United States Patent
Simons et al.

(10) Patent No.: US 11,697,801 B2
(45) Date of Patent: *Jul. 11, 2023

(54) AAV-MEDIATED DELIVERY OF THERAPEUTIC ANTIBODIES TO THE INNER EAR

(71) Applicant: Akouos, Inc., Boston, MA (US)

(72) Inventors: Emmanuel John Simons, Brookline, MA (US); Robert Ng, Newton, MA (US); Michael McKenna, Boston, MA (US)

(73) Assignee: Akouos, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/392,910

(22) Filed: Aug. 3, 2021

(65) Prior Publication Data

US 2021/0363499 A1 Nov. 25, 2021

Related U.S. Application Data

(63) Continuation of application No. 16/955,715, filed as application No. PCT/US2018/066512 on Dec. 19, 2018.

(60) Provisional application No. 62/607,665, filed on Dec. 19, 2017.

(51) Int. Cl.
| | | |
|---|---|---|
| *C12N 7/00* | (2006.01) | |
| *C07K 16/22* | (2006.01) | |
| *A61K 9/00* | (2006.01) | |
| *A61K 48/00* | (2006.01) | |
| *A61P 27/16* | (2006.01) | |

(52) U.S. Cl.
CPC .............. *C12N 7/00* (2013.01); *A61K 9/0046* (2013.01); *A61K 48/005* (2013.01); *A61P 27/16* (2018.01); *C07K 16/22* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter et al. | |
| 4,816,567 A | 3/1989 | Cabilly et al. | |
| 5,122,458 A | 6/1992 | Post et al. | |
| 5,139,941 A | 8/1992 | Muzyczka et al. | |
| 5,168,062 A | 12/1992 | Stinski | |
| 5,478,745 A | 12/1995 | Samulski et al. | |
| 5,741,683 A | 4/1998 | Zhou et al. | |
| 6,001,650 A | 12/1999 | Colosi | |
| 6,054,297 A | 4/2000 | Carter et al. | |
| 6,057,152 A | 5/2000 | Samulski et al. | |
| 6,156,303 A | 12/2000 | Russell et al. | |
| 6,204,059 B1 | 3/2001 | Samulski et al. | |
| 6,268,213 B1 | 7/2001 | Samulski et al. | |
| 6,407,213 B1 | 6/2002 | Carter et al. | |
| 6,491,907 B1 | 12/2002 | Rabinowitz et al. | |
| 6,660,514 B1 | 12/2003 | Zolotukhin et al. | |
| 6,884,879 B1 | 4/2005 | Baca et al. | |
| 6,951,753 B2 | 10/2005 | Shenk et al. | |
| 7,060,269 B1 | 6/2006 | Baca et al. | |
| 7,094,604 B2 | 8/2006 | Snyder et al. | |
| 7,169,901 B2 | 1/2007 | Baca et al. | |
| 7,172,893 B2 | 2/2007 | Rabinowitz et al. | |
| 7,201,898 B2 | 4/2007 | Monahan et al. | |
| 7,229,823 B2 | 6/2007 | Samulski et al. | |
| 7,282,199 B2 | 10/2007 | Gao et al. | |
| 7,297,334 B2 | 11/2007 | Baca et al. | |
| 7,365,166 B2 | 4/2008 | Baca et al. | |
| 7,439,065 B2 | 10/2008 | Ferrari et al. | |
| 7,485,291 B2 | 2/2009 | Fang et al. | |
| 7,498,024 B2 | 3/2009 | Fang et al. | |
| 7,588,772 B2 | 9/2009 | Kay et al. | |
| 7,612,181 B2 | 11/2009 | Wu et al. | |
| 7,662,623 B2 | 2/2010 | Fang et al. | |
| 7,709,224 B2 | 5/2010 | Fang et al. | |
| 7,714,119 B2 | 5/2010 | Fang et al. | |
| 7,790,449 B2 | 9/2010 | Gao et al. | |
| 8,258,268 B2 | 9/2012 | Wu et al. | |
| 8,586,714 B2 | 11/2013 | Ghayur et al. | |

(Continued)

FOREIGN PATENT DOCUMENTS

| | | |
|---|---|---|
| WO | WO-92/022653 A1 | 12/1992 |
| WO | WO-96/037234 A1 | 11/1996 |

(Continued)

OTHER PUBLICATIONS

Fath et al PLoS One, 6 (3) e17596, 1-14 (Year: 2011).*
London et al Laryngoscope, 124:E340-E346 (Year: 2014).*
Suzuki et al Scientific Report, 7(1), 1-10 (Year: 2017).*
Landegger et al Nat Biotechnol. 35(3): 280-284 (Year: 2017).*
Adachi, K. et al., Drawing a high-resolution functional map of adeno-associated virus capsid by massively parallel sequencing, *Nat Commun.*, 5:3075 (2014).
Ahn, S. et al., Intraocular pharmacokinetics of ranibizumab in vitrectomized versus nonvitrectomized eyes, *Invest Ophthalmol Vis Sci.*, 55(1):567-573 (2014).
Akil, O. et al., Dual AAV-mediated gene therapy restores hearing in a DFNB9 mouse model, *Proc Natl Acad Sci USA*, 116(10):4496-4501 (2019).

(Continued)

*Primary Examiner* — Anoop K Singh
(74) *Attorney, Agent, or Firm* — Choate, Hall & Stewart LLP; Stephanie L. Schonewald; Mandeep Kaur

(57) ABSTRACT

Provided herein are methods that include introducing into an inner ear of a mammal a therapeutically effective amount of an adeno-associated virus (AAV) vector that includes a nucleotide sequence encoding (a) a polypeptide including an antibody heavy chain variable domain operably linked to a signal peptide and a polypeptide including an antibody light chain variable domain operably linked to a signal peptide; (b) a polypeptide including an antigen-binding antibody fragment operably linked to a signal peptide; or (c) a soluble vascular endothelial growth factor receptor operably linked to a signal peptide.

25 Claims, 5 Drawing Sheets

Specification includes a Sequence Listing.

(56) References Cited

U.S. PATENT DOCUMENTS

| | | | |
|---|---|---|---|
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |
| 8,822,645 | B2 | 9/2014 | Ghayur et al. |
| 9,079,953 | B2 | 7/2015 | Harding et al. |
| 9,453,241 | B2 | 9/2016 | Pan |
| 10,179,925 | B2 * | 1/2019 | Laird ............ C12Y 203/01046 |
| 10,647,758 | B2 | 5/2020 | Wilson et al. |
| 10,799,566 | B2 * | 10/2020 | High ................. A61K 38/4846 |
| 11,197,937 | B2 | 12/2021 | Tretiakova et al. |
| 2001/0034062 | A1 | 10/2001 | Koenig |
| 2006/0040354 | A1 | 2/2006 | O'Keefe |
| 2006/0110364 | A1 | 5/2006 | Harding |
| 2006/0177819 | A1 | 8/2006 | Smith et al. |
| 2007/0141029 | A1 | 6/2007 | Brough |
| 2009/0215178 | A1 | 8/2009 | Tang |
| 2009/0305344 | A1 | 12/2009 | Polo et al. |
| 2010/0317096 | A1 | 12/2010 | Fang et al. |
| 2010/0322931 | A1 | 12/2010 | Harding et al. |
| 2011/0052576 | A1 | 3/2011 | Ferrara et al. |
| 2011/0065779 | A1 | 3/2011 | Fang et al. |
| 2013/0078260 | A1 | 3/2013 | Cheeseman et al. |
| 2013/0090375 | A1 | 4/2013 | Crystal et al. |
| 2015/0050243 | A1 | 2/2015 | Kaczmarczyk et al. |
| 2015/0147317 | A1 | 5/2015 | Robblee et al. |
| 2015/0182638 | A1 | 7/2015 | Crystal et al. |
| 2015/0210771 | A1 | 7/2015 | Crystal et al. |
| 2016/0243229 | A1 | 8/2016 | Crystal et al. |
| 2016/0289314 | A1 | 10/2016 | Shandilya et al. |
| 2017/0321214 | A1 | 11/2017 | Zhang et al. |
| 2018/0311319 | A1 | 11/2018 | Constable et al. |
| 2018/0369414 | A1 | 12/2018 | Stankovic et al. |
| 2019/0060328 | A1 | 2/2019 | Ibanez et al. |
| 2019/0127455 | A1 | 5/2019 | Simpson et al. |
| 2019/0211091 | A1 * | 7/2019 | Simpson ................ C12N 15/86 |
| 2019/0381194 | A1 | 12/2019 | Tretiakova et al. |
| 2020/0277364 | A1 | 9/2020 | Yoo et al. |
| 2020/0282077 | A1 * | 9/2020 | Kirn ................... A61K 48/0075 |
| 2021/0071149 | A1 | 3/2021 | Simons et al. |
| 2021/0171656 | A1 | 6/2021 | Crystal et al. |
| 2022/0143221 | A1 | 5/2022 | Danos et al. |
| 2022/0195462 | A1 | 6/2022 | Danos et al. |
| 2022/0267739 | A1 | 8/2022 | Simons et al. |
| 2022/0280608 | A1 | 9/2022 | Pakola et al. |
| 2022/0288236 | A1 | 9/2022 | Decibel |
| 2022/0288238 | A1 | 9/2022 | Tretiakova et al. |
| 2023/0057380 | A1 | 2/2023 | Gao et al. |
| 2023/0057519 | A1 | 2/2023 | Simpson et al. |
| 2023/0075045 | A1 | 3/2023 | Wang et al. |

FOREIGN PATENT DOCUMENTS

| | | | |
|---|---|---|---|
| WO | WO-98/10088 A1 | 3/1998 | |
| WO | WO-98/45331 A2 | 10/1998 | |
| WO | WO-00/028004 A1 | 5/2000 | |
| WO | WO-01/059142 A1 | 8/2001 | |
| WO | WO-2003/042397 A2 | 5/2003 | |
| WO | WO-2004/113493 A2 | 12/2004 | |
| WO | WO-2005/017149 A1 | 2/2005 | |
| WO | WO-2005/033321 A2 | 4/2005 | |
| WO | WO-2005/073384 A2 | 8/2005 | |
| WO | WO-2006/12414 A2 | 2/2006 | |
| WO | WO-2006/017325 A2 | 2/2006 | |
| WO | WO-2006/110689 A2 | 10/2006 | |
| WO | WO-2011104307 A2 * | 9/2011 | ......... B01D 15/3804 |
| WO | WO-2012/115980 A1 | 8/2012 | |
| WO | WO-2013/173129 A2 | 11/2013 | |
| WO | WO-2014/043480 A1 | 3/2014 | |
| WO | WO-2014/178078 A2 | 11/2014 | |
| WO | WO-2015/138616 A1 | 9/2015 | |
| WO | WO-2017/040528 A1 | 3/2017 | |
| WO | WO-2017/050825 A1 | 3/2017 | |
| WO | WO-2017040528 A1 * | 3/2017 | ......... A61K 39/0011 |
| WO | WO-2017/075119 A1 | 5/2017 | |
| WO | WO-2017/100791 A1 | 6/2017 | |
| WO | WO-2017/180936 A1 | 10/2017 | |
| WO | WO-2017/181021 A1 | 10/2017 | |
| WO | WO-2017180936 A1 * | 10/2017 | ......... A61K 35/761 |
| WO | WO-2017181021 A1 * | 10/2017 | ......... A61K 48/005 |
| WO | WO-2017/218974 A2 | 12/2017 | |
| WO | WO-2017/218981 A2 | 12/2017 | |
| WO | WO-2019/067540 A1 | 4/2019 | |
| WO | WO-2019/079496 A2 | 4/2019 | |
| WO | WO-2019/104279 A1 | 5/2019 | |
| WO | WO-2019/126329 A1 | 6/2019 | |
| WO | WO-2019116349 A1 * | 6/2019 | ............ C12N 15/11 |
| WO | WO-2019/164854 A1 | 8/2019 | |
| WO | WO-2020/097372 A1 | 5/2020 | |
| WO | WO-2020/206098 A1 | 10/2020 | |
| WO | WO-2020/219868 A1 | 10/2020 | |
| WO | WO-2021/046245 A1 | 3/2021 | |
| WO | WO-2021/071835 A1 | 4/2021 | |
| WO | WO-2021/076794 A1 | 4/2021 | |
| WO | WO-2021/108530 A1 | 6/2021 | |
| WO | WO-2021/255589 A1 | 12/2021 | |
| WO | WO-2021/255590 A1 | 12/2021 | |
| WO | WO-2022/018516 A1 | 1/2022 | |
| WO | WO-2022/051537 A1 | 3/2022 | |
| WO | WO-2022/076549 A1 | 4/2022 | |
| WO | WO-2022/076591 A1 | 4/2022 | |
| WO | WO-2022/076595 A1 | 4/2022 | |
| WO | WO-2022/119839 A1 | 6/2022 | |
| WO | WO-2023/280157 A1 | 1/2023 | |
| WO | WO-2023/284879 A1 | 1/2023 | |

OTHER PUBLICATIONS

Akil, O. et al., Restoration of hearing in the VGLUT3 knockout mouse using virally mediated gene therapy, Neuron, 75(2):283-293 (2012).

Al-Moyed, H. et al., A dual-AAV approach restores fast exocytosis and partially rescues auditory function in deaf otoferlin knock-out mice, EMBO Mol Med., 11(1):e9396 (2019).

Andersen, J. et al., Herpesvirus-Mediated Gene Delivery into the Rat Brain: Specificity and Efficiency of the Neuron-Specific Enolase Promoter, Cell Mol. Neurobiol., 13(5):503-515 (1993).

Andres-Mateos, E. et al., Optimized surgical approach leads to highly efficient AAV gene transfer to inner hair cells in rhesus macaque, American Society of Gene and Cell Therapy Annual Meeting, 22:676 (2019).

Ansari, S. et al., Surgery for vestibular schwannomas: a systematic review of complications by approach, Neurosurg Focus, 33(3):E14 (2012).

Arbuthnot, P. et al., In vitro and in vivo hepatoma cell-specific expression of a gene transferred with an adenoviral vector, Hum Gene Ther., 7(13):1503-1514 (1996).

Askew, C. et al., Tmc gene therapy restores auditory function in deaf mice, Sci Transl Med., 7(295):295ra108 (2015).

Asokan, A. et al., The AAV Vector Toolkit: Poised at the Clinical Crossroads, Molecular Therapy, 20(4):699-708 (2012).

AveXis. 2019. Zolgensma US prescribing information. US Food and Drug Administration. https://www.fda.gov/media/126109/download. Accessed Aug. 31, 2020.

Bakri, S. J. et al., Pharmacokinetics of Intravitreal Ranibizumab (Lucentis), American Academy of Ophthalmology, 14(12):2179-2182 (2007).

Banaszynski, L. A. et al., A rapid, reversible, and tunable method to regulate protein function in living cells using synthetic small molecules, Cell, 126(5): 995-1004 (2012).

Bartoli. M. et al., Noninvasive Monitoring of Therapeutic Gene Transfer in Animal Models of Muscular Dystrophies, Gene Ther. 13:20-28 (2006).

Batt, D. and Carmichael, G., Characterization of the polyomavirus late polyadenylation signal, Mol Cell Biol., 15(9):4783-4790 (1995).

Batt, D. B. and Carmichael, G. G., Characterization of the polyomavirus late polyadenylation signal, Mol. Cell Biol., 15(9):4783-4790 (1995).

Bennett, J. et al., AAV2 gene therapy readministration in three adults with congenital blindness, Sci Transl Med., 4(120):120ra15 (2012).

(56) References Cited

OTHER PUBLICATIONS

Bohne, B. and Harding, G., Degeneration in the cochlea after noise damage: primary versus secondary events, *Am J Otol.*, 21(4):505-509 (2000).
Bonne, N. et al., An allograft mouse model for the study of hearing loss secondary to vestibular schwannoma growth, *J Neurooncol.*, 129(1):47-56 (2016).
Boshart, M. et al., A very strong enhancer is located upstream of an immediate early gene of human cytomegalovirus, Cell, 41(2):521-530 (1985).
Brastianos, P. and Batchelor, T., VEGF inhibitors in brain tumors, *Clin Adv Hematol Oncol.*, 7(11):753-768 (2009).
Bulankina, A. and Moser, T., Neural circuit development in the mammalian cochlea, *Physiology (Bethesda)*, 27(2):100-112 (2012).
Carlson, M. et al., A cross-sectional survey of the North American Skull Base Society: current practice patterns of vestibular schwannoma evaluation and management in North America, *J Neurol Surg B Skull Base*, 79(3):289-296 (2018).
Carlson, M. et al., Long-term quality of life in patients with vestibular schwannoma: an international multicenter cross-sectional study comparing microsurgery, stereotactic radiosurgery, observation, and nontumor controls, *J Neurosurg.*, 122(4):833-842 (2015).
Carneiro, A. et al., Vascular endothelial growth factor plasma levels before and after treatment of neovascular age-related macular degeneration with bevacizumab or ranibizumab, *Acta Ophthalmol.*, 90(1):e25-e30 (2012).
Carvalho, L. et al., Synthetic adeno-associated viral vector efficiently targets mouse and nonhuman primate retina in vivo, *Hum Gene Ther.*, 29(7):771-784 (2018).
Caye-Thomasen, P. et al. Immunohistochemical demonstration of vascular endothelial growth factor in vestibular schwannomas correlates to tumor growth rate, *Laryngoscope*, 113(12):2129-2134 (2003).
Caye-Thomasen, P. et al., VEGF and VEGF receptor-1 concentration in vestibular schwannoma homogenates correlates to tumor growth rate, *Otol Neurotol.*, 26(1):98-101 (2005).
Chen, C. et al., mRNA decay mediated by two distinct AU-rich elements from c-fos and granulocyte-macrophage colony-stimulating factor transcripts: different deadenylation kinetics and uncoupling from translation, *Mol Cell Biol.*, 15(10):5777-5788 (1995).
Chen, H. and Cleck, J., Adverse effects of anticancer agents that target the VEGF pathway, *Nat Rev Clin Oncol.*, 6(8):465-477 (2009).
Chen, J. et al., A cerebellopontine angle mouse model for the investigation of tumor biology, hearing, and neurological function in NF2-related vestibular schwannoma, *Nat Protoc.*, 14(2):541-555 (2019).
Chen, J. et al., Expression of rat bone sialoprotein promoter in transgenic mice, *J Bone Miner Res.*, 11(5):654-664 (1996).
Chen, Q. et al., An AU-rich element in the 3' untranslated region of the spinach chloroplast petD gene participates in sequence-specific RNA-protein complex formation, *Mol Cell Biol.*, 15(4):2010-2018 (1995).
Chen, X. et al., HSV amplicon-mediated neurotrophin-3 expression protects murine spiral ganglion neurons from cisplatin-induced damage, *Mol Ther.*, 3(6):958-963 (2001).
Chien, W. et al., Gene therapy restores hair cell stereocilia morphology in inner ears of deaf whirler mice, *Mol Ther.*, 24(1):17-25 (2016).
Christoforidis, J. et al., PET/CT imaging of 1-124-radiolabeled bevacizumab and ranibizumab after intravitreal injection in a rabbit model, *Invest Ophthalmol Vis Sci.*, 52(8):5899-5903 (2011).
Clinicaltrials.gov. 2020a. NCT02132130: Safety, Tolerability and Efficacy for CGF166 in Patients with Unilateral or Bilateral Severe-to-profound Hearing Loss. National Institutes of Health. Accessed Aug. 31, 2020.
Clinicaltrials.gov. 2020b. NCT03066258: RGX-314 gene therapy for neovascular AMD trial. National Institutes of Health. Accessed Aug. 31, 2020.
Clinicaltrials.gov. 2020c. NCT03748784: ADVM-022 Intravitreal Gene Therapy for Wet AMD (Optic). National Institutes of Health. Accessed Aug. 31, 2020.
Clinicaltrials.gov. 2020d. NCT04418427: ADVM-022 Intravitreal Gene Therapy for DME (Infinity). National Institutes of Health. Accessed Aug. 31, 2020.
Colella, P. et al., Emerging issues in AAV-mediated in vivo gene therapy, *Mol Ther Methods Clin Dev.*, 8:87-104 (2018).
Cotten, M. et al., High-efficiency receptor-mediated delivery of small and large (48 kilobase gene constructs using the endosome-disruption activity of defective or chemically inactivated adenovirus particles, *P.N.A.S. U.S.A.*, 89(13):6094-98 (1992).
Cromie, K. et al., Nanobodies and their Use in GPCR Drug Discovery, *Curr. Top. Med. Chem.*, 15:2543-2557 (2016).
Curiel, D. T., High-efficiency gene transfer employing adenovirus-polylysine-DNA complexes, *Nat Immun.*, 13(2-3):141-64 (1994).
Dai, C. et la., Rhesus cochlear and vestibular functions are preserved after inner ear injection of saline volume sufficient for gene therapy delivery, *J Assoc Res Otolaryngol.*, 18(4):601-617 (2017).
De Felipe, P. and Izqierdo, M., Tricistronic and tetracistronic retroviral vectors for gene transfer, *Hum Gene Ther*, 11(13):1921-1931 (2000).
De Felipe, P. et al., Use of the 2A sequence from foot-and-mouth disease virus in the generation of retroviral vectors for gene therapy, *Gene Ther.*, 6(2):198-208 (1999).
De Fougerolles, A., Delivery vehicles for small interfering RNA in vivo, *Hum Gene Ther.*, 19(2):125-132 (2008).
De Genst, E. et al., Antibody repertoire development in camelids, *Dev Comp Immunol.*, 30(1-2):187-198 (2006).
De Meyer., T. et al., Nanobody-based products as research and diagnostic tools, *Trends Biotechnol.*, 32(5):263-270 (2014).
Digiammarino, E. et al., Design and generation of DVD-lg™ molecules for dual-specific targeting, *Methods Mol Biol.*, 899:145-156 (2012).
Dilwali, S. et al., Secreted factors from human vestibular schwannomas can cause cochlear damage, *Sci Rep.*, 5:18599 (2015).
Dinh, C. et al., Axenograft model of vestibular schwannoma and hearing loss, *Otol Neurotol.*, 39(5):e362-e369 (2018).
Dmitriev, I. et al., An adenovirus vector with genetically modified fibers demonstrates expanded tropism via utilization of a coxsackievirus and adenovirus receptor-independent cell entry mechanism, *J Virol.*, 72(12):9706-9713 (1998).
Doherty, J. and Friedman, R., Controversies in building a management algorithm for vestibular schwannomas, *Curr Opin Otolaryngol Head Neck Surg.*, 14(5):305-313 (2006).
Failla, C. et al., Positive and Negative Regulation of Angiogenesis by Soluble Vascular Endothelial Growth Factor Receptor-1, *Int J Mol Sci.*, 19(5):1306 (2018).
FDA, Applying human factors and usability engineering to medical devices—guidance for industry and Food and Drug Administration staff. In, edited by Food and Drug Administration and Center for Devices and Radiological Health, 49 pages (Feb. 2016).
FDA, Design and analysis of shedding studies for virus or bacteria-based gene therapy and oncolytic products—guidance for industry. In, edited by Food and Drug Administration and Center for Biologies Evaluation and Research, 19 pages (Aug. 2015).
FDA, Evaluation of devices used with Regenerative Medicine Advanced Therapies—guidance for industry. In, edited by Food and Drug Administration, Center for Biologies Evaluation and Research, Center for Devices and Radiological Health and Office of Combination Products, 14 pages (Feb. 2019).
FDA, Principles of premarket pathways for combination products guidance for industry and FDA staff—draft guidance. In, edited by Food and Drug Administration, Office of Combination Products, Center for Biologies Evaluation and Research, Center for Drug Evaluation and Research and Center for Devices and Radiological Health, 24 pages (Feb. 2019).
FDA, Use of International Standard ISO 10993-1, "Biological evaluation of medical devices—Part 1: Evaluation and testing within a risk management process"—guidance for industry and Food and Drug Administration staff. In, edited by Food and Drug Administration and Center for Devices and Radiological Health, 68 pages (Sep. 2020).

(56) References Cited

OTHER PUBLICATIONS

Ferrara, N. et al., Bevacizumab (Avastin), a humanized anti-VEGF monoclonal antibody for cancer therapy, *Biochem Biophys Res Commun.*, 333(2):328-335 (2005).
Fisher, K. et al., Transduction with recombinant adeno-associated virus for gene therapy is limited by leading-strand synthesis, *J Virol.*, 70(1):520-532 (1996).
Flotte, T. et al., A phase I study of an adeno-associated virus-CFTR gene vector in adult CF patients with mild lung disease, *Hum Gene Ther.*, 7(9):1145-1159 (1996).
Flotte, Terence R., Birth of a new therapeutic platform: 47 years of adeno-associated virus biology from virus discovery to licensed gene therapy, *Mol Ther.*, 21(11):1976-1981 (2013).
Francis, S. et al., The adeno-associated viral Anc80 vector efficiently transduces inner ear cells in cynomolgus macaques (*Macaca fascicularis*), *Association for Research in Otolaryngology Midwinter Meeting*, 43:685 (2020).
Fujioka, M. et al., Inflammatory and immune responses in the cochlea: potential therapeutic targets for sensorineural hearing loss, *Front Pharmacol.*, 5:287 (2014).
Furler, S. et al., Recombinant AAV vectors containing the foot and mouth disease virus 2A sequence confer efficient bicistronic gene expression in cultured cells and rat substantia nigra neurons, *Gene Ther.*, 8(11):864-873 (2001).
Gao, G. et al., Clades of Adeno-associated viruses are widely disseminated in human tissues, *J. Virol . . .* 78(12): 6381-6388 (2004).
Gao, X. et al., Anti-VEGF treatment improves neurological function and augments radiation response in NF2 schwannoma model, *Proc Natl Acad Sci USA*, 112(47):14676-14681 (2015).
Gao, Y. et al., The adeno-associated viral AAVAnc80 vector efficiently transduces inner ear cells in olive baboons (*Papio anubis*), *Association for Research in Otolaryngology Midwinter Meeting*, 43:680 (2020).
Garber, K., Bispecific antibodies rise again, *Nat Rev Drug Discov.*, 13(11):799-801 (2014).
Gaudreault, J. et al., Preclinical pharmacokinetics of ranibizumab (rhuFabV2) after a single intravitreal administration, *Invest Ophthalmol Vis Sci.*, 46(2):726-733 (2005).
Gehlhausen, J. et al., A murine model of neurofibromatosis type 2 that accurately phenocopies human schwannoma formation, *Hum Mol Genet.*, 24(1):1-8 (2015).
Genentech. 2017. Lucentis US prescribing information. US Food and Drug Administration. https://www.accessdata.fda.gov/drugsatfda_docs/label/2017/125156s114lbl.pdf., 7 pages, Accessed Aug. 31, 2020.
Giovannini, M. et al., Conditional biallelic Nf2 mutation in the mouse promotes manifestations of human neurofibromatosis type 2, *Genes Dev.*, 14(13):1617-1630 (2000).
Giovannini, M. et al., Schwann cell hyperplasia and tumors in transgenic mice expressing a naturally occurring mutant NF2 protein, *Genes Dev.*, 13(8):978-986 (1999).
Glasscock, M. et al., Twenty-five years of experience with stapedectomy, *Laryngoscope*, 105(9 Pt 1):899-904 (1995).
Golfinos, J. et al., A matched cohort comparison of clinical outcomes following microsurgical resection or stereotactic radiosurgery for patients with small- and medium-sized vestibular schwannomas, *J Neurosurg.*, 125(6):1472-1482 (2016).
Gossen, M. and Bujard, H., Tight control of gene expression in mammalian cells by tetracycline-responsive promoters, *Proc Natl Acad Sci USA*, 89(12):5547-5551 (1992).
Gossen, M. et al., Transcriptional activation by tetracyclines in mammalian cells, *Science*, 268(5218):1766-1769 (1995).
Gutmann, D. and Giovannini, M., Mouse models of neurofibromatosis 1 and 2, *Neoplasia*, 4(4):279-290 (2002).
Gyorgy, B. et al., Gene transfer with AAV9-PHP.B rescues hearing in a mouse model of Usher Syndrome 3A and transduces hair cells in a non-human primate, *Mol Ther Methods Clin Dev.*, 13:1-13 (2019).

Halpin, C. et al., Self-processing 2A-polyproteins—a system for co-ordinate expression of multiple proteins in transgenic plants, *Plant J.*, 17(4):453-45 (1999).
Hamernik, R. et al., Anatomical correlates of impulse noise-induced mechanical damage in the cochlea, *Hear Res.*, 13(3):229-247 (1984).
Hanna, R. et al., Nephrotoxicity induced by intravitreal vascular endothelial growth factor inhibitors: emerging evidence, *Kidney Int.*, 96(3):572-580 (2019).
Hansal, S. et al., Induction of antigen-specific hyporesponsiveness by transplantation of hemopoietic cells containing an MHC class I transgene regulated by a lymphocyte-specific promoter, *J Immunol.*, 161(3):1063-1068 (1998).
Harvey, D. and Caskey, C., Inducible control of gene expression: prospects for gene therapy, *Curr Opin Chem Biol.*, 2(4):512-518 (1998).
Heidel, J. et al., Administration in non-human primates of escalating intravenous doses of targeted nanoparticles containing ribonucleotide reductase subunit M2 siRNA, *Proc Natl Acad Sci USA*, 104(14):5715-5721 (2007).
Hellen, C. and Sarnow, P., Internal ribosome entry sites in eukaryotic mRNA molecules, *Genes Dev.*, 15(13):1593-1612 (2001).
Huang, V. et al., Improvement in patient-reported hearing after treatment with bevacizumab in people with neurofibromatosis type 2, *Otol Neurotol.*, 39(5):632-638 (2018).
Huang, X. et al., Spontaneous tumour shrinkage in 1261 observed patients with sporadic vestibular schwannoma, *J Laryngol Otol.*, 127(8):739-743 (2013).
Hudry, E. et al., Efficient gene transfer to the central nervous system by single-stranded Anc80L65, *Mol Ther Methods Clin Dev.*, 10:197-209 (2018).
Hu-Lieskovan, S. et al., Sequence-specific knockdown of EWS-FLI1 by targeted, nonviral delivery of small interfering RNA inhibits tumor growth in a murine model of metastatic Ewing's sarcoma, *Cancer Res.*, 65(19):8984-8992 (2005).
Husseman, J. and Raphael, Y., Gene Therapy in the Inner Ear Using Adenovirus Vectors, *Adv. Otorhinolaryngol.*, 66:37-51 (2009).
Hutton-Smith, L. et al., A mechanistic model of the intravitreal pharmacokinetics of large molecules and the pharmacodynamic suppression of ocular vascular endothelial growth factor levels by ranibizumab in patients with neovascular age-related macular degeneration, *Mol Pharm.*, 13(9):2941-2950 (2016).
Ikeda, Y. et al., Efficient gene transfer to kidney mesenchymal cells using a synthetic adeno-associated viral vector, *J Am Soc Nephrol.*, 29(9):2287-2297 (2018).
International Search Report for PCT/US2018/066512 (AAV-Mediated Delivery of Therapeutic Antibodies to the Inner Ear, filed Dec. 19, 2018), received from ISA/KR, 7 pages (dated Apr. 17, 2019).
Isgrig, K. et al., AAV2.7m8 is a powerful viral vector for inner ear gene therapy, *Nat. Commun.*, 10(1):427 (2019).
Ito, T. et al., SLC26A4 mutation testing for hearing loss associated with enlargement of the vestibular aqueduct, *World J. Otorhinolaryngol.*, 3(2):26-34 (2013).
Iwamoto, M. et al., A general chemical method to regulate protein stability in the mammalian central nervous system. *Chem Biol.*, 17(9): 981-988 (2010).
Jakob, C. et al., Structure reveals function of the dual variable domain immunoglobulin (DVD-Ig™) molecule, *Mabs*, (3):358-363 (2013).
Jung, J. et al., Secretion of soluble vascular endothelial growth factor receptor 1 (sVEGFR1/sFlt1) requires Arf1, Arf6, and Rab11 GTPases, *PLoS One*, 7(9):e44572, 11 pages (2012).
Kanaan, N. M. et al., Rationally Engineered AAV Capsids Improve Transduction and Volumetric Spread in the CNS, *Mol. Ther. Nucleic Acids*, 8:184-197 (2017).
Kapurch, J. et al., Temporal lobe gliosarcoma after gamma knife radiosurgery for vestibular schwannoma, *Otol Neurotol.*, 37(8):1143-1147 (2016).
Karajannis, M. et al., Sustained imaging response and hearing preservation with low-dose bevacizumab in sporadic vestibular schwannoma, *Neuro Oncol.*, 21(6):822-824 (2019).

(56) References Cited

OTHER PUBLICATIONS

Karch-Georges, A. et al., MRI of endolymphatic hydrops in patients with vestibular schwannomas: a case-controlled study using non-enhanced T2-weighted images at 3 Teslas, *Eur Arch Otorhinolaryngol.*, 276(6):1591-1599 (2019).
Kaul, V. and Cosetti, M., Management of vestibular schwannoma (including NF2): facial nerve considerations, *Otolaryngol Clin North Am.*, 51(6):1193-1212 (2018).
Kelleher, Z. T. and Vos, J. M., Long-term episomal gene delivery in human lymphoid cells using human and avian adenoviral-assisted transfection, *Biotechniques*, 17(6):1110-17 (1994).
Kendall, R. et al,. Identification of a Natural Soluble Form of the Vascular Endothelial Growth Factor Receptor, FLT-1, and Its Heterodimerization with KDR, *Biochem Biophys Res Commun.* 226:324-328 (1996).
Kendall., R. and Thomas, K., Inhibition of vascular endothelial cell growth factor activity by an endogenously encoded soluble receptor, *Proc Natl Acad Sci USA*, 90(22):10705-10709 (1993).
Kijanka, M. et al., Nanobody-based cancer therapy of solid tumors, *Nanomedicine (Lond).*, 10(1):161-174 (2015).
Killeen, D. et al., Long-term effects of bevacizumab on vestibular schwannoma volume in neurofibromatosis type 2 patients, *J Neurol Surg B Skull Base*, 80(5):540-546 (2019).
Kim, H. et al., FcRn receptor-mediated pharmacokinetics of therapeutic IgG in the eye, *Mol Vis.*, 15:2803-2812 (2009).
Kim, M. et al., Methionine sulfoxide reductase B3-targeted in utero gene therapy rescues hearing function in a mouse model of congenital sensorineural hearing loss, *Antioxid Redox Signal*, 24(11):590-602 (2016).
Kim, M. et al., Targeted gene delivery into the mammalian inner ear using synthetic serotypes of adeno-associated virus vectors, *Mol Ther Methods Clin Dev.*, 13:197-204 (2019).
Kirchmann, M. et al., Ten-year follow-up on tumor growth and hearing in patients observed with an intracanalicular vestibular schwannoma, *Neurosurgery*, 80(1):49-56 (2017).
Klettner, A. and Roider, J., Comparison of bevacizumab, ranibizumab, and pegaptanib in vitro: efficiency and possible additional pathways, *Invest Ophthalmol Vis Sci.*, 49(10):4523-4527 (2008).
Klump, H. et al., Retroviral vector-mediated expression of HoxB4 in hematopoietic cells using a novel coexpression strategy, *Gene Ther.*, 8(10):811-817 (2001).
Koen, N. et al., Location of small intracanalicular vestibular schwannomas based on magnetic resonance imaging, *Otolaryngol Head Neck Surg.*, 162(2):211-214 (2020).
Kondziolka, D. et al., The newly diagnosed vestibular schwannoma: radiosurgery, resection, or observation?, *Neurosurg Focus*, 33(3):E8 (2012).
Konishi, T. et al., Effects of chemical alteration in the endolymph on the cochlear potentials, *Acta Otolaryngol.*, 62(4):393-404 (1966).
Koutsimpelas, D. et al., Expression of vascular endothelial growth factor and basic fibroblast growth factor in sporadic vestibular schwannomas correlates to growth characteristics, *Otol Neurotol.*, 28(8):1094-1099 (2007).
Koutsimpelas, D. et al., The VEGF/VEGF-R axis in sporadic vestibular schwannomas correlates with irradiation and disease recurrence, *ORL J Otorhinolaryngol Relat Spec.*, 74(6):330-338 (2012).
Kovaleva, M. et al., Shark variable new antigen receptor biologies—a novel technology platform for therapeutic drug development, *Expert Opin Biol Ther.*, 14(10):1527-1539 (2014).
Krah, S. et al., Single-domain antibodies for biomedical applications, *Immunopharmacol Immunotoxicol.*, 38(1):21-28 (2016).
Kshettry, V. et al., Incidence of vestibular schwannomas in the United States, *J Neurooncol.*, 124(2):223-228 (2015).
Kujawa, S. and Liberman, M. et al., Synaptopathy in the noise-exposed and aging cochlea: Primary neural degeneration in acquired sensorineural hearing loss, *Hear Res.*, 330(Pt B):191-199 (2015).
Landegger, L. et al., A synthetic AAV vector enables safe and efficient gene transfer to the mammalian inner ear, *Nat Biotechnol.*, 35(3):280-284 (2017).
Leabman, M. et al., Effects of altered FcγR binding on antibody pharmacokinetics in cynomolgus monkeys, *Mabs*, 5(6):896-903 (2013).
Lees, K. et al., Natural history ofsporadic vestibular schwannoma: a volumetric study of tumor growth, *Otolaryngol Head Neck Surg.*, 159(3):535-542 (2018).
Levitt, N. et al., Definition of an efficient synthetic poly(A) site, *Genes Dev.*, 3(7):1019-1025 (1989).
Li, S. et al., Effective electrophoretic mobilities and charges of anti-VEGF proteins determined by capillary zone electrophoresis, *J Pharm Biomed Anal.*, 55(3):603-607 (2011).
Li, W. et al., Engineering and selection of shuffled AAV genomes: a new strategy for producing targeted biological nanoparticles, *Mol. Ther.* 16(7):1252-1260 (2008).
Lichtenbeld, H. et al., Effect of local anti-VEGF antibody treatment on tumor microvessel permeability, *Microvasc Res.*, 57(3):357-362 (1999).
Litovsky, Ruth, Development of the auditory system, *Handb Clin Neurol.*, 129:55-72 (2015).
Littman, T. et al., The quinoxalinediones DNOX, CNOX and two related congeners suppress hair cell-to-auditory nerve transmission, *Hear Res.*, 40(1-2):45-53 (1989).
London, N.R. et al., The role of vascular endothelial growth factor and vascular stability in diseases of the ear, *The Laryngoscope*, 124:E340-E346 (2014).
Lu, V. et al., Efficacy and safety of bevacizumab for vestibular schwannoma in neurofibromatosis type 2: a systematic review and meta-analysis of treatment outcomes, *J Neurooncol.*, 144(2):239-248 (2019).
Lysaght, A. et al., Proteome of human perilymph, *J Proteome Res.*, 10(9):3845-3851 (2011).
MacKeith, S. et al., Trends in acoustic neuroma management: a 20-year review of the oxford skull base clinic, *J Neurol Surg B Skull Base*, 74(4):194-200 (2013).
Magari, S. et al., Pharmacologic control of a humanized gene therapy system implanted into nude mice, *J Clin Invest.*, 100(11):2865-2872 (1997).
Mahmud, M. et al., Histopathology of the inner ear in unoperated acoustic neuroma, *Ann Otol Rhinol Laryngol.*, 112(11):979-986 (2003).
Maier, P. et al., Retroviral vectors for gene therapy, *Future Microbiol.*, 5(10):1507-1523 (2010).
Manley, Geoffrey A., Comparative auditory neuroscience: understanding the evolution and function of ears, *J Assoc Res Otolaryngol.*, 18(1):1-24 (2017).
Mattion, N. et al., Foot-and-mouth disease virus 2A protease mediates cleavage in attenuated Sabin 3 poliovirus vectors engineered for delivery of foreign antigens, *J Virol.*, 70(11):8124-8127 (1996).
McClatchey, A. et al., Mice heterozygous for a mutation at the Nf2 tumor suppressor locus develop a range of highly metastatic tumors, *Genes Dev.*, 12(8):1121-1133 (1998).
McClatchey, A. et al., The Nf2 tumor suppressor gene product is essential for extraembryonic development immediately prior to gastrulation, *Genes Dev.*, 11(10):1253-1265 (1997).
Meyer, C. and Holz, F., Preclinical aspects of anti-VEGF agents for the treatment of wet AMD: ranibizumab and bevacizumab, *Eye (Lond).*, 25(6):661-672 (2011).
Miyazaki, J. et al., Expression vector system based on the chicken beta-actin promoter directs efficient production of interleukin-5, *Gene*, 79(2):269-277 (1989).
Morrison, S. et al., Chimeric human antibody molecules: mouse antigen-binding domains with human constant region domains, *Proc Natl Acad Sci USA*, 81(21):6851-6855 (1984).
Mujic-Delic, A. et al., GPCR-targeting nanobodies: attractive research tools, diagnostics, and therapeutics, *Trends Pharmacol Sci.*, 35(5):247-255 (2014).
Murillo, O. et al., Liver expression of a miniATP7B gene results in long-term restoration of copper homeostasis in a Wilson disease model in mice, *Hepatology*, 70(1):108-126 (2019).
Muyldermans, S. et al., Recognition of antigens by single-domain antibody fragments: the superfluous luxury of paired domains, *Trends Biochem Sci.*, 26(4):230-235 (2001).

(56) References Cited

OTHER PUBLICATIONS

Muyldermans, S., Nanobodies: natural single-domain antibodies, *Ann. Rev. Biochem.* 82:775-797 (2013).
Muyldermans, S., Single domain camel antibodies: current status, *J. Biotechnol.*, 74(4):277-302 (2001).
Muzyczka, N., Use of adeno-associated virus as a general transduction vector for mammalian cells, *Curr Top Microbiol Immunol*, 158:97-129 (1992).
Naganawa, S. et al., Endolympathic hydrops in patients with vestibular schwannoma: visualization by non-contrast-enhanced 3D Flair, *Neuroradiology*, 53(12):1009-1015 (2011).
Niwa, H. et al., Efficient selection for high-expression transfectants with a novel eukaryotic vector, *Gene*, 108(2):193-199 (1991).
No Author Listed, High-dose AAV gene therapy deaths, *Nat Biotechnol.*, 38(8):910 (2020).
No, D. et al., Ecdysone-inducible gene expression in mammalian cells and transgenic mice, *Proc Natl Acad Sci USA*, 93(8):3346-3351 (1996).
Nuttall, A. et al., Acute perilymphatic perfusion of the guinea pig cochlea, *Hear Res.*, 6(2):207-221 (1982).
Omichi, R. et al., Hair cell transduction efficiency of single- and dual-AAV serotypes in adult murine cochleae, *Mol Ther Methods Clin Dev.*, 17:1167-1177 (2020).
Orban, T. et al., Applying a "double-feature" promoter to identify cardiomyocytes differentiated from human embryonic stem cells following transposon-based gene delivery, *Stem Cells*, 27(5):1077-1087 (2009).
Orkin, S. et al., Thalassemia due to a mutation in the cleavage-polyadenylation signal of the human beta-globin gene, *EMBO J.*, 4(2):453-456 (1985).
Ostrom, Q. et al., CBTRUS statistical report: primary brain and other central nervous system tumors diagnosed in the United States in 2011-2015, *Neuro Oncol.*, 20(suppl 4):iv1-iv86 (2018).
Paldor, I. et al., Growth rate of vestibular schwannoma, *J Clin Neurosci.*, 32:1-8 (2016).
Pan, B. et al., Gene therapy restores auditory and vestibular function in a mouse model of Usher syndrome type 1c, *Nat Biotechnol.*, 35(3):264-272 (2017).
Papadopoulos, N. et al., Binding and neutralization of vascular endothelial growth factor (VEGF) and related ligands by VEGF Trap, ranibizumab and bevacizumab, *Angiogenesis*, 15(2):171-185 (2012).
Pararas, E. et al., Kinetics of reciprocating drug delivery to the inner ear, *J Control Release*, 152(2):270-277 (2011).
Parente, V. and Corti, S., Advances in spinal muscular atrophy therapeutics, *Ther Adv Neurol Disord.*, 11:1-13 (2018).
Pedrosa, C. et al., Determinants and impact of headache after acoustic neuroma surgery, *Am J Otol.*, 15(6):793-797 (1994).
Pelletier, J. et al., Cap-independent translation of poliovirus mRNA is conferred by sequence elements within the 5' noncoding region., *Mol. Cell. Biol.* 8(3):1103-1112 (1988).
Peris-Celda, M. et al., Main symptom that led to medical evaluation and diagnosis of vestibular schwannoma and patient-reported tumor size: cross-sectional study in 1,304 patients, *J Neurol Surg B Skull Base*, 80(3):316-322 (2019).
Peyre, M. et al., Conservative management of bilateral vestibular schwannomas in neurofibromatosis type 2 patients: hearing and tumor growth results, *Neurosurgery*, 72(6):907-914 (2013).
Piccioli, P. et al., Neuroantibodies: ectopic expression of a recombinant anti-substance P antibody in the central nervous system of transgenic mice, *Neuron*, 15(2):373-384 (1995).
Piccioli, P. et al., Neuroantibodies: molecular cloning of a monoclonal antibody against substance P for expression in the central nervous system, *Proc Natl Acad Sci USA*, 88(13):5611-5615 (1991).
Plotkin, S. et al., Bevacizumab for progressive vestibular schwannoma in neurofibromatosis type 2: a retrospective review of 31 patients, *Otol Neurotol.*, 33(6):1046-1052 (2012).
Plotkin, S. et al., Hearing improvement after bevacizumab in patients with neurofibromatosis type 2, *N Engl J Med.*, 361(4):358-367 (2009).
Plotkin, S. et al., Multicenter, prospective, phase II and biomarker study of high-dose bevacizumab as induction therapy in patients with neurofibromatosis type 2 and progressive vestibular schwannoma, *J Clin Oncol.*, 37(35):3446-3454 (2019).
Poulin, K. et al., Retargeting of adenovirus vectors through genetic fusion of a single-chain or single-domain antibody to capsid protein IX, *J Virol.*, 84(19):10074-10086 (2010).
Proudfoot, N. et al., Integrating mRNA processing with transcription, *Cell*, 108(4):501-512 (2002).
Pryadkina, M. et al., A Comparison of AAV Strategies Distinguishes Overlapping Vectors for Efficient Systemic Delivery of the 6.2 Kb Dysferlin Coding Sequence, *Meth. Clin. Devel.* 2:15009 (2015).
Quesnel, A. et al., Otosclerosis: temporal bone pathology, *Otolaryngol Clin North Am.*, 51(2):291-303 (2018).
Rahbarizadeh, F. et al., Nanobody; an old concept and new vehicle for immunotargeting, *Immunol Invest.*, 40(3):299-338 (2011).
Rask-Andersen, H. et al., Perilymph/modiolar communication routes in the human cochlea, *Ear Hear.*, 27(5):457-465 (2006).
Remenschneider, A. et al., Is the cause of sensorineural hearing loss in patients with facial schwannomas multifactorial?, *Laryngoscope*, 127(7):1676-1682 (2017).
Reznitsky, M. et al., Epidemiology of vestibular schwannomas—prospective 40-year data from an unselected national cohort, *Clin Epidemiol.*, 11:981-986 (2019).
Roesch, S. et al., Functional Testing of SLC26A4 Variants—Clinical and Molecular Analysis of a Cohort with Enlarged Vestibular Aqueduct from Austria, *Int. J. Mol. Sci.* 19(1):209 (2018).
Ronzitti, G. et al., Human immune responses to adeno-associated virus (AAV) Vectors, *Front Immunol.*, 11:670 (2020).
Roosli, C. et al., Dysfunction of the cochlea contributing to hearing loss in acoustic neuromas: an underappreciated entity, *Otol Neurotol.*, 33(3):473-480 (2012).
Rozema, D. et al., Dynamic PolyConjugates for targeted in vivo delivery of siRNA to hepatocytes, *Proc Natl Acad Sci USA*, 104(32):12982-12987 (2007).
Russell, S. et al., Efficacy and safety of voretigene neparvovec (AAV2-hRPE65v2) in patients with RPE65-mediated inherited retinal dystrophy: a randomised, controlled, open-label, phase 3 trial, *Lancet*, 390(10097):849-860 (2017).
Ryan, A. et al., Cellular targeting for cochlear gene therapy, *Adv Otorhinolaryngol.*, 66:99-115 (2009).
Ryan, M. and Drew, J., Foot-and-mouth disease virus 2A oligopeptide mediated cleavage of an artificial polyprotein, EMBO J., 13(4):928-933 (1994).
Saito, K. et al., Expression of Ki-67 antigen and vascular endothelial growth factor in sporadic and neurofibromatosis type 2-associated schwannomas, *Clin Neuropathol.*, 22(1):30-34 (2003).
Sampath, P. et al., Facial nerve injury in acoustic neuroma (vestibular schwannoma) surgery: etiology and prevention, *J Neurosurg.*, 87(1):60-66 (1997).
Sandig, V. et al., HBV-derived promoters direct liver-specific expression of an adenovirally transduced LDL receptor gene, Gene Ther., 3(11):1002-1009 (1996).
Sanofi-Aventis US. 2020. Zaltrap US prescribing information. US Food and Drug Administration. https://www.accessdata.fda.gov/drugsatfda_docs/label/2020/125418s047lbl.pdf. Accessed Aug. 31, 2020.
Sardhara, J. et al., Postoperative tinnitus after vestibular schwannoma surgery: a neglected entity, *Neurol India*, 68(2):333-339 (2020).
Schek, N. et al., Definition of the Upstream Efficiency Element of the Simian Virus 40 Late Polyadenylation Signal by Using in Vitro Analyses, *Mol. Cell Biol.*, 12(12):5386-5393 (1992).
Schmidt-Erfurth, Ursula, Clinical safety of ranibizumab in age-related macular degeneration, *Expert Opin Drug Saf*, 9(1):149-165 (2010).
Schnurman, Z. et la., Volumetric growth rates of untreated vestibular schwannomas, *J Neurosurg.*, 1-7 (2019).
Seol, H. et al., Optimal extent of resection in vestibular schwannoma surgery: relationship to recurrence and facial nerve preservation, *Neurol Med Chir (Tokyo)*, 46(4):176-181 (2006).

(56) References Cited

OTHER PUBLICATIONS

Sharma, A. et al., Transduction efficiency of AAV 2/6, 2/8 and 2/9 vectors for delivering genes in human corneal fibroblasts, *Brain Res Bull.*, 81(2-3):273 (2010).
Shepherd, R. et al., Cochlear pathology following reimplantation of a multichannel scala tympani electrode array in the macaque, *Am J Otol.*, 16(2):186-199 (1995).
Shu, Y. et al., Adenovirus vectors target several cell subtypes of mammalian inner ear in vivo, *Neural Plast.*, 2016:1-8 (2016).
Slattery, W. et al., Vestibular schwannoma growth rates in neurofibromatosis type 2 natural history consortium subjects, *Otol Neurotol.*, 25(5):811-817 (2004).
Spark Therapeutics. 2017. Luxturna US prescribing information. US Food and Drug Administration. https://www.fda.gov/media/109906/download, 16 pages, Accessed Aug. 31, 2020.
Sridhar, T. et al., A novel cholinergic "slow effect" of efferent stimulation on cochlear potentials in the guinea pig, *J Neurosci.*, 15(5 Pt 1):3667-3678 (1995).
Srinivasan, M. et al., Effect of fixatives and tissue processing on the content and integrity of nucleic acids, *Am J Pathol.*, 161(6):1961-1971 (2002).
Stein, G. et al., The osteocalcin gene: a model for multiple parameters of skeletal-specific transcriptional control, *Mol Biol Rep.*, 24(3):185-196 (1997).
Sullivan, J. et al., Convective forces increase rostral delivery of intrathecal radiotracers and antisense oligonucleotides in the cynomolgus monkey nervous system, *J Transl Med.*, 18(1):309 (2020).
Suzuki, J. et al., Cochlear gene therapy with ancestral AAV in adult mice: complete transduction of inner hair cells without cochlear dysfunction, *Sci Rep.*, 7:45524, pp. 1-11 (2017).
Suzuki, J. et al., Round-window delivery of neurotrophin 3 regenerates cochlear synapses after acoustic overexposure, Sci Rep., 6:24907, 11 pages (2016).
Szymanski, P. et al., Development and validation of a robust and versatile one-plasmid regulated gene expression system, Mol Ther., 15(7):1340-1347 (2007).
Talaei, S. et la., Dye tracking following posterior semicircular canal or round window membrane injections suggests a role for the cochlea aqueduct in modulating distribution, *Front Cell Neurosci.*, 13:471, 16 pages (2019).
Tandon, V. et al., Microfabricated infuse-withdraw micropump component for an integrated inner-ear drug-delivery platform, *Biomed Microdevices*, 17(2):37 (2015).
Tandon, V. et al., Microfabricated reciprocating micropump for intracochlear drug delivery with integrated drug/fluid storage and electronically controlled dosing, *Lab Chip.*, 16(5):829-846 (2016).
Tao, Y. et al., Delivery of adeno-associated virus vectors in adult mammalian inner-ear cell subtypes without auditory dysfunction, *Hum Gene Ther.*, 29(4):492-506 (2018).
Thein, S. et al., The polyadenylation site mutation in the alpha-globin gene cluster, Blood, 71(2):313-319 (1988).
Tian, Y. et al., Creation of a transgenic mouse for hair-cell gene targeting by using a modified bacterial artificial chromosome containing Prestin, Dev Dyn., 231(1):199-203 (2004).
Timmers, A. et al., Ocular inflammatory response to intravitreal injection of adeno-associated virus vector: relative contribution of genome and capsid, *Hum Gene Ther.*, 31(1-2):80-89 (2020).
Torres Maldonado, S et al., Recent trends in vestibular schwannoma management: an 11-year analysis of the National Cancer Database, *Otolaryngol Head Neck Surg.*, 161(1):137-143 (2019).
Trapani, I., et al., Effective delivery of large genes to the retina by dual AAV vectors, EMBO Mol Med., 6(2):194-211 (2014).
Tschudi, D. et al., Conservative management of unilateral acoustic neuromas, *Am J Otol.*, 21(5):722-728 (2000).
Van Audenhove, I. and Gettemans, J., Nanobodies as Versatile Tools to Understand, Diagnose, Visualize and Treat Cancer, *EBioMedicine*, 8:40-48 (2016).
Van Bockstaele, F. et al., The development of nanobodies for therapeutic applications, *Curr Opin Investig Drugs*, 10(11):1212-1224 (2009).

Vincke, C. and Muyldermans, S. Introduction to heavy chain antibodies and derived Nanobodies, *Methods Mol Biol.*, 911:15-26 (2012).
Vitosevic, K. et al., Effect of formalin fixation on per amplification of DNA isolated from healthy autopsy tissues, *Acta Histochem*, 120(8):780-788 (2018).
Wang, D. et al., Adeno-associated virus vector as a platform for gene therapy delivery, *Nat Rev Drug Discov.*, 18(5):358-378 (2019).
Wang, L. et al., Single stranded adeno-associated virus achieves efficient gene transfer to anterior segment in the mouse eye, *PLoS One*, 12(8):e0182473, pp. 1-12 (2017).
Wang, Y. et al., Ligand-inducible and liver-specific target gene expression in transgenic mice, *Nat Biotechnol.*, 15(3):239-243 (1997).
Wang, Y., et al., Positive and negative regulation of gene expression in eukaryotic cells with an inducible transcriptional regulator, *Gene Ther.*, 4(5):432-441 (1997).
Wen, H. et al., Characterization of human sclera barrier properties for transscleral delivery of bevacizumab and ranibizumab, *J Pharm Sci.*, 102(3):892-903 (2013).
Wenzel, G. et al., Helper-dependent adenovirus-mediated gene transfer into the adult mouse cochlea, *Otol Neurotol.*, 28(8):1100-1108 (2007).
Wesolowski, J. et al., Single domain antibodies: promising experimental and therapeutic tools in infection and immunity, *Med Microbiol Immunol.*, 198(3):157-174 (2009).
Wolf, A. et al., Risk of radiation-associated intracranial malignancy after stereotactic radiosurgery: a retrospective, multicentre, cohort study, *Lancet Oncol.*, 20(1):159-164 (2019).
Wong, H. et al., Anti-vascular endothelial growth factor therapies as a novel therapeutic approach to treating neurofibromatosis-related tumors, *Cancer Res.*, 70(9):3483-3493 (2010).
Woychik, R. et al., Requirement for the 3' flanking region of the bovine growth hormone gene for accurate polyadenylylation, *Proc Natl Acad Sci USA*, 81(13):3944-3948 (1984).
Wright, C. et al., Ototoxicity of neomycin and polymyxin B following middle ear application in the chinchilla and baboon, *Am J Otol.*, 8(6):495-499 (1987).
Written Opinion for PCT/US2018/066512 (AAV-Mediated Delivery of Therapeutic Antibodies to the Inner Ear, filed Dec. 19, 2018), received from ISA/KR, 19 pages (Apr. 17, 2019).
Xenaki, K. et al., Antibody or antibody fragments: implications for molecular imaging and targeted therapy of solid tumors, *Front Immunol.*, 8:1287 (2017).
Xiao, W. et al. Gene Therapy Vectors Based on Adeno-Associated Virus Type 1, J. Virol., 73(5):3994-4003 (1999).
Yang, J. et al., Comparison of binding characteristics and in vitro activities of three inhibitors of vascular endothelial growth factor A, *Mol Pharm.*, 11(10):3421-3430 (2014).
Yoshimoto, Yuhei, Systematic review of the natural history of vestibular schwannoma, *J Neurosurg.*, 103(1):59-63 (2005).
Yoshimura, H. et al., Enhanced viral-mediated cochlear gene delivery in adult mice by combining canal fenestration with round window membrane inoculation, *Sci Rep.*, 8(1):2980, pp. 1-10 (2018).
Yuan, F. et al., Time-dependent vascular regression and permeability changes in established human tumor xenografts induced by an anti-vascular endothelial growth factor/vascular permeability factor antibody, *Proc Natl Acad Sci USA*, 93(25):14765-14770 (1996).
Zhang, H. et al., Adenovirus-adeno-associated virus hybrid for large-scale recombinant adeno-associated virus production, Human Gene Therapy, 20(9):922-929 (2009).
Zhao, Y. et al., Targeting the cMET pathway augments radiation response without adverse effect on hearing in NF2 schwannoma models, *Proc Natl Acad Sci USA*, 115(9):E2077-E2084 (2018).
Zheng, J. et al., Prestin is the motor protein of cochlear outer hair cells, *Nature*, 405(6783):149-155 (2000).
Zinn, E. et al., In silico reconstruction of the viral evolutionary lineage yields a potent gene therapy vector, *Cell Rep.*, 12(6):1056-1068 (2015).
International Search Report for PCT/US2021/061205, 6 pages (dated Mar. 31, 2022).

(56) References Cited

OTHER PUBLICATIONS

Liu, Y. et al., AAV8-antiVEGFfab Ocular Gene Transfer for Neovascular Age-Related Macular Degeneration, Molecular Therapy, 26(2):542-549 (2017).
Reid, C. et al., Development of an inducible anti-VEGF rAAV gene therapy strategy for the treatment of wet AMD, Scientific Reports, 8(1): p. 11763 (2018).
Written Opinion for PCT/US2021/061205, 10 pages (dated Mar. 31, 2022).
Casset, F. et al., A peptide mimetic of an anti-CD4 monoclonal antibody by rational design, Biochem. Biophys. Res. Commun., 307(1):198-205 (2003).
MacCallum, R.M. et al., Antibody-antigen interactions: contact analysis and binding site topography, J. Mol. Biol., 262(5):732-745 (1996).
Skolnick, J. and Fetrow, J.S., From genes to protein structure and function: novel applications of computational approaches in the genomic era, Trends Biotechnol., 18(1):34-39 (2000).
Vajdos, F.F. et al., Comprehensive functional maps of the antigen-binding site of an anti-ErbB2 antibody obtained with shotgun scanning mutagenesis, J. Mol. Biol., 320(2)415-428 (2002).
Wu, H. et al., Humanization of a murine monoclonal antibody by simultaneous optimization of framework and CDR residues, J. Mol. Biol., 294(1):151-162 (1999).
Zhang, L. et al., Alteration in the IL-2 signal peptide affects secretion of proteins in vitro and in vivo, J. Gene Med., 7(3):354-365 (2005).
Bankoti, K. et al., Advances and challenges in adeno-associated viral inner-ear gene therapy for sensorineural hearing loss, Molecular Therapy: Methods & Clinical Development, 21:209-236 (2021).
Chen, Y. et al., Selection and Analysis of an Optimized Anti-VEGF Anitbody: Crystal Structure of an Affinity-matured Fab in Complex and Antigen, J. Mol. Biol., 293:865-881 (1999).
Gaffen, S.L. and Liu, K.D., Overview of interleukin-2 function, production and clinical applications, Cytokine, 28:109-123 (2004).
Haryadi, R. et al., Optimization of Heavy Chain and Light Chain Signal Peptides for High Level Expression of Therapeutic Antibodies in CHO Cells, PLOS One, 16 pages (2015).
Liu, Y. et al., Promoter effects of adeno-associated viral vector for transgene expression in the cochlea in vivo, Experimental and Molecular Medicine, 39(2):170-175 (2007).
Rudikoff, S. et al., Single amino acid substitution altering antigen-binding specificity, Proc. Natl. Acad. Sci. USA, 79:1979-1983 (1982).
Wu, H. et al. Humanization of a Murine Monoclonal Antibody by Simultaneous Optimization of Framework and CDR Residues, J. Mol. Biol., 294:151-162 (1999).
Liu, H. et al., Current strategies for drug delivery to the inner ear, Acta Pharmaceutica Sinica B, 3(2):86-96 (2013).
Shu, Y. et al., Identification of Adeno-Associated Viral Vectors That Target Neonatal and Adult Mammalian Inner Ear Cell Subtypes, Hum Gene Ther., 27(9):687-99 (2016).

\* cited by examiner

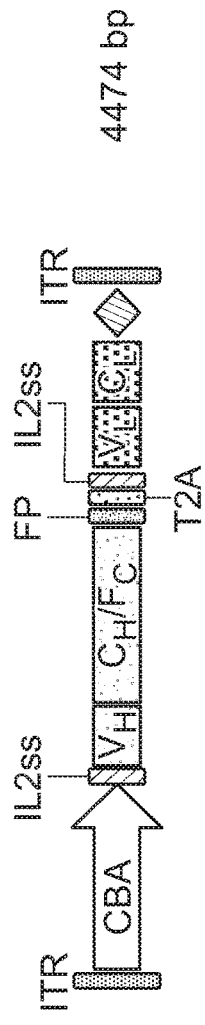
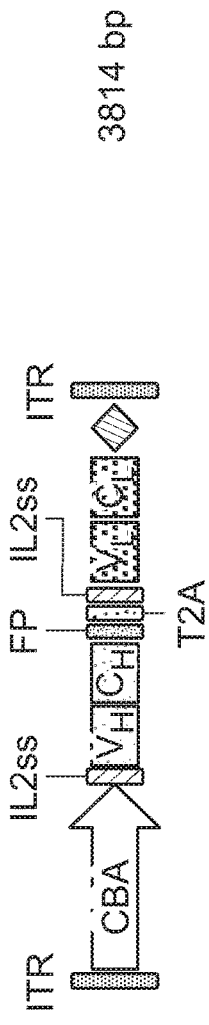
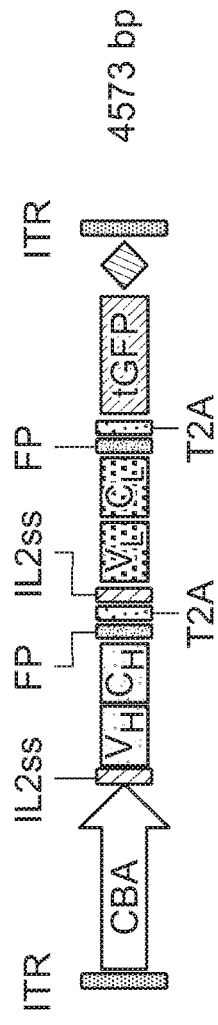
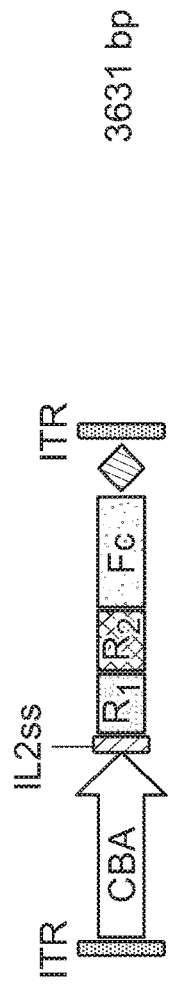
Figure 1A  Avastin / Bevacizumab
Figure 1B  Lucentis / Ranibizumab
Figure 1C  Ranibizumab.T2A.tGFP
Figure 1D  Eylea / Aflibercept

| Loading Sample ID | KD (M) | KD Error | ka (1/Ms) | ka Error | kdis (1/s) | kdis Error |
|---|---|---|---|---|---|---|
| anti-hVEGF MmAb | <1.0E-12 | <1.0E-12 | 2.32E+05 | 7.60E+02 | <1.0E-07 | 1.34E-07 |
| anti-hVEGF MmAb in CM | <1.0E-12 | <1.0E-12 | 2.86E+05 | 8.54E+02 | <1.0E-07 | 1.27E-07 |
| Bevacizumab | <1.0E-12 | 1.32E-12 | 1.62E+05 | 1.43E+03 | <1.0E-07 | 2.14E-07 |
| Parental | N/A | N/A | N/A | N/A | N/A | N/A |

Figure 4C

AAV-MEDIATED DELIVERY OF THERAPEUTIC ANTIBODIES TO THE INNER EAR

CROSS-REFERENCE TO RELATED APPLICATIONS

This application is a Continuation of U.S. patent application Ser. No. 16/955,715, filed Jun. 18, 2020, which claims priority to International Application Serial No. PCT/US2018/066512, filed Dec. 19, 2018, which claims priority to U.S. Provisional Patent Application Ser. No. 62/607,665, filed Dec. 19, 2017; the entire contents of each of which are herein incorporated by reference.

SEQUENCE LISTING

The instant application contains a Sequence Listing which has been submitted electronically in ASCII format and is hereby incorporated by reference in its entirety. Said ASCII copy, created on Jul. 16, 2021, is named "2013615-0474_SL.txt" and is 159,605 bytes in size.

TECHNICAL FIELD

The present disclosure relates generally to the use of nucleic acids to treat hearing loss in a human subject.

BACKGROUND OF THE INVENTION

Sensorinerual hearing loss is hearing loss that is caused by a malfunction of the cells (e.g., hair cells) in an inner ear of a mammal. Non-limiting causes of sensorineural hearing loss include exposure to loud noise, head trauma, viral infection, automimmune inner ear disease, genetic hearing loss, aging, malformations in the inner ear, Meniere's disease, otosclerosis, and tumors.

SUMMARY

The present invention relates to methods that include introducing into an inner ear of a mammal (e.g., a human) a therapeutically effective amount of any adeno-associated virus (AAV) vector that includes a nucleotide sequence encoding: (a) a polypeptide including an antibody heavy chain variable domain operably linked to a signal peptide and a polypeptide including an antibody light chain variable domain operably linked to a signal peptide; or (b) a polypeptide including an antigen-binding antibody fragment operably linked to a signal peptide.

Provided herein are methods for increasing the level of an antibody or an antigen-binding antibody fragment in an inner ear of a mammal in need thereof that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment linked to a signal peptide; wherein the introducing results in an increase in the level of the antibody or the antigen-binding antibody fragment in the inner ear of the mammal.

In some embodiments, the antibody or the antigen-binding antibody fragment binds specifically to vascular endothelial growth factor (VEGF). In some embodiments, the antibody or antigen-binding antibody fragment decreases VEGF activity. In some embodiments of any of the methods described herein, the AAV vector further includes one or both of a promoter and a Kozak sequence that are operably linked to the sequence encoding the antibody or the antigen-binding antibody fragment.

In some embodiments, the AAV vector includes a promoter selected from the group consisting of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified as having an inner ear disorder. In some embodiments of any of the methods described herein, the mammal has been diagnosed as having an inner ear disorder.

In some embodiments of any of the methods described herein, the AAV vector includes a nucleic acid sequence encoding a polypeptide including an antibody heavy chain variable domain operably linked to a signal peptide and a polypeptide including an antibody light chain variable domain operably linked to a signal peptide.

In some embodiments of any of the methods described herein, the AAV vector includes a nucleic acid sequence encoding a polypeptide including an antigen-binding antibody fragment operably linked to a signal.

Also provided herein are methods for treating an inner ear disorder in a mammal in need thereof that include: introducing into the inner ear of the mammal a therapeutically effective amount of an AAV vector that includes a nucleotide sequence encoding: (a) a polypeptide including an antibody heavy chain variable domain operably linked to a signal peptide and a polypeptide including an antibody light chain variable domain operably linked to a signal peptide; or (b) a polypeptide including an antigen-binding antibody fragment linked to a signal peptide; wherein the introducing results in the treatment of the inner ear disorder in the mammal.

In some embodiments of any of the methods described herein, the AAV vector further includes one or both of a promoter and a Kozak sequence that are operably linked to the sequence encoding the antibody or the antigen-binding antibody fragment.

In some embodiments, the AAV vector includes a promoter selected from the group consisting of: an inducible promoter, a constitutive promoter, and a tissue-specific promoter.

In some embodiments of any of the methods described herein, the AAV vector further includes a polyadenylation signal sequence.

In some embodiments of any of the methods described herein, the mammal is a human. In some embodiments of any of the methods described herein, the mammal has been identified as having an inner ear disorder. In some embodiments of any of the methods described herein, the mammal has been diagnosed as having an inner ear disorder.

In some embodiments of any of the methods described herein, the AAV vector includes a nucleic acid sequence encoding a polypeptide including an antibody heavy chain variable domain operably linked to a signal peptide and a polypeptide including an antibody light chain variable domain operably linked to a signal peptide.

In some embodiments of any of the methods described herein, the AAV vector includes a nucleic acid sequence encoding a polypeptide including an antigen-binding antibody fragment operably linked to a signal.

Also provided herein are methods of reducing VEGF activity in an inner ear of a mammal in need thereof that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; wherein the introducing results in a reduction in VEGF activity in the inner ear of the mammal.

In some embodiments of any of the methods described herein, the AAV vector further includes one or both of a promoter and a Kozak sequence that are operably linked to the sequence encoding the antibody or the antigen-binding antibody fragment.

In some embodiments, the AAV vector includes a promoter selected from the group consisting of: an inducible promoter, a constitutive promoter, and a tissue-specific promoter.

In some embodiments of any of the methods described herein, the AAV vector further includes a polyadenylation signal sequence. In some embodiments of any of the methods described herein, the mammal is a human.

In some embodiments of any of the methods described herein, the mammal has been identified or diagnosed as having an acoustic neuroma. In some embodiments, the mammal has been identified or diagnosed as having a vestibular schwannoma. In some embodiments of any of the methods described herein, the mammal has been identified or diagnosed as having a neurofibromatosis type 2.

In some embodiments of any of the methods described herein, the AAV vector includes a nucleic acid sequence encoding a polypeptide including an antibody heavy chain variable domain operably linked to a signal peptide and a polypeptide including an antibody light chain variable domain operably linked to a signal peptide.

In some embodiments of any of the methods described herein, the AAV vector includes a nucleic acid sequence encoding a polypeptide including an antigen-binding antibody fragment operably linked to a signal peptide.

Also provided herein are methods of treating acoustic neuroma, vestibular schwannoma, or neurofibromatosis type 2 in an inner ear of a mammal that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; wherein the introducing results in treatment of acoustic neuroma, vestibular schwannoma, or neurofibromatosis type II, respectively, in the inner ear of the mammal.

In some embodiments of any of the methods described herein, the AAV vector further includes one or both of a promoter and a Kozak sequence that are operably linked to the sequence encoding the antibody or the antigen-binding antibody fragment.

In some embodiments of any of the methods described herein, the AAV vector includes a promoter selected from the group consisting of: an inducible promoter, a constitutive promoter, and a tissue-specific promoter.

In some embodiments of any of the methods described herein, the AAV vector further includes a polyadenylation signal sequence.

In some embodiments of any of the methods described herein, the mammal is a human. In some embodiments of any of the methods described herein, the mammal has been identified or diagnosed as having an acoustic neuroma. In some embodiments of any of the methods described herein, the mammal has been identified or diagnosed as having a vestibular schwannoma. In some embodiments of any of the methods described herein, the mammal has been identified or diagnosed as having neurofibromatosis type 2.

In some embodiments of any of the methods described herein, the AAV vector includes a nucleic acid sequence encoding a polypeptide including an antibody heavy chain variable domain operably linked to a signal peptide and a polypeptide including an antibody light chain variable domain operably linked to a signal peptide.

In some embodiments of any of the methods described herein, the AAV vector includes a nucleic acid sequence encoding a polypeptide including an antigen-binding antibody fragment operably linked to a signal peptide.

In some embodiments of any of the methods described herein, the antibody includes a Fc region that includes one or more amino acid substitutions that decreases the half-life of the antibody in a mammal as compared to a control antibody; or the antigen-binding antibody fragment thereof has a decreased in vivo half-life as compared to a control antigen-binding antibody fragment.

Also provided herein are methods that include introducing into an inner ear of a mammal a therapeutically effective amount of an adeno-associated virus (AAV) vector that includes a nucleotide sequence encoding a soluble vascular endothelial growth factor (VEGF) receptor operably linked to a signal peptide.

Also provided herein are methods for increasing the level of a soluble vascular endothelial growth factor (VEGF) receptor in an inner ear of a mammal in need thereof that include: introducing into the inner ear of the mammal a therapeutically effective amount of an AAV vector that includes a nucleotide sequence encoding a soluble VEGF receptor operably linked to a signal peptide; where the introducing results in an increase in the level of the soluble VEGF receptor in the inner ear of the mammal.

In some embodiments of any of the methods described herein, the soluble VEGF receptor includes a portion of an extracellular region of VEGF receptor-1 (VEGFR-1). In some embodiments of any of the methods described herein, the portion of the extracellular region of VEGFR-1 includes a contiguous sequence from wildtype human VEGFR-1. In some embodiments of any of the methods described herein, the portion of the extracellular region of VEGFR-1 includes one or more immunoglobulin-like domains in the extracellular region from wildtype human VEGFR-1. In some embodiments of any of the methods described herein, the portion of the extracellular region of VEGFR-1 includes a sequence that is at least 90% identical to a contiguous sequence from wildtype human VEGFR-1.

In some embodiments of any of the methods described herein, the soluble VEGF receptor includes a portion of an extracellular region of VEGF receptor-2 (VEGFR-2). In some embodiments of any of the methods described herein, the portion of the extracellular region of VEGFR-2 includes a contiguous sequence from wildtype human VEGFR-2. In some embodiments of any of the methods described herein, the portion of the extracellular region of VEGFR-2 includes one or more immunoglobulin-like domains in the extracellular region from wildtype human VEGFR-2. In some embodiments of any of the methods described herein, the portion of the extracellular region of VEGFR-2 includes a sequence that is at least 90% identical to a contiguous sequence from wildtype human VEGFR-2.

In some embodiments of any of the methods described herein, the soluble VEGF receptor includes a portion of an extracellular region of VEGFR-1 and a portion of an extracellular region of VEGFR-2. In some embodiments of any of the methods described herein, the portion of the extracellular region of VEGFR-1 includes one or more immunoglobulin-like domains in the extracellular region from wildtype human VEGFR-1; and the portion of the extracellular region of VEGFR-2 includes one or more immunoglobulin-like domains in the extracellular region from wildtype human VEGFR-2. In some embodiments of any of the methods described herein, the soluble VEGF receptor is aflibercept.

In some embodiments of any of the methods described herein, the soluble VEGF receptor includes a portion of an extracellular region of VEGF receptor-3 (VEGFR-3). In some embodiments of any of the methods described herein, the portion of the extracellular region of VEGFR-3 includes a contiguous sequence from wildtype human VEGFR-3. In some embodiments of any of the methods described herein, the portion of the extracellular region of VEGFR-3 includes one or more immunoglobulin-like domains in the extracellular region from wildtype human VEGFR-3. In some embodiments of any of the methods described herein, the portion of the extracellular region of VEGFR-3 includes a sequence that is at least 90% identical to a contiguous sequence from wildtype human VEGFR-3. In some embodiments of any of the methods described herein, the soluble VEGF receptor comprises a Fc domain. In some embodiments of any of the methods described herein, the Fc domain is an IgG1 Fc domain. In some embodiments of any of the methods described herein, the IgG1 Fc domain is a human wildtype IgG1 Fc domain.

In some embodiments of any of the methods described herein, the soluble VEGF receptor decreases the ability of a VEGF to bind to one or more of VEGFR-1, VEGFR-2, and VEGFR-3.

In some embodiments of any of the methods described herein, the AAV vector further includes one or both of a promoter and a Kozak sequence that are operably linked to the sequence encoding the soluble VEGF receptor. In some embodiments of any of the methods described herein, the AAV vector includes a promoter selected from the group of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified as having an inner ear disorder. In some embodiments of any of the methods described herein, the mammal has been diagnosed as having an inner ear disorder.

Also provided herein are methods for treating an inner ear disorder in a mammal in need thereof that include: introducing into the inner ear of the mammal a therapeutically effective amount of an AAV vector that includes a nucleotide sequence encoding a soluble vascular endothelial growth factor (VEGF) receptor operably linked to a signal peptide; where the introducing results in the treatment of the inner ear disorder in the mammal.

In some embodiments of any of the methods described herein, the AAV vector further includes one or both of a promoter and a Kozak sequence that are operably linked to the sequence encoding the soluble VEGF receptor. In some embodiments of any of the methods described herein, the AAV vector includes a promoter selected from the group of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified as having an inner ear disorder. In some embodiments of any of the methods described herein, the mammal has been diagnosed as having an inner ear disorder.

Also provided herein are methods of reducing a VEGF activity in an inner ear of a mammal in need thereof that include: introducing into the inner ear of the mammal a therapeutically effective amount of an AAV vector that includes a nucleotide sequence encoding a soluble vascular endothelial growth factor (VEGF) receptor operably linked to a signal peptide; where the introducing results in a reduction in the VEGF activity in the inner ear of the mammal.

In some embodiments of any of the methods described herein, the AAV vector further includes one or both of a promoter and a Kozak sequence that are operably linked to the sequence encoding the soluble VEGF receptor. In some embodiments of any of the methods described herein, the AAV vector includes a promoter selected from the group of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified or diagnosed as having an acoustic neuroma. In some embodiments of any of the methods described herein, the mammal has been identified or diagnosed as having a vestibular schwannoma. In some embodiments of any of the methods described herein, the mammal has been identified or diagnosed as having a neurofibromatosis type 2.

Also provided herein are methods of treating acoustic neuroma, vestibular schwannoma, or neurofibromatosis type 2 in an inner ear of a mammal that include: introducing into the inner ear of the mammal a therapeutically effective amount of an AAV vector that includes a nucleotide sequence encoding a nucleotide sequence encoding a soluble vascular endothelial growth factor (VEGF) receptor operably linked to a signal peptide; where the introducing results in treatment of acoustic neuroma, vestibular schwannoma, or neurofibromatosis type II, respectively, in the inner ear of the mammal.

In some embodiments of any of the methods described herein, the AAV vector further includes one or both of a promoter and a Kozak sequence that are operably linked to the sequence encoding the soluble VEGF receptor. In some embodiments of any of the methods described herein, the AAV vector includes a promoter selected from the group of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified or diagnosed as having an acoustic neuroma. In some embodiments of any of the methods described herein, the mammal has been identified or diagnosed as having a vestibular schwannoma. In some embodiments of any of the methods described herein, the mammal has been identified or diagnosed as having neurofibromatosis type 2.

In some embodiments of any of the methods described herein, the soluble VEGF receptor includes a portion of an extracellular region of VEGF receptor-1 (VEGFR-1). In some embodiments of any of the methods described herein, the portion of the extracellular region of VEGFR-1 includes a contiguous sequence from wildtype human VEGFR-1. In some embodiments of any of the methods described herein, the portion of the extracellular region of VEGFR-1 includes one or more immunoglobulin-like domains in the extracellular region from wildtype human VEGFR-1. In some embodiments of any of the methods described herein, the portion of the extracellular region of VEGFR-1 includes a sequence that is at least 90% identical to a contiguous sequence from wildtype human VEGFR-1.

In some embodiments of any of the methods described herein, the soluble VEGF receptor includes a portion of an extracellular region of VEGF receptor-2 (VEGFR-2). In some embodiments of any of the methods described herein, the portion of the extracellular region of VEGFR-2 includes a contiguous sequence from wildtype human VEGFR-2. In some embodiments of any of the methods described herein, the portion of the extracellular region of VEGFR-2 includes one or more immunoglobulin-like domains in the extracellular region from wildtype human VEGFR-2. In some embodiments of any of the methods described herein, the portion of the extracellular region of VEGFR-2 includes a sequence that is at least 90% identical to a contiguous sequence from wildtype human VEGFR-2.

In some embodiments of any of the methods described herein, the soluble VEGF receptor includes a portion of an extracellular region of VEGFR-1 and a portion of an extracellular region of VEGFR-2. In some embodiments of any of the methods described herein, the portion of the extracellular region of VEGFR-1 includes one or more immunoglobulin-like domains in the extracellular region from wildtype human VEGFR-1; and the portion of the extracellular region of VEGFR-2 includes one or more immunoglobulin-like domains in the extracellular region from wildtype human VEGFR-2. In some embodiments of any of the methods described herein, the soluble VEGF receptor is aflibercept.

In some embodiments of any of the methods described herein, the soluble VEGF receptor includes a portion of an extracellular region of VEGF receptor-3 (VEGFR-3). In some embodiments of any of the methods described herein, the portion of the extracellular region of VEGFR-3 includes a contiguous sequence from wildtype human VEGFR-3. In some embodiments of any of the methods described herein, the portion of the extracellular region of VEGFR-3 includes one or more immunoglobulin-like domains in the extracellular region from wildtype human VEGFR-3. In some embodiments of any of the methods described herein, the portion of the extracellular region of VEGFR-3 includes a sequence that is at least 90% identical to a contiguous sequence from wildtype human VEGFR-3.

In some embodiments of any of the methods described herein, the soluble VEGF receptor comprises a Fc domain. In some embodiments of any of the methods described herein, the Fc domain is an IgG1 Fc domain. In some embodiments of any of the methods described herein, the IgG1 Fc domain is a human wildtype IgG1 Fc domain.

In some embodiments of any of the methods described herein, the soluble VEGF receptor decreases the ability of a VEGF to bind to one or more of VEGFR-1, VEGFR-2, and VEGFR-3. In some embodiments of any of the methods described herein, the AAV vector further includes a secretion sequence.

Unless otherwise specified, a "nucleotide sequence encoding an amino acid sequence" includes all nucleotide sequences that are degenerate versions of each other and thus encode the same amino acid sequence.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "transfected," "transformed," or "transduced" refers to a process by which exogenous nucleic acid is transferred or introduced into a cell. A "transfected," "transformed," or "transduced" mammalian cell is one that has been transfected, transformed, or transduced with exogenous nucleic acid.

The term "expression" refers to the transcription and/or translation of a particular nucleotide sequence encoding a protein.

The term "transient expression" refers to the expression of a non-integrated coding sequence for a short period of time (e.g., hours or days). The coding sequence that is transiently expressed in a cell (e.g., a mammalian cell) is lost upon multiple rounds of cell division.

The term "subject" is intended to include any mammal. In some embodiments, the subject is a rodent (e.g., a rat or mouse), a rabbit, a sheep, a goat, a pig, a dog, a cat, a non-human primate, or a human. In some embodiments, the subject has or is at risk of developing non-syndromic deafness. In some embodiments, the subject has been previously identified as having an inner ear disorder. In some embodiments, the subject has previously been diagnosed as having an inner ear disorder. In some embodiments, the subject has been identified as having drug-induced hearing loss. In some embodiments, the subject is an infant (e.g., a human infant).

A treatment is "therapeutically effective" when it results in a reduction in one or more of the number, severity, and frequency of one or more symptoms of a disease (e.g., non-symptomatic sensorineural hearing loss) in a subject (e.g., a human).

The term "nucleic acid" or "polynucleotide" refers to deoxyribonucleic acid (DNA) or ribonucleic acid (RNA), or a combination thereof, in either single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the nucleic acids described herein, the nucleic acid is DNA. In some embodiments of any of the nucleic acids described herein, the nucleic acid is RNA.

The term "signal peptide" refers to a sequence present on the N-terminus of a nascent secreted protein but is absent in the naturally-occurring mature protein. A "signal peptide" is cleaved by a protease (e.g., a signal peptidase) after the signal peptide is translated. Signal peptides are known in the art. Non-limiting examples of signal peptides include: MEFFKKTALAALVMGFSGAALA (SEQ ID NO: 9) and MKYLLPTAAAGLLLLAAQPAMA (SEQ ID NO: 10).

The term "inner ear disorder" refers to a disorder caused by malfunction of the cells (e.g., hair cells, supporting cells, spiral ganglion neurons, macrophages, or schwann cells) in or around the inner ear of a mammal. Non-limiting examples of inner ear disorders include, e.g., sensorineural hearing loss (SNHL), noise-induced hearing loss, drug-induced hearing loss, age-related hearing loss, acoustic neuroma, neurofibromatosis type 2, auditory neuropathy, noise-induced cochlear synaptopathy without hair cell loss, age-related cochlear synaptopathy, acquired sensorineural hearing loss, and vestibular schwannoma. See, e.g., Kujawa et al., *Hear Res* 330(0 0): 191-199, 2015; and Suzuki et al., *Scientific Reports* 6: 24907. Non-limiting examples of inner ear disorders are described herein and additional examples of inner ear disorders are known in the art.

The term "antibody" means a complex of two or more single polypeptide chains that interact to form at least one antigen-binding domain. Non-limiting examples of an antibody include monoclonal antibodies (for example, full length or intact monoclonal antibodies), polyclonal antibodies, multivalent antibodies, multispecific antibodies (e.g., bispecific, trispecific, etc. antibodies so long as they exhibit the desired biological activity). An antibody can be human, humanized, and/or affinity-matured.

The term "antigen-binding antibody fragment" is a single polypeptide that includes all the amino acids that make up at least one antigen-binding domain (e.g., an scFv).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al, Proc. Natl. Acad. Sci. USA 81:6851-6855 (1984)).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigens. In some examples, an antigen-binding domain can bind to an antigen or epitope with specificity and affinity similar to that of naturally-occurring antibodies. In some embodiments, an antigen-binding domain can include an alternative scaffold. Non-limiting examples of antigen-binding domains are described herein. Additional examples of antigen-binding domains are known in the art. In some examples, an antigen-binding domain can bind to a single antigen.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity between an antigen-binding domain and its corresponding antigen or epitope are known in the art.

The phrase "half-life" refers to the half-life of an antibody, an antigen-binding antibody fragment thereof, or a soluble VEGF receptor in circulation (e.g., blood) of a mammal (e.g., any of the mammals described herein) and is represented by the time required for 50% of an antibody, an antigen-binding antibody fragment thereof, or soluble VEGF receptor to be cleared from the circulation. In some embodiments, an alteration in half-life (e.g., a decrease in half-life of an antibody, an antigen-binding antibody fragment thereof, or soluble VEGF receptor) is determined by comparing the half-life of an antibody, an antigen-binding antibody fragment, or a soluble VEGF receptor in a subject to the half-life of a control antibody, control antigen-binding antibody fragment, or control soluble VEGF receptor in a similar mammal.

In some embodiments, the half-life of an antibody, antigen-binding antibody fragment thereof, or soluble VEGF receptor in a mammal is determined by measuring the level of the antibody, antigen-binding antibody fragment thereof, or soluble VEGF receptor in samples obtained from a subject (e.g., a blood sample) at different time points following systemic administration (e.g., intravenous) administration of any of the AAV vectors described herein. In some embodiments, the level of the antibody, antigen-binding antibody fragment thereof, or soluble VEGF receptor present in samples obtained from a mammal is determined using enzyme-linked immunosorbent assay (ELISA) or another assay known to the art, and the determined level of the antibody, antigen-binding antibody fragment thereof, or soluble VEGF receptor present in the samples is plotted as a function of time using a software program (e.g., GraphPad Prism).

The term "VEGF activity" refers to one or more known activities of a VEGF protein. For example, one activity of a VEGF protein is the ability to bind to one or more VEGF receptors. In another example, one activity of a VEGF protein is the ability of a VEGF to trigger downstream signal transduction pathway(s) in a mammalian cell expressing a VEGF receptor. Methods for detecting one or more activities of VEGF are known in the art.

The term "soluble VEGF receptor" refers to a polypeptide that includes a portion of an extracellular region of one or more mammalian VEGF receptor(s) (e.g., VEGFR-1, VEGFR-2, and VEGFR-3) operably linked to a signal peptide, where the soluble VEGF receptor is capable of specifically binding to one or more mammalian VEGF proteins (e.g., one or more of VEGF-A, VEGF-B, VEGF-C, and VEGF-D). In some examples, a soluble VEGF receptor includes a portion of an extracellular region of VEGFR-1 (e.g., a contiguous sequence from wildtype human VEGFR-1 (e.g., one or more immunoglobulin-like domains in the extracellular region from wildtype human VEGFR-1) or a sequence that is at least 90% identical to a contiguous sequence from wildtype human VEGFR-1). In some examples, a soluble VEGF receptor includes a portion of an extracellular region of VEGFR-2 (e.g., a contiguous sequence from wildtype human VEGFR-2 (e.g., one or more immunoglobulin-like domains in the extracellular region from wildtype human VEGFR-2) or a sequence that is at least 90% identical to a contiguous sequence from wildtype human VEGFR-2). In some examples, a soluble VEGF receptor includes a portion of an extracellular region of VEGFR-1 and a portion of an extracellular region of VEGFR-2 (e.g., one or more immunoglobulin-like domains in the extracellular region from wildtype human VEGFR-1 and one or more immunoglobulin-like domains in the extracellular region from wildtype human VEGFR-2) (e.g., aflibercept). In some examples, a soluble VEGF receptor includes a portion of an extracellular region of VEGFR-3 (e.g., a contiguous sequence from wildtype human VEGFR-3 (e.g., one or more immunoglobulin-like domains in the extracellular region from wildtype human VEGFR-3) or a sequence that is at least 90% identical to a contiguous sequence from wildtype human VEGFR-3).

In some examples, a soluble VEGF receptor can further include a stabilizing domain (e.g., a Fc domain, such as an IgG1 Fc domain (e.g., a human wildtype IgG1 Fc domain). In some examples, the soluble VEGF receptor decreases the ability of a VEGF to bind to one or more (e.g., two or three) of VEGFR-1, VEGFR-2, and VEGFR-3. Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

BRIEF DESCRIPTION OF DRAWINGS

FIG. 1A is an exemplary AAV vector of 4474 bp that includes a sequence encoding bevacizumab (Avastin®).

FIG. 1B is an exemplary AAV vector of 3814 bp that includes a sequence encoding ranibizumab (Lucentis®).

FIG. 1C is an exemplary AAV vector of 4573 bp that includes a sequence encoding ranibizumab and green fluorescent protein (GFP).

FIG. 1D is an exemplary AAV vector of 3631 bp that includes a sequence encoding aflibercept (Eylea®).

FIG. 4C is a table showing the equilibrium dissociation constant ($K_D$) determined from the data shown in FIGS. 3A, 3B, 4A, and 4B (going from the top to the bottom of the table).

DETAILED DESCRIPTION

Figure 2:
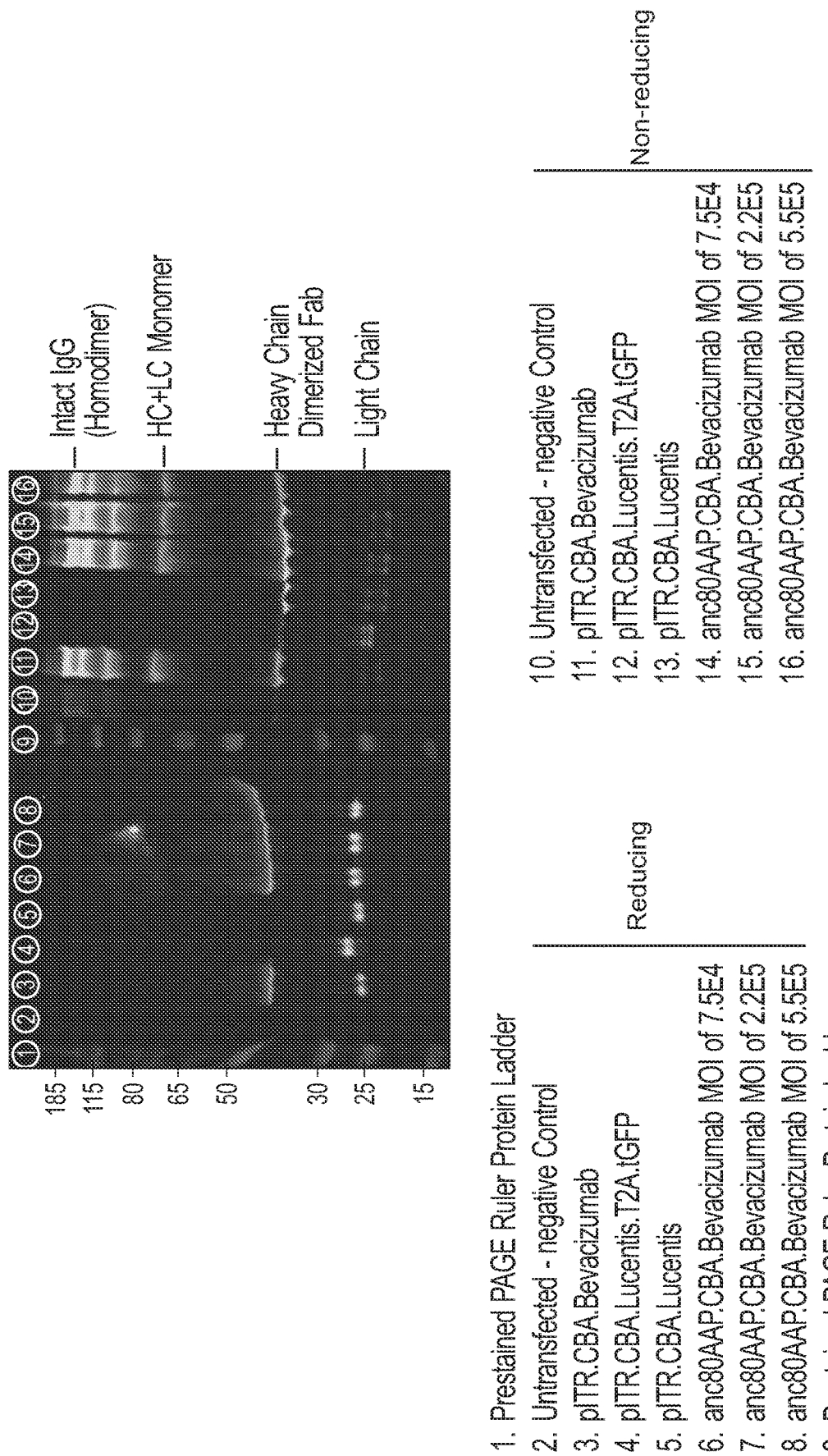
FIG. 2 is a Western blot showing HEK cell expression of different anti-VEGF antibodies or antigen-binding antibody fragments, or soluble VEGF receptors using exemplary AAV vectors described herein. Lane 1: pre-stained PageRuler™ protein ladder. Lane 2: untransfected/negative control. Lane 3: tranfection with the AAV vector shown in FIG. 1A. Lane 4: transfection with the AAV vector shown in FIG. 1C. Lane 5: transfection with the AAV vector shown in FIG. 1B. Lane 6: transfection with the AAV vector shown in FIG. 1A with an multiplicity of infection (MOI) of $7.5 \times 10^4$. Lane 7: transfection with the AAV vector shown in FIG. 1A with an MOI of $2.2 \times 10^5$. Lane 8: transfection with the AAV vector shown in FIG. 1A with an MOI of $5.5 \times 10^5$. Lane 9: prestained PageRuler™ protein ladder. Lane 10: untransfected/negative control. Lane 11: tranfection with the AAV vector shown in FIG. 1A. Lane 12: transfection with the AAV vector shown in FIG. 1C. Lane 13: transfection with the AAV vector shown in FIG. 1B. Lane 14: transfection with the AAV vector shown in FIG. 1A with an multiplicity of infection (MOI) of $7.5 \times 10^4$. Lane 15: transfection with the AAV vector shown in FIG. 1A with an MOI of $2.2 \times 10^5$. Lane 16: transfection with the AAV vector shown in FIG. 1A with an MOI of $5.5 \times 10^5$. Lanes 2-8 contain reduced proteins. Lanes 10-16 contain non-reduced proteins.

Provided herein are methods that include introducing into an inner ear of a mammal a therapeutically effective amount of an adeno-associated virus (AAV) vector that includes a nucleotide sequence encoding: (a) a polypeptide including an antibody heavy chain variable domain operably linked to a signal peptide and a polypeptide including an antibody light chain variable domain operably linked to a signal peptide; or (b) a polypeptide including an antigen-binding antibody fragment (e.g., a Fab or a scFv) operably linked to a signal peptide.

Also provided herein are methods for increasing the level of an antibody or an antigen-binding antibody fragment in an inner ear of a mammal in need thereof, that include: introducing into the inner ear of the mammal a therapeutically effective amount of an AAV vector that includes a nucleotide sequence encoding: (a) a polypeptide including an antibody heavy chain variable domain operably linked to a signal peptide and a polypeptide including an antibody light chain variable domain operably linked to a signal peptide; or (b) a polypeptide including an antigen-binding antibody fragment (e.g., a Fab or a scFv) operably linked to a signal peptide; wherein the introducing results in an increase in the level of the antibody or the antigen-binding antibody fragment in the inner ear of the mammal.

Also provided are methods for treating an inner ear disorder in a mammal in need thereof that include introducing into the inner ear of the mammal a therapeutically effective amount of an AAV vector that includes a nucleotide sequence encoding: (a) a polypeptide including an antibody heavy chain variable domain operably linked to a signal peptide and a polypeptide comprising an antibody light chain variable domain operably linked to a signal peptide; or (b) a polypeptide comprising an antigen-binding antibody fragment linked to a signal peptide; where the introducing results in the treatment of the inner ear disorder in the mammal.

Also provided herein are methods of reducing VEGF activity in an inner ear of a mammal in need thereof that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment (e.g., a Fab or a scFv) operably linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; and wherein the introducing results in a reduction in VEGF activity in the inner ear of the mammal.

Also provided herein are methods of treating acoustic neuroma, vestibular schwannoma, or neurofibromatosis type II in an inner ear of a mammal that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment (e.g., a Fab or a scFv) operably linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; and wherein the introducing results in treatment of acoustic neuroma or vestibular schwannoma in the inner ear of the mammal.

Also provided herein are methods that include introducing into an inner ear of a mammal a therapeutically effective amount of an adeno-associated virus (AAV) vector that include a nucleotide sequence encoding a soluble vascular endothelial growth factor (VEGF) receptor operably linked to a signal peptide.

Also provided herein are methods for increasing the level of a soluble vascular endothelial growth factor (VEGF) receptor in an inner ear of a mammal in need thereof that include introducing into the inner ear of the mammal a therapeutically effective amount of an AAV vector that includes a nucleotide sequence encoding a soluble VEGF receptor operably linked to a signal peptide; where the introducing results in an increase in the level of the soluble VEGF receptor in the inner ear of the mammal.

Also provided herein are methods for treating an inner ear disorder in a mammal in need thereof that include introducing into the inner ear of the mammal a therapeutically effective amount of an AAV vector that includes a nucleotide sequence encoding a soluble vascular endothelial growth factor (VEGF) receptor operably linked to a signal peptide; where the introducing results in the treatment of the inner ear disorder in the mammal.

Also provided herein are methods of reducing a VEGF activity in an inner ear of a mammal in need thereof that include introducing into the inner ear of the mammal a therapeutically effective amount of an AAV vector that includes a nucleotide sequence encoding a soluble vascular endothelial growth factor (VEGF) receptor operably linked to a signal peptide; where the introducing results in a reduction in the VEGF activity in the inner ear of the mammal.

Also provided herein are methods of treating acoustic neuroma, vestibular schwannoma, or neurofibromatosis type 2 in an inner ear of a mammal that include introducing into the inner ear of the mammal a therapeutically effective amount of an AAV vector that includes a nucleotide sequence encoding a nucleotide sequence encoding a soluble vascular endothelial growth factor (VEGF) receptor operably linked to a signal peptide; where the introducing results in treatment of acoustic neuroma, vestibular schwannoma, or neurofibromatosis type II, respectively, in the inner ear of the mammal.

Also provided are kits that include any of the AAV vectors described herein. Additional non-limiting aspects of the compositions, kits, and methods are described herein and can be used in any combination without limitation.

Antibodies and Antigen-Binding Antibody Fragments

In some embodiments, the antibody can be a humanized antibody, a chimeric antibody, or a multivalent antibody. In some embodiments, an antibody or an antigen-binding antibody fragment can be a scFv-Fc, a $V_H$H domain, a $V_{NAR}$ domain, a (scFv)$_2$, a minibody, or a BiTE. In some embodiments, an antibody or an antigen-binding antibody fragment can be a DVD-Ig, and a dual-affinity re-targeting antibody (DART), a triomab, kih IgG with a common LC, a crossmab, an ortho-Fab IgG, a 2-in-1-IgG, IgG-ScFv, scFv$_2$-Fc, a bi-nanobody, tanden antibody, a DART-Fc, a scFv-HAS-scFv, DNL-Fab3, DAF (two-in-one or four-in-one), Duta-Mab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H)IgG, IgG(L)-scFv, scFv-(L)-IgG, IgG (L,H)-Fc, IgG(H)-V, V(H)-IgG, IgG(L)-V, V(L)-IgG, KIH IgG-scFab, 2scFv-IgG, IgG-2scFv, scFv4-Ig, Zybody, DVI-IgG, nanobody, nanobody-HSA, a diabody, a TandAb, scDiabody, scDiabody-CH3, Diabody-CH3, Triple Body, miniantibody, minibody, TriBi minibody, scFv-CH3 KIH, Fab-scFv, scFv-CH-CL-scFv, F(ab')2-scFV2, scFv-KIH, Fab-scFv-Fc, tetravalent HCAb, scDiabody-Fc, diabody-Fc, tandem scFv-Fc, intrabody, dock and lock bispecific antibody, ImmTAC, HSAbody, scDiabody-HAS, tandem scFv, IgG-IgG, Cov-X-Body, and scFv1-PEG-scFv2.

Additional examples of an antibody or an antigen-binding antibody fragment include an Fv fragment, a Fab fragment, a F(ab')2 fragment, and a Fab' fragment. Additional examples of an antibody or an antigen-binding antibody fragment include an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

Any of the antibodies or antigen-binding antibody fragments described herein can bind specifically to VEGF.

A $V_H H$ domain is a single monomeric variable antibody domain that can be found in camelids. A $V_{NAR}$ domain is a single monomeric variable antibody domain that can be found in cartilaginous fish. Non-limiting aspects of $V_H H$ domains and $V_{NAR}$ domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; *Muyldermans, J. Biotechnol.* 74:277-302, 2001; Muyldermans et al., *Trends Biochem. Sci.* 26:230-235, 2001; *Muyldermans, Ann. Rev. Biochem.* 82:775-797, 2013; Rahbarizadeh et al., *Immunol. Invest.* 40:299-338, 2011; Van Audenhove et al., *E Bio Medicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

A "Fv" fragment includes a non-covalently-linked dimer of one heavy chain variable domain and one light chain variable domain.

A "Fab" fragment includes, the constant domain of the light chain and the first constant domain (Cm) of the heavy chain, in addition to the heavy and light chain variable domains of the Fv fragment.

A "F(ab')$_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, *Nature Reviews Drug Discovery* 13:799-801, 2014.

Additional aspects of antibodies and antigen-binding antibody fragments are known in the art.

In some embodiments, any of the antibodies or antigen-binding antibody fragments described herein has a dissociation constant ($K_D$) of less than $1 \times 10^{-5}$ M (e.g., less than $0.5 \times 10^{-5}$ M, less than $1 \times 10^{-6}$ M, less than $0.5 \times 10^{-6}$ M, less than $1 \times 10^{-7}$ M, less than $0.5 \times 10^{-7}$ M, less than $1 \times 10^{-8}$ M, less than $0.5 \times 10^{-8}$ M, less than $1 \times 10^{-9}$ M, less than $0.5 \times 10^{-9}$ M, less than $1 \times 10^{-10}$ M, less than $0.5 \times 10^{-10}$ M, less than $1 \times 10^{-11}$ M, less than $0.5 \times 10^{-11}$ M, or less than $1 \times 10^{-12}$ M), e.g., as measured in phosphate buffered saline using surface plasmon resonance (SPR) for a VEGF protein (e.g., any of the VEGF proteins described herein, e.g., one or more of mature human VEGF-A, mature human VEGF-B, mature human VEGF-C, and mature human VEGF-D).

In some embodiments, any of the antibodies or antigen-binding antibody fragments described herein has a $K_D$ of about $1 \times 10^{-12}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, about $0.5 \times 10^{-10}$ M, about $1 \times 10^{-11}$ M, or about $0.5 \times 10^{-11}$ M (inclusive); about $0.5 \times 10^{-11}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, about $0.5 \times 10^{-10}$ M, or about $1 \times 10^{-11}$ M (inclusive); about $1 \times 10^{-11}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, or about $0.5 \times 10^{-10}$ M (inclusive); about $0.5 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, or about $1 \times 10^{-10}$ M (inclusive); about $1 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, or about $0.5 \times 10^{-9}$ M (inclusive); about $0.5 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, or about $1 \times 10^{-9}$ M (inclusive); about $1 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, or about $0.5 \times 10^{-8}$ M (inclusive); about $0.5 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, or about $1 \times 10^{-8}$ M (inclusive); about $1 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, or about $0.5 \times 10^{-7}$ M (inclusive); about $0.5 \times 10^{-7}$ M to about $1 \times 10^{-5}$ M, about $0.5 \times 10^{-5}$ M, about $1 \times 10^{-6}$ M, about $0.5 \times 10^{-6}$ M, or about $1 \times 10^{-7}$ M (inclusive); about $1 \times 10^{-7}$ M to about $1 \times 10^{-5}$ M, about $0.5 \times 10^{-5}$ M, about $1 \times 10^{-6}$ M, or about $0.5 \times 10^{-6}$ M (inclusive); about $0.5 \times 10^{-6}$ M to about $1 \times 10^{-5}$ M, about $0.5 \times 10^{-5}$ M, or about $1 \times 10^{-6}$ M (inclusive); about $1 \times 10^{-6}$ M to about $1 \times 10^{-5}$ M or about $0.5 \times 10^{-5}$ M (inclusive); or about $0.5 \times 10^{-5}$ M to about $1 \times 10^{-5}$ M (inclusive), e.g., as measured in phosphate buffered saline using surface plasmon resonance (SPR), for a VEGF protein (e.g., any of the VEGF proteins described herein, e.g., one or more of mature human VEGF-A, mature human VEGF-B, mature human VEGF-C, and mature human VEGF-D).

A variety of different methods known in the art can be used to determine the $K_D$ values of any of the antibodies or antigen-binding antibody fragments described herein (e.g., an electrophoretic mobility shift assay, a filter binding assay, surface plasmon resonance, and a biomolecular binding kinetics assay, etc.).

In some embodiments of any of the antibodies and/or antigen-binding antibody fragments described herein, the half-life of the antibody and/or the antigen-binding antibody fragment in a subject (e.g., a human) is decreased about 0.5-fold to about 4-fold (e.g., about 0.5-fold to about 3.5-fold, about 0.5-fold to about 3-fold, about 0.5-fold to about 2.5-fold, about 0.5-fold to about 2-fold, about 0.5-fold to about 1.5-fold, about 0.5-fold to about 1-fold, about 1-fold to about 4-fold, about 1-fold to about 3.5-fold, about 1-fold to about 3-fold, about 1-fold to about 2.5-fold, about 1-fold to about 2-fold, about 1.5-fold to about 4-fold, about 1.5-fold to about 3.5-fold, about 1.5-fold to about 3-fold, about 1.5-fold to about 2.5-fold, about 1.5-fold to about 2-fold, about 2-fold to about 4-fold, about 2-fold to about 3.5-fold, about 2-fold to about 3-fold, about 2-fold to about 2.5-fold, about 2.5-fold to about 4-fold, about 2.5-fold to about 3.5-fold, about 2.5-fold to about 3-fold, about 3-fold to about 4-fold, about 3-fold to about 3.5-fold, or about 3.5-fold to about 4-fold) as compared to the half-life of a control antibody and/or a control antigen-binding antibody fragment (e.g., any of the control antibodies and control antigen-binding antibody fragments described herein) in a similar subject. See, e.g., Leabman et al., *MAbs*. 5(6): 896-903, 2013. In some embodiments, an antibody or antigen-binding antibody fragment described herein has one or more amino acid substitutions in the Fc region that decrease its half-life in a mammal, and a control antibody lacks at least one (e.g., lacks all) of these one or more amino acid substitutions in the Fc region.

VEGF

The VEGF gene encodes vascular endothelial growth factor (VEGF), formerly known as fms-like tyrosine kinase (Flt-1). The VEGF protein is a heparin-biding protein that induces migration and proliferation of vascular endothelial cells.

Non-limiting examples of protein and nucleotide sequences encoding a wildtype VEGF protein are shown below.

```
Human VEGF Transcript Variant 1
Protein Sequence
                                         (SEQ ID NO: 1)
MTDRQTDTAPSPSYHLLPGRRRTVDAAASRGQGPEPAPGGGVE

GVGARGVALKLFVQLLGCSRFGGAVVRAGEAEPSGAARSASSG

REEPQPEEGEEEEKEEERGPQWRLGARKPGSWTGEAAVCADS

APAARAPQALARASGRGGRVARRGAEEESGPPHSPSRRGSASRA

GPGRASETMNFLLSWVHWSLALLLYLHHAKWSQAAPMAEGGGQ

NHHEVVKFMDVYQRSYCHPIETLVDIFQEYPDEIEYIFKPSCV

PLMRCGGCCNDEGLECVPTEESNITMQIMRIKPHQGQHIGEMS

FLQHNKCECRPKKDRARQEKKSVRGKGKGQKRKRKKSRYKSWS

VYVGARCCLMPWSLPGPHPCGPCSERRKHLFVQDPQTCKCSCK

NTDSRCKARQLELNERTCRCDKPRR

Human VEGF Transcript Variant 1 cDNA
                                         (SEQ ID NO: 2)
ct gacggacaga cagacagaca ccgcccccag ccccagctac cacctcctcc ccggccggcg gcggacagtg gacgcggcgg cgagccgcgg gcaggggccg gagcccgcgc ccggaggcgg ggtggagggg gtcggggctc gcggcgtcgc actgaaactt ttcgtccaac ttctgggctg ttctcgcttc ggaggagccg tggtccgcgc ggggaagccgagccgagcg gagccgcgag aagtgctagc tcgggccggg aggagccgca gccggaggag ggggaggagg aagaagagaa ggaagaggag aggggggccgc agtggcgact cggcgctcgg aagccgggct catggacggg tgaggcggcg gtgtgcgcag acagtgctcc agccgcgcgc gctcccagg ccctggcccg ggcctcgggc cgggaggaa gagtagctcg ccgaggcgcc gaggagagcg ggccgcccca cagcccgagc cggagaggga gcgcgagccg cgccggcccc ggtcgggcct ccgaaaccat gaactttctg ctgtcttggg tgcattggag ccttgccttg ctgctctacc tccaccatgc caagtggtcc caggctgcac ccatggcaga aggaggaggg cagaatcatc acgaagtggt gaagttcatg gatgtctatc agcgcagcta ctgccatcca atcgagaccc tggtggacat cttccaggag tacctgatg agatcgagta catcttcaag ccatcctgtg tgccctgat gcgatgcggg ggctgctgca atgacgaggg cctggagtgt gtgcccactg aggagtccaa catcaccatg cagattatgc ggatcaaacc tcaccaaggc cagcacatag gagagatgag cttcctacag cacaacaaat gtgaatgcag accaaagaaa gatagagcaa gacaagaaaa aaaatcagtt cgaggaaagg gaaaggggca aaaacgaaag cgcaagaaat cccggtataa gtcctggagc gtgtacgttg gtgcccgctg ctgtctaatg ccctggagcc tccctggccc ccatccctgt gggccttgct cagagcggag aaagcatttg tttgtacaag atccgcagac gtgtaaatgt tcctgcaaaa acacagactc gcgttgcaag gcgaggcagc ttgagttaaa cgaacgtact tgcagatgtg acaagccgag gcggtga Human VEGF Transcript Variant 3
Protein Sequence
                                         (SEQ ID NO: 3)
MTDRQTDTAPSPSYHLLPGRRRTVDAAASRGQGPEPAPGGGVE

GVGARGVALKLFVQLLGCSRFGGAVVRAGEAEPSGAARSASSG

REEPQPEEGEEEEKEEERGPQWRLGARKPGSWTGEAAVCADS

APAARAPQALARASGRGGRVARRGAEEESGPPHSPSRRGSASRA

GPGRASETMNFLLSWVHWSLALLLYLHHAKWSQAAPMAEGGGQ

NHHEVVKFMDVYQRSYCHPIETLVDIFQEYPDEIEYIFKPSCV

PLMRCGGCCNDEGLECVPTEESNITMQIMRIKPHQGQHIGEMS

FLQHNKCECRPKKDRARQEKKSVRGKGKGQKRKRKKSRPCGPC

SERRKHLFVQDPQTCKCSCKNTDSRCKARQLELNERTCRCDKP

RR

Human VEGF Transcript Variant 3 cDNA
                                         (SEQ ID NO: 4)
ct gacggacaga cagacagaca ccgcccccag ccccagctac cacctcctcc ccggccggcg gcggacagtg gacgcggcgg cgagccgcgg gcaggggccg gagcccgcgc ccggaggcgg ggtggagggg gtcggggctc gcggcgtcgc actgaaactt ttcgtccaac ttctgggctg ttctcgcttc ggaggagccg tggtccgcgc ggggaagccgagccgagcg gagccgcgag aagtgctagc tcgggccggg aggagccgca gccggaggag ggggaggagg aagaagagaa ggaagaggag aggggggccgc agtggcgact cggcgctcgg aagccgggct catggacggg tgaggcggcg gtgtgcgcag acagtgctcc agccgcgcgc
```

```
gctccccagg ccctggcccg ggcctcgggc cggggaggaa gagtagctcg ccgaggcgcc gaggagagcg ggccgcccca cagcccgagc cggagaggga gcgcgagccg cgccggcccc ggtcgggcct ccgaaaccat gaactttctg ctgtcttggg tgcattggag ccttgccttg ctgctctacc tccaccatgc caagtggtcc caggctgcac ccatggcaga aggaggaggg cagaatcatc acgaagtggt gaagttcatg gatgtctatc agcgcagcta ctgccatcca atcgagaccc tggtggacat cttccaggag tacctgatg agatcgagta catcttcaag ccatcctgtg tgccctgat gcgatgcggg ggctgctgca atgacgaggg cctggagtgt gtgcccactg aggagtccaa catcaccatg cagattatgc ggatcaaacc tcaccaaggc cagcacatag gagagatgag cttcctacag cacaacaaat gtgaatgcag accaaagaaa gatagagcaa gacaagaaaa aaaatcagtt cgaggaaagg gaaagggggca aaaacgaaag cgcaagaaat cccgtccctg tgggccttgc tcagagcgga gaaagcattt gtttgtacaa gatccgcaga cgtgtaaatg ttcctgcaaa aacacagact cgcgttgcaa ggcgaggcag cttgagttaa acgaacgtac ttgcagatgt gacaagccga ggcggtga
```

Mature Human VEGF-A
(SEQ ID NO: 13)
apma egggqnhhev vkfmdvyqrs ychpletivd ifqeypdele yifkpscvpi mrcggccnde glecvptees nitmqimrik phqgqhigem sfighnkcec rpkkdrarqe kksvrgkgkg qkrkrkksry kswsvyvgar ccimpwsipg phpcgpcser rkhifvqdpq tckcsckntd srckarqiel nertcrcdkp rr Mature Human VEGF-B
(SEQ ID NO: 14)
pvsqpdapg hqrkvvswid vytratcqpr evvvpitvel mgtvakqlvp scvtvqrcgg ccpddglecv ptgqhqvrmq limirypssq igemsleehs qcecrpkkkd savkpdraat phhrpqprsv pgwdsapgap spadithptp apgpsahaap sttsaltpgp aaaaadaaas svakgga Mature Human VEGF-C
(SEQ ID NO: 15)
Ahynteilk sidnewrktq cmprevcidv gkefgvatnt ffkppcvsvy rcggccnseg iqcmntstsy isktifeitv pisqgpkpvt isfanhtscr cmskidvyrq vhsiirr Mature Human VEGF-D
(SEQ ID NO: 16)
fa atfydietik videewqrtq cspretcvev aseigkstnt ffkppcvnvf rcggccnees licmntstsy iskqlfeisv pitsvpelvp vkvanhtgck ciptaprhpy siirr In some examples of any of the antibodies and antigen-binding fragments thereof described herein, the antibody and antigen-binding fragment can bind to a VEGF antigen (e.g., any of the exemplary VEGF proteins described herein, e.g., one or more of mature human VEGF-A, mature human VEGF-B, mature human VEGF-C, and mature human VEGF-D) (e.g., any of the binding affinities described herein).

In some embodiments described herein, an antibody or antigen-binding antibody fragment can decrease an activity of a VEGF (e.g., one or more of any of the exemplary VEGF proteins described herein, e.g., one or more of mature human VEGF-A, mature human VEGF-B, mature human VEGF-C, and mature human VEGF-D). In some embodiments, an antibody or antigen-binding antibody fragment can block a VEGF (e.g., one or more of any of the exemplary VEGF proteins described herein, e.g., one or more of mature human VEGF-A, mature human VEGF-B, mature human VEGF-C, and mature human VEGF-D) from binding to one or more of its receptors (e.g., one or more VEGF receptors) See, e.g., WO 1998/045331, U.S. Pat. No. 9,079,953, US 2015/0147317, US 2016/0289314, Plotkin et al., Otology & Neurotology 33: 1046-1052 (2012); and Ferrara et al. (2005) Biochem Biophys Res Commun 333(2): 328-335. In some embodiments, an antibody or antigen-binding antibody can decrease downstream signaling (e.g., signaling downstream of a VEGF receptor, e.g., one or more of any of the exemplary VEGF receptors described herein, e.g., one or more of human VEGFR-1, human VEGFR-2, and human VEGFR-3). In some embodiments, a decrease in an activity of a VEGF can be detected indirectly, e.g., through an increase in hearing (e.g., a 1% to about 400% increase (or any of the subranges of this range described herein) in hearing) or a decrease (e.g., a 1% to 99%, a 1% to 95%, a 1% to 90%, a 1% to 85%, a 1% to 80%, a 1% to 75%, a 1% to 70%, a 1% to 65%, a 1% to 60%, a 1% to 55%, a 1% to 50%, a 1% to 45%, a 1% to 40%, a 1% to 35%, a 1% to 30%, a 1% to 25%, a 1% to 20%, a 1% to 15%, a 1% to 10%, a 1% to 5%, a 5% to 99%, a 5% to 95%, a 5% to 90%, a 5% to 85%, a 5% to 80%, a 5% to 75%, a 5% to 70%, a 5% to 65%, a 5% to 60%, a 5% to 55%, a 5% to 50%, a 5% to 45%, a 5% to 40%, a 5% to 35%, a 5% to 30%, a 5% to 25%, a 5% to 20%, a 5% to 15%, a 5% to 10%, a 10% to 99%, a 10% to 95%, a 10% to 90%, a 10% to 85%, a 10% to 80%, a 10% to 75%, a 10% to 70%, a 10% to 65%, a 10% to 60%, a 10% to 55%, a 10% to 50%, a 10% to 45%, a 10% to 40%, a 10% to 35%, a 10% to 30%, a 10% to 25%, a 10% to 20%, a 10% to 15%, a 15% to 99%, a 15% to 95%, a 15% to 90%, a 15% to 85%, a 15% to 80%, a 15% to 75%, a 15% to 70%, a 15% to 65%, a 15% to 60%, a 15% to 55%, a 15% to 50%, a 15% to 45%, a 15% to 40%, a 15% to 35%, a 15% to 30%, a 15% to 25%, a 15% to 20%, a 20% to 99%, a 20% to 95%, a 20% to 90%, a 20% to 85%, a 20% to 80%, a 20% to 75%, a 20% to 70%, a 20% to 65%, a 20% to 60%, a 20% to 55%, a 20% to 50%, a 20% to 45%, a 20% to 40%, a 20% to 35%, a 20% to 30%, a 20% to 25%, a 25% to 99%, a 25% to 95%, a 25% to 90%, a 25% to 85%, a 25% to 80%, a 25% to 75%, a 25% to 70%, a 25% to 65%, a 25% to 60%, a 25% to 55%, a 25% to 50%, a 25% to 45%, a 25% to 40%, a 25% to 35%, a 25% to 30%, a 30% to 99%, a 30% to 95%, a 30% to 90%, a 30% to 85%, a 30% to 80%, a 30% to 75%, a 30% to 70%, a 30% to 65%, a 30% to 60%, a 30% to 55%, a 30% to 50%, a 30% to 45%, a 30% to 40%, a 30% to 35%, a 35% to 99%, a 35% to 95%, a 35% to 90%, a 35% to 85%, a 35% to 80%, a 35% to 75%, a 35% to 70%, a 35% to 65%, a 35% to 60%, a 35% to 55%, a 35% to 50%, a 35% to 45%, a 35% to 40%, a 40% to 99%, a 40% to 95%, a 40% to 90%, a 40% to 85%, a 40% to 80%, a 40% to 75%, a 40% to 70%, a 40% to 65%, a 40% to 60%, a 40% to 55%, a 40% to 50%, a 40% to 45%, a 45% to 99%, a 45% to 95%, a 45% to 90%, a 45% to 85%, a 45% to 80%, a 45% to 75%, a 45% to 70%, a 45% to 65%, a 45% to 60%, a 45% to 55%, a 45% to 50%, a 50% to 99%, a 50% to 95%, a 50% to 90%, a 50% to 85%, a 50% to 80%, a 50% to 75%, a 50% to 70%, a 50% to 65%, a 50% to 60%, a 50% to 55%, a 55% to 99%, a 55% to 95%, a 55% to 90%, a 55% to 85%, a 55% to 80%, a 55% to 75%, a 55% to 70%, a 55% to 65%, a 55% to 60%, a 60% to 99%, a 60% to 95%, a 60% to 90%, a 60% to 85%, a 60% to 80%, a 60% to 75%, a 60% to 70%, a 60% to 65%, a 65% to 99%, a 65% to 95%, a 65% to 90%, a 65% to 85%, a 65% to 80%, a 65% to 75%, a 65% to 70%, a 70% to 99%, a 70% to 95%, a 70% to 90%, a 70% to 85%, a 70% to 80%, a 70% to 75%, a 75% to 99%, a 75% to 95%, a 75% to 90%, a 75% to 85%, a 75% to 80%, a 80% to 99%, a 80% to 95%, a 80% to 90%, a 80% to 85%, a 85% to 99%, a 85% to 95%, a 85% to 90%, a 90% to 99%, a 90% to 95%, or a 95% to 99% decrease) in the size or the severity of one or more symptoms of an acoustic neuroma, vestibular schwannoma, or neurofibromatosis type II in a mammal as compared to the level of hearing or size of an acoustic neuroma, vestibular schwannoma, or neurofibromatosis type II in the mammal, respectively, before administration of any of the AAV vectors described herein. In some embodiments, a decrease in a VEGF activity can be detected in an in vitro assay.

In some embodiments, the antibody that specifically binds to a VEGF is bevacizumab (Avastatin®) or an antigen-binding fragment thereof. Bevacizumab (full size antibody ~150 kDa) inhibits all isoforms of VEGF-A. Bevacizumab received Food and Drug administration (FDA) approval in 2004 for colon cancer for intravenous (IV) dose of 4.0-7.5 mg/kg at 2-3 weeks (plasmatic half life 21 days), for intravetrial (IVT) dose 1.25 mg in 0.05 mL (half-life 5.6 days). Bevacizumab has a $K_D$ for VEGF 165 (VEGF-A) of 58 pM. See, e.g., WO 2017/050825. In some embodiments, the antibody that specifically binds to a VEGF is ranibizumab (Lucentis®), or an antigen-binding fragment thereof. Ranibizumab (~50 kDa) inhibits all isoforms of VEGF-A. Ranibizumab received FDA approval in 2006 for ocular use for intravenous (IV) dose of 4.0-7.5 mg/kg at 2-3 weeks (plasma half life of 0.5 days), for intravetrial (IVT) dose 0.5 mg in 0.05 mL (half-life of 3.2 days). Ranibizumab has a $K_D$ for VEGF 165 (VEGF-A) of 46 pM. See, e.g., WO 2014/178078. In some embodiments, the antibody that specifically binds to VEGF is sevacizumab (APX003/SIM-BD0801), or an antigen-binding fragment thereof.

Amino Acid Encoding Light Chain of Bevacizumab
(SEQ ID NO: 5)
DIQMTQSPSSLSASVGDRVTITCSASQDISNYLNWYQQKPGKAPKVLIYFT

SSLHSGVPSRFSGSGSGTDFTLTISSLQPEDFATYYCQQYSTVPWTFGQGT

KVEIKRTVAAPSVFIFPPSDEQLKSGTASVVCLLNNFYPREAKVQWKVDNA

-continued
LQSGNSQESVTEQDSKDSTYSLSSTLTLSKADYEKHKVYACEVTHQGLSSP

VTKSFNRGEC

Amino Acid Encoding Heavy Chain of Bevacizumab
(SEQ ID NO: 6)
EVQLVESGGGLVQPGGSLRLSCAASGYTFTNYGMNWVRQAPGKGLEWVGWI

NTYTGEPTYAADFKRRFTFSLDTSKSTAYLQMNSLRAEDTAVYYCAKYPHY

YGSSHWYFDVWGQGTLVTVSSASTKGPSVFPLAPSSKSTSGGTAALGCLVK

DYFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK

In some embodiments of the antibodies that specifically bind to VEGF and antigen-binding fragments thereof described herein, the antibody or antigen-binding fragments thereof includes a variable light chain domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the variable light chain domain of bevacizumab, and/or includes a variable heavy chain domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the variable heavy chain domain of bevacizumab.

In some embodiments of the antibodies that specifically bind to VEGF and antigen-binding fragments thereof described herein, the antibody or antigen-binding fragments thereof includes a variable light chain domain that is or includes the variable light chain domain of bevacizumab, and/or a variable heavy chain domain that is or includes the variable heavy chain domain of bevacizumab. In some embodiments of the antibodies that specifically bind to VEGF and antigen-binding fragments thereof described herein, the antibody or antigen-binding fragments thereof includes a variable light chain domain that is or includes the sequence of variable light chain domain of bevacizumab, except that it includes one, two, three, four, five, six, seven, eight, nine, ten, eleven, twelve, thirteen, fourteen, or fifteen amino acid substitutions, and/or includes a variable heavy chain domain that is or includes the sequence of variable heavy chain of bevacizumab, except that it includes one, two, three, four, five, six, seven, eight, nine, ten, eleven, twelve, thirteen, fourteen, or fifteen amino acid substitutions. In some embodiments the first antigen-binding domain includes the three CDRs in the light chain variable domain of bevacizumab, and/or the three CDRs in the heavy chain variable domain of bevacizumab.

Amino Acid Encoding Light Chain of Ranibizumab
(SEQ ID NO: 7)
DIQLTQSPSSLSASVGDRVTITCSASQDISNYLNWYQQKPGKAPKVLIYFT

SSLHSGVPSRFSGSGSGTDFTLTISSLQPEDFATYYCQQYSTVPWTFGQGT

KVEIKRTVAAPSVFIFPPSDEQLKSGTASVVCLLNNFYPREAKVQWKVDNA

```
LQSGNSQESVTEQDSKDSTYSLSSTLTLSKADYEKHKVYACEVTHQGLSSP

VTKSFNRGEC

Amino Acid Encoding Heavy Chain of Ranibizumab
                                         (SEQ ID NO: 8)
EVQLVESGGGLVQPGGSLRLSCAASGYDFTHYGMNWVRQAPGKGLEWVGWI

NTYTGEPTYAADFKRRFTFSLDTSKSTAYLQMNSLRAEDTAVYYCAKYPYY

YGTSHWYFDVWGQGTLVTVSSASTKGPSVFPLAPSSKSTSGGTAALGCLVK

DYFPEPVTVSWNSGALTSGVHTFPAVLQSSGLYSLSSVVTVPSSSLGTQTY

ICNVNHKPSNTKVDKKVEPKSCDKTHL
```

In some embodiments of the antibodies that specifically bind to VEGF and antigen-binding fragments thereof described herein, the antibody or antigen-binding fragments thereof includes a variable light chain domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the variable light chain domain of ranibizumab, and/or includes a variable heavy chain domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the variable heavy chain domain of ranibizumab.

In some embodiments of the antibodies that specifically bind to VEGF and antigen-binding fragments thereof described herein, the antibody or antigen-binding fragments thereof includes a variable light chain domain that is or includes the variable light chain domain of ranibizumab, and/or a variable heavy chain domain that is or includes the variable heavy chain domain of ranibizumab. In some embodiments of the antibodies that specifically bind to VEGF and antigen-binding fragments thereof described herein, the antibody or antigen-binding fragments thereof includes a variable light chain domain that is or includes the sequence of variable light chain domain of ranibizumab, except that it includes one, two, three, four, five, six, seven, eight, nine, ten, eleven, twelve, thirteen, fourteen, or fifteen amino acid substitutions, and/or includes a variable heavy chain domain that is or includes the sequence of variable heavy chain of ranibizumab, except that it includes one, two, three, four, five, six, seven, eight, nine, ten, eleven, twelve, thirteen, fourteen, or fifteen amino acid substitutions. In some embodiments the first antigen-binding domain includes the three CDRs in the light chain variable domain of ranibizumab, and/or the three CDRs in the heavy chain variable domain of ranibizumab.

Soluble VEGF Receptors

A soluble VEGF receptor is a polypeptide that includes a portion of an extracellular region of one or more (e.g., two or three) mammalian VEGF receptor(s) (e.g., one or more of VEGFR-1, VEGFR-2, and VEGFR-3) operably linked to a signal peptide (e.g., any of the exemplary signal peptides described herein), where the soluble VEGF receptor is capable of specifically binding to one or more mammalian VEGF protein(s) (e.g., one or more (e.g., two, three, or four) of VEGF-A, VEGF-B, VEGF-C, and VEGF-D, e.g., one or more (e.g., two, three, or four) of human wildtype VEGF-A, human wildtype VEGF-B, human wildtype VEGF-C, and human wildtype VEGF-D).

In some examples, a soluble VEGF receptor includes a portion (e.g., about 10 amino acids to about 732 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, about 10 amino acids to about 50 amino acids, about 50 amino acids to about 732 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 100 amino acids to about 732 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 732 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 732 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 732 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 732 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 732 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 732 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 732 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 732 amino acids, about 500 amino acids to about 700 amino acids, about 500 amino acids to about 650 amino acids, about 500 amino acids to about 600 amino acids, about 500 amino acids to about 550 amino acids, about 550 amino acids to about 732 amino acids, about 550 amino acids to about 700 amino acids, about 550 amino acids to about 650 amino acids, about 550 amino acids to about 600 amino acids, about 600 amino acids to about 732 amino acids, about 600 amino acids to about 700 amino acids, about 600 amino acids to about 650 amino acids, about 650 amino acids to about 732 amino acids, about 650 amino acids to about 700 amino acids, or about 700 amino acids to about 732 amino acids) of an extracellular region of VEGFR-1 (e.g., a contiguous sequence from wildtype human VEGFR-1 (e.g., a contiguous sequence including one or more (e.g., one, two, three, four, five, six, or seven) immunoglobulin-like domains in the extracellular region from wildtype human VEGFR-1 (e.g., SEQ ID NO: 23) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-1, e.g., a sequence that is at least 80% (e.g., at least 82%, at least 84%, at least 86%, at least 88%, at least 90%, at least 92%, at least 94%, at least 96%, at least 98%, or at least 99%) identical to a contiguous sequence in SEQ ID NO: 23).

In some examples, a soluble VEGF receptor includes a portion (e.g., about 20 amino acids to about 745 amino acids, or any of the subranges of this range described herein) of an extracellular region of VEGFR-2 (e.g., a contiguous sequence from wildtype human VEGFR-2 (e.g., a contiguous sequence including one or more (e.g., one, two, three, four, five, six, or seven) immunoglobulin-like domains in the extracellular region from wildtype human VEGFR-2 (e.g., SEQ ID NO: 26) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-2, e.g., a sequence that is at least 80% (e.g., at least 82%, at least 84%, at least 86%, at least 88%, at least 90%, at least 92%, at least 94%, at least 96%, at least 98%, or at least 99%) identical to a contiguous sequence in SEQ ID NO: 26).

In some examples, a soluble VEGF receptor includes a portion of an extracellular region of VEGFR-1 (e.g., any of the portions of an extracellular region of VEGFR-1 described herein) and a portion of an extracellular region of VEGFR-2 (e.g., any of the portions of an extracellular region of VEGFR-2 described herein). For example, a soluble VEGF receptor can include one or more (e.g., two, three, four, five, six, or seven) immunoglobulin-like domains in the extracellular region from wildtype human VEGFR-1 and one or more (e.g., two, three, four, five, six, or seven) immunoglobulin-like domains in the extracellular region from wildtype human VEGFR-2 (e.g., aflibercept).

In some examples, a soluble VEGF receptor includes a portion (e.g., about 20 amino acids to about 751 amino acids, or any of the subranges of this range described herein) of an extracellular region of VEGFR-3 (e.g., a contiguous sequence from wildtype human VEGFR-3 (e.g., a contiguous sequence including one or more (e.g., one, two, three, four, five, six, or seven) immunoglobulin-like domains in the extracellular region from wildtype human VEGFR-3 (e.g., SEQ ID NO: 29) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-3, e.g., a sequence that is at least 80% (e.g., at least 82%, at least 84%, at least 86%, at least 88%, at least 90%, at least 92%, at least 94%, at least 96%, at least 98%, or at least 99%) identical to a contiguous sequence in SEQ ID NO: 29).

Non-limiting examples of extracellular regions of different mammalian VEGFR-1, different mammalian VEGFR-2, and different mammalian VEGFR-3 are described herein. Non-limiting examples of protein and nucleotide sequences encoding a wildtype VEGF receptor protein are shown below. As one skilled in the art can appreciate, a substitution in an amino acid that is conserved between species is more likely to result in a change in the function of a protein, while a substitution in an amino acid position that is not converved between species is less likely to have an affect on the function of a protein.

Human VEGF Receptor 1 Isoform 2 Protein Sequence
(SEQ ID NO: 17)
MVSYWDTGVLLCALLSCLLLTGSSSGSKLKDPELSLKGTQHIMQAGQTLHL

QCRGEAAHKWSLPEMVSKESERLSITKSACGRNGKQFCSTLTLNTAQANHT

GFYSCKYLAVPTSKKKETESAIYIFISDTGRPFVEMYSEIPEIIHMTEGRE

LVIPCRVTSPNITVTLKKFPLDTLIPDGKRIIWDSRKGFIISNATYKEIGL

LTCEATVNGHLYKTNYLTHRQTNTIIDVQISTPRPVKLLRGHTLVLNCTAT

TPLNTRVQMTWSYPDEKNKRASVRRRIDQSNSHANIFYSVLTIDKMQNKDK

GLYTCRVRSGPSFKSVNTSVHIYDKAFITVKHRKQQVLETVAGKRSYRLSM

KVKAFPSPEVVWLKDGLPATEKSARYLTRGYSLIIKDVTEEDAGNYTILLS

IKQSNVFKNLTATLIVNVKPQIYEKAVSSFPDPALYPLGSRQILTCTAYGI

PQPTIKWFWHPCNHNHSEARCDFCSNNEESFILDADSNMGNRIESITQRMA

IIEGKNKMASTLVVADSRISGIYICIASNKVGTVGRNISFYITDVPNGFHV

NLEKMPTEGEDLKLSCTVNKFLYRDVTWILLRTVNNRTMHYSISKQKMAIT

KEHSITLNLTIMNVSLQDSGTYACRARNVYTGEEILQKKEITIRGEHCNKK

AVFSRISKFKSTRNDCTTQSNVKH

Human VEGF Receptor 1 Isoform 2 cDNA
(SEQ ID NO: 18)
ATGGTCAGCTACTGGGACACCGGGGTCCTGCTGTGCGCGCTGCTCAGCTGT

CTGCTTCTCACAGGATCTAGTTCAGGTTCAAAATTAAAAGATCCTGAACTG

```
AGTTTAAAAGGCACCCAGCACATCATGCAAGCAGGCCAGACACTGCATCTC
CAATGCAGGGGGAAGCAGCCCATAAATGGTCTTTGCCTGAAATGGTGAGT
AAGGAAAGCGAAAGGCTGAGCATAACTAAATCTGCCTGTGGAAGAAATGGC
AAACAATTCTGCAGTACTTTAACCTTGAACACAGCTCAAGCAAACCACACT
GGCTTCTACAGCTGCAAATATCTAGCTGTACCTACTTCAAAGAAGAAGGAA
ACAGAATCTGCAATCTATATATTTATTAGTGATACAGGTAGACCTTTCGTA
GAGATGTACAGTGAAATCCCCGAAATTATACACATGACTGAAGGAAGGGAG
CTCGTCATTCCCTGCCGGGTTACGTCACCTAACATCACTGTTACTTTAAAA
AAGTTTCCACTTGACACTTTGATCCCTGATGGAAAACGCATAATCTGGGAC
AGTAGAAAGGGCTTCATCATATCAAATGCAACGTACAAAGAAATAGGGCTT
CTGACCTGTGAAGCAACAGTCAATGGGCATTTGTATAAGACAAACTATCTC
ACACATCGACAAACCAATACAATCATAGATGTCCAAATAAGCACACCACGC
CCAGTCAAATTACTTAGAGGCCATACTCTTGTCCTCAATTGTACTGCTACC
ACTCCCTTGAACACGAGAGTTCAAATGACCTGGAGTTACCCTGATGAAAAA
AATAAGAGAGCTTCCGTAAGGCGACGAATTGACCAAAGCAATTCCCATGCC
AACATATTCTACAGTGTTCTTACTATTGACAAAATGCAGAACAAAGACAAA
GGACTTTATACTTGTCGTGTAAGGAGTGGACCATCATTCAAATCTGTTAAC
ACCTCAGTGCATATATATGATAAAGCATTCATCACTGTGAAACATCGAAAA
CAGCAGGTGCTTGAAACCGTAGCTGGCAAGCGGTCTTACCGGCTCTCTATG
AAAGTGAAGGCATTTCCCTCGCCGGAAGTTGTATGGTTAAAAGATGGGTTA
CCTGCGACTGAGAAATCTGCTCGCTATTTGACTCGTGGCTACTCGTTAATT
ATCAAGGACGTAACTGAAGAGGATGCAGGGAATTATACAATCTTGCTGAGC
ATAAAACAGTCAAATGTGTTTAAAAACCTCACTGCCACTCTAATTGTCAAT
GTGAAACCCAGATTTACGAAAAGGCCGTGTCATCGTTTCCAGACCCGGCT
CTCTACCCACTGGGCAGCAGACAAATCCTGACTTGTACCGCATATGGTATC
CCTCAACCTACAATCAAGTGGTTCTGGCACCCCTGTAACCATAATCATTCC
GAAGCAAGGTGTGACTTTTGTTCCAATAATGAAGAGTCCTTTATCCTGGAT
GCTGACAGCAACATGGGAAACAGAATTGAGAGCATCACTCAGCGCATGGCA
ATAATAGAAGGAAAGAATAAGATGGCTAGCACCTTGGTTGTGGCTGACTCT
AGAATTTCTGGAATCTACATTTGCATAGCTTCCAATAAAGTTGGGACTGTG
GGAAGAAACATAAGCTTTTATATCACAGATGTGCCAAATGGGTTTCATGTT
AACTTGGAAAAAATGCCGACGGAAGGAGAGGACCTGAAACTGTCTTGCACA
GTTAACAAGTTCTTATACAGAGACGTTACTTGGATTTTACTGCGGACAGTT
AATAACAGAACAATGCACTACAGTATTAGCAAGCAAAAAATGGCCATCACT
AAGGAGCACTCCATCACTCTTAATCTTACCATCATGAATGTTTCCCTGCAA
GATTCAGGCACCTATGCCTGCAGAGCCAGGAATGTATACACAGGGGAAGAA
ATCCTCCAGAAGAAAGAAATTACAATCAGAGGTGAGCACTGCAACAAAAG
GCTGTTTTCTCTCGGATCTCCAAATTTAAAGCACAAGGAATGATTGTACC
ACACAAAGTAATGTAAAACATTAA
```

Human VEGF Receptor 1 Isoform 3 Protein Sequence
(sFlt1-14)
(SEQ ID NO: 19)
MVSYWDTGVLLCALLSCLLLTGSSSGSKLKDPELSLKGTQHIMQAGQTLHL
QCRGEAAHKWSLPEMVSKESERLSITKSACGRNGKQFCSTLTLNTAQANHT
GFYSCKYLAVPTSKKKETESAIYIFISDTGRPFVEMYSEIPEIIHMTEGRE
LVIPCRVTSPNITVTLKKFPLDTLIPDGKRIIWDSRKGFIISNATYKEIGL
LTCEATVNGHLYKTNYLTHRQTNTIIDVQISTPRPVKLLRGHTLVLNCTAT
TPLNTRVQMTWSYPDEKNKRASVRRRIDQSNSHANIFYSVLTIDKMQNKDK
GLYTCRVRSGPSFKSVNTSVHIYDKAFITVKHRKQQVLETVAGKRSYRLSM
KVKAFPSPEVVWLKDGLPATEKSARYLTRGYSLIIKDVTEEDAGNYTILLS
IKQSNVFKNLTATLIVNVKPQIYEKAVSSFPDPALYPLGSRQILTCTAYGI
PQPTIKWFWHPCNHNHSEARCDFCSNNEESFILDADSNMGNRIESITQRMA
IIEGKNKMASTLVVADSRISGIYICIASNKVGTVGRNISFYITDVPNGFHV
NLEKMPTEGEDLKLSCTVNKFLYRDVTWILLRTVNNRTMHYSISKQKMAIT
KEHSITLNLTIMNVSLQDSGTYACRARNVYTGEEILQKKEITIRDQEAPYL
LRNLSDHTVAISSSTTLDCHANGVPEPQITWFKNNHKIQQEPELYTSTSPS
SSSSSPLSSSSSSSSSSSS Human VEGF Receptor 1 Isoform 3 cDNA
(SEQ ID NO: 20)
ATGGTCAGCTACTGGGACACCGGGGTCCTGCTGTGCGCGCTGCTCAGCTGT
CTGCTTCTCACAGGATCTAGTTCAGGTTCAAAATTAAAAGATCCTGAACTG
AGTTTAAAAGGCACCCAGCACATCATGCAAGCAGGCCAGACACTGCATCTC
CAATGCAGGGGGAAGCAGCCCATAAATGGTCTTTGCCTGAAATGGTGAGT
AAGGAAAGCGAAAGGCTGAGCATAACTAAATCTGCCTGTGGAAGAAATGGC
AAACAATTCTGCAGTACTTTAACCTTGAACACAGCTCAAGCAAACCACACT
GGCTTCTACAGCTGCAAATATCTAGCTGTACCTACTTCAAAGAAGAAGGAA
ACAGAATCTGCAATCTATATATTTATTAGTGATACAGGTAGACCTTTCGTA
GAGATGTACAGTGAAATCCCCGAAATTATACACATGACTGAAGGAAGGGAG
CTCGTCATTCCCTGCCGGGTTACGTCACCTAACATCACTGTTACTTTAAAA
AAGTTTCCACTTGACACTTTGATCCCTGATGGAAAACGCATAATCTGGGAC
AGTAGAAAGGGCTTCATCATATCAAATGCAACGTACAAAGAAATAGGGCTT
CTGACCTGTGAAGCAACAGTCAATGGGCATTTGTATAAGACAAACTATCTC
ACACATCGACAAACCAATACAATCATAGATGTCCAAATAAGCACACCACGC
CCAGTCAAATTACTTAGAGGCCATACTCTTGTCCTCAATTGTACTGCTACC
ACTCCCTTGAACACGAGAGTTCAAATGACCTGGAGTTACCCTGATGAAAAA
AATAAGAGAGCTTCCGTAAGGCGACGAATTGACCAAAGCAATTCCCATGCC
AACATATTCTACAGTGTTCTTACTATTGACAAAATGCAGAACAAAGACAAA
GGACTTTATACTTGTCGTGTAAGGAGTGGACCATCATTCAAATCTGTTAAC
ACCTCAGTGCATATATATGATAAAGCATTCATCACTGTGAAACATCGAAAA
CAGCAGGTGCTTGAAACCGTAGCTGGCAAGCGGTCTTACCGGCTCTCTATG
AAAGTGAAGGCATTTCCCTCGCCGGAAGTTGTATGGTTAAAAGATGGGTTA
CCTGCGACTGAGAAATCTGCTCGCTATTTGACTCGTGGCTACTCGTTAATT ATCAAGGACGTAACTGAAGAGGATGCAGGGAATTATACAATCTTGCTGAGC
ATAAAACAGTCAAATGTGTTTAAAAACCTCACTGCCACTCTAATTGTCAAT
GTGAAACCCCAGATTTACGAAAAGGCCGTGTCATCGTTTCCAGACCCGGCT
CTCTACCCACTGGGCAGCAGACAAATCCTGACTTGTACCGCATATGGTATC
CCTCAACCTACAATCAAGTGGTTCTGGCACCCCTGTAACCATAATCATTCC
GAAGCAAGGTGTGACTTTTGTTCCAATAATGAAGAGTCCTTTATCCTGGAT
GCTGACAGCAACATGGGAAACAGAATTGAGAGCATCACTCAGCGCATGGCA
ATAATAGAAGGAAAGAATAAGATGGCTAGCACCTTGGTTGTGGCTGACTCT
AGAATTTCTGGAATCTACATTTGCATAGCTTCCAATAAAGTTGGGACTGTG
GGAAGAAACATAAGCTTTTATATCACAGATGTGCCAAATGGGTTTCATGTT
AACTTGGAAAAAATGCCGACGGAAGGAGAGGACCTGAAACTGTCTTGCACA
GTTAACAAGTTCTTATACAGAGACGTTACTTGGATTTTACTGCGGACAGTT
AATAACAGAACAATGCACTACAGTATTAGCAAGCAAAAAATGGCCATCACT
AAGGAGCACTCCATCACTCTTAATCTTACCATCATGAATGTTTCCCTGCAA
GATTCAGGCACCTATGCCTGCAGAGCCAGGAATGTATACACAGGGGAAGAA
ATCCTCCAGAAGAAAGAAATTACAATCAGAGATCAGGAAGCACCATACCTC
CTGCGAAACCTCAGTGATCACACAGTGGCCATCAGCAGTTCCACCACTTTA
GACTGTCATGCTAATGGTGTCCCCGAGCCTCAGATCACTTGGTTTAAAAAC
AACCACAAAATACAACAAGAGCCTGAACTGTATACATCAACGTCACCATCG
TCATCGTCATCATCACCATTGTCATCATCATCATCATCGTCATCATCATCA
TCATCATAG Human VEGF Receptor 1 Isoform 4 Protein Sequence
(SEQ ID NO: 21)
MVSYWDTGVLLCALLSCLLLTGSSSGSKLKDPELSLKGTQHIMQAGQTLHL
QCRGEAAHKWSLPEMVSKESERLSITKSACGRNGKQFCSTLTLNTAQANHT
GFYSCKYLAVPTSKKKETESAIYIFISDTGRPFVEMYSEIPEIIHMTEGRE
LVIPCRVTSPNITVTLKKFPLDTLIPDGKRIIWDSRKGFIISNATYKEIGL
LTCEATVNGHLYKTNYLTHRQTNTIIDVQISTPRPVKLLRGHTLVLNCTAT
TPLNTRVQMTWSYPDEKNKRASVRRRIDQSNSHANIFYSVLTIDKMQNKDK
GLYTCRVRSGPSFKSVNTSVHIYDKAFITVKHRKQQVLETVAGKRSYRLSM
KVKAFPSPEVVWLKDGLPATEKSARYLTRGYSLIIKDVTEEDAGNYTILLS
IKQSNVFKNLTATLIVNVKPQIYEKAVSSFPDPALYPLGSRQILTCTAYGI
PQPTIKWFWHPCNHNHSEARCDFCSNNEESFILDADSNMGNRIESITQRMA
IIEGKNKLPPANSSFMLPPTSFSSNYFHFLP Human VEGF Receptor 1 Isoform 4 cDNA
(SEQ ID NO: 22)
ATGGTCAGCTACTGGGACACCGGGGTCCTGCTGTGCGCGCTGCTCAGCTGT
CTGCTTCTCACAGGATCTAGTTCAGGTTCAAAATTAAAAGATCCTGAACTG
AGTTTAAAAGGCACCCAGCACATCATGCAAGCAGGCCAGACACTGCATCTC
CAATGCAGGGGGGAAGCAGCCCATAAATGGTCTTTGCCTGAAATGGTGAGT
AAGGAAAGCGAAAGGCTGAGCATAACTAAATCTGCCTGTGGAAGAAATGGC
AAACAATTCTGCAGTACTTTAACCTTGAACACAGCTCAAGCAAACCACACT
GGCTTCTACAGCTGCAAATATCTAGCTGTACCTACTTCAAAGAAGAAGGAA
ACAGAATCTGCAATCTATATATTTATTAGTGATACAGGTAGACCTTTCGTA
GAGATGTACAGTGAAATCCCCGAAATTATACACATGACTGAAGGAAGGGAG
CTCGTCATTCCCTGCCGGGTTACGTCACCTAACATCACTGTTACTTTAAAA
AAGTTTCCACTTGACACTTTGATCCCTGATGGAAAACGCATAATCTGGGAC
AGTAGAAAGGGCTTCATCATATCAAATGCAACGTACAAAGAAATAGGGCTT
CTGACCTGTGAAGCAACAGTCAATGGGCATTTGTATAAGACAAACTATCTC
ACACATCGACAAACCAATACAATCATAGATGTCCAAATAAGCACACCACGC
CCAGTCAAATTACTTAGAGGCCATACTCTTGTCCTCAATTGTACTGCTACC
ACTCCCTTGAACACGAGAGTTCAAATGACCTGGAGTTACCCTGATGAAAAA
AATAAGAGAGCTTCCGTAAGGCGACGAATTGACCAAAGCAATTCCCATGCC
AACATATTCTACAGTGTTCTTACTATTGACAAAATGCAGAACAAAGACAAA
GGACTTTATACTTGTCGTGTAAGGAGTGGACCATCATTCAAATCTGTTAAC
ACCTCAGTGCATATATATGATAAAGCATTCATCACTGTGAAACATCGAAAA
CAGCAGGTGCTTGAAACCGTAGCTGGCAAGCGGTCTTACCGGCTCTCTATG
AAAGTGAAGGCATTTCCCTCGCCGGAAGTTGTATGGTTAAAAGATGGGTTA
CCTGCGACTGAGAAATCTGCTCGCTATTTGACTCGTGGCTACTCGTTAATT
ATCAAGGACGTAACTGAAGAGGATGCAGGGAATTATACAATCTTGCTGAGC
ATAAAACAGTCAAATGTGTTTAAAAACCTCACTGCCACTCTAATTGTCAAT
GTGAAACCCCAGATTTACGAAAAGGCCGTGTCATCGTTTCCAGACCCGGCT
CTCTACCCACTGGGCAGCAGACAAATCCTGACTTGTACCGCATATGGTATC
CCTCAACCTACAATCAAGTGGTTCTGGCACCCCTGTAACCATAATCATTCC
GAAGCAAGGTGTGACTTTTGTTCCAATAATGAAGAGTCCTTTATCCTGGAT
GCTGACAGCAACATGGGAAACAGAATTGAGAGCATCACTCAGCGCATGGCA
ATAATAGAAGGAAAGAATAAGCTTCCACCAGCTAACAGTTCTTTCATGTTG
CCACCTACAAGCTTCTCTTCCAACTACTTCCATTTCCTTCCGTGA Extracellular Region of Wildtype Human VEGFR-1 (the seven
Ig-like domains are shown in bold and underlined)
(SEQ ID NO: 23)
sklk dpelslkgtq himgagqtlh lqcrgeaahk wslpemvske serlsitksa cgrngkqfcs tltlntaqan htgfysckyl avptskkket esaiyifisd tgrpfvemys eipeiihmte grelvipcrv tspnitvtlk kfpldtlipd gkriiwdsrk gfiisnatyk eiglltceat vnghlyktny lthrqtntii dvqistprpv kllrghtlvl nctattplnt

-continued rvqmtwsypd eknkrasvrr ridqsnshan ifysvltidk mqnkdkglyt crvrsgpsfk svntsvhiyd kafitvkhrk qqvletvagk rsyrlsmkvk afpspevvwl kdglpateks aryltrgysl iikdvteeda gnytillsik qsnvfknlta tlivnvkpqi yekavssfpd palyplgsrq iltctaygip qptikwfwhp cnhnhsearc dfcsnneesf ildadsnmgn riesitqrma iiegknkmas tlvvadsris giyiciasnk vgtvgrnisf yitdvpngfh vnlekmpteg edlklsctvn kflyrdvtwi llrtvnnrtm hysiskqkma itkehsitln ltimnvslqd sgtyacrarn vytgeeilqk keitirdqea pyllrnlsdh tvaisssttl dchangvpep qitwfknnhk iqqepgiilg pgsstlfier vteedegvyh ckatnqkgsv essayltvqg tsdksnle

Extracellular Region of Wildtype Mouse VEGFR-1
(SEQ ID NO: 24)
ygsgsklk vpelslkgtq hvmqagqtlf lkcrgeaahs wslpttvsqe dkrlsitpps acgrdnrqfc stltldtaqa nhtglytcry lptstskkkk aessiyifvs dagspfiemh tdipklvhmt egrqliipcr vtspnvtvtl kkfpfdtltp dgqritwdsr rgfiianaty keigllncea tvnghlyqtn ylthrqtnti ldvqirppsp vrllhgqtlv lnctatteln trvqmswnyp gkatkrasir qridrshshn nvfhsvlkin nvesrdkgly tcrvksgssf qsfntsvhvy ekgfisvkhr kqpvqettag rrsyrlsmkv kafpspeivw lkdgspatlk sarylvhgys liikdvtted agdytillgi kqsrlfknlt atlivnvkpq iyeksvsslp spplyplgsr qvltctvygi prptitwlwh pchhnhsker ydfctenees fildpssnlg nriesisqrm tviegtnktv stlvvadsqt pgiyscrafn kigtvernik fyvtdvpngf hvslekmpae gedlklscvv nkflyrditw illrtvnnrt mhhsiskqkm attqdysitl nlviknvsle dsgtyacrar niytgedilr ktevlvrdse aphllqnlsd yevsisgstt ldcqargvpa pqitwfknnh kiqqepgiil gpgnstlfie rvteedegvy rcratnqkga vesaayltvq gtsdksnle Extracellular Region of Wildtype Rat VEGFR-1
(SEQ ID NO: 25)
ycsgsklk gpelslkgtq hvmqagqtlf lkcrgeaahs wslpttvsqe dkklsvtrsa cgrnnrqfcs tltlnmaqan htglyscryl pkstskekkm esaiyifvsd agspfiemhs dipklvhmte greliipcrv tspnitvtlk kfpfdaltpd gqriawdsrr gfiianatyk eiglltceat vnghlyqtsy lthrqtntil dvqisppspv rflrgqtlvl nctvttdlnt rvqmswnypg katkrasirq ridqsnphsn vfhsvlkinn vesrdkglyt crvksgssfr tfntsvhvye kgfisvkhrk qqvqetiagk rshrlsmkvk afpspevvwl kdgvpateks arysvhgysl iikdvtaeda gdytillgik qsklfrnlta tlivnvkpqi yeksvsslps pplyplgsrq vltctvygip qptikwlwhp chynhskern dfcfgseesf ildsssnign riegitqrmm viegtnktvs tlvvadsrtp gsysckafnk igtverdirf yvtdvpngfh vslekipteg edlklscvvs kflyrditwi llrtvnnrtm hhsiskqkma ttqdysitln lviknvsled sgtyacrarn iytgeeilrk tevlvrdlea plllqnlsdh evsisgsttl dcqargvpap qitwfknnhk iqqepgiilg pgnstlfier vteedegvyr cratnqkgvv essayltvqg tsdksnle Extracellular Region of Wildtype Human VEGFR-2
(the seven Ig-like domains are shown in bold and underlined)
(SEQ ID NO: 26)
asvglpsvsld lprlsiqkdi ltikanttlq itcrgqrdld wlwpnnqsgs eqrvevtecs dglfcktlti pkvigndtga ykcfyretdl asviyvyvqd yrspfiasvs dqhgvvyite

```
nknktvvipc lgsisnlnvs lcarypekrf vpdgnriswd skkgftipsy misyagmvfc eakindesyq simyivvvvg yriydvvlsp shgielsvge klvlnctart elnvgidfnw eypsskhqhk klvnrdlktq sgsemkkfls tltidgvtrs dqglytcaas sglmtkknst fvrvhekpfv afgsgmeslv eatvgervri p -continued Extracellular Region of Wildtype Human VEGFR-3
(the seven Ig-like domains are shown in bold)

(SEQ ID NO: 29)

ysmtpp tlniteeshv idtgdslsis crgqhplewa wpgaqeapat gdkdsedtgv vrdcegtdar pyckvlllhe vhandtgsyv cyykyikari egttaassyv fvrdfeqpfi nkpdtllvnr kdamwvpclv sipglnvtlr sqssvlwpdg qevvwddrrg mlvstpllhd alylqcettw gdqdflsnpf lvhitgnely diqllprksl ellvgeklvl nctvwaefns gvtfdwdypg kqaergkwvp errsqqthte lssiltihnv sqhdlgsyvc kanngiqrfr estevivhen pfisvewlkg pileatagde lvklpvklaa ypppefqwyk dgkalsgrhs phalvlkevt eastgtytla lwnsaaglrr nislelvvnv ppqihekeas spsiysrhsr qaltctaygv plplsiqwhw rpwtpckmfa qrslrrrqqq dlmpqcrdwr avttqdavnp iesldtwtef vegknktvsk lvignanvsa mykcvvsnkv gqderliyfy vttipdgfti eskpseelle gqpvllscqa dsykyehlrw yrlnlstlhd ahgnpllldc knvhlfatpl aasleevapg arhatlslsi prvapehegh yvcevqdrrs hdkhchkkyl svqaleaprl tqnltdllvn vsdslemgcl vagahapsiv wykderllee ksgvdladsn qklsiqrvre edagrylcsv cnakgcvnss asvavegsed kgsmeivilv

Extracellular Region of Wildtype Mouse VEGFR-3

(SEQ ID NO: 30)

ysmtpp tlnitedsyv idtgdslsis crgqhplewt wpgagevltt ggkdsedtrv vhdcegtear pyckvlllaq thanntgsyh cyykyikari egttaastyv fvrdfkhpfi nkpdtllvnr kdsmwvpclv sipglnitlr sqssalhpdg qevlwddrrg mrvptqllrd alylqcettw gdqnflsnlf vvhitgnely diqlypkksm ellvgeklvl nctvwaefds gvtfdwdypg kqaerakwvp errsqqthte lssiltihnv sqndlgpyvc eanngiqrfr estevivhek pfisvewlkg pvleatagde lvklpvklaa ypppefqwyk drkavtgrhn phalvlkevt easagvytla lwnsaaglrq nislelvvnv pphihekeas spsiysrhsr qtltctaygv pqplsvqwhw rpwtpcktfa qrslrrrqqr dgmpqcrdwk evttqdavnp iesldswtef vegknktvsk lviqdanvsa mykcvvvnkv gqderliyfy vttipdgfsi esepsedple gqsvrlscra dnytyehlrw yrinlstlhd aqgnpllldc knvhlfatpl eanleeaepg arhatlslni prvapedegd yvcevqdrrs qdkhchkkyl svgaleaprl tqnltdllvn vsdslemrcp vagahvpsiv wykderllek esgidladsn qrlsiqrvre edagrylcsv cnakgcvnss asvavegsed kgsme Extracellular Region of Wildtype Rat VEGFR-3

(SEQ ID NO: 31)

ysmtpp tlnitedsyv idtgdslsis crgqhplewt wrgagevltt ggkdsedtqv vqdcegtear pyckvlslaq thanntgsyy cyykyikari egttaastyv fvrdfeqpfi nkpdtllvnr kdsmwvpclv sipglnitlr sqssvlhpdg qevlwddrrg mrvptlllrd alylqcettw gdqdflsnpf lvhitgnely diqlypkksl ellvgeklvl nctvwaefds gvtfdwdypg kqaerakwvp errsqqthte lssiltihnv sqhdlgpyvc eanngiqqfr estevivhek pfisvewlkg pvleatagde mvklpvklaa ypppefqwyk drkavtgrhn phalvlkevt easagvytla lwnsaaglrq nislelvvnv pphihekeas spsiysrhsr qtltcttygv pqplsvqwhw rpwtpcktfa qrslrrrqpr dgmpqcrdwk evttqdavnp iesldtwtes vegknktvsk lviqdanvsa mykcvvfnkv gqderliyfy vttipdgfsi esepsedple gqsvrlscra dnytyehlrw yrlnlstlhd aqgnpllldc knvhlfatpl eanleeaepg arhatlslni prvapedegd yvcevqdrrs qdkhchkkyl svgaleaprl -continued

```
tqnltdllvn vrtslemrcp vagahvpsiv wykderllek esgidladsn qrlsiqrvre edagrylcsv cnakgcvnss asvavegsed kgsme
```

In some examples, a soluble VEGF receptor can further include a stabilizing domain (e.g., a Fc domain or a portion of a Fc domain). For example, a stabilizing domain can be an IgG1 Fc domain (e.g., a human wildtype IgG1 Fc domain or a portion thereof). For example, a stalizing domain can be an IgG2 Fc domain (e.g., a human wildtype IgG2 Fc domain or a portion thereof). For example, a stabilizing domain can be an IgG3 Fc domain (e.g., a human wildtype IgG3 domain or a portion thereof).

Non-limiting examples of human wildtype IgG1 Fc domain, human wildtype IgG2 Fc domain, and human wildtype IgG3 Fc domain are shown below.

```
Human Wildtype IgG1 Fc Domain
                                    (SEQ ID NO: 32)
pcpapellgg psvflfppkp kdtlmisrtp evtcvvvdvs hedpevkfnw yvdgvevhna ktkpreeqyn styrvvsvlt vlhqdwlngk eykckvsnka lpapiektis kakgqprepq vytlppsrde ltknqvsltc lvkgfypsdi avewesngqp ennykttppv ldsdgsffly skltvdksrw qqgnvfscsv mhealhnhyt qkslslspgk Human Wildtype IgG2 Fc Region
                                    (SEQ ID NO: 33)
vecppcpapp vagpsvflfp pkpkdtlmis rtpevtcvvv dvshedpevq fnwyvdgvev hnaktkpree qfnstfrvvs vltvvhqdwl ngkeykckvs nkglpapiek tisktkgqpr epqvytlpps reemtknqvs ltclvkgfyp sdiavewesn gqpennyktt ppmldsdgsf flyskltvdk srwqqgnvfs csvmhealhn hytqkslsls pgk Human Wildtype IgG3 Fc Region
                                    (SEQ ID NO: 34)
tcprcpapel lggpsvflfp pkpkdtlmis rtpevtcvvv dvshedpevq fkwyvdgvev hnaktkpree qfnstfrvvs vltvlhqdwl ngkeykckvs nkalpapiek tisktkgqpr epqvytlpps reemtknqvs ltclvkgfyp sdiavewess gqpennyktt ppmldsdgsf flyskltvdk srwqqgnifs csvmhealhn rftqkslsls pgk
```

In some embodiments, the soluble VEGF receptor is aflibercept (Eylea®). Aflibercept includes portions of human VEGF receptors 1 and 2 extracellular domains fused to the Fc portion of human IgG1 (size ~115 kDa). Aflibercept inhibits the activity of VEGF-A, VEGF-B, and PIGF. Aflibercept has a $K_D$ for VEGF-A of 0.49 pM. See, e.g., WO 2017/218974.

```
Amino Encoding aflibercept
                                    (SEQ ID NO: 12)
SDTGRPFVEMYSEIPEIIHMTEGRELVIPCRVTSPNITVTLKKFPLDTLIP

DGKRIIWDSRKGFIISNATYKEIGLLTCEATVNGHLYKTNYLTHRQTNTII

DVVLSPSHGIELSVGEKLVLNCTARTELNVGIDFNWEYPSSKHQHKKLVNR

DLKTQSGSEMKKFLSTLTIDGVTRSDQGLYTCAASSGLMTKKNSTFVRVHE

KDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPG
```

In some embodiments of a soluble VEGF receptor includes a sequence that is at least 80% identical (e.g., at least 82%, at least 84%, at least 86%, at least 88%, at least 90%, at least 92%, at least 94%, at least 96%, at least 98%, or at least 99%) identical to SEQ ID NO: 12.

In some embodiments of the soluble VEGF receptor includes an extracellular domain that is or includes the sequence of SEQ ID NO: 12, except that it includes one, two, three, four, five, six, seven, eight, nine, ten, eleven, twelve, thirteen, fourteen, or fifteen amino acid substitutions in the sequence of SEQ ID NO: 12.

Additional examples of soluble VEGF receptors are described in, e.g., Kendall et al., PNAS 90: 10705-10709, 1993; Kendall et al., Biochem Biophys Res Commun 226: 324-328, 1996; Failla et al., Int J Mol Sci 19(5):pii. E1306, 2018; and Jung et al., PLoS One 7(9): e44572.

Vectors

Recombinant AAV vectors or "rAAVs" are typically composed of, at a minimum, a transgene or a portion thereof and a regulatory sequence, and optionally 5' and 3' AAV inverted terminal repeats (ITRs). Such a recombinant AAV vector is packaged into a capsid and delivered to a selected target cell (e.g., a cochlear hair cell).

The AAV sequences of the vector typically comprise the cis-acting 5' and 3' ITR sequences (See, e.g., B. J. Carter, in "Handbook of Parvoviruses", ed., P. Tijsser, CRC Press, pp. 155 168, 1990). Typical AAV ITR sequences are about 145 nucleotides in length. In some embodiments, at least 75% of a typical ITR sequence (e.g., at least 80%, at least 85%, at least 90%, or at least 95%) is incorporated into the AAV vector. The ability to modify these ITR sequences is within the skill of the art. (See, e.g., texts such as Sambrook et al., "Molecular Cloning. A Laboratory Manual", 2d ed., Cold Spring Harbor Laboratory, New York, 1989; and K. Fisher et al., J Virol. 70:520 532, 1996). In some embodiments, any of the coding sequences described herein is flanked by 5' and 3' AAV ITR sequences in the AAV vectors. The AAV ITR sequences may be obtained from any known AAV, including presently identified AAV types.

AAV vectors as described herein may include any of the regulatory elements described herein (e.g., one or more of a promoter, a polyadenylation (poly(A)) signal sequence, and an IRES).

In some embodiments, the vector(s) is an adenovirus (see, e.g., Dmitriev et al. (1998) *J. Virol.* 72: 9706-9713; and Poulin et al., *J. Virol* 8: 10074-10086, 2010). In some embodiments, the vector(s) is a retrovirus (see, e.g., Maier et al. (2010) *Future Microbiol* 5: 1507-23).

The vectors provided herein can be of different sizes. The choice of vector that is used in any of the compositions, kits, and methods described herein may depend on the size of the vector.

In some embodiments, the vector(s) can have a total number of nucleotides of up to 10 kb. In some embodiments, the viral vector(s) can have a total number of nucleotides in the range of about 1 kb to about 2 kb, 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 2 kb to about 9 kb, about 2 kb to about 10 kb, about 3 kb to about 4 kb, about 3 kb to about 5 kb, about 3 kb to about 6 kb, about 3 kb to about 7 kb, about 3 kb to about 8 kb, about 3 kb to about 9 kb, about 3 kb to about 10 kb, about 4 kb to about 5 kb, about 4 kb to about 6 kb, about 4 kb to about 7 kb, about 4 kb to about 8 kb, about 4 kb to about 9 kb, about 4 kb to about 10 kb, about 5 kb to about 6 kb, about 5 kb to about 7 kb, about 5 kb to about 8 kb, about 5 kb to about 9 kb, about 5 kb to about 10 kb, about 6 kb to about 7 kb, about 6 kb to about 8 kb, about 6 kb to about 9 kb, about 6 kb to about 10 kb, about 7 kb to about 8 kb, about 7 kb to about 9 kb, about 7 kb to about 10 kb, about 8 kb to about 9 kb, about 8 kb to about 10 kb, or about 9 kb to about 10 kb.

In some embodiments, the vector(s) is a lentivirus and can have a total number of nucleotides of up to 8 kb. In some examples, the lentivirus(es) can have a total number of nucleotides of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 7 kb, or about 7 kb to about 8 kb.

In some embodiments, the vector(s) is an adenovirus and can have a total number of nucleotides of up to 8 kb. In some embodiments, the adenovirus(es) can have a total number of nucleotides in the range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 7 kh, about 6 kb to about 8 kb, or about 7 kb to about 8 kb.

In some embodiments, the vector(s) is an adeno-associated virus (AAV vector) and can include a total number of nucleotides of up to 5 kb. In some embodiments, the AAV vector(s) can include a total number of nucleotides in the range of about 1 kb to about 2 kb, about 1 kb to about 3 kb, about 1 kb to about 4 kb, about 1 kb to about 5 kb, about 2 kb to about 3 kb, about 2 kb to about 4 kb, about 2 kb to about 5 kb, about 3 kb to about 4 kb, about 3 kb to about 5 kb, or about 4 kb to about 5 kb.

A variety of different methods known in the art can be used to introduce any of vectors disclosed herein into a mammalian cell (e.g., an inner ear cell, a cochlear inner hair cell). Non-limiting examples of methods for introducing nucleic acid into a mammalian cell include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection.

Any of the vectors described herein can further include a control sequence, e.g., a control sequence selected from the group of a transcription initiation sequence, a transcription termination sequence, a promoter sequence, an enhancer sequence, an RNA splicing sequence, a polyadenylation (polyA) signal, and a Kozak consensus sequence. Non-limiting examples of these control sequences are described herein. In some embodiments, a promoter can be a native promoter, a constitutive promoter, an inducible promoter, and/or a tissue-specific promoter.

Promoters

The term "promoter" means a DNA sequence recognized by enzymes/proteins in a mammalian cell required to initiate the transcription of a specific gene. A promoter typically refers to, e.g., a nucleotide sequence to which an RNA polymerase and/or any associated factor binds and at which transcription is initiated. Non-limiting examples of promoters are described herein. Additional examples of promoters are known in the art.

In some embodiments, a vector (e.g., an adeno-associated virus (AAV) vector) encoding an antibody (e.g., an antibody that binds specifically to VEGF or an antigen-binding antibody fragment thereof,) can include a promoter and/or an enhancer. The vector encoding the antibody or antigen-binding antibody fragment can include any of the promoters and/or enhancers described herein or known in the art.

In some embodiments, the promoter is an inducible promoter, a constitutive promoter, a mammalian cell promoter, a viral promoter, a chimeric promoter, an engineered promoter, a tissue-specific promoter, or any other type of promoter known in the art. In some embodiments, the promoter is a RNA polymerase II promoter, such as a mammalian RNA polymerase II promoter. In some embodiments, the promoter is a RNA polymerase III promoter, including, but not limited to, a H1 promoter, a human U6 promoter, a mouse U6 promoter, or a swine U6 promoter. The promoter will generally be one that is able to promote transcription in an inner hair cell In some examples, the promoter is a cochlea-specific promoter or a cochlea-oriented promoter.

A variety of promoters are known in the art that can be used herein. Non-limiting examples of promoters that can be used herein include: human EF1a, human cytomegalovirus (CMV) (U.S. Pat. No. 5,168,062), human ubiquitin C (UBC), mouse phosphoglycerate kinase 1, polyoma adenovirus, simian virus 40 (SV40), β-globin, β-actin, α-fetoprotein, γ-globin, β-interferon, γ-glutamyl transferase, mouse mammary tumor virus (MMTV), Rous sarcoma virus, rat insulin, glyceraldehyde-3-phosphate dehydrogenase, metallothionein II (MT II), amylase, cathepsin, MI muscarinic receptor, retroviral LTR (e.g. human T-cell leukemia virus HTLV), AAV ITR, interleukin-2, collagenase, platelet-derived growth factor, adenovirus 5 E2, stromelysin, murine MX gene, glucose regulated proteins (GRP78 and GRP94), α-2-macroglobulin, vimentin, MHC class I gene H-2κ b, HSP70, proliferin, tumor necrosis factor, thyroid stimulating hormone a gene, immunoglobulin light chain, T-cell receptor, HLA DQα and DQβ, interleukin-2 receptor, MHC class II, MHC class II HLA-DRα, muscle creatine kinase, prealbumin (transthyretin), elastase I, albumin gene, c-fos, c-HA-ras, neural cell adhesion molecule (NCAM), H2B (TH2B) histone, rat growth hormone, human serum amyloid (SAA), troponin I (TN I), duchenne muscular dystrophy, human immunodeficiency virus, and Gibbon Ape Leukemia Virus (GALV) promoters. Additional examples of promoters are known in the art. See, e.g., Lodish, Molecular Cell Biology, Freeman and Company, New York 2007. In some embodiments, the promoter is the CMV immediate early promoter. In some embodiments, the promoter is a CAG promoter or a CAG/CBA promoter.

The term "constitutive" promoter refers to a nucleotide sequence that, when operably linked with a nucleic acid encoding a protein (e.g., an antibody or an antigen-binding antibody fragment), causes RNA to be transcribed from the nucleic acid in a mammalian cell under most or all physiological conditions.

Examples of constitutive promoters include, without limitation, the retroviral Rous sarcoma virus (RSV) LTR promoter, the cytomegalovirus (CMV) promoter (see, e.g., Boshart et al, *Cell* 41:521-530, 1985), the SV40 promoter, the dihydrofolate reductase promoter, the beta-actin promoter, the phosphoglycerol kinase (PGK) promoter, and the EF1-alpha promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Additional examples of inducible promoters are known in the art.

Examples of inducible promoters regulated by exogenously supplied compounds include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, *Proc. Natl. Acad. Sci. U.S.A.* 93:3346-3351, 1996), the tetracycline-repressible system (Gossen et al, *Proc. Natl. Acad. Sci. U.S.A.* 89:5547-5551, 1992), the tetracycline-inducible system (Gossen et al, *Science* 268:1766-1769, 1995, see also Harvey et al, Curr. Opin. Chem. Biol. 2:512-518, 1998), the RU486-inducible system (Wang et al, Nat. Biotech. 15:239-243, 1997) and Wang et al, *Gene Ther.* 4:432-441, 1997), and the rapamycin-inducible system (Magari et al. *J. Clin. Invest.* 100:2865-2872, 1997).

The term "tissue-specific" promoter refers to a promoter that is active only in certain specific cell types and/or tissues (e.g., transcription of a specific gene occurs only within cells expressing transcription regulatory proteins that bind to the tissue-specific promoter).

In some embodiments, the regulatory sequences impart tissue-specific gene expression capabilities. In some cases, the tissue-specific regulatory sequences bind tissue-specific transcription factors that induce transcription in a tissue-specific manner.

Exemplary tissue-specific promoters include but are not limited to the following: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, an alpha-myosin heavy chain (a-MHC) promoter, and a cardiac Troponin T (cTnT) promoter. Additional exemplary promoters include Beta-actin promoter, hepatitis B virus core promoter (Sandig et al., *Gene Ther.* 3:1002-1009, 1996), alpha-fetoprotein (AFP) promoter (Arbuthnot et al., *Hum. Gene Ther.* 7:1503-1514, 1996), bone osteocalcin promoter (Stein et al., *Mol. Biol. Rep.* 24:185-196, 1997); bone sialoprotein promoter (Chen et al., *J. Bone Miner. Res.* 11:654-664, 1996), CD2 promoter (Hansal et al., *J. Immunol.* 161:1063-1068, 1998); immunoglobulin heavy chain promoter; T cell receptor alpha-chain promoter, neuronal such as neuron-specific enolase (NSE) promoter (Andersen et al., *Cell. Mol. Neurobiol.* 13:503-515, 1993), neurofilament light-chain gene promoter (Piccioli et al., *Proc. Natl. Acad. Sci. U.S.A.* 88:5611-5615, 1991), and the neuron-specific vgf gene promoter (Piccioli et al., *Neuron* 15:373-384, 1995).

In some embodiments, the tissue-specific promoter is a cochlea-specific promoter. In some embodiments, the tissue-specific promoter is a cochlear hair cell-specific promoter. Non-limiting examples of cochlear hair cell-specific promoters include but are not limited to: a ATOH1 promoter, a POU4F3 promoter, a LHX3 promoter, a MYO7A promoter, a MYO6 promoter, a α9ACHR promoter, and a α10ACHR promoter. In some embodiments, the promoter is an cochlear hair cell-specific promoter such as a PRESTIN promoter or an ONCOMOD promoter. See, e.g., Zheng et al., Nature 405:149-155, 2000; Tian et al. *Dev. Dyn.* 231:199-203, 2004; and Ryan et al., *Adv. Otorhinolaryngol.* 66: 99-115, 2009.

Enhancers

In some instances, a vector (e.g., an AAV vector) can include an enhancer sequence. The term "enhancer" refers to a nucleotide sequence that can increase the level of transcription of a nucleic acid encoding a protein of interest (e.g., an antibody that binds specifically to VEGF or an antigen-binding antibody fragment thereof, or a soluble VEGF receptor). Enhancer sequences (50-1500 basepairs in length) generally increase the level of transcription by providing additional binding sites for transcription-associated proteins (e.g., transcription factors). In some embodiments, an enhancer sequence is found within an intronic sequence. Unlike promoter sequences, enhancer sequences can act at much larger distance away from the transcription start site (e.g., as compared to a promoter). Non-limiting examples of enhancers include a RSV enhancer, a CMV enhancer, and a SV40 enhancer.

Poly(A) Signal Sequence

In some embodiments, any of the vectors provided herein (e.g., an AAV vector) can include a polyadenylation (poly (A)) signal sequence. Most nascent eukaryotic mRNAs possess a poly(A) tail at their 3' end which is added during a complex process that includes cleavage of the primary transcript and a coupled polyadenylation reaction driven by the poly(A) signal sequence (see, e.g., Proudfoot et al., *Cell* 108:501-512, 2002). The poly(A) tail confers mRNA stability and transferability (Molecular Biology of the Cell, Third Edition by B. Alberts et al., Garland Publishing, 1994). In some embodiments, the poly(A) signal sequence is positioned 3' to the nucleic acid sequence encoding the antibody heavy chain, the antibody light chain, the antigen-binding antibody fragment, or the soluble VEGF receptor.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (e.g., 50, 60, 70, 100, 200, 500, 1000, 2000, 3000, 4000, or 5000) added to the pre-mRNA through the action of an enzyme, polyadenylate polymerase. In higher eukaryotes, the poly(A) tail is added onto transcripts that contain a specific sequence, the polyadenylation (or poly (A)) signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but also can occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, a "poly(A) signal sequence" or "polyadenylation signal sequence" is a sequence that triggers the endonuclease cleavage of an mRNA and the addition of a series of adenosines to the 3' end of the cleaved mRNA.

There are several poly(A) signal sequences that can be used, including those derived from bovine growth hormone (bgh) (Woychik et al., *Proc. Natl. Acad. Sci. U.S.A.* 81(13): 3944-3948, 1984; U.S. Pat. No. 5,122,458), mouse-β-globin, mouse-α-globin (Orkin et al., *EMBO J.* 4(2):453-456, 1985; Thein et al., *Blood* 71(2):313-319, 1988), human collagen, polyoma virus (Batt et al., *Mol. Cell Biol.* 15(9): 4783-4790, 1995), the Herpes simplex virus thymidine kinase gene (HSV TK), IgG heavy-chain gene polyadenylation signal (US 2006/0040354), human growth hormone (hGH) (Szymanski et al., *Mol. Therapy* 15(7):1340-1347, 2007), the group consisting of SV40 poly(A) site, such as the SV40 late and early poly(A) site (Schek et al., *Mol. Cell Biol.* 12(12):5386-5393, 1992).

The poly(A) signal sequence can be AATAAA. The AATAAA sequence may be substituted with other hexanucleotide sequences with homology to AATAAA and that are capable of signaling polyadenylation, including ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, or AATAAG (see, e.g., WO 06/12414).

In some embodiments, the poly(A) signal sequence can be a synthetic polyadenylation site (see, e.g., the pCl-neo expression vector of Promega that is based on Levitt el al, *Genes Dev.* 3(7):1019-1025, 1989). In some embodiments, the poly(A) signal sequence is the polyadenylation signal of soluble neuropilin-1 (sNRP) (AAATAAAATACGAAATG; SEQ ID NO: 11) (see, e.g., WO 05/073384). Additional examples of poly(A) signal sequences are known in the art.

Internal Ribosome Entry Site (IRES)

In some embodiments, a vector (e.g., an adeno-associated virus (AAV) vector) encoding an antibody (e.g., an antibody heavy chain and an antibody light chain), an antigen-binding antibody fragment, or a soluble VEGF receptor can include a polynucleotide internal ribosome entry site (IRES). An IRES sequence is used to produce more than one polypeptide from a single gene transcript. An IRES forms a complex secondary structure that allows translation initiation to occur from any position with an mRNA immediately downstream from where the IRES is located (see, e.g., Pelletier and Sonenberg, *Mol. Cell. Biol.* 8(3):1103-1112, 1988).

There are several IRES sequences known to those in skilled in the art, including those from, e.g., foot and mouth disease virus (FMDV), encephalomyocarditis virus (EMCV), human rhinovirus (HRV), cricket paralysis virus, human immunodeficiency virus (HIV), hepatitis A virus (HAV), hepatitis C virus (HCV), and poliovirus (PV). See e.g., Alberts, Molecular Biology of the Cell, Garland Science, 2002; and Hellen et al., *Genes Dev.* 15(13):1593-612, 2001.

In some embodiments, the IRES sequence that is incorporated into the AAV vector is the foot and mouth disease virus (FMDV) 2A sequence. The Foot and Mouth Disease Virus 2A sequence is a small peptide (approximately 18 amino acids in length) that has been shown to mediate the cleavage of polyproteins (Ryan, M D et al., *EMBO* 4:928-933, 1994; Mattion et al., *J. Virology* 70:8124-8127, 1996; Furler et al., *Gene Therapy* 8:864-873, 2001; and Halpin et al., *Plant Journal* 4:453-459, 1999). The cleavage activity of the 2A sequence has previously been demonstrated in artificial systems including plasmids and gene therapy vectors (AAV and retroviruses) (Ryan et al., *EMBO* 4:928-933, 1994; Mattion et al., *J Virology* 70:8124-8127, 1996; Furler et al., *Gene Therapy* 8:864-873, 2001; and Halpin et al., *Plant Journal* 4:453-459, 1999; de Felipe et al., *Gene Therapy* 6:198-208, 1999; de Felipe et al., *Human Gene Therapy* 11:1921-1931, 2000; and Klump et al., *Gene Therapy* 8:811-817, 2001).

Reporter Sequences

Any of the AAVs provided herein can optionally include a sequence encoding a reporter protein ("a reporter sequence"). Non-limiting examples of reporter sequences include DNA sequences encoding: a beta-lactamase, a beta-galactosidase (LacZ), an alkaline phosphatase, a thymidine kinase, a green fluorescent protein (GFP), a red fluorescent protein, an mCherry fluorescent protein, a yellow fluorescent protein, a chloramphenicol acetyltransferase (CAT), and a luciferase. Additional examples of reporter sequences are known in the art. When associated with regulatory elements which drive their expression, the reporter sequence can provide signals detectable by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry).

In some embodiments, the reporter sequence is the LacZ gene, and the presence of a vector carrying the LacZ gene in a mammalian cell (e.g., a cochlear hair cell) is detected by assays for beta-galactosidase activity. When the reporter is a fluorescent protein (e.g., green fluorescent protein) or luciferase, the presence of a vector carrying the fluorescent protein or luciferase in a mammalian cell (e.g., a cochlear hair cell) may be measured by fluorescent techniques (e.g., fluorescent microscopy or FACS) or light production in a luminometer (e.g., a spectrophotometer or an IVIS imaging instrument). In some embodiments, the reporter sequence can be used to verify the tissue-specific targeting capabilities and tissue-specific promoter regulatory activity of any of the vectors described herein.

Flanking Regions Untranslated Regions (UTRs)

In some embodiments, any of the adeno-associated virus (AAV) vectors can include an untranslated region, such as a 5' UTR or a 3' UTR.

Untranslated regions (UTRs) of a gene are transcribed but not translated. The 5' UTR starts at the transcription start site and continues to the start codon but does not include the start codon. The 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into any of the vectors, compositions, kits, or methods as described herein to enhance the expression of an antibody (e.g., an antibody that binds specifically to VEGF), an antigen-binding antibody fragment (e.g., an antigen-binding fragment that binds specifically to VEGF), or a soluble VEGF receptor.

Natural 5' UTRs include a sequence that plays a role in translation initiation. They harbor signatures like Kozak sequences, which are commonly known to be involved in the process by which the ribosome initiates translation of many genes. Kozak sequences have the consensus sequence CCR (A/G)CCAUGG, where R is a purine (A or G) three bases upstream of the start codon (AUG), and the start codon is followed by another "G". The 5' UTRs have also been known to form secondary structures that are involved in elongation factor binding.

In some embodiments, a 5' UTR is included in any of the vectors described herein. Non-limiting examples of 5' UTRs, including those from the following genes: albumin, serum amyloid A, Apolipoprotein A/B/E, transferrin, alpha fetoprotein, erythropoietin, and Factor VIII, can be used to enhance expression of a nucleic acid molecule, such as a mRNA.

In some embodiments, a 5' UTR from a mRNA that is transcribed by a cell in the cochlea can be included in any of the vectors, compositions, kits, and methods described herein.

3' UTRs are known to have stretches of adenosines and uridines (in the RNA form) or thymidines (in the DNA form) embedded in them. These AU-rich signatures are particularly prevalent in genes with high rates of turnover. Based on their sequence features and functional properties, the AU-rich elements (AREs) can be separated into three classes (Chen et al., *Mol. Cell. Biol.* 15:5777-5788, 1995; Chen et al., *Mol. Cell Biol.* 15:2010-2018, 1995): Class I AREs contain several dispersed copies of an AUUUA motif within U-rich regions. For example, c-Myc and MyoD mRNAs contain class I AREs. Class II AREs possess two or more overlapping UUAUUUA(U/A) (U/A) nonamers. GM-CSF and TNF-alpha mRNAs are examples that contain class II AREs. Class III AREs are less well defined. These U-rich regions do not contain an AUUUA motif. Two well-studied examples of this class are c-Jun and myogenin mRNAs.

Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

In some embodiments, the introduction, removal, or modification of 3' UTR AREs can be used to modulate the stability of an mRNA encoding a protein of interest (e.g., any antibody described herein, any antigen-binding antibody fragment described herein, or any soluble VEGF receptor described herein). In other embodiments, AREs can be removed or mutated to increase the intracellular stability and thus increase translation and production of a protein of interest (e.g., any antibody described herein, any antigen-binding antibody fragment described herein, or any soluble VEGF receptor described herein).

In other embodiments, non-ARE sequences may be incorporated into the 5' or 3' UTRs. In some embodiments, introns or portions of intron sequences may be incorporated into the flanking regions of the polynucleotides in any of the vectors, compositions, kits, and methods provided herein. Incorporation of intronic sequences may increase protein production as well as mRNA levels.

Fc Mutations that Decrease the Half-Life of an Antibody, Antigen-Binding Antibody Fragment, or a Soluble VEGF Receptor in a Mammal Any of the antibodies, antigen-binding antibody fragments, or soluble VEGF receptors described herein can include one or more (e.g., two, three, four, five, six, seven, eight, nine, or ten) amino acid substitutions in the Fc region that decrease the half-life of the antibody, the antigen-binding antibody fragment, or soluble VEGF receptor in a mammal, e.g., as compared to the half-life of an otherwise identical antibody, antigen-binding antibody fragment, or soluble VEGF receptor not including at least one of the one or more amino acid substitutions in the Fc region. Methods for determining the half-life of an antibody, antigen-binding antibody fragment, or soluble VEGF receptor in a mammal are well-known in the art.

Non-limiting examples of point mutations in a Fc mutation that can decrease the half-life of an antibody, an antigen-binding antibody fragment, or soluble VEGF receptor are described in Leabman et al., *MAbs* 5(6):896-903, 2013.

Methods

Also provided herein are methods that include introducing into an inner ear of a mammal a therapeutically effective amount of an adeno-associated virus (AAV) vector that includes a nucleotide sequence encoding (a) a polypeptide including an antibody heavy chain variable domain (e.g., any of the exemplary antibody heavy chain variable domains described herein) operably linked to a signal peptide (e.g., any of the signal peptides described herein) and a polypeptide including an antibody light chain variable domain (e.g., any of the exemplary antibody light chain variable domains described herein) operably linked to a signal peptide (e.g., any of the signal peptides described herein); (b) a polypeptide including an antigen-binding antibody fragment (e.g., a scFv) (e.g., any of the exemplary antigen-binding antibody fragments described herein) operably linked to a signal peptide (e.g., any of the signal peptides described herein), or (c) a soluble VEGF receptor (e.g., any of the soluble VEGF receptors described herein) operably linked to a signal peptide (e.g., any of the signal peptides described herein).

Also provided herein are methods for increasing the level of an antibody or an antigen-binding antibody fragment in an inner ear of a mammal in need thereof, that include: introducing into the inner ear of the mammal a therapeutically effective amount of an AAV vector that includes a nucleotide sequence encoding (a) a polypeptide including an antibody heavy chain variable domain (e.g., any of the antibody heavy chain variable domains described herein) operably linked to a signal peptide and a polypeptide including an antibody light chain variable domain (e.g., any of the antibody light chain variable domains described herein) operably linked to a signal peptide; or (b) a polypeptide including an antigen-binding antibody fragment (e.g., a scFv) (e.g., any of the exemplary antigen-binding antibody fragments described herein) operably linked to a signal peptide (e.g., any of the exemplary signal peptides described herein); where the introducing results in an increase (e.g., a 1% to 400% increase (or any of the subranges of this range described herein), or at least a 1%, at least a 10%, at least a 20%, at least a 30%, at least a 40%, at least a 50%, at least a 60%, at least a 70%, at least a 80%, at least a 90%, at least a 100%, at least a 150%, at least a 200%, at least a 250%, at least a 300%, at least a 350%, at least a 400%, at least a 450%, at least a 500%, at least a 550%, at least a 600%, at least a 650%, at least a 700%, at least a 750%, at least a 800%, at least a 850%, at least a 900%, at least a 950%, at least a 1000%, at least a 1100%, at least a 1200%, at least a 1300%, at least a 1400%, at least a 1500%, at least a 1600%, at least a 1700%, at least a 1800%, at least a 1900%, or at least a 2000% increase) in the level of the antibody or the antigen-binding antibody fragment in the inner ear of the mammal, e.g., as compared to the level of the antibody or the antigen-binding antibody fragment in the inner ear of the mammal prior to the administration.

Also provided herein are methods for increasing the level of a soluble VEGF receptor that include: introducing into the inner ear of the mammal a therapeutically effective amount of an AAV vector that includes a nucleotide sequence encoding a soluble VEGF receptor (e.g., any of the soluble VEGF receptors described herein) operably linked to a signal peptide (e.g., any of the signal peptides described herein); where the introducing results in an increase (e.g., a 1% to 400% increase (or any of the subranges of this range described herein), or at least a 1%, at least a 10%, at least a 20%, at least a 30%, at least a 40%, at least a 50%, at least a 60%, at least a 70%, at least a 80%, at least a 90%, at least a 100%, at least a 150%, at least a 200%, at least a 250%, at least a 300%, at least a 350%, at least a 400%, at least a 450%, at least a 500%, at least a 550%, at least a 600%, at least a 650%, at least a 700%, at least a 750%, at least a 800%, at least a 850%, at least a 900%, at least a 950%, at least a 1000%, at least a 1100%, at least a 1200%, at least a 1300%, at least a 1400%, at least a 1500%, at least a 1600%, at least a 1700%, at least a 1800%, at least a 1900%, or at least a 2000% increase) in the level of the soluble VEGF receptor in the inner ear of the mammal, e.g., as compared to the level of the soluble VEGF receptor in the inner ear of the mammal prior to the administration.

Also provided herein are methods for treating an inner ear disorder in a mammal in need thereof that include introducing into the inner ear of the mammal a therapeutically effective amount of an AAV vector that comprises a nucleotide sequence encoding: (a) a polypeptide including an antibody heavy chain variable domain (e.g., e.g., any of the antibody heavy chain variable domains described herein) operably linked to a signal peptide (e.g., any of the signal peptides described herein) and a polypeptide comprising an antibody light chain variable domain (e.g., any of the antibody light chain variable domains described herein) operably linked to a signal peptide (e.g., any of the signal peptides described herein); (b) a polypeptide including an antigen-binding antibody fragment (e.g., any of the exemplary antigen-binding antibody fragments described herein) linked to a signal peptide (e.g., any of the signal peptides described herein); or (c) a soluble VEGF receptor (e.g., any of the soluble VEGR receptors described herein) operably linked to a signal peptide (e.g., any of the signal peptides described herein), where the introducing results in the treatment of the inner ear disorder in the mammal. In some embodiments, treatment of an inner ear disorder results in a reduction (e.g., a 1% to 100% reduction, or any of the subranges of this range described herein) in the severity, frequency, or number of symptoms of an inner ear disorder in a mammal following the introducing as compared to before the introducing. In some embodiments, treatment of any inner ear disorder results in an increase (e.g., a 1% to 400% increase, or any of the subranges of this range described herein) in the hearing (e.g., one or more metrics of hearing) of the mammal following the introducing as compared to before the introducing.

In some embodiments of any of these methods, the antibody or the antigen-binding antibody fragment, or the soluble VEGF receptor, binds specifically to a vascular endothelial growth factor (VEGF) (e.g., one of more of VEGF-A, VEGF-B, VEGF-C, and VEGF-D, e.g., one or more of human VEGF-A, human VEGF-B, human VEGF-C, and human VEGF-D). In some embodiments of any of these methods, the AAV vector further includes one or both of a promoter and a Kozak sequence that are operably linked to the sequence encoding the antibody or the antigen-binding antibody fragment. In some embodiments wherein the AAV vector comprises a promoter selected from the group consisting of: an inducible promoter, a constitutive promoter, and a tissue-specific promoter. In some embodiments of any of these methods, the AAV vector further includes a polyadenylation signal sequence. In some embodiments of any of these methods, the mammal is a human. In some embodiments of any of these methods, the mammal (e.g., the human) has been identified as having an inner ear disorder. In some embodiments of any of these methods, the mammal (e.g., the human) has previously been diagnosed as having an inner ear disorder. In some embodiments of any of these methods, the vector includes a nucleic acid sequence encoding a polypeptide comprising an antibody heavy chain and an antibody light chain. In some embodiments of any of these methods, the vector includes a nucleic acid sequence encoding an antigen-binding antibody fragment. In some embodiments of any of these methods, the vector include a nucleic acid sequence encoding a soluble VEGF receptor operably linked to a signal peptide.

Also provided herein are methods of reducing a VEGF activity (e.g., one or more of VEGF-A, VEGF-B, VEGF-C, and VEGF-D, e.g., one or more of human VEGF-A, human VEGF-B, human VEGF-C, and human VEGF-D) in an inner ear of a mammal in need thereof that include: introducing into the inner ear of the mammal a therapeutically effective amount of an AAV vector that includes a nucleotide sequence encoding (a) a polypeptide including an antibody heavy chain variable domain (e.g., any of the antibody heavy chain variable domains described herein) operably linked to a signal peptide (e.g., any of the signal peptides described herein) and a polypeptide including an antibody light chain variable domain (e.g., any of the antibody light chain variable domains described herein) operably linked to a signal peptide (e.g., any of the signal peptides described herein); (b) a polypeptide including an antigen-binding antibody fragment (e.g., a Fab or a scFv) (e.g., any of the antigen-binding antibody fragments described herein) operably linked to a signal peptide (e.g., any of the signal peptides described herein); or (c) a soluble VEGF receptor (e.g., any of the soluble VEGF receptors described herein) operably linked to a signal peptide (e.g., any of the signal peptides described herein), where the polypeptide of (a) includes an antibody that binds specifically to a VEGF and reduces a VEGF activity, the polypeptide of (b) includes an antigen-binding antibody fragment that binds specifically to a VEGF and reduces a VEGF activity, or the soluble VEGF receptor of (c) binds specifically to one or more VEGF proteins and reduces the activity of the one or more VEGF proteins; and where the introducing results in a reduction (e.g., a 1% to 100% reduction, or any of the subranges of this range described herein) in a VEGF activity (e.g., an activity of one or more of VEGF-A, VEGF-B, VEGF-C, and VEGF-D, e.g., one or more human VEGF-A, human VEGF-B, human VEGF-C, and human VEGF-D) in the inner ear of the mammal, e.g., as compared to the VEGF activity in the mammal prior to the introducing. A reduction in a VEGF activity in a mammal can be detected using any of the exemplary methods described herein.

Also provided herein are methods of treating acoustic neuroma, vestibular schwannoma, or neurofibromatosis type II (NF2) in an inner ear of a mammal that include: introducing into the inner ear of the mammal a therapeutically effective amount of an AAV vector that includes a nucleotide sequence encoding (a) a polypeptide including an antibody heavy chain variable domain (e.g., any of the antibody heavy chain variable domains described herein) operably linked to a signal peptide (e.g., any of the signal peptides described herein) and a polypeptide including an antibody light chain variable domain (e.g., any of the antibody light chain variable domains described herein) operably linked to a signal peptide (e.g., any of the signal peptides described herein); (b) a polypeptide including an antigen-binding antibody fragment (e.g., a Fab or a scFv) (e.g., any of the antigen-binding antibody fragments described herein) operably linked to a signal peptide (e.g., any of the signal peptides described herein), or (c) a soluble VEGF receptor (e.g., any of the soluble VEGF receptors described herein) operably linked to a signal peptide (e.g., any of the signal peptides described herein); where the polypeptide of (a) encodes an antibody that binds specifically to a VEGF (e.g., one or more of VEGF-A, VEGF-B, VEGF-C, and VEGF-D, e.g., one or more of human VEGF-A, human VEGF-B, human VEGF-C, and human VEGF-D) and reduces the VEGF activity, the polypeptide of (b) encodes an antigen-binding antibody fragment that binds specifically to a VEGF (e.g., one or more of VEGF-A, VEGF-B, VEGF-C, and VEGF-D, e.g., one or more of human VEGF-A, human VEGF-B, human VEGF-C, and human VEGF-D) and reduces the VEGF activity, or the soluble VEGF receptor of (c) binds to specifically to one or more of VEGF-A, VEGF-B, VEGF-C, and VEGF-D (e.g., one or more of human VEGF-A, human VEGF-B, human VEGF-C, and human VEGF-D) and where the introducing results in treatment of acoustic neuroma, vestibular schwannoma, or neurofibromatosis type II (NF2) in the inner ear of the mammal. As described herein, successful treatment of one or more of an acoustic neuroma, vestibular schwannoma, or neurofibromatosis type II can be detected by observing a reduction (e.g., a 1% to 100% decrease, or any of the subranges of this range described herein) in the number, severity, or frequency of one or more symptoms of an acoustic neuroma, vestibular schwannoma, or neurofibromatosis type II, respectively, in the mammal, e.g., as compared to before the introducing step.

In some embodiments of any of these methods, the vector includes a nucleic acid sequence encoding a polypeptide encoding an antibody heavy chain variable domain (e.g., any of the antibody heavy chains described herein) and an antibody light chain variable domain (e.g., any of the antibody light chain variable domains described herein). In some embodiments of any of these methods, the vector includes a nucleic acid sequence encoding a polypeptide comprising an antigen-binding antibody fragment (e.g., any of the antigen-binding antibody fragments described herein). In some embodiments of any of these methods, the vector includes a nucleic acid sequence encoding a soluble VEGF receptor (e.g., any of the soluble VEGF receptors described herein) operably linked to a signal peptide (e.g., any of the signal peptides described herein). In some embodiments of any of these methods, the AAV vector further includes one or both of a promoter and a Kozak sequence that are operably linked to the sequence encoding the antibody or the antigen-binding antibody fragment. In some embodiments, the AAV vector comprises a promoter, where the promoter is selected from the group consisting of: an inducible promoter, a constitutive promoter, or a tissue-specific promoter. In some embodiments, the AAV vector further includes a polyadenylation signal sequence. In some embodiments of any of these methods, the mammal is a human. In some embodiments of any of these methods, the mammal (e.g., the human) has been identified as having an inner ear disorder. In some embodiments of any of these methods, the mammal (e.g., the human) has previously been diagnosed as having an inner ear disorder. In some embodiments of any of these methods, the mammal (e.g., the human) has been identified or diagnosed as having drug-induced hearing loss. In some embodiments of any of these methods, the mammal (e.g., the human) has been identified or diagnosed as having age-related hearing loss.

In some embodiments, the antibody or antigen-binding fragment thereof includes a Fc region that includes one or more point mutations that decrease the half-life of the antibody or antigen-binding antibody fragment in vivo.

In some embodiments of any of these methods, two or more doses of any of the adeno-associated virus (AAV) vectors described herein are introduced or administered into the inner ear of the mammal or subject. Some embodiments of any of these methods can include introducing or administering a first dose of the adeno-associated virus (AAV) vectors into the inner ear of the mammal or subject, assessing hearing function of the mammal or subject following the introducing or the administering of the first dose, and administering an additional dose of the adeno-associated virus (AAV) vector into the inner ear of the mammal or subject found not to have a hearing function within a normal range (e.g., as determined using any test for hearing known in the art).

In some embodiments of any of the methods described herein, the adeno-associated virus (AAV) vectors can be formulated for intra-cochlear administration. In some embodiments of any of the methods described herein, the adeno-associated virus (AAV) vectors described herein can be administered via intra-cochlear administration or local administration. In some embodiments of any of the methods described herein, the adeno-associated virus (AAV) vectors are administered through the use of a medical device (e.g., any of the exemplary medical devices described herein).

In some embodiments, intra-cochlear administration can be performed using any of the methods described herein or known in the art. For example, an adeno-associated virus (AAV) vector can be administered or introduced into the cochlea using the following surgical technique: first using visualization with a 0 degree, 2.5-mm rigid endoscope, the external auditory canal is cleared and a round knife is used to sharply delineate an approximately 5-mm tympanomeatal flap. The tympanomeatal flap is then elevated and the middle ear is entered posteriorly. The chorda tympani nerve is identified and divided, and a currette is used to remove the scutal bone, exposing the round window membrane. To enhance apical distribution of the administered or introduced adeno-associated virus (AAV) vector, a surgical laser may be used to make a small 2-mm fenestration in the oval window to allow for perilymph displacement during trans-round window membrane infusion of the adeno-associated virus (AAV) vectors. The microinfusion device is then primed and brought into the surgical field. The device is maneuvered to the round window, and the tip is seated within the bony round window overhang to allow for penetration of the membrane by the microneedle(s). The footpedal is engaged to allow for a measured, steady infusion of the adeno-associated virus (AAV) vectors. The device is then withdrawn and the round window and stapes foot plate are sealed with a gelfoam patch.

In some embodiments of any of the methods described herein, the subject or mammal is a rodent, a non-human primate, or a human. In some embodiments of any of the methods described herein, the subject or mammal is an adult, a teenager, a juvenile, a child, a toddler, an infant, or a newborn. In some embodiments of any of the methods described herein, the subject or mammal is 1-5, 1-10, 1-20, 1-30, 1-40, 1-50, 1-60, 1-70, 1-80, 1-90, 1-100, 1-110, 2-5, 2-10, 10-20, 20-30, 30-40, 40-50, 50-60, 60-70, 70-80, 80-90, 90-100, 100-110, 10-30, 10-40, 10-50, 10-60, 10-70, 10-80, 10-90, 10-100, 10-110, 20-40, 20-50, 20-60, 20-70, 20-80, 20-90, 20-100, 20-110, 30-50, 30-60, 30-70, 30-80, 30-90, 30-100, 40-60, 40-70, 40-80, 40-90, 40-100, 50-70, 50-80, 50-90, 50-100, 60-80, 60-90, 60-100, 70-90, 70-100, 70-110, 80-100, 80-110, or 90-110 years of age. In some embodiments of any of the methods described herein, the subject or mammal is 1, 2, 3, 4, 5, 6, 7, 8, 9, 10, or 11 months of age.

In some embodiments of any of the methods described herein, the subject or mammal has or is at risk of developing hearing loss (e.g., drug-induced hearing loss). In some embodiments of any of the methods described herein, the subject or mammal has been previously identified as having a mutation in a VEGF gene.

In some embodiments, successful treatment of hearing loss (e.g., drug-induced hearing loss) can be determined in a subject using any of the conventional functional hearing tests known in the art. Non-limiting examples of functional hearing tests are various types of audiometric assays (e.g., pure-tone testing, speech testing, test of the middle ear, auditory brainstem response, and otoacoustic emissions).

Methods for introducing any of the adeno-associated virus (AAV) vectors described herein into a mammalian cell are known in the art (e.g., via lipofection or through the use of a viral vector, e.g., any of the viral vectors described herein).

Pharmaceutical Compositions and Kits

In some embodiments, any of the compositions described herein can further include one or more agents that promote the entry of a nucleic acid or any of the vectors described herein into a mammalian cell (e.g., a liposome or cationic lipid). In some embodiments, any of the vectors described herein can be formulated using natural and/or synthetic polymers. Non-limiting examples of polymers that may be included in any of the compositions described herein can include, but are not limited to, DYNAMIC POLYCONJUGATE® (Arrowhead Research Corp., Pasadena, Calif.), formulations from Mirus Bio (Madison, Wis.) and Roche Madison (Madison, Wis.), PhaseRX polymer formulations such as, without limitation, SMARTT POLYMER TECHNOLOGY® (PhaseRX, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly (lactic-co-glycolic acid) (PLGA) polymers, RONDEL™ (RNAi/Oligonucleotide Nanoparticle Delivery) polymers (Arrowhead Research Corporation, Pasadena, Calif.), and pH responsive co-block polymers, such as, but not limited to, those produced by PhaseRX (Seattle, Wash.). Many of these polymers have demonstrated efficacy in delivering oligonucleotides in vivo into a mammalian cell (see, e.g., deFougerolles, *Human Gene Ther.* 19:125-132, 2008; Rozema et al., *Proc. Natl. Acad. Sci. U.S.A.* 104:12982-12887, 2007; Rozema et al., *Proc. Natl. Acad. Sci. U.S.A.* 104:12982-12887, 2007; Hu-Lieskovan et al., *Cancer Res.* 65:8984-8982, 2005; Heidel et al., *Proc. Natl. Acad. Sci. U.S.A.* 104:5715-5721, 2007).

Any of the compositions described herein can be, e.g., a pharmaceutical composition. A pharmaceutical composition can include any of the compositions described herein and one or more pharmaceutically or physiologically acceptable carriers, diluents, or excipients. Such compositions may comprise one or more buffers, such as neutral-buffered saline, phosphate-buffered saline, and the like; one or more carbohydrates, such as glucose, mannose, sucrose, and dextran; mannitol; one or more proteins, polypeptides, or amino acids, such as glycine; one or more antioxidants; one or more chelating agents, such as EDTA or glutathione; and/or one or more preservatives.

In some embodiments, the composition includes a pharmaceutically acceptable carrier (e.g., phosphate buffered saline, saline, or bacteriostatic water). Upon formulation, solutions will be administered in a manner compatible with the dosage formulation and in such amount as is therapeutically effective. The formulations are easily administered in a variety of dosage forms such as injectable solutions, injectable gels, drug-release capsules, and the like.

As used herein, the term "pharmaceutically acceptable carrier" includes solvents, dispersion media, coatings, antibacterial agents, antifungal agents, and the like that are compatible with pharmaceutical administration. Supplementary active compounds can also be incorporated into any of the compostions described herein.

In some embodiments, a single dose of any of the compositions described herein can include a total sum amount of the at least two different vectors of at least 1 ng, at least 2 ng, at least 4 ng, about 6 ng, about 8 ng, at least 10 ng, at least 20 ng, at least 30 ng, at least 40 ng, at least 50 ng, at least 60 ng, at least 70 ng, at least 80 ng, at least 90 ng, at least 100 ng, at least 200 ng, at least 300 ng, at least 400 ng, at least 500 ng, at least 1 µg, at least 2 µg, at least 4 µg, at least 6 µg, at least 8 µg, at least 10 µg, at least 12 µg, at least 14 µg, at least 16 µg, at least 18 µg, at least 20 µg, at least 22 µg, at least 24 µg, at least 26 µg, at least 28 µg, at least 30 µg at least 32 µg, at least 34 µg, at least 36 µg, at least 38 µg, at least 40 µg, at least 42 µg, at least 44 µg, at least 46 µg, at least 48 µg, at least 50 µg, at least 52 µg, at least 54 µg, at least 56 µg, at least 58 µg, at least 60 µg, at least 62 µg, at least 64 µg, at least 66 µg, at least 68 µg, at least 70 µg, at least 72 µg, at least 74 µg, at least 76 µg, at least 78 µg, at least 80 µg, at least 82 µg, at least 84 µg, at least 86 µg, at least 88 µg, at least 90 µg, at least 92 µg, at least 94 µg, at least 96 µg, at least 98 µg, at least 100 µg, at least 102 µg, at least 104 µg, at least 106 µg, at least 108 µg, at least 110 µg, at least 112 µg, at least 114 µg, at least 116 µg, at least 118 µg, at least 120 µg, at least 122 µg, at least 124 µg, at least 126 µg, at least 128 µg, at least 130 µg at least 132 µg, at least 134 µg, at least 136 µg, at least 138 µg, at least 140 µg, at least 142 µg, at least 144 µg, at least 146 µg, at least 148 µg, at least 150 µg, at least 152 µg, at least 154 µg, at least 156 µg, at least 158 µg, at least 160 µg, at least 162 µg, at least 164 µg, at least 166 µg, at least 168 µg, at least 170 µg, at least 172 µg, at least 174 µg, at least 176 µg, at least 178 µg, at least 180 µg, at least 182 µg, at least 184 µg, at least 186 µg, at least 188 µg, at least 190 µg, at least 192 µg, at least 194 µg, at least 196 µg, at least 198 µg, or at least 200 µg, e.g., in a buffered solution.

The compositions provided herein can be, e.g., formulated to be compatible with their intended route of administration. A non-limiting example of an intended route of administration is local administration (e.g., intra-cochlear administration). In some embodiments, the therapeutic compositions are formulated to include a lipid nanoparticle. In some embodiments, the therapeutic compositions are formulated to include a polymeric nanoparticle. In some embodiments, the therapeutic compositions are formulated to comprise a mini-circle DNA. In some embodiments, the therapeutic compositions are formulated to comprise a CELiD DNA. In some embodiments, the therapeutic compositions are formulated to comprise a synthetic perilymph solution. An exemplary synthetic perilymph solution includes 20-200 mM NaCl; 1-5 mM KCl; 0.1-10 mM $CaCl_2$; 1-10 mM glucose; 2-50 mM HEPES, having a pH of between about 6 and about 9.

Also provided are kits including any of the compositions described herein. In some embodiments, a kit can include a solid composition (e.g., a lyophilized composition including the at least two different vectors described herein) and a liquid for solubilizing the lyophilized composition. In some embodiments, a kit can include a pre-loaded syringe including any of the compositions described herein.

In some embodiments, the kit includes a vial comprising any of the compositions described herein (e.g., formulated as an aqueous composition, e.g., an aqueous pharmaceutical composition).

In some embodiments, the kits can include instructions for performing any of the methods described herein.

Devices and Surgical Methods

Provided herein are therapeutic delivery systems for treating hearing loss (e.g., acoustic neuromas/vestibular schwannomas and associated-hearing loss). In one aspect, the therapeutic delivery systems include i) a medical device capable of creating one or a plurality of incisions in a round window membrane of an inner ear of a human subject in need thereof, and ii) an effective dose of a composition (e.g., any of the compositions described herein). In some embodiments, the medical device includes a plurality of micro-needles.

Also provided herein are surgical methods for treatment of hearing loss (e.g., acoustic neuromas/vestibular schwannomas and associated-hearing loss). In some embodiments, the methods include the steps of: introducing into a cochlea of a human subject a first incision at a first incision point; and administering intra-cochlearly a therapeutically effective amount of any of the compositions provided herein. In some embodiments, the composition is administered to the subject at the first incision point. In some embodiments, the composition is administered to the subject into or through the first incision.

In some embodiments of any of the methods described herein, any of the compositions described herein is administered to the subject into or through the cochlea oval window membrane. In some embodiments of any of the methods described herein, any of the compositions described herein is administered to the subject into or through the cochlea round window membrane. In some embodiments of any of the methods described herein, the composition is administered using a medical device capable of creating a plurality of incisions in the round window membrane. In some embodiments, the medical device includes a plurality of micro-needles. In some embodiments, the medical device includes a plurality of micro-needles including a generally circular first aspect, where each micro-needle has a diameter of at least about 10 microns. In some embodiments, the medical device includes a base and/or a reservoir capable of holding the composition. In some embodiments, the medical device includes a plurality of hollow micro-needles individually including a lumen capable of transferring the composition. In some embodiments, the medical device includes a means for generating at least a partial vacuum.

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations that become evident as a result of the teaching provided herein.

Without further description, it is believed that one of ordinary skill in the art can, using the preceding description and the following illustrative examples, make and utilize the compositions of the present invention and practice the claimed methods. The following working examples specifically point out various aspects of the present invention, and are not to be construed as limiting in any way the remainder of the disclosure.

EXAMPLES

Example 1. Construction of Viral Vectors

Four different recombinant AAV vectors were generated and are shown in FIGS. 1A-D.

The vector in FIG. 1A is an exemplary AAV vector of 4474 bp (SEQ ID NO: 35) that includes the following sub-sequences going in the 5' to 3' direction:

```
                        (5' ITR; SEQ ID NO: 36)
CCTGCAGGCAGCTGCGCGCTCGCTCGCTCACTGAGGCCGCCCGGGCGTCGG

GCGACCTTTGGTCGCCCGGCCTCAGTGAGCGAGCGAGCGCGCAGAGAGGGA

GTGGCCAACTCCATCACTAGGGGTTCCTGCGGCCGCACGCGT;

(CBA sequence; SEQ ID NO: 37)
GACATTGATTATTGACTAGTTATTAATAGTAATCAATTACGGGGTCATTAG

TTCATAGCCCATATATGGAGTTCCGCGTTACATAACTTACGGTAAATGGCC

CGCCTGGCTGACCGCCCAACGACCCCCGCCCATTGACGTCAATAATGACGT

ATGTTCCCATAGTAACGCCAATAGGGACTTTCCATTGACGTCAATGGGTGG

ACTATTTACGGTAAACTGCCCACTTGGCAGTACATCAAGTGTATCATATGC

CAAGTACGCCCCCTATTGACGTCAATGACGGTAAATGGCCCGCCTGGCATT

ATGCCCAGTACATGACCTTATGGGACTTTCCTACTTGGCAGTACATCTACG

TATTAGTCATCGCTATTACCATGGTCGAGGTGAGCCCCACGTTCTGCTTC

ACTCTCCCCATCTCCCCCCCCTCCCCACCCCCAATTTTGTATTTATTTATT

TTTTAATTATTTTGTGCAGCGATGGGGCGGGGGGGGGGGGGGCGCGCGCC

AGGCGGGGCGGGGCGGGGCGAGGGGCGGGGCGGGGCGAGGCGGAGAGGTGC

GGCGGCAGCCAATCAGAGCGGCGCGCTCCGAAAGTTTCCTTTTATGGCGAG

GCGGCGGCGGCGGCGGCCCTATAAAAAGCGAAGCGCGCGGCGGGCGGGAGT
```

CGCTGCGTTGCCTTCGCCCCGTGCCCCGCTCCGCGCCGCCTCGCGCCGCCC

GCCCCGGCTCTGACTGACCGCGTTACTCCCACAGGTGAGCGGGCGGGACGG

CCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTG

CGGGGGGGAGCGGCTCGGGGGTGCGTGCGTGTGTGTGCGTGGGGAGCG

CCGCGTGCGGCCCGCGCTGCCCGGCGGCTGTGAGCGCTGCGGGCGCGGCGC

GGGGCTTTGTGCGCTCCGCGTGTGCGCGAGGGGAGCGCGGCCGGGGCGGT

GCCCCGCGGTGCGGGGGGCTGCGAGGGGAACAAAGGCTGCGTGCGGGGTG

TGTGCGTGGGGGGGTGAGCAGGGGGTGTGGGCGCGGCGGTCGGGCTGTAAC

CCCCCCCTGCACCCCCCTCCCCGAGTTGCTGAGCACGGCCCGGCTTCGGT

GCGGGGCTCCGTGCGGGCGTGGCGCGGGGCTCGCCGTGCCGGGCGGGGG

TGGCGGCAGGTGGGGGTGCCGGGCGGGGCGGGGCCGCCTCGGGCCGGGGAG

GGCTCGGGGAGGGGCGCGGCGGCCCCCGGAGCGCCGGCGGCTGTCGAGGC

GCGGCGAGCCGCAGCCATTGCCTTTTATGGTAATCGTGCGAGAGGGCGCAG

GGACTTCCTTTGTCCCAAATCTGTGCGGAGCCGAAATCTGGGAGGCGCCGC

CGCACCCCCTCTAGCGGGCGCGGGGCGAAGCGGTGCGGCGCCGGCAGGAAG

GAAATGGGCGGGGAGGGCCTTCGTGCGTCGCCGCGCCGCCGTCCCCTTCTC

CCTCTCCAGCCTCGGGGCTGTCCGCGGGGGACGGCTGCCTTCGGGGGGGA

CGGGGCAGGGCGGGGTTCGGCTTCTGGCGTGTGACCGGCGGCTCTAGAGCC

TCTGCTAACCATGTTCATGCCTTCTTCTTTTTCCTACAG;

(spacer; SEQ ID NO: 38)
CTCCTGGGCAACGTGCTGGTTATTGTGACCGGTGCCACC;

(IL-2 secretion signal sequence; SEQ ID NO: 39)
ATGTACCGGATGCAGCTGCTGAGCTGTATCGCCCTGTCTCTGGCCCTGGTC

ACCAATTCT;

(sequence encoding heavy chain of bevacizumab;
SEQ ID NO: 40)
GAGGTGCAGCTGGTGGAATCTGGCGGCGGACTTGTTCAACCTGGCGGCTCT

CTGAGACTGAGCTGTGCCGCTTCTGGCTACACCTTCACCAACTACGGCATG

AACTGGGTCCGACAGGCCCCTGGCAAAGGCCTTGAATGGGTCGGATGGATC

AACACCTACACCGGCGAGCCAACATACGCCGCCGACTTCAAGCGGAGATTC

ACCTTCAGCCTGGACACCAGCAAGAGCACCGCCTACCTGCAGATGAACAGC

CTGAGAGCCGAGGACACCGCCGTGTACTACTGCGCCAAGTATCCCCACTAC

TACGGCAGCAGCCACTGGTACTTTGACGTGTGGGGACAGGGCACACTGGTC

ACAGTGTCTAGCGCCTCTACAAAGGGCCCCAGCGTTTTCCCACTGGCTCCT

AGCAGCAAGTCTACCAGCGGAGGAACAGCCGCTCTGGGCTGTCTGGTCAAG

GACTACTTTCCCGAGCCTGTGACCGTGTCCTGGAATTCTGGCGCTCTGACA

AGCGGCGTGCACACCTTTCCAGCTGTGCTGCAAAGCAGCGGCCTGTACTCT

CTGAGCAGCGTCGTGACAGTGCCAAGCAGCTCTCTGGGCACCCAGACCTAC

ATCTGCAATGTGAACCACAAGCCTAGCAACACCAAGGTGGACAAGAAGGTG

GAACCCAAGAGCTGCGACAAGACCCACACCTGTCCTCCATGTCCTGCTCCA

GAACTGCTCGGCGGACCTTCCGTGTTCCTGTTTCCTCCAAAGCCTAAGGAC

ACCCTGATGATCAGCAGAACCCCTGAAGTGACCTGCGTGGTGGTGGATGTG

TCCCACGAGGATCCCGAAGTGAAGTTCAATTGGTACGTGGACGGCGTGGAA

GTGCACAACGCCAAGACCAAGCCTAGAGAGGAACAGTACAACAGCACCTAC

AGAGTGGTGTCCGTGCTGACCGTGCTGCACCAGGATTGGCTGAACGGCAAA

GAGTACAAGTGCAAGGTGTCCAACAAGGCCCTGCCTGCTCCTATCGAGAAA

ACCATCAGCAAGGCCAAGGGCCAGCCTAGGGAACCCCAGGTTTACACACTG

CCTCCAAGCCGGGAAGAGATGACCAAGAACCAGGTGTCCCTGACCTGCCTC

GTGAAGGGCTTCTACCCTTCCGATATCGCCGTGGAATGGGAGAGCAATGGC

CAGCCAGAGAACAACTACAAGACAACCCCTCCTGTGCTGGACAGCGACGGC

TCATTCTTCCTGTACAGCAAGCTGACAGTGGACAAGTCCAGATGGCAGCAG

GGCAACGTGTTCAGCTGCAGCGTGATGCACGAGGCCCTGCACAACCACTAC

ACCCAGAAGTCTCTGAGCCTGTCTCCTGGCAAG;

(linker sequence; SEQ ID NO: 41)
CGGAAGAGAAGA;

(T2A sequence; SEQ ID NO: 42)
GGCTCTGGCGAAGGCAGAGGCAGCCTGCTTACATGTGGCGACGTGGAAG

AGAACCCCGGACCT;

(IL-2 secretion signal sequence; SEQ ID NO: 43)
ATGTATAGAATGCAGCTCCTGTCCTGCATTGCCCTGAGCCTGGCTCTCGTG

ACCAACAGC;

(sequence encoding light chain of bevacizumab;
SEQ ID NO: 44)
GACATCCAGATGACACAGAGCCCCAGCAGCCTGTCTGCCTCTGTGGGAGAC

AGAGTGACCATCACCTGTAGCGCCAGCCAGGACATCTCCAACTACCTGAAC

TGGTATCAGCAAAAGCCCGGCAAGGCCCCTAAGGTGCTGATCTACTTCACA

AGCAGCCTGCACTCCGGCGTGCCCAGCAGATTTTCTGGCTCTGGCAGCGGC

ACCGACTTCACCCTGACCATATCTAGCCTGCAGCCTGAGGACTTCGCCACC

TACTACTGCCAGCAGTACAGCACCGTGCCTTGGACATTTGGCCAGGGCACA

AAGGTGGAAATCAAGCGGACTGTGGCCGCTCCTAGCGTGTTCATCTTTCCA

CCTAGCGACGAGCAGCTGAAGTCTGGCACAGCCTCTGTCGTGTGCCTGCTG

AACAACTTCTACCCCAGAGAAGCCAAGGTGCAGTGGAAAGTGGACAATGCC

CTGCAGAGCGGCAACAGCCAAGAGAGCGTGACAGAGCAGGACTCCAAGGAT

AGCACCTATAGCCTGAGCAGCACCCTGACACTGAGCAAGGCCGACTACGAG

AAGCACAAAGTGTACGCCTGCGAAGTGACCCACCAGGGCCTTTCTAGCCCT

GTGACCAAGAGCTTCAACCGGGGCGAATGTTAA;

(linker sequence; SEQ ID NO: 45)
GAGCTCGCTGATCAGCCTCGA;

(bovine growth hormone poly A tail sequence;
SEQ ID NO: 46)
CTGTGCCTTCTAGTTGCCAGCCATCTGTTGTTTGCCCCTCCCCCGTGCCTT

CCTTGACCCTGGAAGGTGCCACTCCCACTGTCCTTTCCTAATAAAATGAGG

AAATTGCATCGCATTGTCTGAGTAGGTGTCATTCTATTCTGGGGGGTGGGG

TGGGGCAGGACAGCAAGGGGGAGGATTGGGAAGACAATAGCAGGCATGCTG

GGGATGCGGTGGGCTCTATGG;

(linker sequence; SEQ ID NO: 47)
AAGCTTGAATTCAGCTGACGTGCCTCGGACCGCT;
and (3' ITR; SEQ ID NO: 48)
AGGAACCCCTAGTGATGGAGTTGGCCACTCCCTCTCTGCGCGCTCGCTCG

CTCACTGAGGCCGGGCGACCAAAGGTCGCCCGACGCCCGGGCTTTGCCCG

GGCGGCCTCAGTGAGCGAGCGAGCGCGCAGCTGCCTGCAGG.

The IL-2 signal sequence encoded by each of SEQ ID NOs: 39 and 43 is MYRMQLLSCIALSLALVTNS (SEQ ID NO: 49). The T2A sequence encoded by SEQ ID NO: 42 is GSGEGRGSLLTCGDVEENPGP (SEQ ID NO: 50). SEQ ID NO: 40 encodes the heavy chain of bevacizumab (SEQ ID NO: 6). SEQ ID NO: 44 encodes the light chain of bevacizumab (SEQ ID NO: 5). The last three nucleotides in SEQ ID NO: 44 are a stop codon.

The vector in FIG. 1B is an exemplary AAV vector of 3814 bp (SEQ ID NO: 51) that includes the following sub-sequences going in the 5' to 3' direction:

(3' ITR; SEQ ID NO: 36)
CCTGCAGGCAGCTGCGCGCTCGCTCGCTCACTGAGGCCGCCCGGGCGTCGG

GCGACCTTTGGTCGCCCGGCCTCAGTGAGCGAGCGAGCGCGCAGAGAGGGA

GTGGCCAACTCCATCACTAGGGGTTCCTGCGGCCGCACGCGT;

(CBA sequence; SEQ ID NO: 37)
GACATTGATTATTGACTAGTTATTAATAGTAATCAATTACGGGGTCATTAG

TTCATAGCCCATATATGGAGTTCCGCGTTACATAACTTACGGTAAATGGCC

CGCCTGGCTGACCGCCCAACGACCCCCGCCCATTGACGTCAATAATGACGT

ATGTTCCCATAGTAACGCCAATAGGGACTTTCCATTGACGTCAATGGGTGG

ACTATTTACGGTAAACTGCCCACTTGGCAGTACATCAAGTGTATCATATGC

CAAGTACGCCCCCTATTGACGTCAATGACGGTAAATGGCCCGCCTGGCATT

ATGCCCAGTACATGACCTTATGGGACTTTCCTACTTGGCAGTACATCTACG

TATTAGTCATCGCTATTACCATGGTCGAGGTGAGCCCCACGTTCTGCTTC

ACTCTCCCCATCTCCCCCCCCTCCCCACCCCCAATTTTGTATTTATTTATT

TTTTAATTATTTTGTGCAGCGATGGGGGCGGGGGGGGGGGGGCGCGCGCC

AGGCGGGGCGGGGCGGGGCGAGGGCGGGGCGGGGCGAGGCGGAGAGGTGC

GGCGGCAGCCAATCAGAGCGGCGCGCTCCGAAAGTTTCCTTTTATGGCGAG

GCGGCGGCGGCGGCGGCCCTATAAAAAGCGAAGCGCGCGGCGGGCGGGAGT

CGCTGCGTTGCCTTCGCCCCGTGCCCCGCTCCGCGCCGCCTCGCGCCGCCC

GCCCCGGCTCTGACTGACCGCGTTACTCCCACAGGTGAGCGGGCGGGACGG

CCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTG

CGGGGGGAGCGGCTCGGGGGGTGCGTGCGTGTGTGTGCGTGGGGAGCG

CCGCGTGCGGCCCGCGCTGCCCGGCGGCTGTGAGCGCTGCGGGCGCGGCGC

GGGGCTTTGTGCGCTCCGCGTGTGCGCGAGGGGAGCGCGGCCGGGGGCGGT

GCCCCGCGGTGCGGGGGGGCTGCGAGGGGAACAAAGGCTGCGTGCGGGGTG

TGTGCGTGGGGGGGTGAGCAGGGGGTGTGGGCGCGGCGGTCGGGCTGTAAC

CCCCCCCTGCACCCCCCTCCCCGAGTTGCTGAGCACGGCCCGGCTTCGGGT

GCGGGGCTCCGTGCGGGGCGTGGCGCGGGGCTCGCCGTGCCGGGCGGGGGG

TGGCGGCAGGTGGGGGTGCCGGGCGGGGCGGGGCCGCCTCGGGCCGGGGAG

GGCTCGGGGGAGGGGCGCGGCGGCCCCCGGAGCGCCGGCGGCTGTCGAGGC

GCGGCGAGCCGCAGCCATTGCCTTTTATGGTAATCGTGCGAGAGGGCGCAG

GGACTTCCTTTGTCCCAAATCTGTGCGGAGCCGAAATCTGGGAGGCGCCGC

CGCACCCCCTCTAGCGGGCGCGGGGCGAAGCGGTGCGGCGCCGGCAGGAAG

GAAATGGGCGGGGAGGGCCTTCGTGCGTCGCCGCGCCGCCGTCCCCTTCTC

CCTCTCCAGCCTCGGGGCTGTCCGCGGGGGGACGGCTGCCTTCGGGGGGGA

CGGGGCAGGGCGGGGTTCGGCTTCTGGCGTGTGACCGGCGGCTCTAGAGCC

TCTGCTAACCATGTTCATGCCTTCTTCTTTTTCCTACAG;

(linker sequence; SEQ ID NO: 38)
CTCCTGGGCAACGTGCTGGTTATTGTGACCGGTGCCACC;

(IL-2 secretion signal sequence; SEQ ID NO: 39)
ATGTACCGGATGCAGCTGCTGAGCTGTATCGCCCTGTCTCTGGCCCTGGTC

ACCAATTCT;

(sequence encoding ranibizumab heavy chain; SEQ ID NO: 52)
GAGGTGCAGCTGGTGGAATCTGGCGGCGGACTTGTTCAACCTGGCGGCTCT

CTGAGACTGAGCTGTGCCGCTTCTGGCTACGACTTCACCCACTACGGCATG

AACTGGGTCCGACAGGCCCCTGGCAAAGGCCTTGAATGGGTCGGATGGATC

AACACCTACACCGGCGAGCCAACATACGCCGCCGACTTCAAGCGGAGATTC

ACCTTCAGCCTGGACACCAGCAAGAGCACCGCCTACCTGCAGATGAACAGC

CTGAGAGCCGAGGACACCGCCGTGTACTACTGCGCCAAGTATCCCTACTAC

TACGGCACCAGCCACTGGTACTTTGACGTGTGGGGACAGGGCACACTGGTC

ACAGTGTCTAGCGCCTCTACAAAGGGCCCCAGCGTTTTCCCACTGGCTCCT

AGCAGCAAGTCTACCAGCGGAGGAACAGCCGCTCTGGGCTGTCTGGTCAAG

GACTACTTTCCCGAGCCTGTGACCGTGTCCTGGAATTCTGGCGCTCTGACA

AGCGGCGTGCACACCTTTCCAGCTGTGCTGCAAAGCAGCGGCCTGTACTCT

CTGAGCAGCGTCGTGACAGTGCCAAGCAGCTCTCTGGGCACCCAGACCTAC

ATCTGCAATGTGAACCACAAGCCTAGCAACACCAAGGTGGACAAGAAGGTG

GAACCCAAGAGCTGCGACAAGACCCACACCGGCAAG;

(linker sequence; SEQ ID NO: 41)
CGGAAGAGAAGA;

(T2A sequence; SEQ ID NO: 42)
GGCTCTGGCGAAGGCAGAGGCAGCCTGCTTACATGTGGCGACGTGGAAGAG

AACCCCGGACCT;

(IL-2 signal secretion sequence; SEQ ID NO: 43)
ATGTATAGAATGCAGCTCCTGTCCTGCATTGCCCTGAGCCTGGCTCTCGTG

ACCAACAGC;

(sequence encoding ranibizumab light chain; SEQ ID NO: 53)
GACATCCAGCTGACACAGAGCCCCAGCAGCCTGTCTGCCTCTGTGGGAGAC

AGAGTGACCATCACCTGTAGCGCCAGCCAGGACATCTCCAACTACCTGAAC

TGGTATCAGCAAAAGCCCGGCAAGGCCCCTAAGGTGCTGATCTACTTCACA

AGCAGCCTGCACTCCGGCGTGCCCAGCAGATTTTCTGGCTCTGGCAGCGGC

```
                                                     (linker sequence; SEQ ID NO: 44)
ACCGACTTCACCCTGACCATATCTAGCCTGCAGCCTGAGGACTTCGCCACC

TACTACTGCCAGCAGTACAGCACCGTGCCTTGGACATTTGGCCAGGGCACA

AAGGTGGAAATCAAGCGGACTGTGGCCGCTCCTAGCGTGTTCATCTTTCCA

CCTAGCGACGAGCAGCTGAAGTCTGGCACAGCCTCTGTCGTGTGCCTGCTG

AACAACTTCTACCCCAGAGAAGCCAAGGTGCAGTGGAAAGTGGACAATGCC

CTGCAGAGCGGCAACAGCCAAGAGAGCGTGACAGAGCAGGACTCCAAGGAT

AGCACCTATAGCCTGAGCAGCACCCTGACACTGAGCAAGGCCGACTACGAG

AAGCACAAAGTGTACGCCTGCGAAGTGACCCACCAGGGCCTTTCTAGCCCT

GTGACCAAGAGCTTCAACCGGGGCGAATGTTAA.

(linker sequence; SEQ ID NO: 45)
GAGCTCGCTGATCAGCCTCGA;

(bovine growth hormone poly A tail sequence;
                                             SEQ ID NO: 46)
CTGTGCCTTCTAGTTGCCAGCCATCTGTTGTTTGCCCCTCCCCCGTGCCTT

CCTTGACCCTGGAAGGTGCCACTCCCACTGTCCTTTCCTAATAAAATGAGG

AAATTGCATCGCATTGTCTGAGTAGGTGTCATTCTATTCTGGGGGGTGGGG

TGGGGCAGGACAGCAAGGGGGAGGATTGGGAAGACAATAGCAGGCATGCTG

GGGATGCGGTGGGCTCTATGG;
and
                                         (linker; SEQ ID NO: 47)
AAGCTTGAATTCAGCTGACGTGCCTCGGACCGCT;

(SEQ ID NO: 48)
AGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGG

CGGCCTCAGTGAGCGAGCGAGCGCGCAGCTGCCTGCAGG.

The IL-2 signal sequence encoded by each of SEQ ID NOs: 39 and 43 is MYRMQLLSCIALSLALVTNS (SEQ ID NO: 49). The T2A sequence encoded by SEQ ID NO: 42 is GSGEGRGSLLTCGDVEENPGP (SEQ ID NO: 50). SEQ ID NO: 52 encodes the heavy chain of ranibizumab (EVQLVESGGGLVQPGGSLRLSCAASGYDFTHYGMNWVRQAPGKGLEWVGW

INTYTGEPTYAADFKRRFTFSLDTSKSTAYLQMNSLRAEDTAVYYCAKYPY

YYGTSHWYFDVWGQGTLVTVSSASTKGPSVFPLAPSSKSTSGGTAALGCLV

KDYFPEPVTVSWNSGALTSGVHTFPAVLQSSGLYSLSSVVTVPSSSLGTQT

YICNVNHKPSNTKVDKKVEPKSCDKTHTGK; SEQ ID NO: 54).

SEQ ID NO: 53 encodes the light chain of bevacizumab (SEQ ID NO: 7). The last three nucleotides in SEQ ID NO: 53 are a stop codon.

FIG. 1C is an exemplary AAV vector of 4573 bp (SEQ ID NO: 55) that includes the following sub-sequences going in the 5' to 3' direction:

(5' ITR; SEQ ID NO: 36)
CCTGCAGGCAGCTGCGCGCTCGCTCGCTCACTGAGGCCGCCCGGGCGTCGG

GCGACCTTTGGTCGCCCGGCCTCAGTGAGCGAGCGAGCGCGCAGAGAGGGA

GTGGCCAACTCCATCACTAGGGGTTCCTGCGGCCGCACGCGT;

(CBA sequence; SEQ ID NO: 37)
GACATTGATTATTGACTAGTTATTAATAGTAATCAATTACGGGGTCATTAG

TTCATAGCCCATATATGGAGTTCCGCGTTACATAACTTACGGTAAATGGCC

CGCCTGGCTGACCGCCCAACGACCCCCGCCCATTGACGTCAATAATGACGT

ATGTTCCCATAGTAACGCCAATAGGGACTTTCCATTGACGTCAATGGGTGG

ACTATTTACGGTAAACTGCCCACTTGGCAGTACATCAAGTGTATCATATGC

CAAGTACGCCCCCTATTGACGTCAATGACGGTAAATGGCCCGCCTGGCATT

ATGCCCAGTACATGACCTTATGGGACTTTCCTACTTGGCAGTACATCTACG

TATTAGTCATCGCTATTACCATGGGTCGAGGTGAGCCCCACGTTCTGCTTC

ACTCTCCCCATCTCCCCCCCCTCCCCACCCCCAATTTTGTATTTATTTATT

TTTTAATTATTTTGTGCAGCGATGGGGGCGGGGGGGGGGGGGCGCGCGCC

AGGCGGGGCGGGGCGGGGCGAGGGGCGGGGCGGGGCGAGGCGGAGAGGTGC

GGCGGCAGCCAATCAGAGCGGCGCGCTCCGAAAGTTTCCTTTTATGGCGAG

GCGGCGGCGGCGGCGGCCCTATAAAAAGCGAAGCGCGCGGCGGGCGGGAGT

CGCTGCGTTGCCTTCGCCCCGTGCCCCGCTCCGCGCCGCCTCGCGCCGCCC

GCCCCGGCTCTGACTGACCGCGTTACTCCCACAGGTGAGCGGGCGGGACGG

CCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTG

CGGGGGGGAGCGGCTCGGGGGGTGCGTGCGTGTGTGTGCGTGGGGAGCG

CCGCGTGCGGCCCGCGCTGCCCGGCGGCTGTGAGCGCTGCGGGCGCGGCGC

GGGGCTTTGTGCGCTCCGCGTGTGCGCGAGGGGAGCGCGGCCGGGGGCGGT

GCCCCGCGGTGCGGGGGGCTGCGAGGGGAACAAAGGCTGCGTGCGGGGTG

TGTGCGTGGGGGGGTGAGCAGGGGGTGTGGGCGCGGCGGTCGGGCTGTAAC

CCCCCCCTGCACCCCCCTCCCCGAGTTGCTGAGCACGGCCCGGCTTCGGGT

GCGGGGCTCCGTGCGGGGCGTGGCGCGGGGCTCGCCGTGCCGGGCGGGGG

TGGCGGCAGGTGGGGGTGCCGGCGGGGCGGGCCGCCTCGGGCCGGGAG

GGCTCGGGGAGGGGCGCGGCGGCCCCCGGAGCGCCGGCGGCTGTCGAGGC

GCGGCGAGCCGCAGCCATTGCCTTTTATGGTAATCGTGCGAGAGGGCGCAG

GGACTTCCTTTGTCCCAAATCTGTGCGGAGCCGAAATCTGGGAGGCGCCGC

CGCACCCCCTCTAGCGGGCGCGGGGCGAAGCGGTGCGGCGCCGGCAGGAAG

GAAATGGGCGGGAGGGCCTTCGTGCGTCGCCGCGCCGCCGTCCCCTTCTC

CCTCTCCAGCCTCGGGGCTGTCCGCGGGGGGACGGCTGCCTTCGGGGGGA

CGGGGCAGGGCGGGGTTCGGCTTCTGGCGTGTGACCGGCGGCTCTAGAGCC

TCTGCTAACCATGTTCATGCCTTCTTCTTTTTCCTACAG;

(linker sequence; SEQ ID NO: 38)
CTCCTGGGCAACGTGCTGGTTATTGTGACCGGTGCCACC;

(IL-2 secretion signal sequence; SEQ ID NO: 39)
ATGTACCGGATGCAGCTGCTGAGCTGTATCGCCCTGTCTCTGGCCCTGGTC

ACCAATTCT;

(sequence encoding ranibizumab heavy chain;
                                                    SEQ ID NO: 52)
GAGGTGCAGCTGGTGGAATCTGGCGGCGGACTTGTTCAACCTGGCGGCTCT

CTGAGACTGAGCTGTGCCGCTTCTGGCTACGACTTCACCCACTACGGCATG
```

-continued

AACTGGGTCCGACAGGCCCCTGGCAAAGGCCTTGAATGGGTCGGATGGATC

AACACCTACACCGGCGAGCCAACATACGCCGCCGACTTCAAGCGGAGATTC

ACCTTCAGCCTGGACACCAGCAAGAGCACCGCCTACCTGCAGATGAACAGC

CTGAGAGCCGAGGACACCGCCGTGTACTACTGCGCCAAGTATCCCTACTAC

TACGGCACCAGCCACTGGTACTTTGACGTGTGGGGACAGGGCACACTGGTC

ACAGTGTCTAGCGCCTCTACAAAGGGCCCCAGCGTTTTCCCACTGGCTCCT

AGCAGCAAGTCTACCAGCGGAGGAACAGCCGCTCTGGGCTGTCTGGTCAAG

GACTACTTTCCCGAGCCTGTGACCGTGTCCTGGAATTCTGGCGCTCTGACA

AGCGGCGTGCACACCTTTCCAGCTGTGCTGCAAAGCAGCGGCCTGTACTCT

CTGAGCAGCGTCGTGACAGTGCCAAGCAGCTCTCTGGGCACCCAGACCTAC

ATCTGCAATGTGAACCACAAGCCTAGCAACACCAAGGTGGACAAGAAGGTG

GAACCCAAGAGCTGCGACAAGACCCACACCGGCAAG;

(linker sequence; SEQ ID NO: 41)
CGGAAGAGAAGA;

(T2A sequence; SEQ ID NO: 42)
GGCTCTGGCGAAGGCAGAGGCAGCCTGCTTACATGTGGCGACGTGGAAGAG
AACCCCGGACCT;

(IL-2 signal secretion sequence; SEQ ID NO: 43)
ATGTATAGAATGCAGCTCCTGTCCTGCATTGCCCTGAGCCTGGCTCTCGTG
ACCAACAGC;

(sequence encoding ranibizumab light chain;
SEQ ID NO: 56)
GACATCCAGCTGACACAGAGCCCCAGCAGCCTGTCTGCCTCTGTGGGAGAC

AGAGTGACCATCACCTGTAGCGCCAGCCAGGACATCTCCAACTACCTGAAC

TGGTATCAGCAAAAGCCCGGCAAGGCCCCTAAGGTGCTGATCTACTTCACA

AGCAGCCTGCACTCCGGCGTGCCCAGCAGATTTTCTGGCTCTGGCAGCGGC

ACCGACTTCACCCTGACCATATCTAGCCTGCAGCCTGAGGACTTCGCCACC

TACTACTGCCAGCAGTACAGCACCGTGCCTTGGACATTTGGCCAGGGCACA

AAGGTGGAAATCAAGCGGACTGTGGCCGCTCCTAGCGTGTTCATCTTTCCA

CCTAGCGACGAGCAGCTGAAGTCTGGCACAGCCTCTGTCGTGTGCCTGCTG

AACAACTTCTACCCCAGAGAAGCCAAGGTGCAGTGGAAAGTGGACAATGCC

CTGCAGAGCGGCAACAGCCAAGAGAGCGTGACAGAGCAGGACTCCAAGGAT

AGCACCTATAGCCTGAGCAGCACCCTGACACTGAGCAAGGCCGACTACGAG

AAGCACAAAGTGTACGCCTGCGAAGTGACCCACCAGGGCCTTTCTAGCCCT

GTGACCAAGAGCTTCAACCGGGGCGAATGT;

(linker sequence; SEQ ID NO: 57)
GGCTCCGGAGAGGGCAGAGGAAGTCTGCTAACATGCGGTGACGTCGAGGAG
AATCCTGGCCCA;

(sequence encoding TurboGFP; SEQ ID NO: 58)
ATGGAGAGCGACGAGAGCGGCCTGCCCGCCATGGAGATCGAGTGCCGCATC

ACCGGCACCCTGAACGGCGTGGAGTTCGAGCTGGTGGGCGGCGGAGAGGGC

ACCCCCGAGCAGGGCCGCATGACCAACAAGATGAAGAGCACCAAAGGCGCC

CTGACCTTCAGCCCCTACCTGCTGAGCCACGTGATGGGCTACGGCTTCTAC

CACTTCGGCACCTACCCCAGCGGCTACGAGAACCCCTTCCTGCACGCCATC

AACAACGGCGGCTACACCAACACCCGCATCGAGAAGTACGAGGACGGCGGC

GTGCTGCACGTGAGCTTCAGCTACCGCTACGAGGCCGGCCGCGTGATCGGC

GACTTCAAGGTGATGGGCACCGGCTTCCCCGAGGACAGCGTGATCTTCACC

GACAAGATCATCCGCAGCAACGCCACCGTGGAGCACCTGCACCCCATGGGC

GATAACGATCTGGATGGCAGCTTCACCCGCACCTTCAGCCTGCGCGACGGC

GGCTACTACAGCTCCGTGGTGGACAGCCACATGCACTTCAAGAGCGCCATC

CACCCCAGCATCCTGCAGAACGGGGGCCCCATGTTCGCCTTCCGCCGCGTG

GAGGAGGATCACAGCAACACCGAGCTGGGCATCGTGGAGTACCAGCACGCC

TTCAAGACCCCGGATGCAGATGCCGGTGAAGAATAA;

(linker sequence; SEQ ID NO: 45)
GAGCTCGCTGATCAGCCTCGA;

(bovine growth hormone poly A tail sequence;
SEQ ID NO: 46)
CTGTGCCTTCTAGTTGCCAGCCATCTGTTGTTTGCCCCTCCCCCGTGCCTT

CCTTGACCCTGGAAGGTGCCACTCCCACTGTCCTTTCCTAATAAAATGAGG

AAATTGCATCGCATTGTCTGAGTAGGTGTCATTCTATTCTGGGGGGTGGGG

TGGGGCAGGACAGCAAGGGGGAGGATTGGGAAGACAATAGCAGGCATGCTG

GGGATGCGGTGGGCTCTATGG;

(linker sequence; SEQ ID NO: 47)
AAGCTTGAATTCAGCTGACGTGCCTCGGACCGCT;
and (3' ITR; SEQ ID NO: 48)
AGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGG

CGGCCTCAGTGAGCGAGCGAGCGCGCAGCTGCCTGCAGG.

The IL-2 signal sequence encoded by each of SEQ ID NOs: 39 and 43 is MYRMQLLSCIALSLALVTNS (SEQ ID NO: 49). The T2A sequence encoded by SEQ ID NO: 42 is GSGEGRGSLLTCGDVEENPGP (SEQ ID NO: 50). SEQ ID NO: 52 encodes the heavy chain of ranibizumab (SEQ ID NO: 54). SEQ ID NO: 56 encodes the light chain of bevacizumab (SEQ ID NO: 7). SEQ ID NO: 58 encodes TurboGFP (MESDESGLPAMEIECRITGTLNGVEFELVGGGEGTPEQGRMTNKMKSTKG
ALTFSPYLLSHVMGYGFYHFGTYPSGYENPFLHAINNGGYTNTRIEKYEDG
GVLHVSFSYRYEAGRVIGDFKVMGTGFPEDSVIFTDKIIRSNATVEHLHPM
GDNDLDGSFTRTFSLRDGGYYSSVVDSHMHFKSAIHPSILQNGGPMFAFRR
VEEDHSNTELGIVEYQHAFKTPDADAGEE; SEQ ID NO: 59).

The last three nucleotides in SEQ ID NO: 58 is a stop codon.

FIG. 1D is an exemplary AAV vector of 3631 bp (SEQ ID NO: 60) that includes the following sub-sequences going in the 5' to 3' direction:

(5' ITR; SEQ ID NO: 36)
CCTGCAGGCAGCTGCGCGCTCGCTCGCTCACTGAGGCCGCCCGGGCGTCGG

GCGACCTTTGGTCGCCCGGCCTCAGTGAGCGAGCGAGCGCGCAGAGAGGGA

GTGGCCAACTCCATCACTAGGGGTTCCTGCGGCCGCACGCGT;

(CBA sequence; SEQ ID NO: 37)
GACATTGATTATTGACTAGTTATTAATAGTAATCAATTACGGGGTCATTAG

TTCATAGCCCATATATGGAGTTCCGCGTTACATAACTTACGGTAAATGGCC

CGCCTGGCTGACCGCCCAACGACCCCCGCCCATTGACGTCAATAATGACGT

ATGTTCCCATAGTAACGCCAATAGGGACTTTCCATTGACGTCAATGGGTGG

ACTATTTACGGTAAACTGCCCACTTGGCAGTACATCAAGTGTATCATATGC

CAAGTACGCCCCCTATTGACGTCAATGACGGTAAATGGCCCGCCTGGCATT

ATGCCCAGTACATGACCTTATGGGACTTTCCTACTTGGCAGTACATCTACG

TATTAGTCATCGCTATTACCATGGGTCGAGGTGAGCCCCACGTTCTGCTTC

ACTCTCCCCATCTCCCCCCCCTCCCCACCCCCAATTTTGTATTTATTTATT

TTTTAATTATTTTGTGCAGCGATGGGGGCGGGGGGGGGGGGGCGCGCGCC

AGGCGGGGCGGGGCGGGCGAGGGCGGGGCGGGGCGAGGCGGAGAGGTGC

GGCGGCAGCCAATCAGAGCGGCGCGCTCCGAAAGTTTCCTTTTATGGCGAG

GCGGCGGCGGCGGCGGCCCTATAAAAAGCGAAGCGCGCGGCGGGCGGGAGT

CGCTGCGTTGCCTTCGCCCCGTGCCCCGCTCCGCGCCGCCTCGCGCCGCCC

GCCCCGGCTCTGACTGACCGCGTTACTCCCACAGGTGAGCGGGCGGGACGG

CCCTTCTCCTCCGGGCTGTAATTAGCGCTTGGTTTAATGACGGCTCGTTTC

TTTTCTGTGGCTGCGTGAAAGCCTTAAAGGGCTCCGGGAGGGCCCTTTGTG

CGGGGGGAGCGGCTCGGGGGTGCGTGCGTGTGTGTGCGTGGGGAGCG

CCGCGTGCGGCCCGCGCTGCCCGGCGGCTGTGAGCGCTGCGGGCGCGGCGC

GGGGCTTTGTGCGCTCCGCGTGTGCGCGAGGGGAGCGCGGCCGGGGCGGT

GCCCCGCGGTGCGGGGGGGCTGCGAGGGGAACAAAGGCTGCGTGCGGGTG

TGTGCGTGGGGGGGTGAGCAGGGGGTGTGGGCGCGGCGGTCGGGCTGTAAC

CCCCCCCTGCACCCCCCTCCCCGAGTTGCTGAGCACGGCCCGGCTTCGGT

GCGGGGCTCCGTGCGGGGCGTGGCGCGGGCTCGCCGTGCCGGGCGGGGG

TGGCGGCAGGTGGGGGTGCCGGGCGGGGCGGGCCGCCTCGGGCCGGGAG

GGCTCGGGGGAGGGGCGCGGCGGCCCCGGAGCGCCGGCGGCTGTCGAGGC

GCGGCGAGCCGCAGCCATTGCCTTTTATGGTAATCGTGCGAGAGGGCGCAG

GGACTTCCTTTGTCCCAAATCTGTGCGGAGCCGAAATCTGGGAGGCGCCGC

CGCACCCCCTCTAGCGGGCGCGGGGCGAAGCGGTGCGGCGCCGGCAGGAAG

GAAATGGGCGGGAGGGCCTTCGTGCGTCGCCGCCGCCGCCGTCCCCTTCTC

CCTCTCCAGCCTCGGGGCTGTCCGCGGGGGGACGGCTGCCTTCGGGGGGGA

CGGGGCAGGGCGGGGTTCGGCTTCTGGCGTGTGACCGGCGGCTCTAGAGCC

TCTGCTAACCATGTTCATGCCTTCTTCTTTTTCCTACAG;

(spacer; SEQ ID NO: 38)
CTCCTGGGCAACGTGCTGGTTATTGTGACCGGTGCCACC;

(IL-2 secretion signal sequence; SEQ ID NO: 39)
ATGTACCGGATGCAGCTGCTGAGCTGTATCGCCCTGTCTCTGGCCCTGGTC

ACCAATTCT;

(sequence encoding aflibercept; SEQ ID NO: 61)
AGCGATACCGGCAGACCCTTCGTGGAAATGTACAGCGAGATCCCCGAGATC

ATCCACATGACCGAGGGCAGAGAGCTGGTCATCCCCTGCAGAGTGACAAGC

CCCAACATCACCGTGACTCTGAAGAAGTTCCCTCTGGACACACTGATCCCC

GACGGCAAGAGAATCATCTGGGACAGCCGGAAGGGCTTCATCATCAGCAAC

GCCACCTACAAAGAGATCGGCCTGCTGACCTGTGAAGCCACCGTGAATGGC

CACCTGTACAAGACCAACTACCTGACACACAGACAGACCAACACCATCATC

GACGTGGTGCTGAGCCCTAGCCACGGCATTGAACTGTCTGTGGGCGAGAAG

CTGGTGCTGAACTGTACCGCCAGAACCGAGCTGAACGTGGGCATCGACTTC

AACTGGGAGTACCCCAGCAGCAAGCACCAGCACAAGAAACTGGTCAACCGG

GACCTGAAAACCCAGAGCGGCAGCGAGATGAAGAAATTCCTGAGCACCCTG

ACCATCGACGGCGTGACCAGATCTGACCAGGGCCTGTACACATGTGCCGCC

AGCTCTGGCCTGATGACCAAGAAAAACAGCACCTTCGTGCGGGTGCACGAG

AAGGACAAGACCCACACCTGTCCTCCATGTCCTGCTCCAGAACTGCTCGGC

GGACCTTCCGTGTTCCTGTTTCCTCCAAAGCCTAAGGACACCCTGATGATC

AGCAGAACCCCTGAAGTGACCTGCGTGGTGGTGGATGTGTCCCACGAGGAT

CCCGAAGTGAAGTTCAATTGGTACGTGGACGGCGTGGAAGTGCACAACGCC

AAGACCAAGCCTAGAGAGGAACAGTACAATAGCACCTACAGAGTGGTGTCC

GTGCTGACCGTGCTGCACCAGGATTGGCTGAACGGCAAAGAGTACAAGTGC

AAGGTGTCCAACAAGGCCCTGCCTGCTCCTATCGAGAAAACCATCTCCAAG

GCCAAGGGCCAGCCTAGGGAACCCCAGGTTTACACACTGCCTCCAAGCAGG

GACGAGCTGACAAAGAACCAGGTGTCCCTGACCTGCCTGGTCAAGGGCTTC

TACCCTTCCGATATCGCCGTGGAATGGGAGAGCAATGGCCAGCCTGAGAAC

AACTACAAGACAACCCCTCCTGTGCTGGACAGCGACGGCTCATTCTTCCTG

TACAGCAAGCTGACAGTGGACAAGAGCAGATGGCAGCAGGGCAACGTGTTC

AGCTGCAGCGTGATGCACGAGGCCCTGCACAACCACTACACCCAGAAGTCC

CTGAGCCTGTCTCCTGGATAA;

(linker sequence; SEQ ID NO: 45)
GAGCTCGCTGATCAGCCTCGA;

(bovine growth hormone poly A tail sequence;
SEQ ID NO: 46)
CTGTGCCTTCTAGTTGCCAGCCATCTGTTGTTTGCCCCTCCCCCGTGCCTT

CCTTGACCCTGGAAGGTGCCACTCCCACTGTCCTTTCCTAATAAAATGAGG

AAATTGCATCGCATTGTCTGAGTAGGTGTCATTCTATTCTGGGGGGTGGGG

TGGGGCAGGACAGCAAGGGGGAGGATTGGGAAGACAATAGCAGGCATGCTG

GGGATGCGGTGGGCTCTATGG;

(linker sequence; SEQ ID NO: 47)
AAGCTTGAATTCAGCTGACGTGCCTCGGACCGCT;
and (3' ITR; SEQ ID NO: 48)
AGGAACCCCTAGTGATGGAGTTGGCCACTCCCTCTCTGCGCGCTCGCTCGC

TCACTGAGGCCGGGCGACCAAAGGTCGCCCGACGCCCGGGCTTTGCCCGGG

CGGCCTCAGTGAGCGAGCGAGCGCGCAGCTGCCTGCAGG.

The IL-2 signal sequence encoded by SEQ ID NO: 39 is MYRMQLLSCIALSLALVTNS (SEQ ID NO: 49). SEQ ID NO: 61 encodes aflibercept (SEQ ID NO: 12). The last three nucleotides in SEQ ID NO: 61 is a stop codon.

To determine protein expression driven by the AAV vectors shown in FIGS. 1A-1C, HEK293FT cells were seeded overnight at $7 \times 10^4$ cells/well (400 μL per well) in wells of a 24-well plate. HEK293FT cells were transfected at ~800 ng with the AAV vectors shown in FIGS. 1A-1D using a Jetprime Polypus reagent (used to generate the data in Lanes 2-5 and 10-13 of FIG. 2). HEK293FT cells were also seeded for six hours at $4×10^4$ cells/well (50 μL per well) in wells of a 96-well plate in the presence of 2 μM etoposide (used to generate the data in Lanes 6-8 and 14-16 of FIG. 2). The AAV vector shown in FIG. 1A was added into the media with a multiplicity of infection (MOI) of $7.5×10^4$, $2.2×10^5$, or $5.5×10^5$. The supernatant was harvested at 72 hours post-treatment from well and was loaded onto a 4-12% Bolt protein gel in reducing (lanes 2-8 of FIG. 2) and non-reducing conditions (lanes 10-16 of FIG. 2). An anti-ranibizumab antibody detecting the Fab region was used as a primary antibody, and anti-human IgG was used as the second antibody.

As shown in FIG. 2, the heavy chain and light chain ranibizumab were detected in Lanes 3 and 6-8, and intact ranibizumab (heterodimer) was detected in lanes 11 and 14-16.

Example 2. Binding Activity of Anti-Human VEGF Monoclonal Antibodies

Figure 3B:
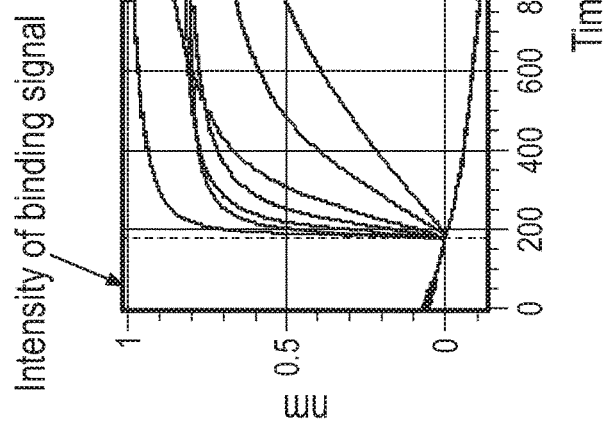
FIG. 3B is a graph showing the affinity of a control anti-hVEGF MmAb in conditioned media (CM) samples using recombinant human VEGF as the binding agent, as measured by Octet® HTX biosensor instrument using the Octet® analysis software, Data Analysis HT10.0. *: anti-hVEGF MmAb was prepared in CM at 100 μg/mL, then diluted to a final concentration of 10 μg/mL in 1× kinetics buffer.
Figure 3A:
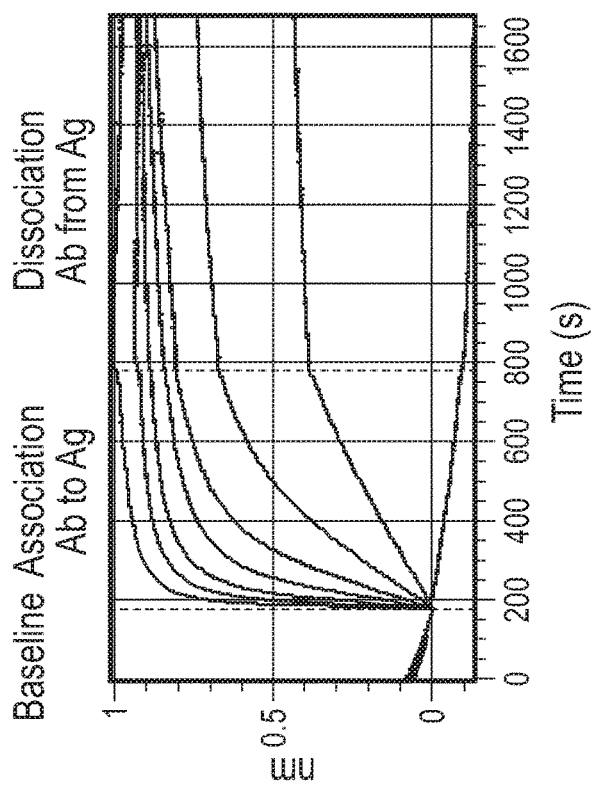
FIG. 3A is a graph showing the affinity of a control mouse anti-human VEGF monoclonal antibody (anti-hVEGF MmAb) in a buffer using recombinant human VEGF as the binding agent, as measured by Octet® HTX biosensor instrument using the Octet® analysis software, Data Analysis HT10.0.
Figures 4A, 4B:
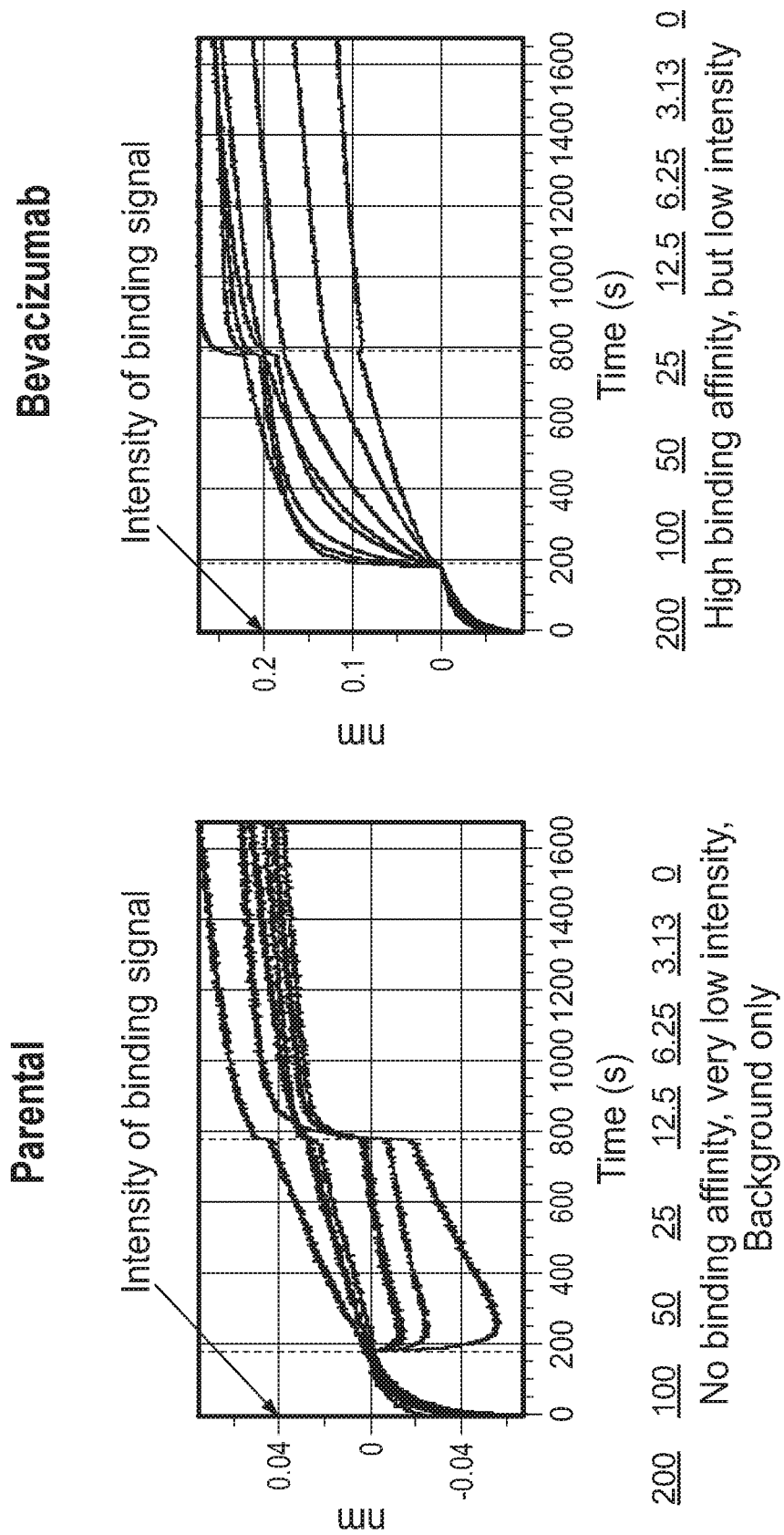
FIG. 4A is a graph showing the affinity of conditioned medium using recombinant human VEGF as the binding agent, as measured by Octet® HTX biosensor instrument using the Octet® analysis software, Data Analysis HT10.0.
FIG. 4B is a graph showing the affinity of culture medium from HEK cells transfected with the AAV vector shown in FIG. 1A using recombinant human VEGF as the binding agent, using by Octet® HTX biosensor instrument using the Octet® analysis software, Data Analysis HT10.0.

A set of experiments were performed to determine the binding activity of bevacizumab produced in HEK293FT cells following transfection with the AAV vector shown in FIG. 1A. A first set of control experiments were performed to calibrate the plasmon surface resonance instrumentation (using a mouse anti-human VEGF monoclonal antibody (anti-hVEGF MmAb; R&D, MAB293-100) in buffer or in conditioned medium (FIGS. 3A and 3B, respectively) using recombinant human VEGF as the binding agent. A second set of experiments were performed to determine the human VEGF-binding activity of control conditioned medium and conditioned medium from HEK293TF cells following transfection with the AAV vector shown in FIG. 1A (FIGS. 4A and 4B, respectively).

The samples, bevacizumab in medium from HEK293TF cells transfected with the AAV vector shown in FIG. 1A or conditioned medium), were prepared by diluting 1:10 in 1× kinetics buffer (Fortebio, 18-1105) into a 384-well sample plate. Anti-hVEGF MmAb (R&D, MAB293-100) was diluted at a concentration of 10 μg/mL as a positive control. The capture agent, recombinant human VEGF (R&D, 293-VE-010) was diluted in a series of 1:2 dilution ratio from 200 nM to 3.125 nM.

The binding affinities of the conditioned medium samples and mouse anti-human VEGF antibody (R&D) samples were measured in 1× kinetics buffer in Octet® HTX biosensor instrument. The binding features and $K_D$ values were generated by the Octet® analysis software, Data Analysis HT10.0. As shown in FIGS. 3A-B, the $K_D$ of anti-hVEGF MmAb in buffer was $<1.0×10^{-12}$ M, and the anti-hVEGF MmAb in conditioned medium was $<1.0×10^{-12}$ M. The conditioned medium itself had no binding affinity and very low intensity (background signal only) (FIG. 4A). In contrast, the conditioned medium including bevacizumab produced by HEK293TF cells transfected with the AAV vector shown in FIG. 1A had high binding affinity, but low intensity (FIG. 4B; $K_D<1.0×10^{-12}$ M). FIG. 4C shows a table of the loading samples and the respective $K_D$, $K_D$ errors, equilibrium association constant ($k_a$), and the dissociation ($k_{dis}$), and $k_{dis}$ error.

In summary, the anti-hVEGF mouse antibody (R&D) showed high binding affinity ($K_D$ was lower than measurable range of $1.0×10^{-12}$ M). The bevacizumab conditioned medium sample showed high binding affinity ($K_D$ was lower than measurable range). No $K_D$ value could be extrapolated from the binding data of control conditioned medium sample.

In sum, these data show that the AAV vectors provided herein can result in expression and secretion of anti-VEGF antibodies and can be used to express anti-VEGF antibodies in the inner ear of a mammal.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. Section headings and any descriptions of materials, methods, and examples are illustrative only and not intended to be limiting.

SEQUENCE LISTING

```
<160> NUMBER OF SEQ ID NOS: 61

<210> SEQ ID NO 1
<211> LENGTH: 412
<212> TYPE: PRT
<213> ORGANISM: Human

<400> SEQUENCE: 1

Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60
```

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
130                 135                 140

Arg Gly Gly Arg Val Ala Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
        290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
        370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 2
<211> LENGTH: 1239
<212> TYPE: DNA
<213> ORGANISM: Human

<400> SEQUENCE: 2
ctgacggaca gacagacaga caccgccccc agccccagct accacctcct ccccggccgg    60
cggcggacag tggacgcggc ggcgagccgc gggcaggggc cggagccgc gcccggaggc    120

```
ggggtggagg gggtcggggc tcgcggcgtc gcactgaaac ttttcgtcca acttctgggc    180
tgttctcgct tcggaggagc cgtggtccgc gcggggaag ccgagccgag cggagccgcg    240
agaagtgcta gctcgggccg ggaggagccg cagccggagg aggggagga ggaagaagag    300 aaggaagagg agaggggcc gcagtggcga ctcggcgctc ggaagccggg ctcatggacg    360
ggtgaggcgg cggtgtgcgc agacagtgct ccagccgcgc gcgctcccca ggccctggcc    420
cgggcctcgg gccggggagg aagagtagct cgccgaggcg ccgaggagag cgggccgccc    480
cacagcccga gccggagagg gagcgcgagc cgcgccggcc ccggtcgggc tccgaaaacc    540
atgaactttc tgctgtcttg ggtgcattgg agccttgcct tgctgctcta cctccaccat    600
gccaagtggt cccaggctgc acccatggca gaaggaggag ggcagaatca tcacgaagtg    660
gtgaagttca tggatgtcta tcagcgcagc tactgccatc caatcgagac cctggtggac    720
atcttccagg agtaccctga tgagatcgag tacatcttca gccatcctg tgtgcccctg    780 atgcgatgcg ggggctgctg caatgacgag ggcctggagt gtgtgccac tgaggagtcc    840 aacatcacca tgcagattat gcggatcaaa cctcaccaag ccagcacat aggagagatg    900 agcttcctac agcacaacaa atgtgaatgc agaccaaaga agatagagc aagacaagaa    960 aaaaaatcag ttcgaggaaa gggaaagggg caaaaacgaa agcgcaagaa atcccggtat   1020
aagtcctgga gcgtgtacgt tggtgcccgc tgctgtctaa tgccctggag cctccctggc   1080
ccccatccct gtgggccttg ctcagagcgg agaaagcatt tgtttgtaca agatccgcag   1140
acgtgtaaat gttcctgcaa aaacacagac tcgcgttgca aggcgaggca gcttgagtta   1200
aacgaacgta cttgcagatg tgacaagccg aggcggtga                          1239
```

<210> SEQ ID NO 3
<211> LENGTH: 389
<212> TYPE: PRT
<213> ORGANISM: Human

<400> SEQUENCE: 3

Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
            290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Pro Cys Gly Pro Cys Ser Glu Arg Arg Lys His Leu Phe
            340                 345                 350

Val Gln Asp Pro Gln Thr Cys Lys Cys Ser Cys Lys Asn Thr Asp Ser
                355                 360                 365

Arg Cys Lys Ala Arg Gln Leu Glu Leu Asn Glu Arg Thr Cys Arg Cys
370                 375                 380

Asp Lys Pro Arg Arg
385

<210> SEQ ID NO 4
<211> LENGTH: 1170
<212> TYPE: DNA
<213> ORGANISM: Human

<400> SEQUENCE: 4
ctgacggaca gacagacaga caccgccccc agccccagct accacctcct ccccggccgg      60
cggcggacag tggacgcggc ggcgagccgc gggcaggggc cggagcccgc gcccggaggc     120
ggggtggagg gggtcggggc tcgcggcgtc gcactgaaac ttttcgtcca acttctgggc     180
tgttctcgct tcggaggagc cgtggtccgc gcggggaaag ccgagccgag cggagccgcg     240
agaagtgcta gctcgggccg ggaggagccg cagccggagg aggggaggag gaagaagag     300 aaggaagagg agaggggcc gcagtggcga ctcggcgctc ggaagccggg ctcatggacg     360
ggtgaggcgg cggtgtgcgc agacagtgct ccagccgcgc gcgctcccca ggccctggcc     420
cgggcctcgg gccggggagg aagagtagct cgccgaggcg ccgaggagag cgggccgccc     480
cacagcccga gccggagagg gagcgcgagc cgcgccggcc ccggtcgggc ctccgaaacc     540
atgaactttc tgctgtcttg ggtgcattgg agccttgcct tgctgctcta cctccaccat     600
gccaagtggt cccaggctgc acccatggca gaaggaggag ggcagaatca tcacgaagtg     660
gtgaagttca tggatgtcta tcagcgcagc tactgccatc caatcgagac cctggtggac     720
atcttccagg agtaccctga tgagatcgag tacatcttca agccatcctg tgtgccctg      780 atgcgatgcg ggggctgctg caatgacgag ggcctggagt gtgtgcccac tgaggagtcc     840
aacatcacca tgcagattat gcggatcaaa cctcaccaag ccagcacat aggagagatg     900

```
agcttcctac agcacaacaa atgtgaatgc agaccaaaga aagatagagc aagacaagaa    960
aaaaaatcag ttcgaggaaa gggaaagggg caaaaacgaa agcgcaagaa atcccgtccc   1020
tgtgggcctt gctcagagcg gagaaagcat tgtttgtac aagatccgca gacgtgtaaa    1080
tgttcctgca aaacacaga ctcgcgttgc aaggcgaggc agcttgagtt aaacgaacgt    1140
acttgcagat gtgacaagcc gaggcggtga                                    1170
```

<210> SEQ ID NO 5
<211> LENGTH: 214
<212> TYPE: PRT
<213> ORGANISM: Artificial
<220> FEATURE:
<223> OTHER INFORMATION: Bevacizumab light chain variable domain

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 6
<211> LENGTH: 453
<212> TYPE: PRT
<213> ORGANISM: Artificial
<220> FEATURE:
<223> OTHER INFORMATION: Bevacizumab heavy chain variable domain

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30
```

```
Gly Met Asn Trp Val Arg Gln Ala Pro Gly Lys Gly Leu Glu Trp Val
            35                  40                  45
Gly Trp Ile Asn Thr Tyr Thr Gly Glu Pro Thr Tyr Ala Ala Asp Phe
 50                  55                  60
Lys Arg Arg Phe Thr Phe Ser Leu Asp Thr Ser Lys Ser Thr Ala Tyr
 65                  70                  75                  80
Leu Gln Met Asn Ser Leu Arg Ala Glu Asp Thr Ala Val Tyr Tyr Cys
                 85                  90                  95
Ala Lys Tyr Pro His Tyr Gly Ser Ser His Trp Tyr Phe Asp Val
             100                 105                 110
Trp Gly Gln Gly Thr Leu Val Thr Val Ser Ser Ala Ser Thr Lys Gly
             115                 120                 125
Pro Ser Val Phe Pro Leu Ala Pro Ser Ser Lys Ser Thr Ser Gly Gly
     130                 135                 140
Thr Ala Ala Leu Gly Cys Leu Val Lys Asp Tyr Phe Pro Glu Pro Val
 145                 150                 155                 160
Thr Val Ser Trp Asn Ser Gly Ala Leu Thr Ser Gly Val His Thr Phe
                 165                 170                 175
Pro Ala Val Leu Gln Ser Ser Gly Leu Tyr Ser Leu Ser Ser Val Val
             180                 185                 190
Thr Val Pro Ser Ser Ser Leu Gly Thr Gln Thr Tyr Ile Cys Asn Val
         195                 200                 205
Asn His Lys Pro Ser Asn Thr Lys Val Asp Lys Lys Val Glu Pro Lys
     210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                 245                 250                 255
Leu Met Ile Ser Arg Thr Pro Glu Val Thr Cys Val Val Val Asp Val
             260                 265                 270
Ser His Glu Asp Pro Glu Val Lys Phe Asn Trp Tyr Val Asp Gly Val
         275                 280                 285
Glu Val His Asn Ala Lys Thr Lys Pro Arg Glu Glu Gln Tyr Asn Ser
     290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                 325                 330                 335
Pro Ile Glu Lys Thr Ile Ser Lys Ala Lys Gly Gln Pro Arg Glu Pro
             340                 345                 350
Gln Val Tyr Thr Leu Pro Pro Ser Arg Glu Glu Met Thr Lys Asn Gln
         355                 360                 365
Val Ser Leu Thr Cys Leu Val Lys Gly Phe Tyr Pro Ser Asp Ile Ala
     370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                 405                 410                 415
Thr Val Asp Lys Ser Arg Trp Gln Gln Gly Asn Val Phe Ser Cys Ser
             420                 425                 430
Val Met His Glu Ala Leu His Asn His Tyr Thr Gln Lys Ser Leu Ser
         435                 440                 445
Leu Ser Pro Gly Lys
```

```
<210> SEQ ID NO 7
<211> LENGTH: 214
<212> TYPE: PRT
<213> ORGANISM: Artificial
<220> FEATURE:
<223> OTHER INFORMATION: Ranibizumab light chain variable domain

<400> SEQUENCE: 7

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 231
<212> TYPE: PRT
<213> ORGANISM: Artificial
<220> FEATURE:
<223> OTHER INFORMATION: Ranibizumab heavy chain variable domain

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80
```

```
Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230

<210> SEQ ID NO 9
<211> LENGTH: 22
<212> TYPE: PRT
<213> ORGANISM: Artificial
<220> FEATURE:
<223> OTHER INFORMATION: Signal peptide

<400> SEQUENCE: 9

Met Glu Phe Phe Lys Lys Thr Ala Leu Ala Ala Leu Val Met Gly Phe
1               5                   10                  15

Ser Gly Ala Ala Leu Ala
            20

<210> SEQ ID NO 10
<211> LENGTH: 22
<212> TYPE: PRT
<213> ORGANISM: Artificial
<220> FEATURE:
<223> OTHER INFORMATION: Signal peptide

<400> SEQUENCE: 10

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 11
<211> LENGTH: 17
<212> TYPE: DNA
<213> ORGANISM: Human

<400> SEQUENCE: 11
aaataaaata cgaaatg                                                  17

<210> SEQ ID NO 12
<211> LENGTH: 431
<212> TYPE: PRT
<213> ORGANISM: Artificial
<220> FEATURE:
<223> OTHER INFORMATION: Aflibercept
```

<400> SEQUENCE: 12

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
```

405                 410                 415
Leu His Asn His Tyr Thr Gln Lys Ser Leu Ser Leu Ser Pro Gly
            420                 425                 430

<210> SEQ ID NO 13
<211> LENGTH: 206
<212> TYPE: PRT
<213> ORGANISM: Human

<400> SEQUENCE: 13

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Tyr Val Gly Ala Arg
    130                 135                 140

Cys Cys Leu Met Pro Trp Ser Leu Pro Gly Pro His Pro Cys Gly Pro
145                 150                 155                 160

Cys Ser Glu Arg Arg Lys His Leu Phe Val Gln Asp Pro Gln Thr Cys
                165                 170                 175

Lys Cys Ser Cys Lys Asn Thr Asp Ser Arg Cys Lys Ala Arg Gln Leu
            180                 185                 190

Glu Leu Asn Glu Arg Thr Cys Arg Cys Asp Lys Pro Arg Arg
        195                 200                 205

<210> SEQ ID NO 14
<211> LENGTH: 186
<212> TYPE: PRT
<213> ORGANISM: Human

<400> SEQUENCE: 14

Pro Val Ser Gln Pro Asp Ala Pro Gly His Gln Arg Lys Val Val Ser
1               5                   10                  15

Trp Ile Asp Val Tyr Thr Arg Ala Thr Cys Gln Pro Arg Glu Val Val
            20                  25                  30

Val Pro Leu Thr Val Glu Leu Met Gly Thr Val Ala Lys Gln Leu Val
            35                  40                  45

Pro Ser Cys Val Thr Val Gln Arg Cys Gly Gly Cys Cys Pro Asp Asp
    50                  55                  60

Gly Leu Glu Cys Val Pro Thr Gly Gln His Gln Val Arg Met Gln Ile
65                  70                  75                  80

Leu Met Ile Arg Tyr Pro Ser Ser Gln Leu Gly Glu Met Ser Leu Glu
                85                  90                  95

Glu His Ser Gln Cys Glu Cys Arg Pro Lys Lys Lys Asp Ser Ala Val

```
            100                 105                 110
Lys Pro Asp Arg Ala Thr Pro His His Arg Pro Gln Pro Arg Ser
            115                 120                 125

Val Pro Gly Trp Asp Ser Ala Pro Gly Ala Pro Ser Pro Ala Asp Ile
            130                 135                 140

Thr His Pro Thr Pro Ala Pro Gly Pro Ser Ala His Ala Ala Pro Ser
145                 150                 155                 160

Thr Thr Ser Ala Leu Thr Pro Gly Pro Ala Ala Ala Ala Asp Ala
                    165                 170                 175

Ala Ala Ser Ser Val Ala Lys Gly Gly Ala
            180                 185

<210> SEQ ID NO 15
<211> LENGTH: 116
<212> TYPE: PRT
<213> ORGANISM: Human

<400> SEQUENCE: 15

Ala His Tyr Asn Thr Glu Ile Leu Lys Ser Ile Asp Asn Glu Trp Arg
1               5                   10                  15

Lys Thr Gln Cys Met Pro Arg Glu Val Cys Ile Asp Val Gly Lys Glu
                20                  25                  30

Phe Gly Val Ala Thr Asn Thr Phe Phe Lys Pro Pro Cys Val Ser Val
            35                  40                  45

Tyr Arg Cys Gly Gly Cys Cys Asn Ser Glu Gly Leu Gln Cys Met Asn
    50                  55                  60

Thr Ser Thr Ser Tyr Leu Ser Lys Thr Leu Phe Glu Ile Thr Val Pro
65                  70                  75                  80

Leu Ser Gln Gly Pro Lys Pro Val Thr Ile Ser Phe Ala Asn His Thr
                85                  90                  95

Ser Cys Arg Cys Met Ser Lys Leu Asp Val Tyr Arg Gln Val His Ser
            100                 105                 110

Ile Ile Arg Arg
            115

<210> SEQ ID NO 16
<211> LENGTH: 117
<212> TYPE: PRT
<213> ORGANISM: Human

<400> SEQUENCE: 16

Phe Ala Ala Thr Phe Tyr Asp Ile Glu Thr Leu Lys Val Ile Asp Glu
1               5                   10                  15

Glu Trp Gln Arg Thr Gln Cys Ser Pro Arg Glu Thr Cys Val Glu Val
                20                  25                  30

Ala Ser Glu Leu Gly Lys Ser Thr Asn Thr Phe Phe Lys Pro Pro Cys
            35                  40                  45

Val Asn Val Phe Arg Cys Gly Gly Cys Cys Asn Glu Glu Ser Leu Ile
    50                  55                  60

Cys Met Asn Thr Ser Thr Ser Tyr Ile Ser Lys Gln Leu Phe Glu Ile
65                  70                  75                  80

Ser Val Pro Leu Thr Ser Val Pro Glu Leu Val Pro Val Lys Val Ala
                85                  90                  95

Asn His Thr Gly Cys Lys Cys Leu Pro Thr Ala Pro Arg His Pro Tyr
            100                 105                 110

Ser Ile Ile Arg Arg
```

-continued

```
              115

<210> SEQ ID NO 17
<211> LENGTH: 687
<212> TYPE: PRT
<213> ORGANISM: Human

<400> SEQUENCE: 17

Met Val Ser Tyr Trp Asp Thr Gly Val Leu Leu Cys Ala Leu Leu Ser
1               5                   10                  15

Cys Leu Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365
```

```
Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685

<210> SEQ ID NO 18
<211> LENGTH: 2064
<212> TYPE: DNA
<213> ORGANISM: Human

<400> SEQUENCE: 18
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca gggggaagc agcccataaa      180 tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
```

```
gaatctgcaa tctatatatt tattagtgat acaggtagac ctttcgtaga gatgtacagt      420
gaaatccccg aaattataca catgactgaa ggaagggagc tcgtcattcc ctgccgggtt      480
acgtcaccta acatcactgt tactttaaaa agtttccac ttgacactt gatccctgat       540 ggaaaacgca taatctggga cagtagaaag ggcttcatca tatcaaatgc aacgtacaaa      600
gaaatagggc ttctgacctg tgaagcaaca gtcaatgggc atttgtataa gacaaactat     660
ctcacacatc gacaaaccaa tacaatcata gatgtccaaa taagcacacc acgcccagtc      720
aaattactta gaggccatac tcttgtcctc aattgtactg ctaccactcc cttgaacacg      780
agagttcaaa tgacctggag ttaccctgat gaaaaaaata gagagcttc cgtaaggcga       840 cgaattgacc aaagcaattc ccatgccaac atattctaca gtgttcttac tattgacaaa      900
atgcagaaca aagacaaagg actttatact tgtcgtgtaa ggagtggacc atcattcaaa      960
tctgttaaca cctcagtgca tatatatgat aaagcattca tcactgtgaa acatcgaaaa     1020
cagcaggtgc ttgaaaccgt agctggcaag cggtcttacc ggctctctat gaaagtgaag     1080
gcatttccct cgccggaagt tgtatggtta aaagatgggt tacctgcgac tgagaaatct     1140
gctcgctatt tgactcgtgg ctactcgtta attatcaagg acgtaactga agaggatgca     1200
gggaattata caatcttgct gagcataaaa cagtcaaatg tgtttaaaaa cctcactgcc     1260
actctaattg tcaatgtgaa accccagatt tacgaaaagg ccgtgtcatc gtttccagac     1320
ccggctctct acccactggg cagcagacaa atcctgactt gtaccgcata tggtatccct     1380
caacctacaa tcaagtggtt ctggcacccc tgtaaccata atcattccga agcaaggtgt     1440
gacttttgtt ccaataatga agagtccttt atcctggatg ctgacagcaa catgggaaac     1500
agaattgaga gcatcactca gcgcatggca ataatagaag gaagaataa gatggctagc      1560 accttggttg tggctgactc tagaatttct ggaatctaca tttgcatagc ttccaataaa     1620
gttgggactg tgggaagaaa cataagcttt tatatcacag atgtgccaaa tgggtttcat     1680
gttaacttgg aaaaatgcc gacggaagga gaggacctga actgtcttg cacagttaac      1740 aagttcttat acagagacgt tacttggatt ttactgcgga cagttaataa cagaacaatg     1800
cactacagta ttagcaagca aaaatggcc atcactaagg agcactccat cactcttaat      1860
cttaccatca tgaatgtttc cctgcaagat tcaggcacct atgcctgcag agccaggaat     1920
gtatacacag gggaagaaat cctccagaag aaagaaatta caatcagagg tgagcactgc     1980
aacaaaaagg ctgttttctc tcggatctcc aaatttaaaa gcacaaggaa tgattgtacc     2040
acacaaagta atgtaaaaca ttaa                                            2064
```

<210> SEQ ID NO 19
<211> LENGTH: 733
<212> TYPE: PRT
<213> ORGANISM: Human

<400> SEQUENCE: 19

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

-continued

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
    355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
    435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser 485                 490                 495
Asn Met Gly Asn Arg Ile Glu Ser Ile Thr Gln Arg Met Ala Ile Ile
                500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
        530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
            660                 665                 670
Ala Ile Ser Ser Ser Thr Thr Leu Asp Cys His Ala Asn Gly Val Pro
        675                 680                 685
Glu Pro Gln Ile Thr Trp Phe Lys Asn Asn His Lys Ile Gln Gln Glu
    690                 695                 700
Pro Glu Leu Tyr Thr Ser Thr Ser Pro Ser Ser Ser Ser Ser Ser Pro
705                 710                 715                 720
Leu Ser Ser Ser Ser Ser Ser Ser Ser Ser Ser Ser
                725                 730

<210> SEQ ID NO 20
<211> LENGTH: 2202
<212> TYPE: DNA
<213> ORGANISM: Human

<400> SEQUENCE: 20
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca ggggggaagc agcccataaa     180
tggtctttgc ctgaaatggt gagtaaggaa agcgaaaggc tgagcataac taatctgcc      240 tgtggaagaa atggcaaaca attctgcagt acttaaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ctttcgtaga gatgtacagt     420
gaaatccccg aaattataca catgactgaa ggaagggagc tcgtcattcc ctgccgggtt     480
acgtcaccta acatcactgt tactttaaaa agtttccac ttgacacttt gatccctgat      540
ggaaaacgca taatctggga cagtagaaag ggcttcatca tatcaaatgc aacgtacaaa     600
gaaatagggc ttctgacctg tgaagcaaca gtcaatgggc atttgtataa gacaaactat     660
ctcacacatc gacaaaccaa tacaatcata gatgtccaaa taagcacacc acgcccagtc     720

```
aaattactta gaggccatac tcttgtcctc aattgtactg ctaccactcc cttgaacacg      780
agagttcaaa tgacctggag ttaccctgat gaaaaaaata agagagcttc cgtaaggcga      840
cgaattgacc aaagcaattc ccatgccaac atattctaca gtgttcttac tattgacaaa      900
atgcagaaca agacaaagg actttatact tgtcgtgtaa ggagtggacc atcattcaaa      960
tctgttaaca cctcagtgca tatatatgat aaagcattca tcactgtgaa acatcgaaaa     1020
cagcaggtgc ttgaaaccgt agctggcaag cggtcttacc ggctctctat gaaagtgaag     1080
gcatttccct cgccggaagt tgtatggtta aaagatgggt tacctgcgac tgagaaatct     1140
gctcgctatt tgactcgtgg ctactcgtta attatcaagg acgtaactga agaggatgca     1200
gggaattata caatcttgct gagcataaaa cagtcaaatg tgtttaaaaa cctcactgcc     1260
actctaattg tcaatgtgaa accccagatt tacgaaaagg ccgtgtcatc gtttccagac     1320
ccggctctct acccactggg cagcagacaa atcctgactt gtaccgcata tggtatccct     1380
caacctacaa tcaagtggtt ctggcacccc tgtaaccata atcattccga agcaaggtgt     1440
gactttgtt ccaataatga agagtccttt atcctggatg ctgacagcaa catgggaaac     1500
agaattgaga gcatcactca gcgcatggca ataatagaag gaaagaataa gatggctagc     1560
accttggttg tggctgactc tagaatttct ggaatctaca tttgcatagc ttccaataaa     1620
gttgggactg tgggaagaaa cataagcttt tatatcacag atgtgccaaa tgggtttcat     1680
gttaacttgg aaaaaatgcc gacggaagga gaggacctga actgtcttg cacagttaac     1740
aagttcttat acagagacgt tacttggatt ttactgcgga cagttaataa cagaacaatg     1800
cactacagta ttagcaagca aaaaatggcc atcactaagg agcactccat cactcttaat     1860
cttaccatca tgaatgtttc cctgcaagat tcaggcacct atgcctgcag agccaggaat     1920
gtatacacag gggaagaaat cctccagaag aaagaaatta caatcagaga tcaggaagca     1980
ccatacctcc tgcgaaacct cagtgatcac acagtggcca tcagcagttc caccacttta     2040
gactgtcatg ctaatggtgt ccccgagcct cagatcactt ggtttaaaaa caaccacaaa     2100
atacaacaag agcctgaact gtatacatca acgtcaccat cgtcatcgtc atcatcacca     2160
ttgtcatcat catcatcatc gtcatcatca tcatcatcat ag                        2202
```

<210> SEQ ID NO 21
<211> LENGTH: 541
<212> TYPE: PRT
<213> ORGANISM: Human

<400> SEQUENCE: 21

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110
```

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
            130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
            245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
            290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
            450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Leu Pro Pro Ala Asn Ser Ser Phe Met Leu Pro
            515                 520                 525

Pro Thr Ser Phe Ser Ser Asn Tyr Phe His Phe Leu Pro

<210> SEQ ID NO 22
<211> LENGTH: 1626
<212> TYPE: DNA
<213> ORGANISM: Human

<400> SEQUENCE: 22

```
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca gggggaagc agcccataaa      180
tggtctttgc ctgaaatggt gagtaaggaa agcgaaaggc tgagcataac taaatctgcc    240
tgtggaagaa atggcaaaca attctgcagt actttaacct tgaacacagc tcaagcaaac    300
cacactggct tctacagctg caaatatcta gctgtaccta cttcaaagaa gaaggaaaca    360
gaatctgcaa tctatatatt tattagtgat acaggtagac ctttcgtaga gatgtacagt    420
gaaatccccg aaattataca catgactgaa ggaagggagc tcgtcattcc ctgccgggtt    480
acgtcaccta acatcactgt tactttaaaa agtttccac ttgacacttt gatccctgat     540
ggaaaacgca taatctggga cagtagaaag ggcttcatca tatcaaatgc aacgtacaaa    600
gaaatagggc ttctgacctg tgaagcaaca gtcaatgggc atttgtataa gacaaactat    660
ctcacacatc gacaaaccaa tacaatcata gatgtccaaa taagcacacc acgcccagtc    720
aaattactta gaggccatac tcttgtcctc aattgtactg ctaccactcc cttgaacacg    780
agagttcaaa tgacctggag ttaccctgat gaaaaaaata gagagcttc cgtaaggcga    840
cgaattgacc aaagcaattc ccatgccaac atattctaca gtgttcttac tattgacaaa    900
atgcagaaca agacaaagg actttatact tgtcgtgtaa ggagtggacc atcattcaaa    960
tctgttaaca cctcagtgca tatatatgat aaagcattca tcactgtgaa acatcgaaaa   1020
cagcaggtgc ttgaaaccgt agctggcaag cggtcttacc ggctctctat gaaagtgaag   1080
gcatttcct cgccggaagt tgtatggtta aaagatgggt acctgcgac tgagaaatct    1140
gctcgctatt tgactcgtgg ctactcgtta attatcaagg acgtaactga agaggatgca   1200
gggaattata caatcttgct gagcataaaa cagtcaaatg tgtttaaaaa cctcactgcc   1260
actctaattg tcaatgtgaa accccagatt tacgaaaagg ccgtgtcatc gtttccagac   1320
ccggctctct acccactggg cagcagacaa atcctgactt gtaccgcata tggtatccct   1380
caacctacaa tcaagtggtt ctggcacccc tgtaaccata atcattccga agcaaggtgt   1440
gactttttgtt ccaataatga agagtccttt atcctggatg ctgacagcaa catgggaaac   1500
agaattgaga gcatcactca gcgcatggca ataatagaag gaagaataa gcttccacca   1560
gctaacagtt ctttcatgtt gccacctaca agcttctctt ccaactactt ccatttcctt   1620
ccgtga                                                               1626
```

<210> SEQ ID NO 23
<211> LENGTH: 732
<212> TYPE: PRT
<213> ORGANISM: Human

<400> SEQUENCE: 23

```
Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30
```

-continued

His Lys Trp Ser Leu Pro Glu Met Val Ser Lys Glu Ser Glu Arg Leu
            35                  40                  45

Ser Ile Thr Lys Ser Ala Cys Gly Arg Asn Gly Lys Gln Phe Cys Ser
        50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Glu Thr Glu Ser
                85                  90                  95

Ala Ile Tyr Ile Phe Ile Ser Asp Thr Gly Arg Pro Phe Val Glu Met
                100                 105                 110

Tyr Ser Glu Ile Pro Glu Ile Ile His Met Thr Glu Gly Arg Glu Leu
            115                 120                 125

Val Ile Pro Cys Arg Val Thr Ser Pro Asn Ile Thr Val Thr Leu Lys
        130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Gln Ile
        195                 200                 205

Ser Thr Pro Arg Pro Val Lys Leu Leu Arg Gly His Thr Leu Val Leu
210                 215                 220

Asn Cys Thr Ala Thr Thr Pro Leu Asn Thr Arg Val Gln Met Thr Trp
225                 230                 235                 240

Ser Tyr Pro Asp Glu Lys Asn Lys Arg Ala Ser Val Arg Arg Ile
                245                 250                 255

Asp Gln Ser Asn Ser His Ala Asn Ile Phe Tyr Ser Val Leu Thr Ile
                260                 265                 270

Asp Lys Met Gln Asn Lys Asp Lys Gly Leu Tyr Thr Cys Arg Val Arg
            275                 280                 285

Ser Gly Pro Ser Phe Lys Ser Val Asn Thr Ser Val His Ile Tyr Asp
            290                 295                 300

Lys Ala Phe Ile Thr Val Lys His Arg Lys Gln Gln Val Leu Glu Thr
305                 310                 315                 320

Val Ala Gly Lys Arg Ser Tyr Arg Leu Ser Met Lys Val Lys Ala Phe
                325                 330                 335

Pro Ser Pro Glu Val Val Trp Leu Lys Asp Gly Leu Pro Ala Thr Glu
            340                 345                 350

Lys Ser Ala Arg Tyr Leu Thr Arg Gly Tyr Ser Leu Ile Ile Lys Asp
            355                 360                 365

Val Thr Glu Glu Asp Ala Gly Asn Tyr Thr Ile Leu Leu Ser Ile Lys
370                 375                 380

Gln Ser Asn Val Phe Lys Asn Leu Thr Ala Thr Leu Ile Val Asn Val
385                 390                 395                 400

Lys Pro Gln Ile Tyr Glu Lys Ala Val Ser Ser Phe Pro Asp Pro Ala
            405                 410                 415

Leu Tyr Pro Leu Gly Ser Arg Gln Ile Leu Thr Cys Thr Ala Tyr Gly
                420                 425                 430

Ile Pro Gln Pro Thr Ile Lys Trp Phe Trp His Pro Cys Asn His Asn
            435                 440                 445

```
His Ser Glu Ala Arg Cys Asp Phe Cys Ser Asn Asn Glu Glu Ser Phe
            450                 455                 460
Ile Leu Asp Ala Asp Ser Asn Met Gly Asn Arg Ile Glu Ser Ile Thr
465                 470                 475                 480
Gln Arg Met Ala Ile Ile Glu Gly Lys Asn Lys Met Ala Ser Thr Leu
            485                 490                 495
Val Val Ala Asp Ser Arg Ile Ser Gly Ile Tyr Ile Cys Ile Ala Ser
            500                 505                 510
Asn Lys Val Gly Thr Val Gly Arg Asn Ile Ser Phe Tyr Ile Thr Asp
            515                 520                 525
Val Pro Asn Gly Phe His Val Asn Leu Glu Lys Met Pro Thr Glu Gly
530                 535                 540
Glu Asp Leu Lys Leu Ser Cys Thr Val Asn Lys Phe Leu Tyr Arg Asp
545                 550                 555                 560
Val Thr Trp Ile Leu Leu Arg Thr Val Asn Asn Arg Thr Met His Tyr
            565                 570                 575
Ser Ile Ser Lys Gln Lys Met Ala Ile Thr Lys Glu His Ser Ile Thr
            580                 585                 590
Leu Asn Leu Thr Ile Met Asn Val Ser Leu Gln Asp Ser Gly Thr Tyr
            595                 600                 605
Ala Cys Arg Ala Arg Asn Val Tyr Thr Gly Glu Glu Ile Leu Gln Lys
610                 615                 620
Lys Glu Ile Thr Ile Arg Asp Gln Glu Ala Pro Tyr Leu Leu Arg Asn
625                 630                 635                 640
Leu Ser Asp His Thr Val Ala Ile Ser Ser Thr Thr Leu Asp Cys
            645                 650                 655
His Ala Asn Gly Val Pro Glu Pro Gln Ile Thr Trp Phe Lys Asn Asn
            660                 665                 670
His Lys Ile Gln Gln Glu Pro Gly Ile Ile Leu Gly Pro Gly Ser Ser
            675                 680                 685
Thr Leu Phe Ile Glu Arg Val Thr Glu Glu Asp Glu Gly Val Tyr His
            690                 695                 700
Cys Lys Ala Thr Asn Gln Lys Gly Ser Val Glu Ser Ser Ala Tyr Leu
705                 710                 715                 720
Thr Val Gln Gly Thr Ser Asp Lys Ser Asn Leu Glu
            725                 730

<210> SEQ ID NO 24
<211> LENGTH: 737
<212> TYPE: PRT
<213> ORGANISM: Mouse

<400> SEQUENCE: 24

Tyr Gly Ser Gly Ser Lys Leu Lys Val Pro Glu Leu Ser Leu Lys Gly
1               5                   10                  15
Thr Gln His Val Met Gln Ala Gly Gln Thr Leu Phe Leu Lys Cys Arg
            20                  25                  30
Gly Glu Ala Ala His Ser Trp Ser Leu Pro Thr Thr Val Ser Gln Glu
            35                  40                  45
Asp Lys Arg Leu Ser Ile Thr Pro Pro Ser Ala Cys Gly Arg Asp Asn
            50                  55                  60
Arg Gln Phe Cys Ser Thr Leu Thr Leu Asp Thr Ala Gln Ala Asn His
65                  70                  75                  80
Thr Gly Leu Tyr Thr Cys Arg Tyr Leu Pro Thr Ser Thr Ser Lys Lys
            85                  90                  95
```

```
Lys Lys Ala Glu Ser Ser Ile Tyr Ile Phe Val Ser Asp Ala Gly Ser
            100                 105                 110

Pro Phe Ile Glu Met His Thr Asp Ile Pro Lys Leu Val His Met Thr
            115                 120                 125

Glu Gly Arg Gln Leu Ile Ile Pro Cys Arg Val Thr Ser Pro Asn Val
            130                 135                 140

Thr Val Thr Leu Lys Lys Phe Pro Phe Asp Thr Leu Thr Pro Asp Gly
145                 150                 155                 160

Gln Arg Ile Thr Trp Asp Ser Arg Arg Gly Phe Ile Ile Ala Asn Ala
                165                 170                 175

Thr Tyr Lys Glu Ile Gly Leu Leu Asn Cys Glu Ala Thr Val Asn Gly
            180                 185                 190

His Leu Tyr Gln Thr Asn Tyr Leu Thr His Arg Gln Thr Asn Thr Ile
            195                 200                 205

Leu Asp Val Gln Ile Arg Pro Pro Ser Pro Val Arg Leu Leu His Gly
210                 215                 220

Gln Thr Leu Val Leu Asn Cys Thr Ala Thr Thr Glu Leu Asn Thr Arg
225                 230                 235                 240

Val Gln Met Ser Trp Asn Tyr Pro Gly Lys Ala Thr Lys Arg Ala Ser
                245                 250                 255

Ile Arg Gln Arg Ile Asp Arg Ser His Ser His Asn Asn Val Phe His
            260                 265                 270

Ser Val Leu Lys Ile Asn Asn Val Glu Ser Arg Asp Lys Gly Leu Tyr
            275                 280                 285

Thr Cys Arg Val Lys Ser Gly Ser Ser Phe Gln Ser Phe Asn Thr Ser
            290                 295                 300

Val His Val Tyr Glu Lys Gly Phe Ile Ser Val Lys His Arg Lys Gln
305                 310                 315                 320

Pro Val Gln Glu Thr Thr Ala Gly Arg Arg Ser Tyr Arg Leu Ser Met
                325                 330                 335

Lys Val Lys Ala Phe Pro Ser Pro Glu Ile Val Trp Leu Lys Asp Gly
            340                 345                 350

Ser Pro Ala Thr Leu Lys Ser Ala Arg Tyr Leu Val His Gly Tyr Ser
            355                 360                 365

Leu Ile Ile Lys Asp Val Thr Thr Glu Asp Ala Gly Asp Tyr Thr Ile
            370                 375                 380

Leu Leu Gly Ile Lys Gln Ser Arg Leu Phe Lys Asn Leu Thr Ala Thr
385                 390                 395                 400

Leu Ile Val Asn Val Lys Pro Gln Ile Tyr Glu Lys Ser Val Ser Ser
                405                 410                 415

Leu Pro Ser Pro Pro Leu Tyr Pro Leu Gly Ser Arg Gln Val Leu Thr
            420                 425                 430

Cys Thr Val Tyr Gly Ile Pro Arg Pro Thr Ile Thr Trp Leu Trp His
            435                 440                 445

Pro Cys His His Asn His Ser Lys Glu Arg Tyr Asp Phe Cys Thr Glu
            450                 455                 460

Asn Glu Glu Ser Phe Ile Leu Asp Pro Ser Ser Asn Leu Gly Asn Arg
465                 470                 475                 480

Ile Glu Ser Ile Ser Gln Arg Met Thr Val Ile Glu Gly Thr Asn Lys
                485                 490                 495

Thr Val Ser Thr Leu Val Val Ala Asp Ser Gln Thr Pro Gly Ile Tyr
            500                 505                 510
```

Ser Cys Arg Ala Phe Asn Lys Ile Gly Thr Val Glu Arg Asn Ile Lys
            515                 520                 525

Phe Tyr Val Thr Asp Val Pro Asn Gly Phe His Val Ser Leu Glu Lys
    530                 535                 540

Met Pro Ala Glu Gly Glu Asp Leu Lys Leu Ser Cys Val Val Asn Lys
545                 550                 555                 560

Phe Leu Tyr Arg Asp Ile Thr Trp Ile Leu Leu Arg Thr Val Asn Asn
                565                 570                 575

Arg Thr Met His His Ser Ile Ser Lys Gln Lys Met Ala Thr Thr Gln
                580                 585                 590

Asp Tyr Ser Ile Thr Leu Asn Leu Val Ile Lys Asn Val Ser Leu Glu
                595                 600                 605

Asp Ser Gly Thr Tyr Ala Cys Arg Ala Arg Asn Ile Tyr Thr Gly Glu
            610                 615                 620

Asp Ile Leu Arg Lys Thr Glu Val Leu Val Arg Asp Ser Glu Ala Pro
625                 630                 635                 640

His Leu Leu Gln Asn Leu Ser Asp Tyr Glu Val Ser Ile Ser Gly Ser
                645                 650                 655

Thr Thr Leu Asp Cys Gln Ala Arg Gly Val Pro Ala Pro Gln Ile Thr
                660                 665                 670

Trp Phe Lys Asn Asn His Lys Ile Gln Gln Glu Pro Gly Ile Ile Leu
                675                 680                 685

Gly Pro Gly Asn Ser Thr Leu Phe Ile Glu Arg Val Thr Glu Glu Asp
            690                 695                 700

Glu Gly Val Tyr Arg Cys Arg Ala Thr Asn Gln Lys Gly Ala Val Glu
705                 710                 715                 720

Ser Ala Ala Tyr Leu Thr Val Gln Gly Thr Ser Asp Lys Ser Asn Leu
                725                 730                 735

Glu

<210> SEQ ID NO 25
<211> LENGTH: 736
<212> TYPE: PRT
<213> ORGANISM: Rat

<400> SEQUENCE: 25

Tyr Cys Ser Gly Ser Lys Leu Lys Gly Pro Glu Leu Ser Leu Lys Gly
1               5                   10                  15

Thr Gln His Val Met Gln Ala Gly Gln Thr Leu Phe Leu Lys Cys Arg
                20                  25                  30

Gly Glu Ala Ala His Ser Trp Ser Leu Pro Thr Thr Val Ser Gln Glu
            35                  40                  45

Asp Lys Lys Leu Ser Val Thr Arg Ser Ala Cys Gly Arg Asn Asn Arg
        50                  55                  60

Gln Phe Cys Ser Thr Leu Thr Leu Asn Met Ala Gln Ala Asn His Thr
65                  70                  75                  80

Gly Leu Tyr Ser Cys Arg Tyr Leu Pro Lys Ser Thr Ser Lys Glu Lys
                85                  90                  95

Lys Met Glu Ser Ala Ile Tyr Ile Phe Val Ser Asp Ala Gly Ser Pro
                100                 105                 110

Phe Ile Glu Met His Ser Asp Ile Pro Lys Leu Val His Met Thr Glu
            115                 120                 125

Gly Arg Glu Leu Ile Ile Pro Cys Arg Val Thr Ser Pro Asn Ile Thr
        130                 135                 140

```
Val Thr Leu Lys Lys Phe Pro Phe Asp Ala Leu Thr Pro Asp Gly Gln
145                 150                 155                 160

Arg Ile Ala Trp Asp Ser Arg Gly Phe Ile Ile Ala Asn Ala Thr
            165                 170                 175

Tyr Lys Glu Ile Gly Leu Leu Thr Cys Glu Ala Thr Val Asn Gly His
                180                 185                 190

Leu Tyr Gln Thr Ser Tyr Leu Thr His Arg Gln Thr Asn Thr Ile Leu
            195                 200                 205

Asp Val Gln Ile Ser Pro Pro Ser Pro Val Arg Phe Leu Arg Gly Gln
            210                 215                 220

Thr Leu Val Leu Asn Cys Thr Val Thr Thr Asp Leu Asn Thr Arg Val
225                 230                 235                 240

Gln Met Ser Trp Asn Tyr Pro Gly Lys Ala Thr Lys Arg Ala Ser Ile
                245                 250                 255

Arg Gln Arg Ile Asp Gln Ser Asn Pro His Ser Asn Val Phe His Ser
            260                 265                 270

Val Leu Lys Ile Asn Asn Val Glu Ser Arg Asp Lys Gly Leu Tyr Thr
            275                 280                 285

Cys Arg Val Lys Ser Gly Ser Ser Phe Arg Thr Phe Asn Thr Ser Val
    290                 295                 300

His Val Tyr Glu Lys Gly Phe Ile Ser Val Lys His Arg Lys Gln Gln
305                 310                 315                 320

Val Gln Glu Thr Ile Ala Gly Lys Arg Ser His Arg Leu Ser Met Lys
                325                 330                 335

Val Lys Ala Phe Pro Ser Pro Glu Val Val Trp Leu Lys Asp Gly Val
                340                 345                 350

Pro Ala Thr Glu Lys Ser Ala Arg Tyr Ser Val His Gly Tyr Ser Leu
            355                 360                 365

Ile Ile Lys Asp Val Thr Ala Glu Asp Ala Gly Asp Tyr Thr Ile Leu
    370                 375                 380

Leu Gly Ile Lys Gln Ser Lys Leu Phe Arg Asn Leu Thr Ala Thr Leu
385                 390                 395                 400

Ile Val Asn Val Lys Pro Gln Ile Tyr Glu Lys Ser Val Ser Ser Leu
                405                 410                 415

Pro Ser Pro Pro Leu Tyr Pro Leu Gly Ser Arg Gln Val Leu Thr Cys
            420                 425                 430

Thr Val Tyr Gly Ile Pro Gln Pro Thr Ile Lys Trp Leu Trp His Pro
        435                 440                 445

Cys His Tyr Asn His Ser Lys Glu Arg Asn Asp Phe Cys Phe Gly Ser
    450                 455                 460

Glu Glu Ser Phe Ile Leu Asp Ser Ser Ser Asn Ile Gly Asn Arg Ile
465                 470                 475                 480

Glu Gly Ile Thr Gln Arg Met Met Val Ile Glu Gly Thr Asn Lys Thr
                485                 490                 495

Val Ser Thr Leu Val Val Ala Asp Ser Arg Thr Pro Gly Ser Tyr Ser
            500                 505                 510

Cys Lys Ala Phe Asn Lys Ile Gly Thr Val Glu Arg Asp Ile Arg Phe
    515                 520                 525

Tyr Val Thr Asp Val Pro Asn Gly Phe His Val Ser Leu Glu Lys Ile
        530                 535                 540

Pro Thr Glu Gly Glu Asp Leu Lys Leu Ser Cys Val Val Ser Lys Phe
545                 550                 555                 560

Leu Tyr Arg Asp Ile Thr Trp Ile Leu Leu Arg Thr Val Asn Asn Arg
```

-continued

```
                565                 570                 575
Thr Met His His Ser Ile Ser Lys Gln Lys Met Ala Thr Thr Gln Asp
            580                 585                 590
Tyr Ser Ile Thr Leu Asn Leu Val Ile Lys Asn Val Ser Leu Glu Asp
            595                 600                 605
Ser Gly Thr Tyr Ala Cys Arg Ala Arg Asn Ile Tyr Thr Gly Glu Glu
            610                 615                 620
Ile Leu Arg Lys Thr Glu Val Leu Val Arg Asp Leu Glu Ala Pro Leu
625                 630                 635                 640
Leu Leu Gln Asn Leu Ser Asp His Glu Val Ser Ile Ser Gly Ser Thr
                645                 650                 655
Thr Leu Asp Cys Gln Ala Arg Gly Val Pro Ala Pro Gln Ile Thr Trp
            660                 665                 670
Phe Lys Asn Asn His Lys Ile Gln Gln Glu Pro Gly Ile Ile Leu Gly
            675                 680                 685
Pro Gly Asn Ser Thr Leu Phe Ile Glu Arg Val Thr Glu Glu Asp Glu
            690                 695                 700
Gly Val Tyr Arg Cys Arg Ala Thr Asn Gln Lys Gly Val Val Glu Ser
705                 710                 715                 720
Ser Ala Tyr Leu Thr Val Gln Gly Thr Ser Asp Lys Ser Asn Leu Glu
                725                 730                 735

<210> SEQ ID NO 26
<211> LENGTH: 745
<212> TYPE: PRT
<213> ORGANISM: Human

<400> SEQUENCE: 26

Ala Ser Val Gly Leu Pro Ser Val Ser Leu Asp Leu Pro Arg Leu Ser
1               5                   10                  15
Ile Gln Lys Asp Ile Leu Thr Ile Lys Ala Asn Thr Thr Leu Gln Ile
            20                  25                  30
Thr Cys Arg Gly Gln Arg Asp Leu Asp Trp Leu Trp Pro Asn Asn Gln
        35                  40                  45
Ser Gly Ser Glu Gln Arg Val Glu Val Thr Glu Cys Ser Asp Gly Leu
    50                  55                  60
Phe Cys Lys Thr Leu Thr Ile Pro Lys Val Ile Gly Asn Asp Thr Gly
65                  70                  75                  80
Ala Tyr Lys Cys Phe Tyr Arg Glu Thr Asp Leu Ala Ser Val Ile Tyr
                85                  90                  95
Val Tyr Val Gln Asp Tyr Arg Ser Pro Phe Ile Ala Ser Val Ser Asp
            100                 105                 110
Gln His Gly Val Val Tyr Ile Thr Glu Asn Lys Asn Lys Thr Val Val
        115                 120                 125
Ile Pro Cys Leu Gly Ser Ile Ser Asn Leu Asn Val Ser Leu Cys Ala
    130                 135                 140
Arg Tyr Pro Glu Lys Arg Phe Val Pro Asp Gly Asn Arg Ile Ser Trp
145                 150                 155                 160
Asp Ser Lys Lys Gly Phe Thr Ile Pro Ser Tyr Met Ile Ser Tyr Ala
                165                 170                 175
Gly Met Val Phe Cys Glu Ala Lys Ile Asn Asp Glu Ser Tyr Gln Ser
            180                 185                 190
Ile Met Tyr Ile Val Val Val Gly Tyr Arg Ile Tyr Asp Val Val
        195                 200                 205
```

-continued

Leu Ser Pro Ser His Gly Ile Glu Leu Ser Val Gly Glu Lys Leu Val
210                 215                 220

Leu Asn Cys Thr Ala Arg Thr Glu Leu Asn Val Gly Ile Asp Phe Asn
225                 230                 235                 240

Trp Glu Tyr Pro Ser Ser Lys His Gln His Lys Lys Leu Val Asn Arg
                245                 250                 255

Asp Leu Lys Thr Gln Ser Gly Ser Glu Met Lys Lys Phe Leu Ser Thr
            260                 265                 270

Leu Thr Ile Asp Gly Val Thr Arg Ser Asp Gln Gly Leu Tyr Thr Cys
        275                 280                 285

Ala Ala Ser Ser Gly Leu Met Thr Lys Lys Asn Ser Thr Phe Val Arg
290                 295                 300

Val His Glu Lys Pro Phe Val Ala Phe Gly Ser Gly Met Glu Ser Leu
305                 310                 315                 320

Val Glu Ala Thr Val Gly Glu Arg Val Arg Ile Pro Ala Lys Tyr Leu
                325                 330                 335

Gly Tyr Pro Pro Pro Glu Ile Lys Trp Tyr Lys Asn Gly Ile Pro Leu
                340                 345                 350

Glu Ser Asn His Thr Ile Lys Ala Gly His Val Leu Thr Ile Met Glu
                355                 360                 365

Val Ser Glu Arg Asp Thr Gly Asn Tyr Thr Val Ile Leu Thr Asn Pro
370                 375                 380

Ile Ser Lys Glu Lys Gln Ser His Val Val Ser Leu Val Val Tyr Val
385                 390                 395                 400

Pro Pro Gln Ile Gly Glu Lys Ser Leu Ile Ser Pro Val Asp Ser Tyr
                405                 410                 415

Gln Tyr Gly Thr Thr Gln Thr Leu Thr Cys Thr Val Tyr Ala Ile Pro
                420                 425                 430

Pro Pro His His Ile His Trp Tyr Trp Gln Leu Glu Glu Cys Ala
                435                 440                 445

Asn Glu Pro Ser Gln Ala Val Ser Val Thr Asn Pro Tyr Pro Cys Glu
450                 455                 460

Glu Trp Arg Ser Val Glu Asp Phe Gln Gly Gly Asn Lys Ile Glu Val
465                 470                 475                 480

Asn Lys Asn Gln Phe Ala Leu Ile Glu Gly Lys Asn Lys Thr Val Ser
                485                 490                 495

Thr Leu Val Ile Gln Ala Ala Asn Val Ser Ala Leu Tyr Lys Cys Glu
                500                 505                 510

Ala Val Asn Lys Val Gly Arg Gly Glu Arg Val Ile Ser Phe His Val
                515                 520                 525

Thr Arg Gly Pro Glu Ile Thr Leu Gln Pro Asp Met Gln Pro Thr Glu
530                 535                 540

Gln Glu Ser Val Ser Leu Trp Cys Thr Ala Asp Arg Ser Thr Phe Glu
545                 550                 555                 560

Asn Leu Thr Trp Tyr Lys Leu Gly Pro Gln Pro Leu Pro Ile His Val
                565                 570                 575

Gly Glu Leu Pro Thr Pro Val Cys Lys Asn Leu Asp Thr Leu Trp Lys
                580                 585                 590

Leu Asn Ala Thr Met Phe Ser Asn Ser Thr Asn Asp Ile Leu Ile Met
                595                 600                 605

Glu Leu Lys Asn Ala Ser Leu Gln Asp Gln Gly Asp Tyr Val Cys Leu
                610                 615                 620

Ala Gln Asp Arg Lys Thr Lys Lys Arg His Cys Val Val Arg Gln Leu

```
                625                 630                 635                 640
            Thr Val Leu Glu Arg Val Ala Pro Thr Ile Thr Gly Asn Leu Glu Asn
                                645                 650                 655

Gln Thr Thr Ser Ile Gly Glu Ser Ile Glu Val Ser Cys Thr Ala Ser
                            660                 665                 670

Gly Asn Pro Pro Gln Ile Met Trp Phe Lys Asp Asn Glu Thr Leu
                        675                 680                 685

Val Glu Asp Ser Gly Ile Val Leu Lys Asp Gly Asn Arg Asn Leu Thr
                        690                 695                 700

Ile Arg Arg Val Arg Lys Glu Asp Glu Gly Leu Tyr Thr Cys Gln Ala
            705                 710                 715                 720

Cys Ser Val Leu Gly Cys Ala Lys Val Glu Ala Phe Phe Ile Ile Glu
                            725                 730                 735

Gly Ala Gln Glu Lys Thr Asn Leu Glu
                        740                 745

<210> SEQ ID NO 27
<211> LENGTH: 743
<212> TYPE: PRT
<213> ORGANISM: Mouse

<400> SEQUENCE: 27

Ala Ser Val Gly Leu Pro Gly Asp Phe Leu His Pro Lys Leu Ser
1               5                   10                  15

Thr Gln Lys Asp Ile Leu Thr Ile Leu Ala Asn Thr Thr Leu Gln Ile
                20                  25                  30

Thr Cys Arg Gly Gln Arg Asp Leu Asp Trp Leu Trp Pro Asn Ala Gln
            35                  40                  45

Arg Asp Ser Glu Glu Arg Val Leu Val Thr Glu Cys Gly Gly Gly Asp
50                  55                  60

Ser Ile Phe Cys Lys Thr Leu Thr Ile Pro Arg Val Val Gly Asn Asp
65                  70                  75                  80

Thr Gly Ala Tyr Lys Cys Ser Tyr Arg Asp Val Asp Ile Ala Ser Thr
                85                  90                  95

Val Tyr Val Tyr Val Arg Asp Tyr Arg Ser Pro Phe Ile Ala Ser Val
                100                 105                 110

Ser Asp Gln His Gly Ile Val Tyr Ile Thr Glu Asn Lys Asn Lys Thr
            115                 120                 125

Val Val Ile Pro Cys Arg Gly Ser Ile Ser Asn Leu Asn Val Ser Leu
130                 135                 140

Cys Ala Arg Tyr Pro Glu Lys Arg Phe Val Pro Asp Gly Asn Arg Ile
145                 150                 155                 160

Ser Trp Asp Ser Glu Ile Gly Phe Thr Leu Pro Ser Tyr Met Ile Ser
                165                 170                 175

Tyr Ala Gly Met Val Phe Cys Glu Ala Lys Ile Asn Asp Glu Thr Tyr
                180                 185                 190

Gln Ser Ile Met Tyr Ile Val Val Val Gly Tyr Arg Ile Tyr Asp
            195                 200                 205

Val Ile Leu Ser Pro Pro His Glu Ile Glu Leu Ser Ala Gly Glu Lys
210                 215                 220

Leu Val Leu Asn Cys Thr Ala Arg Thr Glu Leu Asn Val Gly Leu Asp
225                 230                 235                 240

Phe Thr Trp His Ser Pro Pro Ser Lys Ser His His Lys Lys Ile Val
                245                 250                 255
```

```
Asn Arg Asp Val Lys Pro Phe Pro Gly Thr Val Ala Lys Met Phe Leu
            260                 265                 270

Ser Thr Leu Thr Ile Glu Ser Val Thr Lys Ser Asp Gln Gly Glu Tyr
            275                 280                 285

Thr Cys Val Ala Ser Ser Gly Arg Met Ile Lys Arg Asn Arg Thr Phe
        290                 295                 300

Val Arg Val His Thr Lys Pro Phe Ile Ala Phe Gly Ser Gly Met Lys
305                 310                 315                 320

Ser Leu Val Glu Ala Thr Val Gly Ser Gln Val Arg Ile Pro Val Lys
                325                 330                 335

Tyr Leu Ser Tyr Pro Ala Pro Asp Ile Lys Trp Tyr Arg Asn Gly Arg
            340                 345                 350

Pro Ile Glu Ser Asn Tyr Thr Met Ile Val Gly Asp Glu Leu Thr Ile
            355                 360                 365

Met Glu Val Thr Glu Arg Asp Ala Gly Asn Tyr Thr Val Ile Leu Thr
        370                 375                 380

Asn Pro Ile Ser Met Glu Lys Gln Ser His Met Val Ser Leu Val Val
385                 390                 395                 400

Asn Val Pro Pro Gln Ile Gly Glu Lys Ala Leu Ile Ser Pro Met Asp
                405                 410                 415

Ser Tyr Gln Tyr Gly Thr Met Gln Thr Leu Thr Cys Thr Val Tyr Ala
            420                 425                 430

Asn Pro Pro Leu His His Ile Gln Trp Tyr Trp Gln Leu Glu Glu Ala
            435                 440                 445

Cys Ser Tyr Arg Pro Gly Gln Thr Ser Pro Tyr Ala Cys Lys Glu Trp
450                 455                 460

Arg His Val Glu Asp Phe Gln Gly Gly Asn Lys Ile Glu Val Thr Lys
465                 470                 475                 480

Asn Gln Tyr Ala Leu Ile Glu Gly Lys Asn Lys Thr Val Ser Thr Leu
            485                 490                 495

Val Ile Gln Ala Ala Asn Val Ser Ala Leu Tyr Lys Cys Glu Ala Ile
            500                 505                 510

Asn Lys Ala Gly Arg Gly Glu Arg Val Ile Ser Phe His Val Ile Arg
            515                 520                 525

Gly Pro Glu Ile Thr Val Gln Pro Ala Ala Gln Pro Thr Glu Gln Glu
            530                 535                 540

Ser Val Ser Leu Leu Cys Thr Ala Asp Arg Asn Thr Phe Glu Asn Leu
545                 550                 555                 560

Thr Trp Tyr Lys Leu Gly Ser Gln Ala Thr Ser Val His Met Gly Glu
            565                 570                 575

Ser Leu Thr Pro Val Cys Lys Asn Leu Asp Ala Leu Trp Lys Leu Asn
            580                 585                 590

Gly Thr Met Phe Ser Asn Ser Thr Asn Asp Ile Leu Ile Val Ala Phe
            595                 600                 605

Gln Asn Ala Ser Leu Gln Asp Gln Gly Asp Tyr Val Cys Ser Ala Gln
            610                 615                 620

Asp Lys Lys Thr Lys Lys Arg His Cys Leu Val Lys Gln Leu Ile Ile
625                 630                 635                 640

Leu Glu Arg Met Ala Pro Met Ile Thr Gly Asn Leu Glu Asn Gln Thr
                645                 650                 655

Thr Thr Ile Gly Glu Thr Ile Glu Val Thr Cys Pro Ala Ser Gly Asn
            660                 665                 670

Pro Thr Pro His Ile Thr Trp Phe Lys Asp Asn Glu Thr Leu Val Glu
```

```
              675                 680                 685
Asp Ser Gly Ile Val Leu Arg Asp Gly Asn Arg Asn Leu Thr Ile Arg
    690                 695                 700

Arg Val Arg Lys Glu Asp Gly Gly Leu Tyr Thr Cys Gln Ala Cys Asn
705                 710                 715                 720

Val Leu Gly Cys Ala Arg Ala Glu Thr Leu Phe Ile Ile Glu Gly Ala
                725                 730                 735

Gln Glu Lys Thr Asn Leu Glu
            740

<210> SEQ ID NO 28
<211> LENGTH: 741
<212> TYPE: PRT
<213> ORGANISM: Rat

<400> SEQUENCE: 28

Ala Ser Val Gly Leu Pro Gly Asp Ser Leu His Pro Pro Lys Leu Ser
1               5                   10                  15

Thr Gln Lys Asp Ile Leu Thr Ile Leu Ala Asn Thr Thr Leu Gln Ile
            20                  25                  30

Thr Cys Arg Gly Gln Arg Asp Leu Asp Trp Leu Trp Pro Asn Thr Pro
        35                  40                  45

Arg Asp Ser Glu Glu Arg Val Leu Val Thr Glu Cys Gly Asp Ser Ile
50                  55                  60

Phe Cys Lys Thr Leu Thr Val Pro Arg Val Val Gly Asn Asp Thr Gly
65                  70                  75                  80

Ala Tyr Lys Cys Phe Tyr Arg Asp Thr Asp Val Ser Ser Ile Val Tyr
                85                  90                  95

Val Tyr Val Gln Asp His Arg Ser Pro Phe Ile Ala Ser Val Ser Asp
            100                 105                 110

Glu His Gly Ile Val Tyr Ile Thr Glu Asn Lys Asn Lys Thr Val Val
        115                 120                 125

Ile Pro Cys Arg Gly Ser Ile Ser Asn Leu Asn Val Ser Leu Cys Ala
130                 135                 140

Arg Tyr Pro Glu Lys Arg Phe Val Pro Asp Gly Asn Arg Ile Ser Trp
145                 150                 155                 160

Asp Ser Glu Lys Gly Phe Thr Ile Pro Ser Tyr Met Ile Ser Tyr Ala
                165                 170                 175

Gly Met Val Phe Cys Glu Ala Lys Ile Asn Asp Glu Thr Tyr Gln Ser
            180                 185                 190

Ile Met Tyr Ile Val Leu Val Gly Tyr Arg Ile Tyr Asp Val Val
        195                 200                 205

Leu Ser Pro Pro His Glu Ile Glu Leu Ser Ala Gly Glu Lys Leu Val
210                 215                 220

Leu Asn Cys Thr Ala Arg Thr Glu Leu Asn Val Gly Leu Asp Phe Ser
225                 230                 235                 240

Trp Gln Phe Pro Ser Ser Lys His Gln His Lys Lys Ile Val Asn Arg
                245                 250                 255

Asp Val Lys Ser Leu Pro Gly Thr Val Ala Lys Met Phe Leu Ser Thr
            260                 265                 270

Leu Thr Ile Asp Ser Val Thr Lys Ser Asp Gln Gly Glu Tyr Thr Cys
        275                 280                 285

Thr Ala Tyr Ser Gly Leu Met Thr Lys Lys Asn Lys Thr Phe Val Arg
290                 295                 300
```

```
Val His Thr Lys Pro Phe Ile Ala Phe Gly Ser Gly Met Lys Ser Leu
305                 310                 315                 320

Val Glu Ala Thr Val Gly Ser Gln Val Arg Ile Pro Val Lys Tyr Leu
                325                 330                 335

Ser Tyr Pro Ala Pro Asp Ile Lys Trp Tyr Arg Asn Gly Arg Pro Ile
            340                 345                 350

Glu Ser Asn Tyr Thr Met Ile Val Gly Asp Glu Leu Thr Ile Met Glu
        355                 360                 365

Val Ser Glu Arg Asp Ala Gly Asn Tyr Thr Val Ile Leu Thr Asn Pro
    370                 375                 380

Ile Ser Met Glu Lys Gln Ser His Met Val Ser Leu Val Val Asn Val
385                 390                 395                 400

Pro Pro Gln Ile Gly Glu Lys Ala Leu Ile Ser Pro Met Asp Ser Tyr
                405                 410                 415

Gln Tyr Gly Thr Met Gln Thr Leu Thr Cys Thr Val Tyr Ala Asn Pro
            420                 425                 430

Pro Leu His His Ile Gln Trp Tyr Trp Gln Leu Glu Glu Ala Cys Ser
        435                 440                 445

Tyr Arg Pro Ser Gln Thr Asn Pro Tyr Thr Cys Lys Glu Trp Arg His
    450                 455                 460

Val Lys Asp Phe Gln Gly Gly Asn Lys Ile Glu Val Thr Lys Asn Gln
465                 470                 475                 480

Tyr Ala Leu Ile Glu Gly Lys Asn Lys Thr Val Ser Thr Leu Val Ile
                485                 490                 495

Gln Ala Ala Tyr Val Ser Ala Leu Tyr Lys Cys Glu Ala Ile Asn Lys
            500                 505                 510

Ala Gly Arg Gly Glu Arg Val Ile Ser Phe His Val Ile Arg Gly Pro
        515                 520                 525

Glu Ile Thr Val Gln Pro Ala Thr Gln Pro Thr Glu Arg Glu Ser Met
    530                 535                 540

Ser Leu Leu Cys Thr Ala Asp Arg Asn Thr Phe Glu Asn Leu Thr Trp
545                 550                 555                 560

Tyr Lys Leu Gly Ser Gln Ala Thr Ser Val His Met Gly Glu Ser Leu
                565                 570                 575

Thr Pro Val Cys Lys Asn Leu Asp Ala Leu Trp Lys Leu Asn Gly Thr
            580                 585                 590

Val Phe Ser Asn Ser Thr Asn Asp Ile Leu Ile Val Ala Phe Gln Asn
        595                 600                 605

Ala Ser Leu Gln Asp Gln Gly Asn Tyr Val Cys Ser Ala Gln Asp Lys
    610                 615                 620

Lys Thr Lys Lys Arg His Cys Leu Val Lys Gln Leu Val Ile Leu Glu
625                 630                 635                 640

Arg Met Ala Pro Met Ile Thr Gly Asn Leu Glu Asn Gln Thr Thr Thr
                645                 650                 655

Ile Gly Glu Thr Ile Glu Val Val Cys Pro Thr Ser Gly Asn Pro Thr
            660                 665                 670

Pro Leu Ile Thr Trp Phe Lys Asp Asn Glu Thr Leu Val Glu Asp Ser
        675                 680                 685

Gly Ile Val Leu Lys Asp Gly Asn Arg Asn Leu Thr Ile Arg Arg Val
    690                 695                 700

Arg Lys Glu Asp Gly Gly Leu Tyr Thr Cys Gln Ala Cys Asn Val Leu
705                 710                 715                 720

Gly Cys Ala Arg Ala Glu Thr Leu Phe Ile Ile Glu Gly Val Gln Glu
```

725                 730                 735

Lys Thr Asn Leu Glu
            740

<210> SEQ ID NO 29
<211> LENGTH: 756
<212> TYPE: PRT
<213> ORGANISM: Human

<400> SEQUENCE: 29

Tyr Ser Met Thr Pro Thr Leu Asn Ile Thr Glu Glu Ser His Val
1               5                   10                  15

Ile Asp Thr Gly Asp Ser Leu Ser Ile Ser Cys Arg Gly Gln His Pro
                20                  25                  30

Leu Glu Trp Ala Trp Pro Gly Ala Gln Glu Ala Pro Ala Thr Gly Asp
            35                  40                  45

Lys Asp Ser Glu Asp Thr Gly Val Val Arg Asp Cys Glu Gly Thr Asp
50                  55                  60

Ala Arg Pro Tyr Cys Lys Val Leu Leu Leu His Glu Val His Ala Asn
65                  70                  75                  80

Asp Thr Gly Ser Tyr Val Cys Tyr Tyr Lys Tyr Ile Lys Ala Arg Ile
                85                  90                  95

Glu Gly Thr Thr Ala Ala Ser Ser Tyr Val Phe Val Arg Asp Phe Glu
                100                 105                 110

Gln Pro Phe Ile Asn Lys Pro Asp Thr Leu Leu Val Asn Arg Lys Asp
            115                 120                 125

Ala Met Trp Val Pro Cys Leu Val Ser Ile Pro Gly Leu Asn Val Thr
            130                 135                 140

Leu Arg Ser Gln Ser Ser Val Leu Trp Pro Asp Gly Gln Glu Val Val
145                 150                 155                 160

Trp Asp Asp Arg Arg Gly Met Leu Val Ser Thr Pro Leu Leu His Asp
                165                 170                 175

Ala Leu Tyr Leu Gln Cys Glu Thr Thr Trp Gly Asp Gln Asp Phe Leu
                180                 185                 190

Ser Asn Pro Phe Leu Val His Ile Thr Gly Asn Glu Leu Tyr Asp Ile
            195                 200                 205

Gln Leu Leu Pro Arg Lys Ser Leu Glu Leu Leu Val Gly Glu Lys Leu
        210                 215                 220

Val Leu Asn Cys Thr Val Trp Ala Glu Phe Asn Ser Gly Val Thr Phe
225                 230                 235                 240

Asp Trp Asp Tyr Pro Gly Lys Gln Ala Glu Arg Gly Lys Trp Val Pro
                245                 250                 255

Glu Arg Arg Ser Gln Gln Thr His Thr Glu Leu Ser Ser Ile Leu Thr
            260                 265                 270

Ile His Asn Val Ser Gln His Asp Leu Gly Ser Tyr Val Cys Lys Ala
        275                 280                 285

Asn Asn Gly Ile Gln Arg Phe Arg Glu Ser Thr Glu Val Ile Val His
        290                 295                 300

Glu Asn Pro Phe Ile Ser Val Glu Trp Leu Lys Gly Pro Ile Leu Glu
305                 310                 315                 320

Ala Thr Ala Gly Asp Glu Leu Val Lys Leu Pro Val Lys Leu Ala Ala
                325                 330                 335

Tyr Pro Pro Pro Glu Phe Gln Trp Tyr Lys Asp Gly Lys Ala Leu Ser
            340                 345                 350

```
Gly Arg His Ser Pro His Ala Leu Val Leu Lys Glu Val Thr Glu Ala
            355                 360                 365

Ser Thr Gly Thr Tyr Thr Leu Ala Leu Trp Asn Ser Ala Ala Gly Leu
    370                 375                 380

Arg Arg Asn Ile Ser Leu Glu Leu Val Val Asn Val Pro Pro Gln Ile
385                 390                 395                 400

His Glu Lys Glu Ala Ser Ser Pro Ser Ile Tyr Ser Arg His Ser Arg
                405                 410                 415

Gln Ala Leu Thr Cys Thr Ala Tyr Gly Val Pro Leu Pro Leu Ser Ile
                420                 425                 430

Gln Trp His Trp Arg Pro Trp Thr Pro Cys Lys Met Phe Ala Gln Arg
        435                 440                 445

Ser Leu Arg Arg Arg Gln Gln Gln Asp Leu Met Pro Gln Cys Arg Asp
    450                 455                 460

Trp Arg Ala Val Thr Thr Gln Asp Ala Val Asn Pro Ile Glu Ser Leu
465                 470                 475                 480

Asp Thr Trp Thr Glu Phe Val Glu Gly Lys Asn Lys Thr Val Ser Lys
                485                 490                 495

Leu Val Ile Gln Asn Ala Asn Val Ser Ala Met Tyr Lys Cys Val Val
            500                 505                 510

Ser Asn Lys Val Gly Gln Asp Glu Arg Leu Ile Tyr Phe Tyr Val Thr
        515                 520                 525

Thr Ile Pro Asp Gly Phe Thr Ile Glu Ser Lys Pro Ser Glu Glu Leu
    530                 535                 540

Leu Glu Gly Gln Pro Val Leu Leu Ser Cys Gln Ala Asp Ser Tyr Lys
545                 550                 555                 560

Tyr Glu His Leu Arg Trp Tyr Arg Leu Asn Leu Ser Thr Leu His Asp
                565                 570                 575

Ala His Gly Asn Pro Leu Leu Leu Asp Cys Lys Asn Val His Leu Phe
            580                 585                 590

Ala Thr Pro Leu Ala Ala Ser Leu Glu Glu Val Ala Pro Gly Ala Arg
        595                 600                 605

His Ala Thr Leu Ser Leu Ser Ile Pro Arg Val Ala Pro Glu His Glu
    610                 615                 620

Gly His Tyr Val Cys Glu Val Gln Asp Arg Arg Ser His Asp Lys His
625                 630                 635                 640

Cys His Lys Lys Tyr Leu Ser Val Gln Ala Leu Glu Ala Pro Arg Leu
                645                 650                 655

Thr Gln Asn Leu Thr Asp Leu Leu Val Asn Val Ser Asp Ser Leu Glu
            660                 665                 670

Met Gln Cys Leu Val Ala Gly Ala His Ala Pro Ser Ile Val Trp Tyr
        675                 680                 685

Lys Asp Glu Arg Leu Leu Glu Glu Lys Ser Gly Val Asp Leu Ala Asp
690                 695                 700

Ser Asn Gln Lys Leu Ser Ile Gln Arg Val Arg Glu Glu Asp Ala Gly
705                 710                 715                 720

Arg Tyr Leu Cys Ser Val Cys Asn Ala Lys Gly Cys Val Asn Ser Ser
                725                 730                 735

Ala Ser Val Ala Val Glu Gly Ser Glu Asp Lys Gly Ser Met Glu Ile
            740                 745                 750

Val Ile Leu Val
    755
```

<210> SEQ ID NO 30
<211> LENGTH: 751
<212> TYPE: PRT
<213> ORGANISM: Mouse

<400> SEQUENCE: 30

Tyr Ser Met Thr Pro Pro Thr Leu Asn Ile Thr Glu Asp Ser Tyr Val
1               5                   10                  15

Ile Asp Thr Gly Asp Ser Leu Ser Ile Ser Cys Arg Gly Gln His Pro
            20                  25                  30

Leu Glu Trp Thr Trp Pro Gly Ala Gln Glu Val Leu Thr Thr Gly Gly
        35                  40                  45

Lys Asp Ser Glu Asp Thr Arg Val Val His Asp Cys Glu Gly Thr Glu
50                  55                  60

Ala Arg Pro Tyr Cys Lys Val Leu Leu Leu Ala Gln Thr His Ala Asn
65                  70                  75                  80

Asn Thr Gly Ser Tyr His Cys Tyr Tyr Lys Tyr Ile Lys Ala Arg Ile
                85                  90                  95

Glu Gly Thr Thr Ala Ala Ser Thr Tyr Val Phe Val Arg Asp Phe Lys
            100                 105                 110

His Pro Phe Ile Asn Lys Pro Asp Thr Leu Leu Val Asn Arg Lys Asp
        115                 120                 125

Ser Met Trp Val Pro Cys Leu Val Ser Ile Pro Gly Leu Asn Ile Thr
130                 135                 140

Leu Arg Ser Gln Ser Ser Ala Leu His Pro Asp Gly Gln Glu Val Leu
145                 150                 155                 160

Trp Asp Asp Arg Arg Gly Met Arg Val Pro Thr Gln Leu Leu Arg Asp
                165                 170                 175

Ala Leu Tyr Leu Gln Cys Glu Thr Thr Trp Gly Asp Gln Asn Phe Leu
            180                 185                 190

Ser Asn Leu Phe Val Val His Ile Thr Gly Asn Glu Leu Tyr Asp Ile
        195                 200                 205

Gln Leu Tyr Pro Lys Lys Ser Met Glu Leu Leu Val Gly Glu Lys Leu
210                 215                 220

Val Leu Asn Cys Thr Val Trp Ala Glu Phe Asp Ser Gly Val Thr Phe
225                 230                 235                 240

Asp Trp Asp Tyr Pro Gly Lys Gln Ala Glu Arg Ala Lys Trp Val Pro
                245                 250                 255

Glu Arg Arg Ser Gln Gln Thr His Thr Glu Leu Ser Ser Ile Leu Thr
            260                 265                 270

Ile His Asn Val Ser Gln Asn Asp Leu Gly Pro Tyr Val Cys Glu Ala
        275                 280                 285

Asn Asn Gly Ile Gln Arg Phe Arg Glu Ser Thr Glu Val Ile Val His
290                 295                 300

Glu Lys Pro Phe Ile Ser Val Glu Trp Leu Lys Gly Pro Val Leu Glu
305                 310                 315                 320

Ala Thr Ala Gly Asp Glu Leu Val Lys Leu Pro Val Lys Leu Ala Ala
                325                 330                 335

Tyr Pro Pro Pro Glu Phe Gln Trp Tyr Lys Asp Arg Lys Ala Val Thr
            340                 345                 350

Gly Arg His Asn Pro His Ala Leu Val Leu Lys Glu Val Thr Glu Ala
        355                 360                 365

Ser Ala Gly Val Tyr Thr Leu Ala Leu Trp Asn Ser Ala Ala Gly Leu
370                 375                 380

-continued

```
Arg Gln Asn Ile Ser Leu Glu Leu Val Val Asn Val Pro Pro His Ile
385                 390                 395                 400

His Glu Lys Glu Ala Ser Ser Pro Ser Ile Tyr Ser Arg His Ser Arg
            405                 410                 415

Gln Thr Leu Thr Cys Thr Ala Tyr Gly Val Pro Gln Pro Leu Ser Val
        420                 425                 430

Gln Trp His Trp Arg Pro Trp Thr Pro Cys Lys Thr Phe Ala Gln Arg
            435                 440                 445

Ser Leu Arg Arg Gln Gln Arg Asp Gly Met Pro Gln Cys Arg Asp
    450                 455                 460

Trp Lys Glu Val Thr Thr Gln Asp Ala Val Asn Pro Ile Glu Ser Leu
465                 470                 475                 480

Asp Ser Trp Thr Glu Phe Val Glu Gly Lys Asn Lys Thr Val Ser Lys
                485                 490                 495

Leu Val Ile Gln Asp Ala Asn Val Ser Ala Met Tyr Lys Cys Val Val
            500                 505                 510

Val Asn Lys Val Gly Gln Asp Glu Arg Leu Ile Tyr Phe Tyr Val Thr
        515                 520                 525

Thr Ile Pro Asp Gly Phe Ser Ile Glu Ser Glu Pro Ser Glu Asp Pro
    530                 535                 540

Leu Glu Gly Gln Ser Val Arg Leu Ser Cys Arg Ala Asp Asn Tyr Thr
545                 550                 555                 560

Tyr Glu His Leu Arg Trp Tyr Arg Leu Asn Leu Ser Thr Leu His Asp
                565                 570                 575

Ala Gln Gly Asn Pro Leu Leu Leu Asp Cys Lys Asn Val His Leu Phe
            580                 585                 590

Ala Thr Pro Leu Glu Ala Asn Leu Glu Glu Ala Glu Pro Gly Ala Arg
        595                 600                 605

His Ala Thr Leu Ser Leu Asn Ile Pro Arg Val Ala Pro Glu Asp Glu
    610                 615                 620

Gly Asp Tyr Val Cys Glu Val Gln Asp Arg Arg Ser Gln Asp Lys His
625                 630                 635                 640

Cys His Lys Lys Tyr Leu Ser Val Gln Ala Leu Glu Ala Pro Arg Leu
                645                 650                 655

Thr Gln Asn Leu Thr Asp Leu Leu Val Asn Val Ser Asp Ser Leu Glu
            660                 665                 670

Met Arg Cys Pro Val Ala Gly Ala His Val Pro Ser Ile Val Trp Tyr
        675                 680                 685

Lys Asp Glu Arg Leu Leu Glu Lys Glu Ser Gly Ile Asp Leu Ala Asp
690                 695                 700

Ser Asn Gln Arg Leu Ser Ile Gln Arg Val Arg Glu Glu Asp Ala Gly
705                 710                 715                 720

Arg Tyr Leu Cys Ser Val Cys Asn Ala Lys Gly Cys Val Asn Ser Ser
                725                 730                 735

Ala Ser Val Ala Val Glu Gly Ser Glu Asp Lys Gly Ser Met Glu
            740                 745                 750
```

<210> SEQ ID NO 31
<211> LENGTH: 751
<212> TYPE: PRT
<213> ORGANISM: Rat

<400> SEQUENCE: 31

```
Tyr Ser Met Thr Pro Pro Thr Leu Asn Ile Thr Glu Asp Ser Tyr Val
1               5                   10                  15
```

```
Ile Asp Thr Gly Asp Ser Leu Ser Ile Ser Cys Arg Gly Gln His Pro
            20                  25                  30
Leu Glu Trp Thr Trp Arg Gly Ala Gln Glu Val Leu Thr Gly Gly
        35                  40                  45
Lys Asp Ser Glu Asp Thr Gln Val Val Gln Asp Cys Glu Gly Thr Glu
50                  55                  60
Ala Arg Pro Tyr Cys Lys Val Leu Ser Leu Ala Gln Thr His Ala Asn
65                  70                  75                  80
Asn Thr Gly Ser Tyr Tyr Cys Tyr Tyr Lys Tyr Ile Lys Ala Arg Ile
                85                  90                  95
Glu Gly Thr Thr Ala Ala Ser Thr Tyr Val Phe Val Arg Asp Phe Glu
                100                 105                 110
Gln Pro Phe Ile Asn Lys Pro Asp Thr Leu Leu Val Asn Arg Lys Asp
        115                 120                 125
Ser Met Trp Val Pro Cys Leu Val Ser Ile Pro Gly Leu Asn Ile Thr
        130                 135                 140
Leu Arg Ser Gln Ser Ser Val Leu His Pro Asp Gly Gln Glu Val Leu
145                 150                 155                 160
Trp Asp Asp Arg Arg Gly Met Arg Val Pro Thr Leu Leu Arg Asp
                165                 170                 175
Ala Leu Tyr Leu Gln Cys Glu Thr Thr Trp Gly Asp Gln Asp Phe Leu
                180                 185                 190
Ser Asn Pro Phe Leu Val His Ile Thr Gly Asn Glu Leu Tyr Asp Ile
        195                 200                 205
Gln Leu Tyr Pro Lys Lys Ser Leu Glu Leu Leu Val Gly Glu Lys Leu
        210                 215                 220
Val Leu Asn Cys Thr Val Trp Ala Glu Phe Asp Ser Gly Val Thr Phe
225                 230                 235                 240
Asp Trp Asp Tyr Pro Gly Lys Gln Ala Glu Arg Ala Lys Trp Val Pro
                245                 250                 255
Glu Arg Arg Ser Gln Gln Thr His Thr Glu Leu Ser Ser Ile Leu Thr
                260                 265                 270
Ile His Asn Val Ser Gln His Asp Leu Gly Pro Tyr Val Cys Glu Ala
        275                 280                 285
Asn Asn Gly Ile Gln Gln Phe Arg Glu Ser Thr Glu Val Ile Val His
        290                 295                 300
Glu Lys Pro Phe Ile Ser Val Glu Trp Leu Lys Gly Pro Val Leu Glu
305                 310                 315                 320
Ala Thr Ala Gly Asp Glu Met Val Lys Leu Pro Val Lys Leu Ala Ala
                325                 330                 335
Tyr Pro Pro Pro Glu Phe Gln Trp Tyr Lys Asp Arg Lys Ala Val Thr
                340                 345                 350
Gly Arg His Asn Pro His Ala Leu Val Leu Lys Glu Val Thr Glu Ala
        355                 360                 365
Ser Ala Gly Val Tyr Thr Leu Ala Leu Trp Asn Ser Ala Ala Gly Leu
        370                 375                 380
Arg Gln Asn Ile Ser Leu Glu Leu Val Val Asn Val Pro Pro His Ile
385                 390                 395                 400
His Glu Lys Glu Ala Ser Ser Pro Ser Ile Tyr Ser Arg His Ser Arg
                405                 410                 415
Gln Thr Leu Thr Cys Thr Thr Tyr Gly Val Pro Gln Pro Leu Ser Val
        420                 425                 430
```

-continued

Gln Trp His Trp Arg Pro Trp Thr Pro Cys Lys Thr Phe Ala Gln Arg
            435                 440                 445

Ser Leu Arg Arg Arg Gln Pro Arg Asp Gly Met Pro Gln Cys Arg Asp
    450                 455                 460

Trp Lys Glu Val Thr Thr Gln Asp Ala Val Asn Pro Ile Glu Ser Leu
465                 470                 475                 480

Asp Thr Trp Thr Glu Ser Val Glu Gly Lys Asn Lys Thr Val Ser Lys
                485                 490                 495

Leu Val Ile Gln Asp Ala Asn Val Ser Ala Met Tyr Lys Cys Val Val
            500                 505                 510

Phe Asn Lys Val Gly Gln Asp Glu Arg Leu Ile Tyr Phe Tyr Val Thr
    515                 520                 525

Thr Ile Pro Asp Gly Phe Ser Ile Glu Ser Glu Pro Ser Glu Asp Pro
530                 535                 540

Leu Glu Gly Gln Ser Val Arg Leu Ser Cys Arg Ala Asp Asn Tyr Thr
545                 550                 555                 560

Tyr Glu His Leu Arg Trp Tyr Arg Leu Asn Leu Ser Thr Leu His Asp
                565                 570                 575

Ala Gln Gly Asn Pro Leu Leu Leu Asp Cys Lys Asn Val His Leu Phe
            580                 585                 590

Ala Thr Pro Leu Glu Ala Asn Leu Glu Glu Ala Glu Pro Gly Ala Arg
    595                 600                 605

His Ala Thr Leu Ser Leu Asn Ile Pro Arg Val Ala Pro Glu Asp Glu
610                 615                 620

Gly Asp Tyr Val Cys Glu Val Gln Asp Arg Arg Ser Gln Asp Lys His
625                 630                 635                 640

Cys His Lys Lys Tyr Leu Ser Val Gln Ala Leu Glu Ala Pro Arg Leu
                645                 650                 655

Thr Gln Asn Leu Thr Asp Leu Leu Val Asn Val Arg Thr Ser Leu Glu
            660                 665                 670

Met Arg Cys Pro Val Ala Gly Ala His Val Pro Ser Ile Val Trp Tyr
    675                 680                 685

Lys Asp Glu Arg Leu Leu Glu Lys Glu Ser Gly Ile Asp Leu Ala Asp
690                 695                 700

Ser Asn Gln Arg Leu Ser Ile Gln Arg Val Arg Glu Glu Asp Ala Gly
705                 710                 715                 720

Arg Tyr Leu Cys Ser Val Cys Asn Ala Lys Gly Cys Val Asn Ser Ser
                725                 730                 735

Ala Ser Val Ala Val Glu Gly Ser Glu Asp Lys Gly Ser Met Glu
            740                 745                 750

<210> SEQ ID NO 32
<211> LENGTH: 220
<212> TYPE: PRT
<213> ORGANISM: Human

<400> SEQUENCE: 32

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

-continued

```
Arg Glu Glu Gln Tyr Asn Ser Thr Tyr Arg Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Ser Asn Gly Gln Pro
145                 150                 155                 160

Glu Asn Asn Tyr Lys Thr Thr Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 33
<211> LENGTH: 223
<212> TYPE: PRT
<213> ORGANISM: Human

<400> SEQUENCE: 33

Val Glu Cys Pro Pro Cys Pro Ala Pro Pro Val Ala Gly Pro Ser Val
  1               5                  10                  15

Phe Leu Phe Pro Pro Lys Pro Lys Asp Thr Leu Met Ile Ser Arg Thr
                 20                  25                  30

Pro Glu Val Thr Cys Val Val Asp Val Ser His Glu Asp Pro Glu
             35                  40                  45

Val Gln Phe Asn Trp Tyr Val Asp Gly Val Glu Val His Asn Ala Lys
 50                  55                  60

Thr Lys Pro Arg Glu Glu Gln Phe Asn Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
```

<210> SEQ ID NO 34
<211> LENGTH: 223
<212> TYPE: PRT
<213> ORGANISM: Human

<400> SEQUENCE: 34

Thr Cys Pro Arg Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Lys Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Ser
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Ile Phe Ser Cys Ser Val Met His Glu Ala Leu
        195                 200                 205

His Asn Arg Phe Thr Gln Lys Ser Leu Ser Leu Ser Pro Gly Lys
    210                 215                 220

<210> SEQ ID NO 35
<211> LENGTH: 4474
<212> TYPE: DNA
<213> ORGANISM: Artificial Sequence
<220> FEATURE:
<223> OTHER INFORMATION: pITR.CBA.Bevacizumab

<400> SEQUENCE: 35
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120 agggggttcct gcggccgcac gcgtgacatt gattattgac tagttattaa tagtaatcaa    180
ttacggggtc attagttcat agcccatata tggagttccg cgttacataa cttacggtaa     240
atggcccgcc tggctgaccg cccaacgacc cccgcccatt gacgtcaata atgacgtatg     300
ttcccatagt aacgccaata gggactttcc attgacgtca tgggtggac tatttacggt      360 aaactgccca cttggcagta catcaagtgt atcatatgcc aagtacgccc cctattgacg     420
tcaatgacgg taaatggccc gcctggcatt atgcccagta catgacctta tgggactttc     480
ctacttggca gtacatctac gtattagtca tcgctattac catgggtcga ggtgagcccc    540

-continued

```
acgttctgct tcactctccc catctccccc ccctccccac ccccaatttt gtatttattt    600
attttttaat tattttgtgc agcgatgggg gcggggggg gggggggcgcg cgccaggcgg    660 ggcggggcgg ggcgagggc ggggcgggc gaggcggaga ggtgcggcgg cagccaatca    720
gagcggcgcg ctccgaaagt ttcctttat ggcgaggcgg cggcggcggc ggccctataa    780
aaagcgaagc gcgcggcggg cgggagtcgc tgcgttgcct tcgccccgtg ccccgctccg    840
cgccgcctcg cgccgcccgc cccggctctg actaccgcg ttactcccac aggtgagcgg    900
gcgggacggc ccttctcctc cgggctgtaa ttagcgcttg gtttaatgac ggctcgtttc    960
ttttctgtgt ctgcgtgaaa gccttaaagg gctccgggag ggcccttgt gcgggggga    1020 gcggctcggg gggtgcgtgc gtgtgtgtgt gcgtggggag cgccgcgtgc ggcccgcgct    1080 gcccggcgg tgtgagcgct gcgggcgcg cgcggggctt tgtgcgctcc gcgtgtgcgc    1140
gaggggagcg cggccggggg cggtgccccg cggtgcgggg gggctgcgag gggaacaaag    1200
gctgcgtgcg gggtgtgtgc gtgggggggt gagcagggg tgtgggcgcg gcggtcgggc    1260 tgtaacccc ccctgcaccc ccctccccga gttgctgagc acggcccggc ttcgggtgcg    1320
gggctccgtg cggggcgtgg cgcggggctc gccgtgccgg gcgggggtg gcggcaggtg    1380 ggggtgccgg gcggggcggg gccgcctcgg gccggggagg gctcggggga ggggcgcggc    1440
ggcccccgga gcgccggcgg ctgtcgaggc gcggcgagcc gcagccattg ccttttatgg    1500
taatcgtgcg agagggcgca gggacttcct ttgtcccaaa tctgtgcgga gccgaaatct    1560
gggaggcgcc gccgcacccc ctctagcggg cgcggggcga agcggtgcgg cgccggcagg    1620
aaggaaatgg gcgggaggg ccttcgtgcg tcgccgcgcc gccgtcccct tctccctctc    1680
cagcctcggg gctgtccgcg gggggacggc tgccttcggg ggggacgggg cagggcgggg    1740
ttcggcttct ggcgtgtgac cggcggctct agagcctctg ctaaccatgt tcatgccttc    1800
ttctttttcc tacagctcct gggcaacgtg ctggttattg tgaccggtgc caccatgtac    1860
cggatgcagc tgctgagctg tatcgccctg tctctggccc tggtcaccaa ttctgaggtg    1920
cagctggtgg aatctggcgg cggacttgtt caacctggcg gctctctgag actgagctgt    1980
gccgcttctg gctacacctt caccaactac ggcatgaact gggtccgaca ggcccctggc    2040
aaaggccttg aatgggtcgg atggatcaac acctacaccg gcgagccaac atacgccgcc    2100
gacttcaagc ggagattcac cttcagcctg gacaccagca gagcaccgc ctacctgcag    2160 atgaacagcc tgagagccga ggacaccgcc gtgtactact gcgccaagta tccccactac    2220
tacggcagca gccactggta ctttgacgtg tggggacagg gcacactggt cacagtgtct    2280
agcgcctcta caaagggccc cagcgttttc ccactggctc ctagcagcaa gtctaccagc    2340
ggaggaacag ccgctctggg ctgtctggtc aaggactact tcccgagcc tgtgaccgtg    2400 tcctggaatt ctggcgctct gacaagcggc gtgcacacct ttccagctgt gctgcaaagc    2460
agcggcctgt actctctgag cagcgtcgtg acagtgccaa gcagctctct gggcacccag    2520
acctacatct gcaatgtgaa ccacaagcct agcaacacca aggtggacaa gaaggtggaa    2580
cccaagagct gcgacaagac ccacacctgt cctccatgtc ctgctccaga actgctcggc    2640
ggaccttccg tgttcctgtt tcctccaaag cctaaggaca ccctgatgat cagcagaacc    2700
cctgaagtga cctgcgtggt ggtggatgtg tcccacgagg atcccgaagt gaagttcaat    2760
tggtacgtgg acggcgtgga agtgcacaac gccaagacca agcctagaga ggaacagtac    2820
aacagcacct acagagtggt gtccgtgctg accgtgctgc accaggattg gctgaacggc    2880
```

| aaagagtaca agtgcaaggt gtccaacaag gccctgcctg ctcctatcga gaaaaccatc | 2940 |
| agcaaggcca agggccagcc tagggaaccc caggtttaca cactgcctcc aagccgggaa | 3000 |
| gagatgacca agaaccaggt gtccctgacc tgcctcgtga agggcttcta cccttccgat | 3060 |
| atcgccgtgg aatgggagag caatggccag ccagagaaca actacaagac aaccectcct | 3120 |
| gtgctggaca gcgacggctc attcttcctg tacagcaagc tgacagtgga caagtccaga | 3180 |
| tggcagcagg gcaacgtgtt cagctgcagc gtgatgcacg aggccctgca caaccactac | 3240 |
| acccagaagt ctctgagcct gtctcctggc aagcggaaga aagaggctc tggcgaaggc | 3300 |
| agaggcagcc tgcttacatg tggcgacgtg aagagaaacc ccggacctat gtatagaatg | 3360 |
| cagctcctgt cctgcattgc cctgagcctg gctctcgtga ccaacagcga catccagatg | 3420 |
| acacagagcc ccagcagcct gtctgcctct gtgggagaca gagtgaccat cacctgtagc | 3480 |
| gccagccagg acatctccaa ctacctgaac tggtatcagc aaaagcccgg caaggcccct | 3540 |
| aaggtgctga tctacttcac aagcagcctg cactccggcg tgcccagcag attttctggc | 3600 |
| tctggcagcg gcaccgactt caccctgacc atatctagcc tgcagcctga ggacttcgcc | 3660 |
| acctactact gccagcagta cagcaccgtg ccttggacat ttggccaggg cacaaaggtg | 3720 |
| gaaatcaagc ggactgtggc cgctcctagc gtgttcatct ttccacctag cgacgagcag | 3780 |
| ctgaagtctg gcacagcctc tgtcgtgtgc ctgctgaaca acttctaccc cagagaagcc | 3840 |
| aaggtgcagt ggaaagtgga caatgccctg cagagcggca cagccaaga gagcgtgaca | 3900 |
| gagcaggact ccaaggatag cacctatagc ctgagcagca ccctgacact gagcaaggcc | 3960 |
| gactacgaga agcacaaagt gtacgcctgc gaagtgaccc accagggcct ttctagccct | 4020 |
| gtgaccaaga gcttcaaccg gggcgaatgt taagagctcg ctgatcagcc tcgactgtgc | 4080 |
| cttctagttg ccagccatct gttgtttgcc cctcccccgt gccttccttg acctggaag | 4140 |
| gtgccactcc cactgtcctt tcctaataaa atgaggaaat tgcatcgcat tgtctgagta | 4200 |
| ggtgtcattc tattctgggg ggtggggtgg gcaggacag caaggggag gattgggaag | 4260 |
| acaatagcag gcatgctggg gatgcggtgg gctctatgga agcttgaatt cagctgacgt | 4320 |
| gcctcggacc gctaggaacc cctagtgatg gagttggcca ctccctctct gcgcgctcgc | 4380 |
| tcgctcactg aggccgggcg accaaaggtc gcccgacgcc cgggctttgc ccgggcggcc | 4440 |
| tcagtgagcg agcgagcgcg cagctgcctg cagg | 4474 |

```
<210> SEQ ID NO 36
<211> LENGTH: 144
<212> TYPE: DNA
<213> ORGANISM: Artificial Sequence
<220> FEATURE:
<223> OTHER INFORMATION: ITR sequence

<400> SEQUENCE: 36
```

| cctgcaggca gctgcgcgct cgctcgctca ctgaggccgc ccgggcgtcg gcgacctttg | 60 |
| ggtcgcccgg cctcagtgag cgagcgagcg cgcagagagg gagtggccaa ctccatcact | 120 |
| aggggttcct gcggccgcac gcgt | 144 |

```
<210> SEQ ID NO 37
<211> LENGTH: 1671
<212> TYPE: DNA
<213> ORGANISM: Artificial Sequence
<220> FEATURE:
<223> OTHER INFORMATION: CBA sequence

<400> SEQUENCE: 37
```

| | | | | | |
|---|---|---|---|---|---|
| gacattgatt | attgactagt | tattaatagt | aatcaattac | ggggtcatta | gttcatagcc | 60 |
| catatatgga | gttccgcgtt | acataactta | cggtaaatgg | cccgcctggc | tgaccgccca | 120 |
| acgaccccg | cccattgacg | tcaataatga | cgtatgttcc | catagtaacg | ccaataggga | 180 |
| ctttccattg | acgtcaatgg | gtggactatt | tacggtaaac | tgcccacttg | gcagtacatc | 240 |
| aagtgtatca | tatgccaagt | acgccccta | ttgacgtcaa | tgacggtaaa | tggcccgcct | 300 |
| ggcattatgc | ccagtacatg | accttatggg | actttcctac | ttggcagtac | atctacgtat | 360 |
| tagtcatcgc | tattaccatg | gtcgaggtg | agccccacgt | tctgcttcac | tctccccatc | 420 |
| tcccccccct | ccccaccccc | aattttgtat | ttatttattt | tttaattatt | ttgtgcagcg | 480 |
| atggggggcgg | ggggggggg | ggcgcgcgcc | aggcggggcg | gggcggggcg | aggggcgggg | 540 |
| cggggcgagg | cggagaggtg | cggcggcagc | caatcagagc | ggcgcgctcc | gaaagtttcc | 600 |
| ttttatggcg | aggcggcggc | ggcggcggcc | ctataaaaag | cgaagcgcgc | ggcgggcggg | 660 |
| agtcgctgcg | ttgccttcgc | cccgtgcccc | gctccgcgcc | gcctcgcgcc | gcccgccccg | 720 |
| gctctgactg | accgcgttac | tcccacaggt | gagcgggcgg | gacggccctt | ctcctccggg | 780 |
| ctgtaattag | cgcttggttt | aatgacggct | cgtttctttt | ctgtggctgc | gtgaaagcct | 840 |
| taaagggctc | cggagggcc | ctttgtgcgg | ggggagcgg | ctcgggggt | gcgtgcgtgt | 900 |
| gtgtgtgcgt | ggggagcgcc | gcgtgcggcc | cgcgctgccc | ggcggctgtg | agcgctgcgg | 960 |
| gcgcggcgcg | gggctttgtg | cgctccgcgt | gtgcgcgagg | ggagcgcggc | cggggcggt | 1020 |
| gccccgcgt | gcgggggggc | tgcgagggga | acaaaggctg | cgtgcgggt | gtgtgcgtgg | 1080 |
| gggggtgagc | aggggtgtg | ggcgcggcgg | tcgggctgta | accccccct | gcaccccct | 1140 |
| ccccgagttg | ctgagcacgg | cccggcttcg | ggtgcgggc | tccgtgcggg | gcgtggcgcg | 1200 |
| gggctcgccg | tgccgggcgg | gggtggcgg | caggtgggg | tgccgggcgg | ggcggggccg | 1260 |
| cctcggggccg | gggagggctc | gggggagggg | cgcggcggcc | cccggagcgc | cggcggctgt | 1320 |
| cgaggcgcgg | cgagccgcag | ccattgcctt | ttatggtaat | cgtgcgagag | ggcgcaggga | 1380 |
| cttcctttgt | cccaaatctg | tgcggagccg | aaatctggga | ggcgccgccg | cacccctct | 1440 |
| agcgggcgcg | gggcgaagcg | gtgcggcgcc | ggcaggaagg | aaatgggcgg | ggagggcctt | 1500 |
| cgtgcgtcgc | cgcgccgccg | tccccttctc | cctctccagc | ctcggggctg | tccgcggggg | 1560 |
| gacggctgcc | ttcggggggg | acgggcagg | gcggggttcg | gcttctggcg | tgtgaccggc | 1620 |
| ggctctagag | cctctgctaa | ccatgttcat | gccttcttct | ttttcctaca | g | 1671 |

<210> SEQ ID NO 38
<211> LENGTH: 39
<212> TYPE: DNA
<213> ORGANISM: Artificial Sequence
<220> FEATURE:
<223> OTHER INFORMATION: spacer

<400> SEQUENCE: 38
ctcctgggca acgtgctggt tattgtgacc ggtgccacc         39

<210> SEQ ID NO 39
<211> LENGTH: 60
<212> TYPE: DNA
<213> ORGANISM: Artificial Sequence
<220> FEATURE:
<223> OTHER INFORMATION: IL-2 secretion signal sequence

<400> SEQUENCE: 39
atgtaccgga tgcagctgct gagctgtatc gccctgtctc tggccctggt caccaattct    60

<210> SEQ ID NO 40
<211> LENGTH: 1359
<212> TYPE: DNA
<213> ORGANISM: Artificial Sequence
<220> FEATURE:
<223> OTHER INFORMATION: Sequence encoding heavy chain of bevacizumab

<400> SEQUENCE: 40
gaggtgcagc tggtggaatc tggcggcgga cttgttcaac ctggcggctc tctgagactg    60
agctgtgccg cttctggcta caccttcacc aactacggca tgaactgggt ccgacaggcc   120
cctggcaaag gccttgaatg gtcggatgg atcaacacct acaccggcga gccaacatac    180
gccgccgact tcaagcggag attcaccttc agcctggaca ccagcaagag caccgcctac   240
ctgcagatga acagcctgag agccgaggac accgccgtgt actactgcgc caagtatccc   300
cactactacg gcagcagcca ctggtacttt gacgtgtggg gacagggcac actggtcaca   360
gtgtctagcg cctctacaaa gggccccagc gttttcccac tggctcctag cagcaagtct   420
accagcggag aacagccgc tctgggctgt ctggtcaagg actactttcc cgagcctgtg   480
accgtgtcct ggaattctgg cgctctgaca agcggcgtgc acacctttcc agctgtgctg   540
caaagcagcg gcctgtactc tctgagcagc gtcgtgacag tgccaagcag ctctctgggc   600
acccagacct acatctgcaa tgtgaaccac aagcctagca caccaaggt ggacaagaag    660
gtggaaccca gagctgcga caagacccac acctgtcctc catgtcctgc tccagaactg   720
ctcggcggac cttccgtgtt cctgtttcct ccaaagccta aggacaccct gatgatcagc   780
agaaccctg aagtgacctg cgtggtggtg gatgtgtccc acgaggatcc cgaagtgaag    840
ttcaattggt acgtggacgg cgtggaagtg cacaacgcca agaccaagcc tagagaggaa   900
cagtacaaca gcacctacag agtggtgtcc gtgctgaccg tgctgcacca ggattggctg   960
aacggcaaag agtacaagtg caaggtgtcc aacaaggccc tgcctgctcc tatcgagaaa  1020
accatcagca aggccaaggg ccagcctagg gaaccccagg tttacacact gcctccaagc  1080
cgggaagaga tgaccaagaa ccaggtgtcc ctgacctgcc tcgtgaaggg cttctacccc  1140
tccgatatcg ccgtggaatg ggagagcaat ggccagccag agaacaacta caagacaacc  1200
cctcctgtgc tggacagcga cggctcattc ttcctgtaca gcaagctgac agtggacaag  1260
tccagatggc agcagggcaa cgtgttcagc tgcagcgtga tgcacgaggc cctgcacaac  1320
cactacaccc agaagtctct gagcctgtct cctggcaag                         1359

<210> SEQ ID NO 41
<211> LENGTH: 12
<212> TYPE: DNA
<213> ORGANISM: Artificial Sequence
<220> FEATURE:
<223> OTHER INFORMATION: Linker sequence

<400> SEQUENCE: 41
cggaagagaa ga                                                        12

<210> SEQ ID NO 42
<211> LENGTH: 63
<212> TYPE: DNA
<213> ORGANISM: Artificial Sequence
<220> FEATURE:
<223> OTHER INFORMATION: T2A sequence

<400> SEQUENCE: 42

```
ggctctggcg aaggcagagg cagcctgctt acatgtggcg acgtggaaga gaacccccgga    60 cct                                                                   63

<210> SEQ ID NO 43
<211> LENGTH: 60
<212> TYPE: DNA
<213> ORGANISM: Artificial Sequence
<220> FEATURE:
<223> OTHER INFORMATION: IL-2 secretion signal sequence

<400> SEQUENCE: 43
atgtatagaa tgcagctcct gtcctgcatt gccctgagcc tggctctcgt gaccaacagc    60

<210> SEQ ID NO 44
<211> LENGTH: 645
<212> TYPE: DNA
<213> ORGANISM: Artificial Sequence
<220> FEATURE:
<223> OTHER INFORMATION: Sequence encoding light chain of bevacizumab

<400> SEQUENCE: 44
gacatccaga tgacacagag ccccagcagc ctgtctgcct ctgtgggaga cagagtgacc    60
atcacctgta gcgccagcca ggacatctcc aactacctga actggtatca gcaaaagccc   120
ggcaaggccc ctaaggtgct gatctacttc acaagcagcc tgcactccgg cgtgcccagc   180
agattttctg gctctggcag cggcaccgac ttcaccctga ccatatctag cctgcagcct   240
gaggacttcg ccacctacta ctgccagcag tacagcaccg tgccttggac atttggccag   300
ggcacaaagg tggaaatcaa gcggactgtg gccgctccta gcgtgttcat ctttccacct   360
agcgacgagc agctgaagtc tggcacagcc tctgtcgtgt gcctgctgaa caacttctac   420
cccagagaag ccaaggtgca gtggaaagtg gacaatgccc tgcagagcgg caacagccaa   480
gagagcgtga cagagcagga ctccaaggat agcacctata gcctgagcag caccctgaca   540
ctgagcaagg ccgactacga aagcacaaaa gtgtacgcct gcgaagtgac ccaccagggc   600
ctttctagcc ctgtgaccaa gagcttcaac cggggcgaat gttaa                   645

<210> SEQ ID NO 45
<211> LENGTH: 21
<212> TYPE: DNA
<213> ORGANISM: Artificial Sequence
<220> FEATURE:
<223> OTHER INFORMATION: Linker sequence

<400> SEQUENCE: 45
gagctcgctg atcagcctcg a                                               21

<210> SEQ ID NO 46
<211> LENGTH: 225
<212> TYPE: DNA
<213> ORGANISM: Artificial Sequence
<220> FEATURE:
<223> OTHER INFORMATION: Bovine growth hormone polyA tail sequence

<400> SEQUENCE: 46
ctgtgccttc tagttgccag ccatctgttg tttgcccctc cccgtgcct tccttgaccc     60 tggaaggtgc cactcccact gtcctttcct aataaaatga ggaaattgca tcgcattgtc   120
tgagtaggtg tcattctatt ctgggggtg gggtggggca ggacagcaag ggggaggatt   180
gggaagacaa tagcaggcat gctggggatg cggtgggctc tatgg                   225
```

<210> SEQ ID NO 47
<211> LENGTH: 34
<212> TYPE: DNA
<213> ORGANISM: Artificial Sequence
<220> FEATURE:
<223> OTHER INFORMATION: Linker sequence

<400> SEQUENCE: 47
aagcttgaat tcagctgacg tgcctcggac cgct        34

<210> SEQ ID NO 48
<211> LENGTH: 141
<212> TYPE: DNA
<213> ORGANISM: Artificial Sequence
<220> FEATURE:
<223> OTHER INFORMATION: ITR

<400> SEQUENCE: 48
aggaacccct agtgatggag ttggccactc cctctctgcg cgctcgctcg ctcactgagg    60
ccgggcgacc aaaggtcgcc cgacgcccgg gctttgcccg gcggcctcag tgagcgagc    120 gagcgcgcag ctgcctgcag g                                              141

<210> SEQ ID NO 49
<211> LENGTH: 20
<212> TYPE: PRT
<213> ORGANISM: Artificial Sequence
<220> FEATURE:
<223> OTHER INFORMATION: IL-2 signal sequence

<400> SEQUENCE: 49

Met Tyr Arg Met Gln Leu Leu Ser Cys Ile Ala Leu Ser Leu Ala Leu
1               5                   10                  15

Val Thr Asn Ser
            20

<210> SEQ ID NO 50
<211> LENGTH: 21
<212> TYPE: PRT
<213> ORGANISM: Artificial Sequence
<220> FEATURE:
<223> OTHER INFORMATION: T2A sequence

<400> SEQUENCE: 50

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 51
<211> LENGTH: 3814
<212> TYPE: DNA
<213> ORGANISM: Artificial Sequence
<220> FEATURE:
<223> OTHER INFORMATION: pITR.CBA.lucentis

<400> SEQUENCE: 51
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact    120
aggggttcct gcggccgcac gcgtgacatt gattattgac tagttattaa tagtaatcaa    180
ttacggggtc attagttcat agcccatata tggagttccg cgttacataa cttacggtaa    240
atggcccgcc tggctgaccg cccaacgacc cccgcccatt gacgtcaata atgacgtatg    300

-continued

```
ttcccatagt aacgccaata gggactttcc attgacgtca atgggtggac tatttacggt      360
aaactgccca cttggcagta catcaagtgt atcatatgcc aagtacgccc cctattgacg      420
tcaatgacgg taaatggccc gcctggcatt atgcccagta catgacccta tgggactttc      480
ctacttggca gtacatctac gtattagtca tcgctattac catgggtcga ggtgagcccc      540
acgttctgct tcactctccc catctccccc cctccccac ccccaatttt gtatttattt       600
attttttaat tattttgtgc agcgatgggg gcggggggggg gggggcgcg cgccaggcgg       660 ggcggggcgg ggcgaggggc ggggcggggc gaggcggaga ggtgcggcgg cagccaatca      720
gagcggcgcg ctccgaaagt ttccttttat ggcgaggcgg cggcggcggc ggccctataa      780
aaagcgaagc gcgcggcggg cgggagtcgc tgcgttgcct tcgccccgtg ccccgctccg      840
cgccgcctcg cgccgcccgc cccggctctg actgaccgcg ttactcccac aggtgagcgg      900
gcgggacggc ccttctcctc cgggctgtaa ttagcgcttg gtttaatgac ggctcgtttc      960
ttttctgtgg ctgcgtgaaa gccttaaagg gctccgggag ggccctttgt gcggggggga     1020
gcggctcggg gggtgcgtgc gtgtgtgtgt gcgtggggag cgccgcgtgc ggcccgcgct     1080 gcccggcgg tgtgagcgct gcgggcgcgg cgcggggctt tgtgcgctcc gcgtgtgcgc      1140
gaggggagcg cggccggggg cggtgccccg cggtgcgggg gggctgcgag gggaacaaag     1200
gctgcgtgcg gggtgtgtgc gtgggggggt gagcaggggg tgtgggcgcg gcggtcgggc     1260
tgtaaccccc ccctgcaccc ccctcccga gttgctgagc acggcccggc ttcgggtgcg      1320
gggctccgtg cggggcgtgg cgcggggctc gccgtgccgg gcggggggtg gcggcaggtg     1380
ggggtgccgg gcggggcggg gccgcctcgg gccggggagg gctcggggga ggggcgcggc     1440
ggcccccgga gcgccggcgg ctgtcgaggc gcggcgagcc gcagccattg ccttttatgg     1500
taatcgtgcg agagggcgca gggacttcct ttgtcccaaa tctgtgcgga gccgaaatct     1560
gggaggcgcc gccgcacccc ctctagcggg cgcggggcga agcggtgcgg cgccggcagg     1620
aaggaaatgg gcggggaggg ccttcgtgcg tcgccgcgcc gccgtcccct tctccctctc     1680
cagcctcggg gctgtccgcg gggggacggc tgccttcggg ggggacgggg cagggcgggg     1740
ttcggcttct ggcgtgtgac cggcggctct agagcctctg ctaaccatgt tcatgccttc     1800 ttcttttttcc tacagctcct gggcaacgtg ctggttattg tgaccggtgc caccatgtac     1860
cggatgcagc tgctgagctg tatcgccctg tctctggccc tggtcaccaa ttctgaggtg     1920
cagctggtgg aatctggcgg cggacttgtt caacctggcg gctctctgag actgagctgt     1980
gccgcttctg gctacgactt cacccactac ggcatgaact gggtccgaca ggcccctggc     2040
aaaggccttg aatgggtcgg atggatcaac acctacaccg gcgagccaac atacgccgcc     2100
gacttcaagc ggagattcac cttcagcctg gacaccagca gagcaccgc ctacctgcag      2160 atgaacagcc tgagagccga ggacaccgcc gtgtactact gcgccaagta tccctactac     2220
tacggcacca gccactggta ctttgacgtg tggggacagg gcacactggt cacagtgtct     2280
agcgcctcta caaagggccc cagcgttttc ccactggctc ctagcagcaa gtctaccagc     2340
ggaggaacag ccgctctggg ctgtctggtc aaggactact tcccgagcc tgtgaccgtg     2400 tcctggaatt ctggcgctct gacaagcggc gtgcacacct tccagctgt gctgcaaagc      2460 agcggcctgt actctctgag cagcgtcgtg acagtgccaa gcagctctct gggcacccag     2520
acctacatct gcaatgtgaa ccacaagcct agcaacacca aggtggacaa gaaggtggaa     2580
cccaagagct gcgacaagac ccacaccggc aagcggaaga gaaggagggctc tggcgaaggc     2640
```

| | |
|---|---|
| agaggcagcc tgcttacatg tggcgacgtg aagagaacc ccggacctat gtatagaatg | 2700 |
| cagctcctgt cctgcattgc cctgagcctg gctctcgtga ccaacagcga catccagctg | 2760 |
| acacagagcc ccagcagcct gtctgcctct gtgggagaca gagtgaccat cacctgtagc | 2820 |
| gccagccagg acatctccaa ctacctgaac tggtatcagc aaaagcccgg caaggcccct | 2880 |
| aaggtgctga tctacttcac aagcagcctg cactccggcg tgcccagcag attttctggc | 2940 |
| tctggcagcg gcaccgactt caccctgacc atatctagcc tgcagcctga ggacttcgcc | 3000 |
| acctactact gccagcagta cagcaccgtg ccttggacat ttggccaggg cacaaaggtg | 3060 |
| gaaatcaagc ggactgtggc cgctcctagc gtgttcatct ttccacctag cgacgagcag | 3120 |
| ctgaagtctg gcacagcctc tgtcgtgtgc ctgctgaaca acttctaccc cagagaagcc | 3180 |
| aaggtgcagt ggaaagtgga caatgccctg cagagcggca acagccaaga gagcgtgaca | 3240 |
| gagcaggact ccaaggatag cacctatagc ctgagcagca ccctgacact gagcaaggcc | 3300 |
| gactacgaga agcacaaagt gtacgcctgc gaagtgaccc accagggcct ttctagccct | 3360 |
| gtgaccaaga gcttcaaccg gggcgaatgt taagagctcg ctgatcagcc tcgactgtgc | 3420 |
| cttctagttg ccagccatct gttgtttgcc ctccccgt gccttccttg accctggaag | 3480 |
| gtgccactcc cactgtcctt tcctaataaa atgaggaaat tgcatcgcat tgtctgagta | 3540 |
| ggtgtcattc tattctgggg ggtggggtgg ggcaggacag caaggggag gattgggaag | 3600 |
| acaatagcag gcatgctggg gatgcggtgg gctctatgga agcttgaatt cagctgacgt | 3660 |
| gcctcggacc gctaggaacc cctagtgatg gagttggcca ctccctctct gcgcgctcgc | 3720 |
| tcgctcactg aggccgggcg accaaaggtc gcccgacgcc cgggctttgc ccgggcggcc | 3780 |
| tcagtgagcg agcgagcgcg cagctgcctg cagg | 3814 |

<210> SEQ ID NO 52
<211> LENGTH: 699
<212> TYPE: DNA
<213> ORGANISM: Artificial Sequence
<220> FEATURE:
<223> OTHER INFORMATION: Sequence encoding ranibizumab heavy chain

<400> SEQUENCE: 52

| | |
|---|---|
| gaggtgcagc tggtggaatc tggcggcgga cttgttcaac ctggcggctc tctgagactg | 60 |
| agctgtgccg cttctggcta cgacttcacc cactacggca tgaactgggt ccgacaggcc | 120 |
| cctggcaaag gccttgaatg ggtcggatgg atcaacacct acaccggcga gccaacatac | 180 |
| gccgccgact tcaagcggag attcaccttc agcctggaca ccagcaagag caccgcctac | 240 |
| ctgcagatga acagcctgag agccgaggac accgccgtgt actactgcgc caagtatccc | 300 |
| tactactacg gcaccagcca ctggtacttt gacgtgtggg gacagggcac actggtcaca | 360 |
| gtgtctagcg cctctacaaa gggcccagc gttttcccac tggctcctag cagcaagtct | 420 |
| accagcggag gaacagccgc tctggctgt ctggtcaagg actactttcc cgagcctgtg | 480 |
| accgtgtcct ggaattctgg cgctctgaca agcggcgtgc acacctttcc agctgtgctg | 540 |
| caaagcagcg gcctgtactc tctgagcagc gtcgtgacag tgccaagcag ctctctgggc | 600 |
| acccagacct acatctgcaa tgtgaaccac aagcctagca cac caaggt ggacaagaag | 660 |
| gtggaaccca agagctgcga caagacccac accggcaag | 699 |

<210> SEQ ID NO 53
<211> LENGTH: 645
<212> TYPE: DNA
<213> ORGANISM: Artificial Sequence
<220> FEATURE:
<223> OTHER INFORMATION: Sequence encoding ranibizumab light chain

<400> SEQUENCE: 53

| | | | | | |
|---|---|---|---|---|---|
| gacatccagc | tgacacagag | ccccagcagc | ctgtctgcct | ctgtgggaga | cagagtgacc | 60 |
| atcacctgta | gcgccagcca | ggacatctcc | aactacctga | actggtatca | gcaaaagccc | 120 |
| ggcaaggccc | ctaaggtgct | gatctacttc | acaagcagcc | tgcactccgg | cgtgcccagc | 180 |
| agattttctg | gctctggcag | cggcaccgac | ttcaccctga | ccatatctag | cctgcagcct | 240 |
| gaggacttcg | ccacctacta | ctgccagcag | tacagcaccg | tgccttggac | atttggccag | 300 |
| ggcacaaagg | tggaaatcaa | gcggactgtg | gccgctccta | gcgtgttcat | ctttccacct | 360 |
| agcgacgagc | agctgaagtc | tggcacagcc | tctgtcgtgt | gcctgctgaa | caacttctac | 420 |
| cccagagaag | ccaaggtgca | gtggaaagtg | gacaatgccc | tgcagagcgg | caacagccaa | 480 |
| gagagcgtga | cagagcagga | ctccaaggat | agcacctata | gcctgagcag | caccctgaca | 540 |
| ctgagcaagg | ccgactacga | gaagcacaaa | gtgtacgcct | gcgaagtgac | ccaccagggc | 600 |
| ctttctagcc | ctgtgaccaa | gagcttcaac | cggggcgaat | gttaa | | 645 |

<210> SEQ ID NO 54
<211> LENGTH: 233
<212> TYPE: PRT
<213> ORGANISM: Artificial Sequence
<220> FEATURE:
<223> OTHER INFORMATION: Ranibizumab Heavy Chain

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Gly Lys
225                 230

<210> SEQ ID NO 55
<211> LENGTH: 4573
<212> TYPE: DNA
<213> ORGANISM: Artificial Sequence
<220> FEATURE:
<223> OTHER INFORMATION: pITR.CBA.Lucentis.tGFP

<400> SEQUENCE: 55

| | | | | | |
|---|---|---|---|---|---|
| cctgcaggca | gctgcgcgct | cgctcgctca | ctgaggccgc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggccgcac | gcgtgacatt | gattattgac | tagttattaa | tagtaatcaa | 180 |
| ttacggggtc | attagttcat | agcccatata | tggagttccg | cgttacataa | cttacggtaa | 240 |
| atggcccgcc | tggctgaccg | cccaacgacc | cccgcccatt | gacgtcaata | atgacgtatg | 300 |
| ttcccatagt | aacgccaata | gggactttcc | attgacgtca | atgggtggac | tatttacggt | 360 |
| aaactgccca | cttggcagta | catcaagtgt | atcatatgcc | aagtacgccc | cctattgacg | 420 |
| tcaatgacgg | taaatggccc | gcctggcatt | atgcccagta | catgacctta | tgggactttc | 480 |
| ctacttggca | gtacatctac | gtattagtca | tcgctattac | catgggtcga | ggtgagcccc | 540 |
| acgttctgct | tcactctccc | catctccccc | cctccccac | cccaattttg | tatttattt | 600 |
| attttttaat | tattttgtgc | agcgatgggg | gcggggggg | ggggggcgcg | cgccaggcgg | 660 |
| ggcggggcgg | ggcgaggggc | ggggcgggggc | gaggcggaga | ggtgcggcgg | cagccaatca | 720 |
| gagcggcgcg | ctccgaaagt | ttccttttat | ggcgaggcgg | cggcggcggc | ggccctataa | 780 |
| aaagcgaagc | gcgcggcggg | cgggagtcgc | tgcgttgcct | tcgccccgtg | ccccgctccg | 840 |
| cgccgcctcg | cgccgcccgc | cccggctctg | actgaccgcg | ttactcccac | aggtgagcgg | 900 |
| gcgggacggc | ccttctcctc | cgggctgtaa | ttagcgcttg | gtttaatgac | ggctcgtttc | 960 |
| ttttctgtgg | ctgcgtgaaa | gccttaaagg | gctccgggag | ggccctttgt | gcgggggga | 1020 |
| gcggctcggg | gggtgcgtgc | gtgtgtgtgt | gcgtggggag | cgccgcgtgc | ggcccgcgct | 1080 |
| gcccggcggc | tgtgagcgct | gcgggcgcgg | cgcggggctt | tgtgcgctcc | gcgtgtgcgc | 1140 |
| gaggggagcg | cggccggggg | cggtgccccg | cggtgcgggg | gggctgcgag | gggaacaaag | 1200 |
| gctgcgtgcg | gggtgtgtgc | gtgggggggt | gagcaggggg | tgtgggcgcg | gcggtcgggc | 1260 |
| tgtaaccccc | ccctgcaccc | ccctccccga | gttgctgagc | acggcccggc | ttcgggtgcg | 1320 |
| gggctccgtg | cggggcgtgg | cgcggggctc | gccgtgccgg | gcgggggtg | gcggcaggtg | 1380 |
| ggggtgccgg | gcggggcggg | gccgcctcgg | gccggggagg | gctcggggga | ggggcgcggc | 1440 |
| ggcccccgga | gcgccggcgg | ctgtcgaggc | gcggcgagcc | gcagccattg | ccttttatgg | 1500 |
| taatcgtgcg | agagggcgca | gggacttcct | ttgtcccaaa | tctgtgcgga | gccgaaatct | 1560 |
| gggaggcgcc | gccgcacccc | ctctagcggg | cgcggggcga | agcggtgcgg | cgccggcagg | 1620 |
| aaggaaatgg | gcggggaggg | ccttcgtgcg | tcgccgcgcc | gccgtcccct | tctccctctc | 1680 |
| cagcctcggg | gctgtccgcg | gggggacggc | tgccttcggg | ggggacgggg | cagggcgggg | 1740 |
| ttcggcttct | ggcgtgtgac | cggcggctct | agagcctctg | ctaaccatgt | tcatgccttc | 1800 |
| ttctttttcc | tacagctcct | gggcaacgtg | ctggttattg | tgaccggtgc | caccatgtac | 1860 |
| cggatgcagc | tgctgagctg | tatcgccctg | tctctggccc | tggtcaccaa | ttctgaggtg | 1920 |
| cagctggtgg | aatctggcgg | cggacttgtt | caacctggcg | gctctctgag | actgagctgt | 1980 |

```
gccgcttctg gctacgactt cacccactac ggcatgaact gggtccgaca ggcccctggc    2040
aaaggccttg aatgggtcgg atggatcaac acctacaccg gcgagccaac atacgccgcc    2100
gacttcaagc ggagattcac cttcagcctg acaccagca agagcaccgc ctacctgcag     2160
atgaacagcc tgagagccga ggacaccgcc gtgtactact gcgccaagta tccctactac    2220
tacggcacca gccactggta ctttgacgtg tggggacagg gcacactggt cacagtgtct    2280
agcgcctcta caaagggccc cagcgttttc ccactggctc ctagcagcaa gtctaccagc    2340
ggaggaacag ccgctctggg ctgtctggtc aaggactact tcccgagcc tgtgaccgtg     2400 tcctggaatt ctggcgctct gacaagcggc gtgcacacct tccagctgt gctgcaaagc     2460 agcggcctgt actctctgag cagcgtcgtg acagtgccaa gcagctctct gggcacccag    2520
acctacatct gcaatgtgaa ccacaagcct agcaacacca aggtggacaa gaaggtggaa    2580
cccaagagct gcgacaagac ccacaccggc aagcggaaga agagggctc tggcgaaggc     2640 agaggcagcc tgcttacatg tggcgacgtg aagagaacc ccggacctat gtatagaatg      2700
cagctcctgt cctgcattgc cctgagcctg gctctcgtga ccaacagcga catccagctg    2760
acacagagcc ccagcagcct gtctgcctct gtgggagaca gagtgaccat cacctgtagc    2820
gccagccagg acatctccaa ctacctgaac tggtatcagc aaaagccccg caaggcccct    2880
aaggtgctga tctacttcac aagcagcctg cactccggcg tgcccagcag attttctggc    2940
tctggcagcg gcaccgactt caccctgacc atatctagcc tgcagcctga ggacttcgcc    3000
acctactact gccagcagta cagcaccgtg ccttggacat ttggccaggg cacaaaggtg    3060
gaaatcaagc ggactgtggc cgctcctagc gtgttcatct tcccacctag cgacgagcag    3120
ctgaagtctg gcacagcctc tgtcgtgtgc ctgctgaaca acttctaccc cagagaagcc    3180
aaggtgcagt ggaaagtgga caatgccctg cagagcggca cagccaaga gagcgtgaca     3240 gagcaggact ccaaggatag cacctatagc ctgagcagca ccctgacact gagcaaggcc    3300
gactacgaga agcacaaagt gtacgcctgc gaagtgaccc accagggcct ttctagccct    3360
gtgaccaaga gcttcaaccg gggcgaatgt ggctccggag agggcagagg aagtctgcta    3420
acatgcggtg acgtcgagga gaatcctggc ccaatggaga gcgacgagag cggcctgccc    3480
gccatggaga tcgagtgccg catcaccggc accctgaacg gcgtggagtt cgagctggtg    3540
ggcggcggag agggcacccc cgagcagggc cgcatgacca caagatgaa gagcaccaaa      3600 ggcgccctga ccttcagccc ctacctgctg agccacgtga tgggctacgg cttctaccac    3660
ttcggcaccc tcccccagcgg ctacgagaac ccccttcctgc acgccatcaa caacggcggc   3720
tacaccaaca cccgcatcga gaagtacgag gacggcggcg tgctgcacgt gagcttcagc    3780
taccgctacg aggccggccg cgtgatcggc gacttcaagg tgatgggcac cggcttcccc    3840
gaggacagcg tgatcttcac cgacaagatc atccgcagca acgccaccgt ggagcacctg    3900
caccccatgg gcgataacga tctgatggc agcttcaccc gcaccttcag cctgcgcgac      3960
ggcggctact acagctccgt ggtggacagc acatgcact tcaagagcgc catccacccc      4020
agcatcctgc agaacggggg ccccatgttc gccttccgcc gcgtggagga ggatcacagc    4080
aacaccgagc tgggcatcgt ggagtaccag cacgccttca agaccccgga tgcagatgcc    4140
ggtgaagaat aagagctcgc tgatcagcct cgactgtgcc ttctagttgc cagccatctg    4200
ttgtttgccc ctccccgtg ccttccttga ccctggaagg tgccactccc actgtccttt      4260
cctaataaaa tgaggaaatt gcatcgcatt gtctgagtag gtgtcattct attctggggg    4320
gtggggtggg gcaggacagc aagggggagg attgggaaga caatagcagg catgctgggg    4380
```

```
atgcggtggg ctctatggaa gcttgaattc agctgacgtg cctcggaccg ctaggaaccc    4440
ctagtgatgg agttggccac tccctctctg cgcgctcgct cgctcactga ggccgggcga    4500
ccaaaggtcg cccgacgccc gggctttgcc cgggcggcct cagtgagcga gcgagcgcgc    4560
agctgcctgc agg                                                       4573
```

<210> SEQ ID NO 56
<211> LENGTH: 642
<212> TYPE: DNA
<213> ORGANISM: Artificial Sequence
<220> FEATURE:
<223> OTHER INFORMATION: Sequence encoding ranibizumab light chain

<400> SEQUENCE: 56

```
gacatccagc tgacacagag ccccagcagc ctgtctgcct ctgtgggaga cagagtgacc      60
atcacctgta gcgccagcca ggacatctcc aactacctga actggtatca gcaaaagccc     120
ggcaaggccc ctaaggtgct gatctacttc acaagcagcc tgcactccgg cgtgcccagc     180 agatttctg  gctctggcag cggcaccgac ttcaccctga ccatatctag cctgcagcct     240
gaggacttcg ccacctacta ctgccagcag tacagcaccg tgccttggac atttggccag     300
ggcacaaagg tggaaatcaa gcggactgtg gccgctccta gcgtgttcat ctttccacct     360
agcgacgagc agctgaagtc tggcacagcc tctgtcgtgt gcctgctgaa caacttctac     420
cccagagaag ccaaggtgca gtggaaagtg gacaatgccc tgcagagcgg caacagccaa     480
gagagcgtga cagagcagga ctccaaggat agcacctata gcctgagcag caccctgaca     540
ctgagcaagg ccgactacga aagcacaaaa gtgtacgcct gcgaagtgac ccaccagggc     600 cttttctagcc ctgtgaccaa gagcttcaac cggggcgaat gt                       642
```

<210> SEQ ID NO 57
<211> LENGTH: 63
<212> TYPE: DNA
<213> ORGANISM: Artificial Sequence
<220> FEATURE:
<223> OTHER INFORMATION: Linker sequence

<400> SEQUENCE: 57

```
ggctccggag agggcagagg aagtctgcta acatgcggtg acgtcgagga gaatcctggc      60
cca                                                                   63
```

<210> SEQ ID NO 58
<211> LENGTH: 699
<212> TYPE: DNA
<213> ORGANISM: Artificial Sequence
<220> FEATURE:
<223> OTHER INFORMATION: Sequence encoding Turbo GFP

<400> SEQUENCE: 58

```
atggagagcg acgagagcgg cctgcccgcc atggagatcg agtgccgcat caccggcacc      60
ctgaacggcg tggagttcga gctggtgggc ggcggagagg gcaccccga gcagggccgc     120 atgaccaaca agatgaagag caccaaaggc gccctgacct tcagcccta cctgctgagc     180 cacgtgatgg gctacggctt ctaccacttc ggcacctacc ccagcggcta cgagaacccc     240
ttcctgcacg ccatcaacaa cggcggctac accaacaccc gcatcgagaa gtacgaggac     300
ggcgccgtgc tgcacgtgag cttcagctac cgctacgagg ccggccgcgt gatcggcgac     360
ttcaaggtga tgggcaccgg cttccccgag gacagcgtga tcttcaccga caagatcatc     420
```

```
cgcagcaacg ccaccgtgga gcacctgcac cccatgggcg ataacgatct ggatggcagc    480
ttcacccgca ccttcagcct gcgcgacggc ggctactaca gctccgtggt ggacagccac    540
atgcacttca gagcgccat ccaccccagc atcctgcaga acggggcc catgttcgcc       600 ttccgccgcg tggaggagga tcacagcaac accgagctgg gcatcgtgga gtaccagcac    660
gccttcaaga ccccggatgc agatgccggt gaagaataa                           699
```

<210> SEQ ID NO 59
<211> LENGTH: 232
<212> TYPE: PRT
<213> ORGANISM: Artificial Sequence
<220> FEATURE:
<223> OTHER INFORMATION: Turbo GFP

<400> SEQUENCE: 59

```
Met Glu Ser Asp Glu Ser Gly Leu Pro Ala Met Glu Ile Glu Cys Arg
1               5                   10                  15

Ile Thr Gly Thr Leu Asn Gly Val Glu Phe Glu Leu Val Gly Gly Gly
                20                  25                  30

Glu Gly Thr Pro Glu Gln Gly Arg Met Thr Asn Lys Met Lys Ser Thr
            35                  40                  45

Lys Gly Ala Leu Thr Phe Ser Pro Tyr Leu Leu Ser His Val Met Gly
        50                  55                  60

Tyr Gly Phe Tyr His Phe Gly Thr Tyr Pro Ser Gly Tyr Glu Asn Pro
65                  70                  75                  80

Phe Leu His Ala Ile Asn Asn Gly Gly Tyr Thr Asn Thr Arg Ile Glu
                85                  90                  95

Lys Tyr Glu Asp Gly Gly Val Leu His Val Ser Phe Ser Tyr Arg Tyr
            100                 105                 110

Glu Ala Gly Arg Val Ile Gly Asp Phe Lys Val Met Gly Thr Gly Phe
        115                 120                 125

Pro Glu Asp Ser Val Ile Phe Thr Asp Lys Ile Ile Arg Ser Asn Ala
    130                 135                 140

Thr Val Glu His Leu His Pro Met Gly Asp Asn Asp Leu Asp Gly Ser
145                 150                 155                 160

Phe Thr Arg Thr Phe Ser Leu Arg Asp Gly Gly Tyr Tyr Ser Ser Val
                165                 170                 175

Val Asp Ser His Met His Phe Lys Ser Ala Ile His Pro Ser Ile Leu
            180                 185                 190

Gln Asn Gly Gly Pro Met Phe Ala Phe Arg Arg Val Glu Gly Asp His
        195                 200                 205

Ser Asn Thr Glu Leu Gly Ile Val Glu Tyr Gln His Ala Phe Lys Thr
    210                 215                 220

Pro Asp Ala Asp Ala Gly Glu Glu
225                 230
```

<210> SEQ ID NO 60
<211> LENGTH: 3631
<212> TYPE: DNA
<213> ORGANISM: Artificial Sequence
<220> FEATURE:
<223> OTHER INFORMATION: pITR.CBA.Eylea

<400> SEQUENCE: 60

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact    120
```

-continued

| | | | | |
|---|---|---|---|---|
| agggggttcct | gcggccgcac | gcgtgacatt | gattattgac | tagttattaa | tagtaatcaa | 180 |
| ttacggggtc | attagttcat | agcccatata | tggagttccg | cgttacataa | cttacggtaa | 240 |
| atggcccgcc | tggctgaccg | cccaacgacc | cccgcccatt | gacgtcaata | atgacgtatg | 300 |
| ttcccatagt | aacgccaata | gggactttcc | attgacgtca | atgggtggac | tatttacggt | 360 |
| aaactgccca | cttggcagta | catcaagtgt | atcatatgcc | aagtacgccc | cctattgacg | 420 |
| tcaatgacgg | taaatggccc | gcctggcatt | atgcccagta | catgacctta | tgggactttc | 480 |
| ctacttggca | gtacatctac | gtattagtca | tcgctattac | catgggtcga | ggtgagcccc | 540 |
| acgttctgct | tcactctccc | catctccccc | cctccccac | cccaatttt | gtatttattt | 600 |
| atttttaat | tattttgtgc | agcgatgggg | gcggggggg | ggggggcgcg | cgccaggcgg | 660 |
| ggcggggcgg | ggcgagggc | ggggcgggc | gaggcggaga | ggtgcggcgg | cagccaatca | 720 |
| gagcggcgcg | ctccgaaagt | ttccttttat | ggcgaggcgg | cggcggcggc | ggccctataa | 780 |
| aaagcgaagc | gcgcggcggg | cgggagtcgc | tgcgttgcct | tcgccccgtg | ccccgctccg | 840 |
| cgccgcctcg | cgccgcccgc | cccggctctg | actgaccgcg | ttactcccac | aggtgagcgg | 900 |
| gcgggacggc | ccttctcctc | cgggctgtaa | ttagcgcttg | gtttaatgac | ggctcgtttc | 960 |
| ttttctgtgg | ctgcgtgaaa | gccttaaagg | gctccgggag | ggccctttgt | gcgggggga | 1020 |
| gcggctcggg | gggtgcgtgc | gtgtgtgtgt | gcgtggggag | cgccgcgtgc | ggcccgcgct | 1080 |
| gcccggcgg | tgtgagcgct | gcgggcgcgg | cgcggggctt | tgtgcgctcc | gcgtgtgcgc | 1140 |
| gaggggagcg | cggccggggg | cggtgccccg | cggtgcgggg | gggctgcgag | gggaacaaag | 1200 |
| gctgcgtgcg | gggtgtgtgc | gtgggggggt | gagcaggggg | tgtgggcgcg | gcggtcgggc | 1260 |
| tgtaacccc | ccctgcaccc | ccctccccga | gttgctgagc | acggcccggc | ttcgggtgcg | 1320 |
| gggctccgtg | cggggcgtgg | cgcggggctc | gccgtgccgg | gcggggggtg | gcggcaggtg | 1380 |
| ggggtgccgg | gcggggcggg | gccgcctcgg | gccggggagg | gctcgggggga | ggggcgcggc | 1440 |
| ggcccccgga | gcgccggcgg | ctgtcgaggc | gcggcgagcc | gcagccattg | ccttttatgg | 1500 |
| taatcgtgcg | agagggcgca | gggacttcct | ttgtcccaaa | tctgtgcgga | gccgaaatct | 1560 |
| gggaggcgcc | gccgcacccc | ctctagcggg | cgcggggcga | agcggtgcgg | cgccggcagg | 1620 |
| aaggaaatgg | gcggggaggg | ccttcgtgcg | tcgccgcgcc | gccgtccct | tctccctctc | 1680 |
| cagcctcggg | gctgtccgcg | gggggacggc | tgccttcggg | ggggacgggg | cagggcgggg | 1740 |
| ttcggcttct | ggcgtgtgac | cggcggctct | agagcctctg | ctaaccatgt | tcatgccttc | 1800 |
| ttctttttcc | tacagctcct | gggcaacgtg | ctggttattg | tgaccggtgc | caccatgtac | 1860 |
| cggatgcagc | tgctgagctg | tatcgccctg | tctctggccc | tggtcaccaa | ttctagcgat | 1920 |
| accggcagac | ccttcgtgga | aatgtacagc | gagatcccg | agatcatcca | catgaccgag | 1980 |
| ggcagagagc | tggtcatccc | ctgcagagtg | acaagcccca | acatcaccgt | gactctgaag | 2040 |
| aagttccctc | tggacacact | gatccccgac | ggcaagagaa | tcatctggga | cagccggaag | 2100 |
| ggcttcatca | tcagcaacgc | cacctacaaa | gagatcggcc | tgctgacctg | tgaagccacc | 2160 |
| gtgaatggcc | acctgtacaa | gaccaactac | ctgacacaca | gacagaccaa | caccatcatc | 2220 |
| gacgtggtgc | tgagccctag | ccacggcatt | gaactgtctg | tgggcgagaa | gctggtgctg | 2280 |
| aactgtaccg | ccagaaccga | gctgaacgtg | ggcatcgact | tcaactggga | gtaccccagc | 2340 |
| agcaagcacc | agcacaagaa | actggtcaac | cgggacctga | aaacccagag | cggcagcgag | 2400 |
| atgaagaaat | tcctgagcac | cctgaccatc | gacggcgtga | ccagatcgga | ccagggcctg | 2460 |
| tacacatgtg | ccgccagctc | tggcctgatg | accaagaaaa | acagcacctt | cgtgcgggtg | 2520 |

-continued

```
cacgagaagg acaagaccca cacctgtcct ccatgtcctg ctccagaact gctcggcgga    2580
ccttccgtgt tcctgtttcc tccaaagcct aaggacaccc tgatgatcag cagaaccccc    2640
gaagtgacct gcgtggtggt ggatgtgtcc cacgaggatc ccgaagtgaa gttcaattgg    2700
tacgtggacg gcgtggaagt gcacaacgcc aagaccaagc ctagagagga acagtacaat    2760
agcacctaca gagtggtgtc cgtgctgacc gtgctgcacc aggattggct gaacggcaaa    2820
gagtacaagt gcaaggtgtc caacaaggcc ctgcctgctc tatcgagaa aaccatctcc     2880 aaggccaagg gccagcctag ggaaccccag gtttacacac tgcctccaag cagggacgag    2940
ctgacaaaga accaggtgtc cctgacctgc ctggtcaagg gcttctaccc ttccgatatc    3000
gccgtggaat gggagagcaa tggccagcct gagaacaact acaagacaac ccctcctgtg    3060
ctggacagcg acggctcatt cttcctgtac agcaagctga cagtggacaa gagcagatgg    3120
cagcagggca acgtgttcag ctgcagcgtg atgcacgagg ccctgcacaa ccactacacc    3180
cagaagtccc tgagcctgtc tcctggataa gagctcgctg atcagcctcg actgtgcctt    3240
ctagttgcca gccatctgtt gtttgcccct ccccgtgcc ttccttgacc ctggaaggtg     3300
ccactcccac tgtcctttcc taataaaatg aggaaattgc atcgcattgt ctgagtaggt    3360
gtcattctat tctggggggt ggggtggggc aggacagcaa gggggaggat tgggaagaca    3420
atagcaggca tgctggggat gcggtgggct ctatggaagc ttgaattcag ctgacgtgcc    3480
tcggaccgct aggaacccct agtgatggag ttggccactc cctctctgcg cgctcgctcg    3540
ctcactgagg ccgggcgacc aaaggtcgcc cgacgcccgg gctttgcccg ggcggcctca    3600
gtgagcgagc gagcgcgcag ctgcctgcag g                                   3631
```

<210> SEQ ID NO 61
<211> LENGTH: 1296
<212> TYPE: DNA
<213> ORGANISM: Artificial Sequence
<220> FEATURE:
<223> OTHER INFORMATION: Sequence encoding aflibercept

<400> SEQUENCE: 61

```
agcgataccg gcagacccct cgtggaaatg tacagcgaga tccccgagat catccacatg      60
accgagggca gagagctggt catcccctgc agagtgacaa gccccaacat caccgtgact     120
ctgaagaagt tccctctgga cactctgatc ccgacggca gagaatcat ctgggacagc       180 cggaagggct tcatcatcag caacgccacc tacaaagaga tcggcctgct gacctgtgaa     240
gccaccgtga atggccacct gtacaagacc aactacctga cacacagaca gaccaacacc    300
atcatcgacg tggtgctgag ccctagccac ggcattgaac tgtctgtggg cgagaagctg    360
gtgctgaact gtaccgccag aaccgagctg aacgtgggca tcgacttcaa ctgggagtac    420
cccagcagca agcaccagca caagaaactg gtcaaccggg acctgaaaac ccagagcggc    480
agcgagatga gaaattcct gagcaccctg accatcgacg gcgtgaccag atctgaccag    540
ggcctgtaca catgtgccgc cagctctggc ctgatgacca gaaaaacag caccttcgtg    600 cgggtgcacg agaaggacaa gacccacacc tgtcctccat gtcctgctcc agaactgctc    660 ggcggaccctt ccgtgttcct gtttcctcca aagcctaagg acaccctgat gatcagcaga    720 accccctgaag tgacctgcgt ggtggtggat gtgtcccacg aggatcccga agtgaagttc    780
aattggtacg tggacggcgt ggaagtgcac aacgccaaga ccaagcctag agaggaacag    840
tacaatagca cctacagagt ggtgtccgtg ctgaccgtgc tgcaccagga ttggctgaac    900
```

```
ggcaaagagt acaagtgcaa ggtgtccaac aaggccctgc ctgctcctat cgagaaaacc    960
atctccaagg ccaagggcca gcctagggaa ccccaggttt acacactgcc tccaagcagg   1020
gacgagctga caaagaacca ggtgtccctg acctgcctgg tcaagggctt ctacccttcc   1080
gatatcgccg tggaatggga gagcaatggc cagcctgaga acaactacaa gacaaccccct  1140 cctgtgctgg acagcgacgg ctcattcttc ctgtacagca agctgacagt ggacaagagc   1200
agatggcagc agggcaacgt gttcagctgc agcgtgatgc acgaggccct gcacaaccac   1260
tacacccaga agtccctgag cctgtctcct ggataa                             1296
```

What is claimed is:

1. An adeno-associated virus (AAV) vector comprising a nucleotide sequence which comprises:
   (i) a first coding sequence that encodes a first polypeptide comprising an antibody heavy chain variable domain operably linked to a first signal peptide, and a second coding sequence that encodes a second polypeptide comprising an antibody light chain variable domain operably linked to a second signal peptide, wherein the sequence encoding the antibody heavy chain variable domain consists of SEQ ID NO: 52, and the sequence encoding the antibody light chain variable domain consists of SEQ ID NO: 53, and
   (ii) a sequence encoding a thosea asigna virus 2A (T2A) peptide that is present between the first coding sequence and the second coding sequence, wherein the first and second polypeptides together specifically bind to one or more mammalian VEGF proteins.

2. A kit comprising the adeno-associated virus (AAV) vector of claim 1.

3. A composition comprising an adeno-associated virus (AAV) vector and a pharmaceutically acceptable carrier, wherein the AAV vector comprises a nucleotide sequence comprising:
   (i) a first coding sequence that encodes a first polypeptide comprising an antibody heavy chain variable domain operably linked to a first signal peptide, and a second coding sequence that encodes a second polypeptide comprising an antibody light chain variable domain operably linked to a second signal peptide, wherein the sequence encoding the antibody heavy chain variable domain consists of SEQ ID NO: 52, and the sequence encoding the antibody light chain variable domain consists of SEQ ID NO: 53, and
   (ii) a sequence encoding a thosea asigna virus 2A (T2A) peptide that is present between the first coding sequence and the second coding sequence, wherein the first and second polypeptides together specifically bind to one or more mammalian VEGF proteins, and
   wherein the composition is formulated for intra-cochlear administration.

4. The AAV vector of claim 1, wherein the nucleotide sequence comprises one or both of (i) a promoter and (ii) a Kozak sequence.

5. The AAV vector of claim 4, wherein the promoter is an inducible promoter, a constitutive promoter, or a tissue-specific promoter.

6. The AAV vector of claim 5, wherein the constitutive promoter is a CAG promoter, a CBA promoter, or a CMV promoter.

7. The AAV vector of claim 1, wherein the nucleotide sequence comprises a polyadenylation signal sequence.

8. The AAV vector of claim 1, wherein the first polypeptide comprises the amino acid sequence of SEQ ID NO: 54.

9. The AAV vector of claim 1, wherein the second polypeptide comprises the amino acid sequence of SEQ ID NO: 7.

10. The AAV vector of claim 1, wherein one or both of the first and second signal peptides comprise an IL2 signal peptide.

11. The AAV vector of claim 1, wherein the nucleotide sequence further comprises two AAV inverted terminal repeats (ITRs), wherein the two AAV ITRs flank both of the coding sequences.

12. The AAV vector of claim 11, wherein the two AAV ITRs are AAV2 ITRs, or are derived from AAV2 ITRs.

13. The AAV vector of claim 11, wherein one of the two ITRs comprises the nucleotide sequence as set forth in SEQ ID NO: 36.

14. The AAV vector of claim 11, wherein one of the two ITRs comprises the nucleotide sequence as set forth in SEQ ID NO: 48.

15. The composition of claim 3, wherein the nucleotide sequence comprises one or both of (i) a promoter and (ii) a Kozak sequence.

16. The composition of claim 15, wherein the promoter is an inducible promoter, a constitutive promoter, or a tissue-specific promoter.

17. The composition of claim 16, wherein the constitutive promoter is a CAG promoter, a CBA promoter, or a CMV promoter.

18. The composition of claim 3, wherein the nucleotide sequence comprises a polyadenylation signal sequence.

19. The composition of claim 3, wherein the first polypeptide comprises the amino acid sequence of SEQ ID NO: 54.

20. The composition of claim 3, wherein the second polypeptide comprises the amino acid sequence of SEQ ID NO: 7.

21. The composition of claim 3, wherein one or both of the first and second signal peptide comprises an IL2 signal peptide.

22. The composition of claim 3, wherein the nucleotide sequence further comprises two AAV inverted terminal repeats (ITRs), wherein the two AAV ITRs flank both of the coding sequences.

23. The composition of claim 22, wherein the two AAV ITRs are AAV2 ITRs, or are derived from AAV2 ITRs.

24. The composition of claim 22, wherein one of the two ITRs comprises the nucleotide sequence as set forth in SEQ ID NO: 36.

25. The composition of claim 22, wherein one of the two ITRs comprises the nucleotide sequence as set forth in SEQ ID NO: 48.

\* \* \* \* \*